US007527933B2

(12) United States Patent
Sahin et al.

(10) Patent No.: US 7,527,933 B2
(45) Date of Patent: May 5, 2009

(54) GENETIC PRODUCTS DIFFERENTIALLY EXPRESSED IN TUMORS AND THE USE THEREOF

(75) Inventors: Ugur Sahin, Mainz (DE); Ozlem Türeci, Mainz (DE); Michael Koslowski, Köln (DE)

(73) Assignee: Ganymed Pharmaceuticals AGMA (US)

( * ) Notice: Subject to any disclaimer, the term of this patent is extended or adjusted under 35 U.S.C. 154(b) by 0 days.

(21) Appl. No.: 10/537,002

(22) PCT Filed: Nov. 21, 2003

(86) PCT No.: PCT/EP03/13091

§ 371 (c)(1), (2), (4) Date: May 20, 2005

(87) PCT Pub. No.: WO2004/047863

PCT Pub. Date: Jun. 10, 2004

(65) Prior Publication Data

US 2006/0035852 A1 Feb. 16, 2006

(30) Foreign Application Priority Data

Nov. 22, 2002 (DE) ................................ 102 54 601

(51) Int. Cl.
*G01N 33/53* (2006.01)
*G01N 33/574* (2006.01)

(52) U.S. Cl. ....................................... 435/7.1; 435/7.23

(58) Field of Classification Search ...................... 435/4
See application file for complete search history.

(56) References Cited

U.S. PATENT DOCUMENTS 6,235,481 B1 5/2001 Horikawa et al. .............. 435/6

FOREIGN PATENT DOCUMENTS

| | | |
|---|---|---|
| WO | WO 99/64452 A1 | 12/1999 |
| WO | WO 00/08206 | 2/2000 |
| WO | WO 00/12708 | 3/2000 |
| WO | WO 00/15659 | 3/2000 |
| WO | WO 0015659 A2 * | 3/2000 |
| WO | WO 00/20447 | 4/2000 |
| WO | WO 00/78961 | 12/2000 |
| WO | WO 01/16318 | 3/2001 |
| WO | WO 01/27257 A1 | 4/2001 |
| WO | WO 01/48192 | 7/2001 |
| WO | WO 01/55314 | 8/2001 |
| WO | WO 01/55318 | 8/2001 |
| WO | WO 01/55326 | 8/2001 |
| WO | WO 01/62920 A2 | 8/2001 |
| WO | WO 0154708 A1 * | 8/2001 |
| WO | WO 01/68848 | 9/2001 |
| WO | WO 01/75067 A2 | 10/2001 |
| WO | WO 01/77137 | 10/2001 |
| WO | WO 01/90357 | 11/2001 |
| WO | WO 02/14500 A2 | 2/2002 |
| WO | WO 02/18576 | 3/2002 |
| WO | WO 02/20569 | 3/2002 |
| WO | WO 02/061087 A2 | 8/2002 |
| WO | WO 02/103028 A2 | 12/2002 |

OTHER PUBLICATIONS

Herbert et al (The Dictionary of Immunology, Academic Press, 3rd Edition, London, 1985, p. 58-59).*

Greenbaum et al. (Genome Biology, 2003, vol. 4, Issue 9, pp. 117.1-117.8).*

Brennan et al. (J. Autoimmunity, 1989, 2 (suppl.): 177-186).*

Zimmer (Cell Motility and the Cytoskeleton, 1991. 20:325-337).*

Hell et al. (Laboratory Investigation, 1995, 73: 492-496).*

Fu et al. (EMBO J., 1996, 15:4392-4401).*

Vallejo et al. (Biochimie, 2000 82:1129-1133).*

Jang et al. (Clinical Exp. Metastasis, 1997, 15: 469-483).*

Drexler et al (Leukemia and Lymphoma, 1993, 9:1-25).*

Zellner et al (Clin. Can. Res., 1998, 4:1797-17802).*

Embleton et al (Immunol Ser, 1984, 23:181-207).*

Hsu (in Tissue Culture Methods and Applications, Kruse and Patterson, Eds, 1973, Academic Press, NY, see abstract, p. 764).*

Taber's Cyclopedic Medical Dictionary (1985, F.A. Davis Company, Philadelphia, p. 274).*

Busken, C et al, (Digestive Disease Week Abstracts and Itinerary Planner, 2003, abstract No. 850).*

Krontiris and Capizzi (Internal Medicine, 4th Edition, Editor-in-chief Jay Stein, Elsevier Science, 1994 Chapters 71-72, pp. 699-715).*

Sanda et al. (J. Pathology 2006, 208:633-642).*

Sahin et al. (Clinical Cancer Res., Dec. 2008, 14:7624-7634).*

Baranova et al., "In Silico Screening for Tumour-Specific Expressed Sequences in Human Genome", FEBS Letters, 508:143-148 (2001).

Engberg et al., "Recombinant antibodies with the antigen-specific MHC restricted specificity of T cells: Novel Reagents for Basic and Clinical Investigations and Immunotherapy", Immunotechnology, 4:273-278 (1999).

(Continued)

*Primary Examiner*—Karen A Canella
*Assistant Examiner*—Peter J Reddig
(74) *Attorney, Agent, or Firm*—McAndrews, Held & Malloy, Ltd.

(57) ABSTRACT

The invention relates to the identification of genetic products expressed in association with tumors and to coding nucleic acids for the expressed products. An embodiment of the invention also relates to the therapy and diagnosis of disease in which the genetic products are aberrantly expressed in association with tumors, proteins, polypeptides and peptides which are expressed in association with tumors, and to the nucleic acids coding for the polypeptides, peptides and proteins.

5 Claims, 57 Drawing Sheets

OTHER PUBLICATIONS

Koslowski et al., "Multiple Splice Variants of Lactate Dehydrogenase C Selectively Expressed in Human Cancer", Cancer Research, 62:6750-6755 (2002).
O'Dowd et al., "Discovery of Three Novel G-Protein-Coupled Receptor Genes", Genomics, 47:310-313 (1998).
Reiter et al., "Peptide-specific killing of antigen-presenting cells by a recombinant antibody-toxin fusion protein targeted to Major Histocompatibility Complex/Peptide Class I Complexes with T Cell Receptor-like Specificity", Proc. Natl. Acad. Sci. USA, 94:4631-4636 (1997).
Durand et al., *Clinical Chemistry*, 46:795-805 (2000).
Hakomori S., *Cancer Research*, 56:5309-5318 (1996).
Pardoll D., *Nature Medicine Vaccine Supplement*, 4:525-531 (1998).
Sahin et al., *Current Opinion in Immunolgy*, 9:709-716 (1997).
Scheurle et al., *Cancer Research*, 60:4037-4043 (2000).
Schmitt et al., *Nucleic Acids Research*, 27:4251-4260 (1999).
van der Bruggen et al., *Science*, 254:1643-1647 (1991).
Vasmatzis et al., *Proc. Natl. Acad. Sci. USA*, 95:300-304 (1998).
Okazaki, Y., et al., "Analysis of the mouse transcriptome based on functional annotation of 60,770 full-length cDNAs." *Nature*. (2002). 420(6915):563-573.
International Search Report in European Patent Application No. EP 03773719.4 (Mailing Date: May 11, 2007).
Lemon, W.J., et al. "Identification of candidate lung cancer susceptibility genes in mouse using oligonucleotide arrays." *Journal of Medical Genetics*. (2002). 39:644-655.
Niimi, T., et al. "claudin-18, a novel downstream target gene for the T/EBP/NKX2.1 homeodomain transcription factor, encodes lung- and stomach-specific isoforms through alternative splicing." *Molecular and Cellular Biology*. (2001). 21(21):7380-7390.
Engberg, J., et al. "Recombinant antibodies with the antigen-specific, MHC restricted specificity of T cells: novel reagents for basic and clinical investigations and immunotherapy." *Immunotechnology*. (1999). 4:273-278.
Rudolph, M. & Wilson, I.A. "The specificity of TCR/pMHC interaction." *Current Opinion in Immunology*. (2002). 14:52-65.

* cited by examiner

Fig. 8
NT
Colon
Colon carcinoma

A

B

| Cancer type | Expression | % |
|---|---|---|
| colorektal, primary | 19/20 | 95 |
| colorektal, metast. | 14/15 | 93 |

Potential glycosylation site

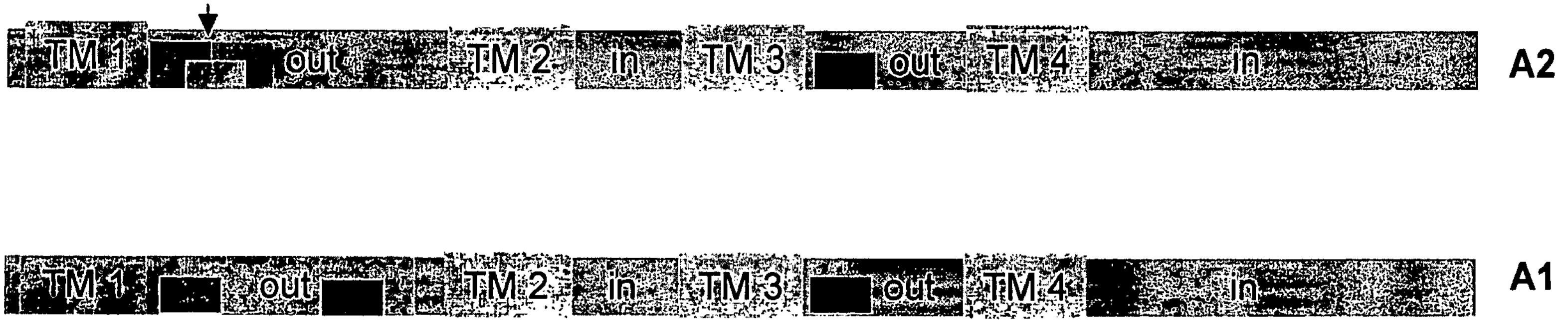

Predicted glycosylation sites (amino acid positions)

Gastric variant

| SeqName | Position | Potential Jury NGlyc Agreement | Result |
|---|---|---|---|
| Sequence | 37 | 0.7219 (9/9) | ++ |
| Sequence | 38 | 0.6502 (8/9) | + |
| Sequence | 45 | 0.6026 (8/9) | + |
| Sequence | 116 | 0.5713 (7/9) | + |
| Sequence | 141 | 0.6348 (7/9) | + |
| Sequence | 146 | 0.5187 (6/9) | + |
| Sequence | 153 | 0.4696 (5/9) | - |
| Sequence | 205 | 0.6011 (8/9) | + |
| Sequence | 234 | 0.3960 (8/9) | - |
| Sequence | 237 | 0.4602 (6/9) | - |

Lung variant

| SeqName | Position | Potential Jury NGlyc Agreement | Result |
|---|---|---|---|
| Sequence | 38 | 0.7102 (9/9) | ++ |
| Sequence | 116 | 0.5713 (7/9) | + |
| Sequence | 141 | 0.6347 (7/9) | + |
| Sequence | 146 | 0.5186 (6/9) | + |
| Sequence | 153 | 0.4696 (5/9) | - |
| Sequence | 205 | 0.6009 (8/9) | + |
| Sequence | 234 | 0.3956 (8/9) | - |
| Sequence | 237 | 0.4603 (6/9) | - |

A. B.

A. B. C.

A. B. C.

A. B. C.

A. B. C.

Fig. 30
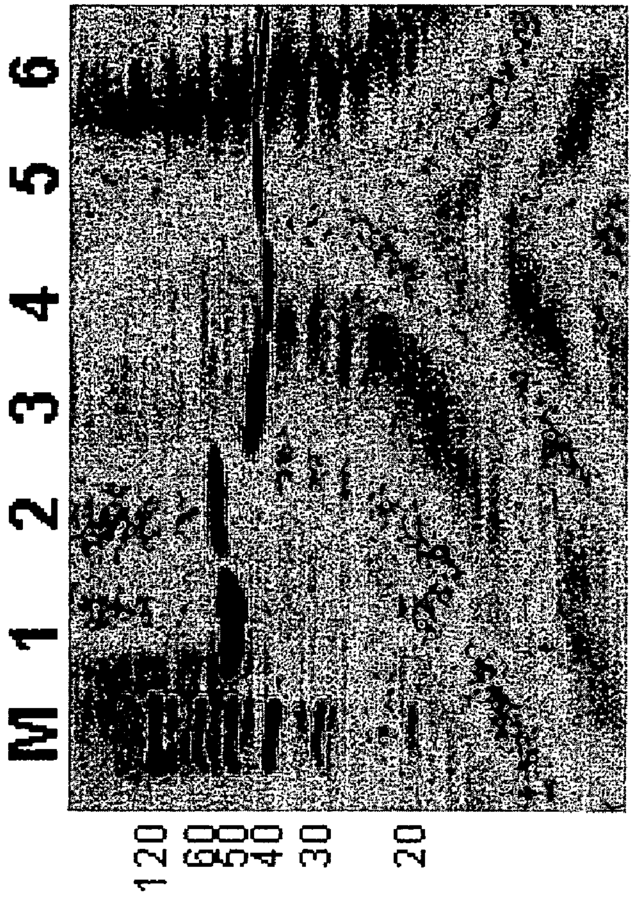
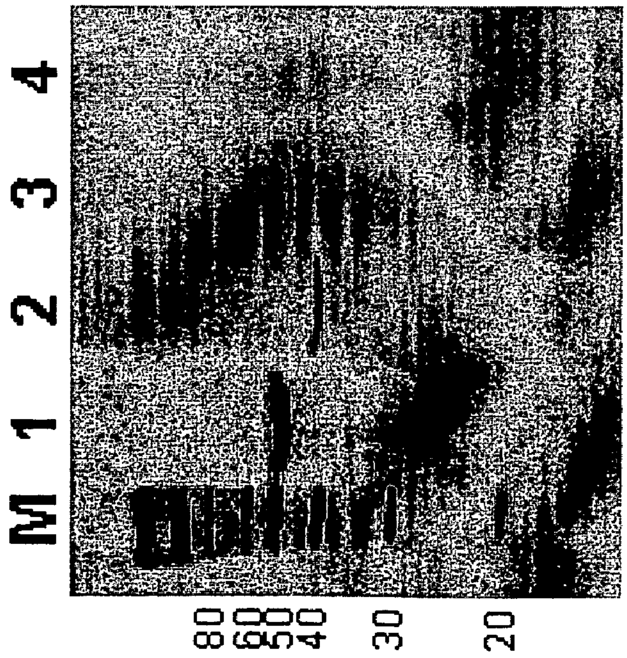

Fig. 33
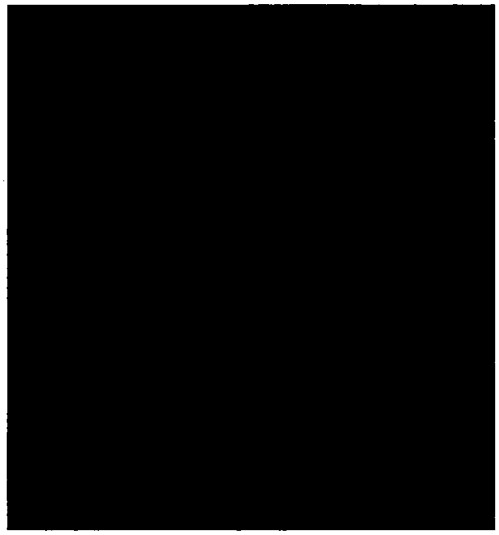
A.
B.

| ID | Sequence |
|---|---|
| #1 | caggccagagtcccagctgtcctggactctgctgtggggaagggctgatgcaggtgtgga<br>gtcaaatgtgggtgcctcctgcagccgggtgccaggaggggtggaggggccaccctgggc<br>tttgtccgggagcctggtcttcccgtccttgggctgacaggtgctgctgcctctgagccc<br>tccctgctaagagctgtgtgctgggtaaggctggtggccctttgggctccctgtccagga<br>tttgtgctctggagggtagggcttgctgggctggggactggaggggaacgtggagctcct<br>tctgcctcctttcctgccccatgacagcaggcagatcccaggagagaagagctcaggaga<br>tgggaagaggatctgtccaggggttagacctcaagggtgacttggagttctttacggcac<br>ccatgctttctttgaggagttttgtgtttgtgggtgtggggtcggggctcacctcctccc<br>acatccctgcccagaggtggcagagtgggggcagtgccttgctcccccctgctcgctctc<br>tgctgacctccggctccctgtgctgccccaggaccatgaatggcacctacaacacctgtg<br>gctccagcgacctcacctggcccccagcgatcaagctgggcttctacgcctacttgggcg<br>tcctgctggtgctaggcctgctgctcaacagcctggcgctctgggtgttctgctgccgca<br>tgcagcagtggacggagacccgcatctacatgaccaacctggcggtggccgacctctgcc<br>tgctgtgcaccttgcccttcgtgctgcactccctgcgagacacctcagacacgccgctgt<br>gccagctctcccagggcatctacctgaccaacaggtacatgagcatcagcctggtcacgg<br>ccatcgccgtggaccgctatgtggccgtgcggcacccgctgcgtgcccgcgggctgcggt<br>cccccaggcaggctgcggccgtgtgcgcggtcctctgggtgctggtcatcggctccctgg<br>tggctcgctggctcctggggattcaggagggcggcttctgcttcaggagcacccggcaca<br>atttcaactccatggcgttcccgctgctgggattctacctgcccctggccgtggtggtct<br>tctgctccctgaaggtggtgactgccctggcccagaggccacccaccgacgtggggcagg<br>cagaggccacccgcaaggctgcccgcatggtctgggccaacctcctggtgttcgtggtct<br>gcttcctgcccctgcacgtggggctgacagtgcgcctcgcagtgggctggaacgcctgtg<br>ccctcctggagacgatccgtcgcgccctgtacataaccagcaagctctcagatgccaact<br>gctgcctggacgccatctgctactactacatggccaaggagttccaggaggcgtctgcac<br>tggccgtggctcccagtgctaaggcccacaaaagccaggactctctgtgcgtgaccctcg<br>cctaagaggcgtgctgtgggcgctgtgggccaggtctcgggggctccgggaggtgctgcc<br>tgccaggggaagctggaaccagtagcaaggagcccgggatcagccctgaactcactgtgt<br>attctcttggagccttgggtgggcagggacggcccaggtacctgctctcttgggaagaga<br>gagggacagggacaagggcaagaggactgaggccagagcaaggccaatgtcagagacccc<br>cgggatggggcctcacacttgccacccccagaaccagctcacctggccagagtgggttcc<br>tgctggccagggtgcagccttgatgacacctgccgctgcccctcggggctggaataaaac<br>tccccacccagagtc |
| #2 | ATGAAGACGTTGCTGTTGGACTTGGCTTTGTGGTCACTGCTCTTCCAGCCCGGGTGGCTGTCCTTTAGTT<br>CCCAGGTGAGTCAGAACTGCCACAATGGCAGCTATGAAATCAGCGTCCTGATGATGGGCAACTCAGCCTT<br>TGCAGAGCCCCTGAAAAACTTGGAAGATGCGGTGAATGAGGGGCTGGAAATAGTGAGAGGACGTCTGCAA<br>AATGCTGGCCTAAATGTGACTGTGAACGCTACTTTCATGTATTCGGATGGTCTGATTCATAACTCAGGCG<br>ACTGCCGGAGTAGCACCTGTGAAGGCCTCGACCTACTCAGGAAAATTTCAAATGCACAACGGATGGGCTG<br>TGTCCTCATAGGGCCCTCATGTACATACTCCACCTTCCAGATGTACCTTGACACAGAATTGAGCTACCCC<br>ATGATCTCAGCTGGAAGTTTTGGATTGTCATGTGACTATAAAGAAACCTTAACCAGGCTGATGTCTCCAG<br>CTAGAAAGTTGATGTACTTCTTGGTTAACTTTTGGAAAACCAACGATCTGCCCTTCAAAACTTATTCCTG<br>GAGCACTTCGTATGTTTACAAGAATGGTACAGAAACTGAGGACTGTTTCTGGTACCTTAATGCTCTGGAG<br>GCTAGCGTTTCCTATTTCTCCCACGAACTCGGCTTTAAGGTGGTGTTAAGACAAGATAAGGAGTTTCAGG<br>ATATCTTAATGGACCACAACAGGAAAAGCAATGTGATTATTATGTGTGGTGGTCCAGAGTTCCTCTACAA<br>GCTGAAGGGTGACCGAGCAGTGGCTGAAGACATTGTCATTATTCTAGTGGATCTTTTCAATGACCAGTAC<br>TTGGAGGACAATGTCACAGCCCCTGACTATATGAAAAATGTCCTTGTTCTGACGCTGTCTCCTGGAATT<br>CCCTTCTAAATAGCTCTTTCTCCAGGAATCTATCACCAACAAAACGAGACTTTGCTCTTGCCTATTTGAA<br>TGGAATCCTGCTCTTTGGACATATGCTGAAGATATTTCTTGAAAATGGAGAAAATATTACCACCCCCAAA<br>TTTGCTCATGCTTTCAGGAATCTCACTTTTGAAGGGTATGACGGTCCAGTGACCTTGGATGACTGGGGG<br>ATGTTGACAGTACCATGGTGCTTCTGTATACCTCTGTGGACACCAAGAAATACAAGGTTCTTTTGACCTA<br>TGATACCCACGTAAATAAGACCTATCCTGTGGATATGAGCCCCACATTCACTTGGAAGAACTCTAAACTT<br>CCTAATGATATTACAGGCCGGGGCCCTCAGATCCTGATGATTGCAGTCTTCACCCTCACTGGAGCTGTGG<br>TGCTGCTCCTGCTCGTCGCTCTCCTGATGCTCAGAAAATATAGAAAAGATTATGAACTTCGTCAGAAAAA<br>ATGGTCCCACATTCCTCCTGAAAATATCTTTCCTCTGGAGACCAATGAGACCAATCATGTTAGCCTCAAG<br>ATCGATGATGACAAAAGACGAGATACAATCCAGAGACTACGACAGTGCAAATACGACAAAAAGCGAGTGA<br>TTCTCAAAGATCTCAAGCACAATGATGGTAATTTCACTGAAAAACAGAAGATAGAATTGAACAAGTTGCT<br>TCAGATTGACTATTACAACCTGACCAAGTTCTACGGCACAGTGAAACTTGATACCATGATCTTCGGGGTG<br>ATAGAATACTGTGAGAGAGGATCCCTCCGGGAAGTTTTAAATGACACAATTTCCTACCCTGATGGCACAT<br>TCATGGATTGGGAGTTTAAGATCTCTGTCTTGTATGACATTGCTAAGGGAATGTCATATCTGCACTCCAG<br>TAAGACAGAAGTCCATGGTCGTCTGAAATCTACCAACTGCGTAGTGGACAGTAGAATGGTGGTGAAGATC |

| | |
|---|---|
| | ACTGATTTTGGCTGCAATTCCATTTTACCTCCAAAAAAGGACCTGTGGACAGCTCCAGAGCACCTCCGCC AAGCCAACATCTCTCAGAAAGGAGATGTGTACAGCTATGGGATCATCGCACAGGAGATCATTCTGCGGAA AGAAACCTTCTACACTTTGAGCTGTCGGGACCGGAATGAGAAGATTTTCAGAGTGGAAAATTCCAATGGA ATGAAACCCTTCCGCCCAGATTTATTCTTGGAAACAGCAGAGGAAAAAGAGCTAGAAGTGTACCTACTTG TAAAAAACTGTTGGGAGGAAGATCCAGAAAAGAGACCAGATTTCAAAAAAATTGAGACTACACTTGCCAA GATATTTGGACTTTTTCATGACCAAAAAAATGAAAGCTATATGGATACCTTGATCCGACGTCTACAGCTA TATTCTCGAAACCTGGAACATCTGGTAGAGGAAAGGACACAGCTGTACAAGGCAGAGAGGGACAGGGCTG ACAGACTTAACTTTATGTTGCTTCCAAGGCTAGTGGTAAAGTCTCTGAAGGAGAAAGGCTTTGTGGAGCC GGAACTATATGAGGAAGTTACAATCTACTTCAGTGACATTGTAGGTTTCACTACTATCTGCAAATACAGC ACCCCCATGGAAGTGGTGGACATGCTTAATGACATCTATAAGAGTTTTGACCACATTGTTGATCATCATG ATGTCTACAAGGTGGAAACCATCGGTGATGCGTACATGGTGGCTAGTGGTTTGCCTAAGAGAAATGGCAA TCGGCATGCAATAGACATTGCCAAGATGGCCTTGGAAATCCTCAGCTTCATGGGGACCTTTGAGCTGGAG CATCTTCCTGGCCTCCCAATATGGATTCGCATTGGAGTTCACTCTGGTCCCTGTGCTGCTGGAGTTGTGG GAATCAAGATGCCTCGTTATTGTCTATTTGGAGATACGGTCAACACAGCCTCTAGGATGGAATCCACTGG CCTCCCTTTGAGAATTCACGTGAGTGGCTCCACCATAGCCATCCTGAAGAGAACTGAGTGCCAGTTCCTT TATGAAGTGAGAGGAGAAACATACTTAAAGGGAAGAGGAAATGAGACTACCTACTGGCTGACTGGGATGA AGGACCAGAAATTCAACCTGCCAACCCCTCCTACTGTGGAGAATCAACAGCGTTTGCAAGCAGAATTTTC AGACATGATTGCCAACTCTTTACAGAAAAGACAGGCAGCAGGGATAAGAAGCCAAAAACCCAGACGGGTA GCCAGCTATAAAAAAGGCACTCTGGAATACTTGCAGCTGAATACCACAGACAAGGAGAGCACCTATTTTT AA |
| #3 | ATGAAGACGTTGCTGTTGGACTTGGCTTTGTGGTCACTGCTCTTCCAGCCCGGGTGGCTGTCCTTTAGTT CCCAGGTGAGTCAGAACTGCCACAATGGCAGCTATGAAATCAGCGTCCTGATGATGGGCAACTCAGCCTT TGCAGAGCCCCTGAAAAACTTGGAAGATGCGGTGAATGAGGGGCTGGAAATAGTGAGAGGACGTCTGCAA AATGCTGGCCTAAATGTGACTGTGAACGCTACTTTCATGTATTCGGATGGTCTGATTCATAACTCAGGCG ACTGCCGGAGTAGCACCTGTGAAGGCCTCGACCTACTCAGGAAAATTTCACCTTGA |
| #4 | ATGAAGACGTTGCTGTTGGACTTGGCTTTGTGGTCACTGCTCTTCCAGCCCGGGTGGCTGTCCTTTAGTT CCCAGGTGAGTCAGAACTGCCACAATGGCAGCTATGAAATCAGCGTCCTGATGATGGGCAACTCAGCCTT TGCAGAGCCCCTGAAAAACTTGGAAGATGCGGTGAATGAGGGGCTGGAAATAGTGAGAGGACGTCTGCAA AATGCTGGCCTAAATGTGACTGTGAACGCTACTTTCATGTATTCGGATGGTCTGATTCATAACTCAGGCG ACTGCCGGAGTAGCACCTGTGAAGGCCTCGACCTACTCAGGAAAATTTCAAATGCACAACGGATGGGCTG TGTCCTCATAGGGCCCTCATGTACATACTCCACCTTCCAGATGTACCTTGACACAGAATTGAGCTACCCC ATGATCTCAGCTGGAAGTTTTGGATTGTCATGTGACTATAAAGAAACCTTAACCAGGCTGATGTCTCCAG CTAGAAAGTTGATGTACTTCTTGGTTAACTTTTGGAAAACCAACGATCTGCCCTTCAAAACTTATTCCTG GAGCACTTCGTATGTTTACAAGAATGGTACAGAAACTGAGGACTGTTTCTGGTACCTTAATGCTCTGGAG GCTAGCGTTTCCTATTTCTCCCACGAACTCGGCTTTAAGGTGGTGTTAAGACAAGATAAGGAGTTTCAGG ATATCTTAATGGACCACAACAGGAAAAGCAATGTGACCAGTACTTGGAGGACAATGTCACAGCCCCTGAC TATATGA |
| #5 | ATGAAGACGTTGCTGTTGGACTTGGCTTTGTGGTCACTGCTCTTCCAGCCCGGGTGGCTGTCCTTTAGTT CCCAGGTGAGTCAGAACTGCCACAATGGCAGCTATGAAATCAGCGTCCTGATGATGGGCAACTCAGCCTT TGCAGAGCCCCTGAAAAACTTGGAAGATGCGGTGAATGAGGGGCTGGAAATAGTGAGAGGACGTCTGCAA AATGCTGGCCTAAATGTGACTGTGAACGCTACTTTCATGTATTCGGATGGTCTGATTCATAACTCAGGCG ACTGCCGGAGTAGCACCTGTGAAGGCCTCGACCTACTCAGGAAAATTTCAAATGCACAACGGATGGGCTG TGTCCTCATAGGGCCCTCATGTACATACTCCACCTTCCAGATGTACCTTGACACAGAATTGAGCTACCCC ATGATCTCAGCTGGAAGTTTTGGATTGTCATGTGACTATAAAGAAACCTTAACCAGGCTGATGTCTCCAG CTAGAAAGTTGATGTACTTCTTGGTTAACTTTTGGAAAACCAACGATCTGCCCTTCAAAACTTATTCCTG GAGCACTTCGTATGTTTACAAGAATGGTACAGAAACTGAGGACTGTTTCTGGTACCTTAATGCTCTGGAG GCTAGCGTTTCCTATTTCTCCCACGAACTCGGCTTTAAGGTGGTGTTAAGACAAGATAAGGAGTTTCAGG ATATCTTAATGGACCACAACAGGAAAAGCAATGTGATTATTATGTGTGGTGGTCCAGAGTTCCTCTACAA GCTGAAGGGTGACCGAGCAGTGGCTGAAGACATTGTCATTATTCTAGTGGATCTTTTCAATGACCAGTAC TTGGAGGACAATGTCACAGCCCCTGACTATATGAAAAATGTCCTTGTTCTGACGCTGTCTCCTGGGAATT CCCTTCTAAATAGCTCTTTCTCCAGGAATCTATCACCAACAAAACGAGACTTTGCTCTTGCCTATTTGAA TGGAATCCTGCTCTTTGGACATATGCTGAAGATATTTCTTGAAAATGGAGAAAATATTACCACCCCCAAA TTTGCTCATGCTTTCAGGAATCTCACTTTTGAAGGGTATGACGGTCCAGTGACCTTGGATGACTGGGGGG ATGTTGACAGTACCATGGTGCTTCTGTATACCTCTGTGGACACCAAGAAATACAAGGTTCTTTTGACCTA TGATACCCACGTAAATAAGACCTATCCTGTGGATATGAGCCCCACATTCACTTGGAAGAACTCTAAACTT CCTAATGATATTACAGGCCGGGGCCCTCAGATCCTGATGATTGCAGTCTTCACCCTCACTGGAGCTGTGG TGCTGCTCCTGCTCGTCGCTCTCCTGATGCTCAGAAAATATAGAAAAGATTATGAACTTCGTCAGAAAAA ATGGTCCCACATTCCTCCTGAAAATATCTTTCCTCTGGAGACCAATGAGACCAATCATGTTAGCCTCAAG ATCGATGATGACAAAAGACGAGATACAATCCAGAGACTACGACAGTGCAAATACGACAAAAAGCGAGTGA |

| | |
|---|---|
| | TTCTCAAAGATCTCAAGCACAATGATGGTAATTTCACTGAAAAACAGAAGATAGAATTGAACAAGATTGA<br>CTATTACAACCTGACCAAGTTCTACGGCACAGTGAAACTTGATACCATGATCTTCGGGGTGATAGAATAC<br>TGTGAGAGAGGATCCCTCCGGGAAGTTTTAAATGACACAATTTCCTACCCTGATGGCACATTCATGGATT<br>GGGAGTTTAAGATCTCTGTCTTGTATGACATTGCTAAGGGAATGTCATATCTGCACTCCAGTAAGACAGA<br>AGTCCATGGTCGTCTGAAATCTACCAACTGCGTAGTGGACAGTAGAATGGTGGTGAAGATCACTGATTTT<br>GGCTGCAATTCCATTTTACCTCCAAAAAGGACCTGTGGACAGCTCCAGAGCACCTCCGCCAAGCCAACA<br>TCTCTCAGAAAGGAGATGTGTACAGCTATGGGATCATCGCACAGGAGATCATTCTGCGGAAAGAAACCTT<br>CTACACTTTGAGCTGTCGGGACCGGAATGAGAAGATTTTCAGAGTGGAAAATTCCAATGGAATGAAACCC<br>TTCCGCCCAGATTTATTCTTGGAAACAGCAGAGGAAAAAGAGCTAGAAGTGTACCTACTTGTAAAAAACT<br>GTTGGGAGGAAGATCCAGAAAAGAGACCAGATTTCAAAAAAATTGAGACTACACTTGCCAAGATATTTGG<br>ACTTTTTCATGACCAAAAAAATGAAAGCTATATGGATACCTTGATCCGACGTCTACAGCTATATTCTCGA<br>AACCTGGAACATCTGGTAGAGGAAAGGACACAGCTGTACAAGGCAGAGAGGGACAGGGCTGACAGACTTA<br>ACTTTATGTTGCTTCCAAGGCTAGTGGTAAAGTCTCTGAAGGAGAAAGGCTTTGTGGAGCCGGAACTATA<br>TGAGGAAGTTACAATCTACTTCAGTGACATTGTAGGTTTCACTACTATCTGCAAATACAGCACCCCCATG<br>GAAGTGGTGGACATGCTTAATGACATCTATAAGAGTTTTGACCACATTGTTGATCATCATGATGTCTACA<br>AGGTGGAAACCATCGGTGATGCGTACATGGTGGCTAGTGGTTTGCCTAAGAGAAATGGCAATCGGCATGC<br>AATAGACATTGCCAAGATGGCCTTGGAAATCCTCAGCTTCATGGGGACCTTTGAGCTGGAGCATCTTCCT<br>GGCCTCCCAATATGGATTCGCATTGGAGTTCACTCTGGTCCCTGTGCTGCTGGAGTTGTGGGAATCAAGA<br>TGCCTCGTTATTGTCTATTTGGAGATACGGTCAACACAGCCTCTAGGATGGAATCCACTGGCCTCCCTTT<br>GAGAATTCACGTGAGTGGCTCCACCATAGCCATCCTGAAGAGAACTGAGTGCCAGTTCCTTTATGAAGTG<br>AGAGGAGAAACATACTTAAAGGGAAGAGGAAATGAGACTACCTACTGGCTGACTGGGATGAAGGACCAGA<br>AATTCAACCTGCCAACCCCTCCTACTGTGGAGAATCAACAGCGTTTGCAAGCAGAATTTTCAGACATGAT<br>TGCCAACTCTTTACAGAAAAGACAGGCAGCAGGGATAAGAAGCCAAAAACCCAGACGGGTAGCCAGCTAT<br>AAAAAAGGCACTCTGGAATACTTGCAGCTGAATACCACAGACAAGGAGAGCACCTATTTTTAA |
| #6 | ggggacactttgtatggcaagtggaaccactggcttggtg<br>gattttgctagatttttctgatttttaaactcctgaaaaatatcccagataactgtcatgaagctggtaacta<br>tcttcct<br>gctggtgaccatcagcctttgtagttactctgctactgcc<br>ttcctcatcaacaaagtgccccttcctgttgacaagttggcacctttacctctggacaacattcttcccttta<br>tggatcc<br>attaaagcttcttctgaaaactctgggcatttctgttgag<br>caccttgtggaggggctaaggaagtgtgtaaatgagctgggaccagaggcttctgaagctgtgaagaaactgc<br>tggaggc<br>gctatcacacttggtgtgacatcaagataaagagcggagg<br>tggatggggatggaagatgatgctcctatcctccctgcctgaaacctgttctaccaattatagatcaaatgcc<br>ctaaaatgtagtgacccgtgaaaaggacaaataaagcaatgaatactaaaaaaaaaaaaaaaaaa<br>aaaaaaaaaa |
| #7 | ATGGCCGTGACTGCCTGTCAGGGCTTGGGGTTCGTGGTTTCACTGATTGGGATTGCGGGCATCATTGCTG<br>CCACCTGCATGGACCAGTGGAGCACCCAAGACTTGTACAACAACCCCGTAACAGCTGTTTTCAACTACCA<br>GGGGCTGTGGCGCTCCTGTGTCCGAGAGAGCTCTGGCTTCACCGAGTGCCGGGGCTACTTCACCCTGCTG<br>GGGCTGCCAGCCATGCTGCAGGCAGTGCGAGCCCTGATGATCGTAGGCATCGTCCTGGGTGCCATTGGCC<br>TCCTGGTATCCATCTTTGCCCTGAAATGCATCCGCATTGGCAGCATGGAGGACTCTGCCAAAGCCAACAT<br>GACACTGACCTCCGGGATCATGTTCATTGTCTCAGGTCTTTGTGCAATTGCTGGAGTGTCTGTGTTTGCC<br>AACATGCTGGTGACTAACTTCTGGATGTCCACAGCTAACATGTACACCGGCATGGGTGGATGGTGCAGA<br>CTGTTCAGACCAGGTACACATTTGGTGCGGCTCTGTTCGTGGGCTGGGTCGCTGGAGGCCTCACACTAAT<br>TGGGGGTGTGATGATGTGCATCGCCTGCCGGGGCCTGGCACCAGAAGAAACCAACTACAAAGCCGTTTCT<br>TATCATGCCTCAGGCCACAGTGTTGCCTACAAGCCTGGAGGCTTCAAGGCCAGCACTGGCTTTGGGTCCA<br>ACACCAAAAACAAGAAGATATACGATGGAGGTGCCCGCACAGAGGACGAGGTACAATCTTATCCTTCCAA<br>GCACGACTATGTGTAA |
| #8 | tgcgccaccatggccgtgactgcctgtcagggcttggggttcgtggtttcactgattggg<br>attgcgggcatcattgctgccacctgcatggaccagtggagcacccaagacttgtacaac<br>aaccccgtaacagctgttttcaactaccaggggctgtggcgctcctgtgtccgagagagc |
| #9 | MNGTYNTCGSSDLTWPPAIKLGFYAYLGVLLVLGLLLNSLALWVFCCRMQQWTETRIYMT<br>NLAVADLCLLCTLPFVLHSLRDTSDTPLCQLSQGIYLTNRYMSISLVTAIAVDRYVAVRH<br>PLRARGLRSPRQAAAVCAVLWVLVIGSLVARWLLGIQEGGFCFRSTRHNFNSMRFPLLGF |

| | |
|---|---|
| | YLPLAVVVFCSLKVVTALAQRPPTDVGQAEATRKAARMVWANLLVFVVCFLPLHVGLTVR<br>LAVGWNACALLETIRRALYITSKLSDANCCLDAICYYYMAKEFQEASALAVAPRAKAHKS<br>QDSLCVTLA |
| #10 | MTAGRSQERRAQEMGRGSVQGLDLKGDLEFFTAPMLSLRSFVFVGVGSGLTSSHIPAQRWAEWGQCLAPPARS<br>LLTSGSLCCPRTMNGTYNTCGSSDLTWPPAIKLGFYAYLGVLLVLGL<br>LLNSLALWVFCCRMQQWTETRIYMTNLAVADLCLLCTLPFVLHSLRDTSDTPLCQLSQGI<br>YLTNRYMSISLVTAIAVDRYVAVRHPLRARGLRSPRQAAAVCAVLWVLVIGSLVARWLLG<br>IQEGGFCFRSTRHNFNSMAFPLLGFYLPLAVVVFCSLKVVTALAQRPPTDVGQAEATRKA<br>ARMVWANLLVFVVCFLPLHVGLTVRLAVGWNACALLETIRRALYITSKLSDANCCLDAIC<br>YYYMAKEFQEASALAVAPSAKAHKSQDSLCVTLA |
| #11 | MKTLLLDLALWSLLFQPGWLSFSSQVSQNCHNGSYEISVLMMGNSAFAEPLKNLEDAVNEGLEIVRGRLQ<br>NAGLNVTVNATFMYSDGLIHNSGDCRSSTCEGLDLLRKISNAQRMGCVLIGPSCTYSTFQMYLDTELSYP<br>MISAGSFGLSCDYKETLTRLMSPARKLMYFLVNFWKTNDLPFKTYSWSTSYVYKNGTETEDCFWYLNALE<br>ASVSYFSHELGFKVVLRQDKEFQDILMDHNRKSNVIIMCGGPEFLYKLKGDRAVAEDIVIILVDLFNDQY<br>LEDNVTAPDYMKNVLVLTLSPGNSLLNSSFSRNLSPTKRDFALAYLNGILLFGHMLKIFLENGENITTPK<br>FAHAFRNLTFEGYDGPVTLDDWGDVDSTMVLLYTSVDTKKYKVLLTYDTHVNKTYPVDMSPTFTWKNSKL<br>PNDITGRGPQILMIAVFTLTGAVVLLLLVALLMLRKYRKDYELRQKKWSHIPPENIFPLETNETNHVSLK<br>IDDDKRRDTIQRLRQCKYDKKRVILKDLKHNDGNFTEKQKIELNKLLQIDYYNLTKFYGTVKLDTMIFGV<br>IEYCERGSLREVLNDTISYPDGTFMDWEFKISVLYDIAKGMSYLHSSKTEVHGRLKSTNCVVDSRMVVKI<br>TDFGCNSILPPKKDLWTAPEHLRQANISQKGDVYSYGIIAQEIILRKETFYTLSCRDRNEKIFRVENSNG<br>MKPFRPDLFLETAEEKELEVYLLVKNCWEEDPEKRPDFKKIETTLAKIFGLFHDQKNESYMDTLIRRLQL<br>YSRNLEHLVEERTQLYKAERDRADRLNFMLLPRLVVKSLKEKGFVEPELYEEVTIYFSDIVGFTTICKYS<br>TPMEVVDMLNDIYKSFDHIVDHHDVYKVETIGDAYMVASGLPKRNGNRHAIDIAKMALEILSFMGTFELE<br>HLPGLPIWIRIGVHSGPCAAGVVGIKMPRYCLFGDTVNTASRMESTGLPLRIHVSGSTIAILKRTECQFL<br>YEVRGETYLKGRGNETTYWLTGMKDQKFNLPTPPTVENQQRLQAEFSDMIANSLQKRQAAGIRSQKPRRV<br>ASYKKGTLEYLQLNTTDKESTYF* |
| #12 | MKTLLLDLALWSLLFQPGWLSFSSQVSQNCHNGSYEISVLMMGNSAFAEPLKNLEDAVNEGLEIVRGRLQ<br>NAGLNVTVNATFMYSDGLIHNSGDCRSSTCEGLDLLRKISP* |
| #13 | MKTLLLDLALWSLLFQPGWLSFSSQVSQNCHNGSYEISVLMMGNSAFAEPLKNLEDAVNEGLEIVRGRLQ<br>NAGLNVTVNATFMYSDGLIHNSGDCRSSTCEGLDLLRKISNAQRMGCVLIGPSCTYSTFQMYLDTELSYP<br>MISAGSFGLSCDYKETLTRLMSPARKLMYFLVNFWKTNDLPFKTYSWSTSYVYKNGTETEDCFWYLNALE<br>ASVSYFSHELGFKVVLRQDKEFQDILMDHNRKSNVTSTWRTMSQPLTI* |
| #14 | MKTLLLDLALWSLLFQPGWLSFSSQVSQNCHNGSYEISVLMMGNSAFAEPLKNLEDAVNEGLEIVRGRLQ<br>NAGLNVTVNATFMYSDGLIHNSGDCRSSTCEGLDLLRKISNAQRMGCVLIGPSCTYSTFQMYLDTELSYP<br>MISAGSFGLSCDYKETLTRLMSPARKLMYFLVNFWKTNDLPFKTYSWSTSYVYKNGTETEDCFWYLNALE<br>ASVSYFSHELGFKVVLRQDKEFQDILMDHNRKSNVIIMCGGPEFLYKLKGDRAVAEDIVIILVDLFNDQY<br>LEDNVTAPDYMKNVLVLTLSPGNSLLNSSFSRNLSPTKRDFALAYLNGILLFGHMLKIFLENGENITTPK<br>FAHAFRNLTFEGYDGPVTLDDWGDVDSTMVLLYTSVDTKKYKVLLTYDTHVNKTYPVDMSPTFTWKNSKL<br>PNDITGRGPQILMIAVFTLTGAVVLLLLVALLMLRKYRKDYELRQKKWSHIPPENIFPLETNETNHVSLK<br>IDDDKRRDTIQRLRQCKYDKKRVILKDLKHNDGNFTEKQKIELNKIDYYNLTKFYGTVKLDTMIFGVIEY<br>CERGSLREVLNDTISYPDGTFMDWEFKISVLYDIAKGMSYLHSSKTEVHGRLKSTNCVVDSRMVVKITDF<br>GCNSILPPKKDLWTAPEHLRQANISQKGDVYSYGIIAQEIILRKETFYTLSCRDRNEKIFRVENSNGMKP<br>FRPDLFLETAEEKELEVYLLVKNCWEEDPEKRPDFKKIETTLAKIFGLFHDQKNESYMDTLIRRLQLYSR<br>NLEHLVEERTQLYKAERDRADRLNFMLLPRLVVKSLKEKGFVEPELYEEVTIYFSDIVGFTTICKYSTPM<br>EVVDMLNDIYKSFDHIVDHHDVYKVETIGDAYMVASGLPKRNGNRHAIDIAKMALEILSFMGTFELEHLP<br>GLPIWIRIGVHSGPCAAGVVGIKMPRYCLFGDTVNTASRMESTGLPLRIHVSGSTIAILKRTECQFLYEV<br>RGETYLKGRGNETTYWLTGMKDQKFNLPTPPTVENQQRLQAEFSDMIANSLQKRQAAGIRSQKPRRVASY<br>KKGTLEYLQLNTTDKESTYF* |
| #15 | MKLVTIFLLVTISLCSYSATAKLINKCPLPVDKLAPLPLDNILPFMDPLK<br>LLLKTLGISVEHLVEGLRKCVNELGPEASEAVKKLLEALSHLV |
| #16 | MAVTACQGLGFVVSLIGIAGIIAATCMDQWSTQDLYNNPVTAVFNYQGLWRSCVRESSGFTECRGYFTLL |

| | |
|---|---|
| | GLPAMLQAVRALMIVGIVLGAIGLLVSIFALKCIRIGSMEDSAKANMTLTSGIMFIVSGLCAIAGVSVFA NMLVTNFWMSTANMYTGMGGMVQTVQTRYTFGAALFVGWVAGGLTLIGGVMMCIACRGLAPEETNYKAVS YHASGHSVAYKPGGFKASTGFGSNTKNKKIYDGGARTEDEVQSYPSKHDYV* |
| #17 | DQWSTQDLYN |
| #18 | NNPVTAVFNYQ |
| #19 | MAVTACQGLGFVVSLIGIAGIIAATCMDQWSTQDLYNNPVTAVFNYQ |
| #20 | AGGTACATGAGCATCAGCCTG |
| #21 | GCAGCAGTTGGCATCTGAGAG |
| #22 | GCAATAGACATTGCCAAGATG |
| #23 | AACGCTGTTGATTCTCCACAG |
| #24 | GGATCCTCCTTTAGTTCCCAGGTGAGTCAGAAC |
| #25 | TGCTCTGGAGGCTAGCGTTTC |
| #26 | ACCAATCATGTTAGCCTCAAG |
| #27 | AGCTATGGGATCATCGCACAG |
| #28 | CCTTTGAGCTGGAGCATCTTC |
| #29 | CTTTCTAGCTGGAGACATCAG |
| #30 | CACCATGGTACTGTCAACATC |
| #31 | ATGTCATACAAGACAGAGATC |
| #32 | TCTGCCTTGTACAGCTGTGTC |
| #33 | TCTGTGGTATTCAGCTGCAAG |
| #34 | TACTCAGGAAAATTTCACCTTG |
| #35 | GACCACAACAGGAAAAGCAATGTGACC |

| | |
|---|---|
| #36 | GATAGAATTGAACAAGATTGAC |
| #37 | CAGCCTTTGTAGTTACTCTGC |
| #38 | TGTCACACCAAGTGTGATAGC |
| #39 | GGTTCGTGGTTTCACTGATTGGGATTGC |
| #40 | CGGCTTTGTAGTTGGTTTCTTCTGGTG |
| #41 | ctattgaagccacctgctcaggacaatgaaattcttcagttacattctggtttatcgccg<br>atttctcttcgtggttttcactgtgttggttttactacctctgcccatcgtcctccacac<br>caaggaagcagaatgtgcctacacactctttgtggtcgccacattttggctcacagaagc<br>attgcctctgtcggtaacagctttgctacctagtttaatgttacccatgtttgggatcat<br>gccttctaagaaggtggcatctgcttatttcaaggattttcacttactgctaattggagt<br>tatctgtttagcaacatccatagaaaaatggaatttgcacaagagaattgctctgaaaat<br>ggtgatgatggttggtgtaaatcctgcatggctgacgctggggttcatgagcagcactgc<br>ctttttgtctatgtggctcagcaacacctcgacggctgccatggtgatgcccattgcgga<br>ggctgtagtgcagcagatcatcaatgcagaagcagaggtcgaggccactcagatgactta<br>cttcaacggatcaaccaaccacggactagaaattgatgaaagtgttaatggacatgaaat<br>aaatgagaggaaagagaaaacaaaaccagttccaggatacaataatgatacagggaaaat<br>ttcaagcaaggtggagttggaaaagaactcaggcatgagaaccaaatatcgaacaaagaa<br>gggccacgtgacacgtaaacttacgtgtttgtgcattgcctactcttctaccattggtgg<br>actgacaacaatcactggtacctccaccaacttgatctttgcagagtatttcaatacacg<br>ctatcctgactgtcgttgcctcaactttggatcatggtttacgttttccttcccagctgc<br>ccttatcattctactcttatcctggatctggcttcagtggcttttcctaggattcaattt<br>taaggagatgttcaaatgtggcaaaaccaaaacagtccaacaaaaagcttgtgctgaggt<br>gattaagcaagaataccaaaagcttgggccaataaggtatcaagaaattgtgaccttggt<br>cctcttcattataatggctctgctatggtttagtcgagaccccggatttgttcctggttg<br>gtctgcactttttttcagagtaccctggttttgctacagattcaactgttgctttacttat<br>agggctgctattctttcttatcccagctaagacactgactaaaactacacctacaggaga<br>aattgttgcttttgattactctccactgattacttggaaagaattccagtcattcatgcc<br>ctgggatatagccattcttgttggtggagggtttgccctggcagatggttgtgaggagtc<br>tggattatctaagtggataggaaataaattatctcctctgggttcattaccagcatggct<br>aataattctgatatcttctttgatggtgacatctttaactgaggtagccagcaatccagc<br>taccattacactctttctcccaatattatctccattggccgaagccattcatgtgaaccc<br>tctttatattctgataccttctactctgtgtacttcatttgcattcctcctaccagtagc<br>aaatccacccaatgctattgtcttttcatatggtcatctgaaagtcattgacatggttaa<br>agctggacttggtgtcaacattgttggtgttgctgtggttatgcttggcatatgtacttg<br>gattgtacccatgtttgacctctacacttacccttcgtgggctcctgctatgagtaatga<br>gaccatgccataataagcacaaaatttctgactatcttgcggtaatttctggaagacatt<br>aatgattgactgtaaaatgtggctctaaataactaatgacacacatttaaatcagttatg<br>gtgtagctgctgcaattcccgtgaatacccgaaacctgctggtataactcagagtccata<br>tttgttattgcagtgcaactaaagagcatctatgtgccttcatcaagaagcccatgtttt<br>gagattttgctcatgaaccatctgcaacttgcttcatcataagaataatttataacttga<br>ccttcaaagagattagagcatttgtttcatcttacagttggagttcaatgtaacattta<br>aatgcaatttattatttcagaaatttcccatgaaactaaaaatagaaaataagatataca<br>agttaattcggtacttggataaatcatttctgcattgttgttccagagaatttgctgaga<br>aatcaaagccatggtcatctggtgatgaagagaaaaggttaatctaaatgatatgtgcat<br>ttcctcatttaaaaaatccaattggattattcttaatatatacatgtaatatgaaaattg<br>agattgaagcactaattccaaaattatggctgaatatactaaataacagaaaagttacag<br>ataagaatttatttctactgaactctatagttagtgtaatataattcatattttatgat<br>attggcacactgagaaattcattttgtagagctatggataaggcttgctatgatttgcac<br>tattagtacagtatagttagaaaggaaagctgaacactataaaactattaacatatttc<br>gtatatgagtaacaactttgcttaagtgtttatcttagttcagaaatacataatgtcata<br>tgttaaaaataaagagatgtagaaatctaaatgaattatcactgtgtatacagacagaaa<br>aatcacataactctggtgtgttaacattgcaatgaaaaaatgaaaaaaagaaggaaaaaa<br>gaataagaatgaaaactgctgacgtattacaaaacagaaaaataaatgatttaaatcaa |

| | |
|---|---|
| | atcaaaagaaaaaaactaaacatttaaacaaaaatgggataagaatagtcttctagaag<br>tgaggatgcgtaaaagaatgagtttccaattaccctgatgtgacaattacacattgtaga<br>caggtagcaaaatatcacatacacccccaaaatatgtacaaatattatatatcaataaat<br>aaatttttaaagagtaagtgctattggcattccaaaattcagctaaaggaaaaatgatca<br>aaaacaaagtaaggtgcacagttagcaaaagatgcagatgttatatcacagcaattctca<br>tgctaaaaatacaacaaaagacaaagcaaaaaataaacctttgcttttttttttttttt<br>ttttttttttgagacggagtctcgctctgtcgcccaggctggagtgcagtggcgggatct<br>cggctcactgcaagctccgcctcccaggttcacgccattctcctgcctcagccaaacctt<br>tgctattttttaatcttcgttggcactttccagctgttactgaccttgtcatttttttgttc<br>aaataagattatttacaaacttattcttgaaactaaatatagtaaagagggttttttaaaa<br>taatatttaacatacgaattattaattggccatgttcattatttatctatgtttattaat<br>gggccaatgcaaaaaatcatttttttcaaagaaaaatttgtccatgtaaagcttaaattat<br>aatattgctgctttgtataactcttctatgtttattctattcatttgttcctttccctac<br>catattttacacatgtatttataatctgtagtatttattacatttctgctttttttctagt<br>cattcaatttatcactgctgaattgcatcagatcatggatgcatttttattatgaaaaaa<br>taaaatgacttttcaaattaaaaaaaaaaaaaa |
| #42 | caggacaatgaaattcttcagttacattctggtttatcgccgatttctcttcgtggttttcactgtgttggtt<br>ttactacctctgcccatcgtcctccacaccaaggaagcagaatgtgcctacacactctttgtggtcgccacat<br>tttggctcacagaagcattgcctctgtcggtaacagctttgctacctagtttaatgttacccatgtttgggat<br>catgccttctaagaaggtggcatctgcttatttcaaggattttcacttactgctaattggagttatctgttta<br>gcaacatccatagaaaaatggaatttgcacaagagaattgctctgaaaatggtgatgatggttggtgtaaatc<br>ctgcatggctgacgctggggttcatgagcagcactgcctttttgtctatgtggctcagcaacacctcgacggc<br>tgccatggtgatgcccattgcggaggctgtagtgcagcagatcatcaatgcagaagcagaggtcgaggccact<br>cagatgacttacttcaacggatcaaccaaccacggactagaaattgatgaaagtgttaatggacatgaaataa<br>atgagaggaaagagaaaacaaaaccagttccaggatacaataatgatacagggaaaatttcaagcaaggtgga<br>gttggaaaagactgtttaactactgaaatgaagctattctcctgactaaacataactgaaaaaccattcatta<br>aatg |
| #43 | gccactcagatgacttacttcaacggatcaaccaaccacggactagaaattgatgaaagtgttaatggacatg<br>aaataaatgagaggaaagagaaaacaaaaccagttccaggatacaataatgatacagggaaaatttcaagcaa<br>ggtggagttggaaaagcactggaaacttgcagttcaagatggctccccatctccctctgtccattctgtatcg<br>cagctagctgctcaaggaaaggagaaagtggaaggcatatgtacttagaaattattctattactttcctggat<br>ttaagagtattcagattttctatttcaacatcaaacaattgcattttttaaaaagaaatttatgtgttccatgt<br>caaatttagtagtgtgtggttgtttataatattttcttatatctacttaatttctatagtatttatagttata<br>tgtctttatttctaacatttttcttgtgcttttaaagattatttaaagattattttttaaataatctttatttc<br>atttaaataaaatattttatttaagtct |
| #44 | cacggactagaaattgatgaaagtgttaatggacatgaaataaatgagaggaaagagaaaacaaaaccagttc<br>caggatacaataatgatacagggaaaatttcaagcaaggtggagttggaaaagaactcaggcatgagaaccaa<br>atatcgaacaaagaagggccacgtgacacgtaaacttacgtgtttgtgcattgcctactcttctaccattggt<br>ggactgacaacaatcactggtacctccaccaacttgatctttgcagagtatttcaatacattccatccacaca<br>gaagaggagatcgtacaaggcatgtacaccaggaggcagaaatttgaggcatatcttggaactctgtctacca<br>catcctgaacatcacacagtttccactcttgttgccttcaatcctgagaatgcatccaggagccattctgttt<br>tatgtcaattactaattagatcatgtcacgttactaacttactacgttccaattagtccttattgcatttgta<br>ataaaatccgcatactttcggactggctacaaggttatacatgat |
| #45 | MKFFSYILVYRRFLFVVFTVLVLLPLPIVLHTKEAECAYTLFVV<br>ATFWLTEALPLSVTALLPSLMLPMFGIMPSKKVASAYFKDFHLLLIGVICLATSIEKW<br>NLHKRIALKMVMMVGVNPAWLTLGFMSSTAFLSMWLSNTSTAAMVMPIAEAVVQQIIN<br>AEAEVEATQMTYFNGSTNHGLEIDESVNGHEINERKEKTKPVPGYNNDTGKISSKVEL<br>EKNSGMRTKYRTKKGHVTRKLTCLCIAYSSTIGGLTTITGTSTNLIFAEYFNTRYPDC<br>RCLNFGSWFTFSFPAALIILLLSWIWLQWLFLGFNFKEMFKCGKTKTVQQKACAEVIK<br>QEYQKLGPIRYQEIVTLVLFIIMALLWFSRDPGFVPGWSALFSEYPGFATDSTVALLI<br>GLLFFLIPAKTLTKTTPTGEIVAFDYSPLITWKEFQSFMPWDIAILVGGGFALADGCE<br>ESGLSKWIGNKLSPLGSLPAWLIILISSLMVTSLTEVASNPATITLFLPILSPLAEAI<br>HVNPLYILIPSTLCTSFAFLLPVANPPNAIVFSYGHLKVIDMVKAGLGVNIVGVAVVM<br>LGICTWIVPMFDLYTYPSWAPAMSNETMP" |

| | |
|---|---|
| #46 | RTMKFFSYILVYRRFLFVVFTVLVLLPLPIVLHTKEAECAYTLFVVATFWLTEALPLSVTALLPSLMLPMFGI MPSKKVASAYFKDFHLLLIGVICLATSIEKWNLHKRIALKMVMMVGVNPAWLTLGFMSSTAFLSMWLSNTSTA AMVMPIAEAVVQQIINAEAEVEATQMTYFNGSTNHGLEIDESVNGHEINERKEKTKPVPGYNNDTGKISSKVE LEKTV* |
| #47 | ATQMTYFNGSTNHGLEIDESVNGHEINERKEKTKPVPGYNNDTGKISSKVELEKHWKLAVQDGSPSPSVHSVS QLAAQGKEKVEGICT* |
| #48 | HGLEIDESVNGHEINERKEKTKPVPGYNNDTGKISSKVELEKNSGMRTKYRTKKGHVTRKLTCLCIAYSSTIG GLTTIITGTSTNLIFAEYFNTFHPHRRGDRTRHVHQEAEI* |
| #49 | CCAGCTTTAACCATGTCAATG |
| #50 | CAGATGGTTGTGAGGAGTCTG |
| #51 | TGCTAATGCTTTTGGTACAAATGGATGTGGAATATAATTGAATATTTTCTTGTTTAAGGGGAGCATGAAGAGG TGTTGAGGTTATGTCAAGCATCTGGCACAGCTGAAGGCAGATGGAAATATTTACAAGTACGCAATTTGAGACT AAGATATTGTTATCATTCTCCTATTGAAGACAAGAGCAATAGTAAAACACATCAGGTCAGGGGGTTAAAGACC TGTGATAAACCACTTCCGATAAGTTGGAAACGTGTGTCTATATTTTCATATCTGTATATATATAATGGTAAAG AAAGACACCTTCGTAACCCGCATTTTCCAAAGAGAGGAATCACAGGGAGATGTACAGCAATGGGGCCATTTAA GAGTTCTGTGTTCATCTTGATTCTTCACCTTCTAGAAGGGGCCCTGAGTAATTCACTCATTCAGCTGAACAAC AATGGCTATGAAGGCATTGTCGTTGCAATCGACCCCAATGTGCCAGAAGATGAAACACTCATTCAACAAATAA AGGACATGGTGACCCAGGCATCTCTGTATCTGTTTGAAGCTACAGGAAAGCGATTTTATTTCAAAAATGTTGC CATTTTGATTCCTGAAACATGGAAGACAAAGGCTGACTATGTGAGACCAAAACTTGAGACCTACAAAAATGCT GATGTTCTGGTTGCTGAGTCTACTCCTCCAGGTAATGATGAACCCTACACTGAGCAGATGGGCAACTGTGGAG AGAAGGGTGAAAGGATCCACCTCACTCCTGATTTCATTGCAGGAAAAAAGTTAGCTGAATATGGACCACAAGG TAAGGCATTTGTCCATGAGTGGGCTCATCTACGATGGGGAGTATTTGACGAGTACAATAATGATGAGAAATTC TACTTATCCAATGGAAGAATACAAGCAGTAAGATGTTCAGCAGGTATTACTGGTACAAATGTAGTAAAGAAGT GTCAGGGAGGCAGCTGTTACACCAAAAGATGCACATTCAATAAAGTTACAGGACTCTATGAAAAAGGATGTGA GTTTGTTCTCCAATCCCGCCAGACGGAGAAGGCTTCTATAATGTTTGCACAACATGTTGATTCTATAGTTGAA TTCTGTACAGAACAAAACCACAACAAAGAAGCTCCAAACAAGCAAAATCAAAAATGCAATCTCCGAAGCACAT GGGAAGTGATCCGTGATTCTGAGGACTTTAAGAAAACCACTCCTATGACAACACAGCCACCAAATCCCACCTT CTCATTGCTGCAGATTGGACAAAGAATTGTGTGTTTAGTCCTTGACAAATCTGGAAGCATGGCGACTGGTAAC CGCCTCAATCGACTGAATCAAGCAGGCCAGCTTTTCCTGCTGCAGACAGTTGAGCTGGGGTCCTGGGTTGGGA TGGTGACATTTGACAGTGCTGCCCATGTACAAAGTGAACTCATACAGATAAACAGTGGCAGTGACAGGGACAC ACTCGCCAAAAGATTACCTGCAGCAGCTTCAGGAGGGACGTCCATCTGCAGCGGGCTTCGATCGGCATTTACT GTGATTAGGAAGAAATATCCAACTGATGGATCTGAAATTGTGCTGCTGACGGATGGGGAAGACAACACTATAA GTGGGTGCTTTAACGAGGTCAAACAAAGTGGTGCCATCATCCACACAGTCGCTTTGGGGCCCTCTGCAGCTCA AGAACTAGAGGAGCTGTCCAAAATGACAGGAGGTTTACAGACATATGCTTCAGATCAAGTTCAGAACAATGGC CTCATTGATGCTTTTGGGGCCCTTTCATCAGGAAATGGAGCTGTCTCTCAGCGCTCCATCCAGCTTGAGAGTA AGGGATTAACCCTCCAGAACAGCCAGTGGATGAATGGCACAGTGATCGTGGACAGCACCGTGGGAAAGGACAC TTTGTTTCTTATCACCTGGACAACGCAGCCTCCCCAAATCCTTCTCTGGGATCCCAGTGGACAGAAGCAAGGT GGCTTTGTAGTGGACAAAAACACCAAAATGGCCTACCTCCAAATCCCAGGCATTGCTAAGGTTGGCACTTGGA AATACAGTCTGCAAGCAAGCTCACAAACCTTGACCCTGACTGTCACGTCCCGTGCGTCCAATGCTACCCTGCC TCCAATTACAGTGACTTCCAAAACGAACAAGGACACCAGCAAATTCCCCAGCCCTCTGGTAGTTTATGCAAAT ATTCGCCAAGGAGCCTCCCCAATTCTCAGGGCCAGTGTCACAGCCCTGATTGAATCAGTGAATGGAAAAACAG TTACCTTGGAACTACTGGATAATGGAGCAGGTGCTGATGCTACTAAGGATGACGGTGTCTACTCAAGGTATTT CACAACTTATGACACGAATGGTAGATACAGTGTAAAAGTGCGGGCTCTGGGAGGAGTTAACGCAGCCAGACGG AGAGTGATACCCCAGCAGAGTGGAGCACTGTACATACCTGGCTGGATTGAGAATGATGAAATACAATGGAATC CACCAAGACCTGAAATTAATAAGGATGATGTTCAACACAAGCAAGTGTGTTTCAGCAGAACATCCTCGGGAGG CTCATTTGTGGCTTCTGATGTCCCAAATGCTCCCATACCTGATCTCTTCCCACCTGGCCAAATCACCGACCTG AAGGCGGAAATTCACGGGGGCAGTCTCATTAATCTGACTTGGACAGCTCCTGGGGATGATTATGACCATGGAA CAGCTCACAAGTATATCATTCGAATAAGTACAAGTATTCTTGATCTCAGAGACAAGTTCAATGAATCTCTTCA AGTGAATACTACTGCTCTCATCCCAAAGGAAGCCAACTCTGAGGAAGTCTTTTTGTTTAAACCAGAAAACATT ACTTTTGAAAATGGCACAGATCTTTTCATTGCTATTCAGGCTGTTGATAAGGTCGATCTGAAATCAGAAATAT CCAACATTGCACGAGTATCTTTGTTTATTCCTCCACAGACTCCGCCAGAGACACCTAGTCCTGATGAAACGTC TGCTCCTTGTCCTAATATTCATATCAACAGCACCATTCCTGGCATTCACATTTTAAAAATTATGTGGAAGTGG ATAGGAGAACTGCAGCTGTCAATAGCCTAGGGCTGAATTTTTGTCAGATAAATAAAATAAATCATTCATCCTT TTTTGATTATAAAATTTTCTAAAATGTATTTAGACTTCCTGTAGGGGGCGATATACTAAATGTATATAGTA |

| | |
|---|---|
| | CATTTATACTAAATGTATTCCTGTAGGGGGCGATATACTAAATGTATTTAGACTTCCTGTAGGGGGCGATAA<br>AATAAAATGCTAAACAACTGGGTAAA |
| #52 | AATTAAATTATGAGAATTAAAAAGACAACATTGAGCAGAGATGAAAAAGGAAGGGAGGAAAAGGTGGAAAAGA<br>AAAGAAGACAAGAAGCGAGTAGTGGTCTCTAACTTGCTCTTTGAAGGATGGTCTCACAAAGAGAACCCCAACA<br>GACATCATCGTGGGAATCAAATCAAGACCAGCAAGTACACCGTGTTGTCCTTCGTCCCCAAAAACATTTTTGA<br>GCAGCTACACCGGTTTGCCAATCTCTATTTTGTGGGCATTGCGGTTCTGAATTTTATCCCTGTGGTCAATGCT<br>TTCCAGCCTGAGGTGAGCATGATACCAATCTGTGTTATCCTGGCAGTCACTGCCATCAAGGACGCTTGGGAAG<br>ACCTCCGGAGGTACAAATCGGATAAAGTCATCAATAACCGAGAGTGCCTCATCTACAGCAGAAAAGAGCAGAC<br>CTATGTGCAGAAGTGCTGGAAGGATGTGCGTGTGGGAGACTTCATCCAAATGAAATGCAATGAGATTGTCCCA<br>GCAGACATACTCCTCCTTTTTTCCTCTGACCCCAATGGGATATGCCATCTGGAAACTGCCAGCTTGGATGGAG<br>AGACAAACCTCAAGCAAAGACGTGTCGTGAAGGGCTTCTCACAGCAGGAGGTACAGTTCGAACCAGAGCTTTT<br>CCACAATACCATCGTGTGTGAGAAACCCAACAACCACCTCAACAAATTTAAGGGTTATATGGAGCATCCTGAC<br>CAGACCAGGACTGGCTTTGGCTGTGAGAGTCTTCTGCTTCGAGGCTGCACCATCAGAAACACCGAGATGGCTG<br>TTGGCATTGTCATCTATGCAGGCCATGAGACGAAAGCCATGCTGAACAACAGTGGCCCCCGGTACAAACGCAG<br>CAAGATTGAGCGGCGCATGAATATAGACATCTTCTTCTGCATTGGGATCCTCATCCTCATGTGCCTTATTGGA<br>GCTGTAGGTCACAGCATCTGGAATGGGACCTTTGAAGAACACCCTCCCTTCGATGTGCCAGATGCCAATGGCA<br>GCTTCCTTCCCAGTGCCCTTGGGGGCTTCTACATGTTCCTCACAATGATCATCCTGCTCCAGGTGCTGATCCC<br>CATCTCTTTGTATGTCTCCATTGAGCTGGTGAAGCTCGGGCAAGTGTTCTTCTTGAGCAATGACCTTGACCTG<br>TATGATGAAGAGACCGATTTATCCATTCAATGTCGAGCCCTCAACATCGCAGAGGACTTGGGCCAGATCCAGT<br>ACATCTTCTCCGATAAGACGGGGACCCTGACAGAGAACAAGATGGTGTTCCGACGTTGCACCATCATGGGCAG<br>CGAGTATTCTCACCAAGAAAATGGTATAGAAGCTCCCAAGGGCTCCATCCCTCTTTCTAAAAGGAAATACCCT<br>GCTCTCCTAAGAAACGAGGAGATAAAAGACATTCTCCTGGCTCTCTTAGAGGCTGTGTGGCATTTCCACAAGT<br>TGCTTCCTGTATCCCTGTGGTCTTCCTTGTCACAGATCAGGGCTGTTCCAATTACTTGTAAACTTTCATTTGT<br>TTACAAAGGTTAGAAGTTATCCCATATGTGGTTCCCCTTCAGCTGATCTTTGTCTGGTGCCAGACAAAGCACT<br>TTATGAGACGAGTTTTTTATCTGTCAGCAATGGATTGGAGACATTTCCCAATTGTGTGCCAGTCACACAACCA<br>AGGCTTAGGAATTTCTCAGGCCACCTTACCTGACATGTCAGGGCAGGTCTGTGTCTAGGTGCATGGTCAGATT<br>TAATACATCCAGAAGATGTCTTCTATTCTAACAGATCTCTTAGCTTGTCACTGAGGCAAAGTTTTGATTTAGG<br>AGATAGGGCTATAAAATGCCTGGACTGTTACCTTGCATGGACTGAATATGACTCATAAAACTGATCTGATTCC<br>TTCAGCCATCATCTGCCCAACTTGGTTCCCCTCCCCACCCCCCCACAACACACACACACACACTTTCTAAGAAAA<br>GAAAAGAAATTCTTTTTTTTCAATACTTTAAGTTCTGGGATACATGTGCAGAATGTGCAGGTTTGTTACATAG<br>GTATACATGTGTCATGGTGGTTTGCAGCACCCACCAACCCATCATCTACCTTAGGTATTTCTCCTAATGCTAT<br>CCCTCCCCTAGCCCCCAACCCCCCGATGGGCTCCAGTGTGTGATGTTCCCCTCCATGTCCATGTGTTCTCATT<br>GTTCAATTCCCACTTATGAGTGAGAACATGCAGTATTTGGTTTTCTGTTCTTGTGTTAGTTTGCTGATGGTTT<br>CCTGTTCATCCGTGTCCCTGCAAAGGACATGAACTCATCCTTTTTTATGGCTGCATAATATTCCATGGTGTAT<br>ATGTGCCACATTTTCTTTATCCAGTCTATCGCTGATGGGCACTGGGGTTGGTTCCAAGTCTTTGCTATTGTGA<br>ACAGTGCTGCAATAAACTTACATGTGCATGTGTCTTTAGTAGAATGATTTATAATCCTTTGGGTATATACCCA<br>GTAATGGGATTGCTGGTCAAATGGTATTTCTGGTTCTAGATCCTTGAGGAATCTTTGTCTTCCACAATGGTTG<br>AACTAATTTGTACTCCCACCAACAGTGTAAAAGTATTCCTGTTTCTCTACATCCTCTTCAGCATCTGTTGTGT<br>CCTGACATTTTAATGATCACTATTCTCACTGGCGTGAGATGTTATCTCATTGTGGTTTTGATTTGCATTTCTC<br>TAATGACCAGTAATGATGAGCTTTTTTTCATATGTTTGTTGGCTGCATAAATGTCTTCTTTTGAGAAGTGTCT<br>GTTCATATCCTTCACCCATTTTTTGAAGAAAACAAACTCTTAAGAGAGCAGTATTCATTCTTTTGAGTGTGAG<br>GGATGGAGAAAGAGAAAGATGGAGAGAGTATTATAAGCAGCTGTATCCCCTTTGCCATGGTGATAGCAGACCA<br>TTCACATGGGAGCTTCTGGTCTCTTTGTAATAATAATAAGAGCCACATTACCAGTACTTAGAGTATGCTAGTT<br>ATTTTAACACATTGTATCATTAAATCTTCAAAACATCCCTATGAGTTAGAAACCTAAAAAAAAAAAAAAAAAA<br>A |
| #53 | CTCATTTTGATGTCTAGAATCAGGGGATCCAGGATCATCACCAAGGTCATTTTCCCAGGTATGGAGGGGTCTT<br>TCTGCTTCTTTCTTGTCATGCACAGCTGCTGAGGAAGGGGCTGGGAGTAAAGACAGTGAAATGGGGAGGAGGA<br>GTCCATTCAAACCGAGAAACAAAGTGTTTGGTTTTTCTTACCCCTGGTGTAGAAGCTACCAACCTTTTCCAAG<br>AAAGAGGGCCTGGCCCCCTTCTCGGGTCTGGCTGGGTGCCTGCTGTGCCTCTCTGGCCTCCCCTCCGAAGGGC<br>ACCATTCCCTCGGGTGAGTACTACCGGCCTGCACCGTCTTCCAGTGGGGACAGCCTGAGAAGAGAGTCTGGGG<br>CCTTACTTCAGTACCTTCCTTCACTGGCCTCACCCTGTGCAAATCATGCCACACGCTGCAGCCTCCTTTTCCC<br>TATCTATAAAATAAAAATGACCCTGCTCTATCTCACTGGGCTGGCAAGAACACACTGTTGTTGCCTTGCAGAC<br>AGATGTGCTGAGGCTGTAGAAAGTGCTTTTTATTTGGTTGGGAGCTTGTGCATAAATGCGAGAGGGGCTGCAC<br>ATCTGACGGACTAGAGGTGACTCATGGCTGAACCGGAACAGGACATCGGGGAGAAGCCAGCAGCCATGCTGAA<br>CTCTCCACAGGGCCCTGTGAAAAGCTCTTCACCTCCTCTGCCCTCTGGATCTAGTGAAGCCTATTCATCCTTC<br>AGATGTCAGCTCAAATAATCAACCTTCATGGAGGCCTCCCTTGACCCCTAACATGCTTTCAAAGTACTGTGTA<br>TTTCACATTCATCATGCCCCGACAACTGTGATTTCCCATTTATTAATATCTGTCTCTTCTGCTGGCCTGCAAA<br>CTCCAGGAGCACAGAGACATCTTTGGGATTTTTGAACATGATTTCCCCAGGGCTTAGCCCAGTGCCTGGTGCA<br>AAGCAGGCTTTCAACATGTTCAGTGGATATTGTAAGAAAGAAAGAAATACACAAAAGGCCTGGCATATGCAAA<br>GCACTCTAAATATTCACTCCTTTCCCTTCCCTCTGGGTGAGAAAATTTCTCCTTATAAAGACACCCTCCTAAC<br>TGTATCTCTGCTAGAGAACTGAAGACATAAAGCACTCTGTGCCAAAAATATTTAAGTAAAACTTGAGCTAAG<br>CACAGAGATTATAAATATTTCTTCCCCAGATTACGCACCATTTAAAAATACTGTCTCAGCTCCTTTTCATGAT |

| | |
|---|---|
| | TTGGGTGGTGATTAAAGAAAATTACTCTTCAAGACTGAAAGTCATTACTGCCCTTTTCCTGACTTGCCTTTTC<br>CCTTGAGAAGGGGAGGATAAGCTGCAGGGCAGGAAGTGGAAGTGGGGCATCCTTGTCCTTTGTCTGGCAGACA<br>GCCAACTGGTCAGGTACTGCTCCTTCTCAACTCTTTCCTGATTCCCAGGTGAATATAAACAAGAAGGCACAAA<br>TCCACACTTGCCAACAACGGACCCAAGTGATAACAAGAAACCCAGTGACACCTGTCTAGGTGAAGACTCAGCC<br>CCTATGTGACCAGGTTGCAAAGCCAAACTGACCATCTGCTTTCCATTTGGACTTTTAGTTCATACTGTATCTT<br>CTCAGGACAGTTAAGTTGGAATACAATGCCACTGTCCTGAAAGATGGTAGAATTATCCTATTTCTGGAGGAGT<br>GGGGGTGGTGGGTAGGAATCTCAAGAGCGATTTGCTCCTCTGCACAATAGCTTCTTTAAGGACACCAGGGCCC<br>CCAGGGCTATACATTTCCCTGAAGCTTTCCAGATAAGCAACAAGGTATGAGCACCTGCTATGTATTGCCCAAG<br>GGTGATGTGTTTAAATATCCATTGCATATTTTAAATCCTTGGCTGGCTTAAAGCTGCAAGCTTTCTGTCTTCA<br>GTGGATATAATGGGGGCATACATCCCAGAGCTTGCCCAACACTCCAAGAAAAGAACCCTCAGCTAATGCAAAG<br>TGTGTATGTGCCCATGAAAGCTCCATGTCTACTTAACATTCAGTTTTTAGGATTATTTATGCTGTAATAATAG<br>ATATGAAAATCTCTGACAGGTATTTTGTTTCCTTTACAAACTGTATTTGAATTTATGGGTGATTTAGAGCTTG<br>TGTTTAAAGTCAGAATTCAGAACCCCAAAGAAAATGACTTCATTGAAATTGAACTGAAGAGACAAGAACTGAG<br>TTACCAAAACCTACTAAACGTGAGTTGCTGTGAACTGGGGATTAAACCAGAACGAGTGGAGAAGATCAGAAAG<br>CTACCAAACACACTGCTCAGAAAGGACAAAGACATTCGAAGACTGCGGGACTTTCAGGAAGTGGAACTCATTT<br>TAATGAAAAATGGAAGCTCCAGATTGACAGAATATGTGCCATCTCTGACAGAAAGGCCCTGCTATGATAGCAA<br>AGCTGCAAAAATGACTTATTAAATACTCCCAGGAATGGCCGCGCATGGTGGCTCACCCCCTGTAATCCCAGCA<br>CTTTGGGAAGCCAAGGTGGGCGGATCACCTGAGGTCAGGAGTTCTAGACCAGCCTGGCCAACATATAGTGAAA<br>CCCAGTCTCTACTAAAAAAAATACAAAAATTAGCTAGGTGTGGTGGCGCACACCTGTAGTAGTCCCAGCTACA<br>TGGGAAGCTGAGGCAGGAGAATCACCTGAACCCAGGAGGCAGAGGTTGCAGTGAGCTGAGATTGCGCCACTGC<br>ACTCCAGCCTGGCGACAGAGCAAGACTCTGTCTCTCAAAATAAATAAATAAATAAATAAATAAATAAATAAAT<br>AATC |
| #54 | GCCCGGGAGAGGAGAGGAGCGGGCCGAGGACTCCAGCGTGCCCAGGTCTGGCATCCTGCACTTGCTGCCCTCT<br>GACACCTGGGAAGATGGCCGGCCCGTGGACCTTCACCCTTCTCTGTGGTTTGCTGGCAGCCACCTTGATCCAA<br>GCCACCCTCAGTCCCACTGCAGTTCTCATCCTCGGCCCAAAAGTCATCAAAGAAAAGCTGACACAGGAGCTGA<br>AGGACCACAACGCCACCAGCATCCTGCAGCAGCTGCCGCTGCTCAGTGCCATGCGGGAAAAGCCAGCCGGAGG<br>CATCCCTGTGCTGGGCAGCCTGGTGAACACCGTCCTGAAGCACATCATCTGGCTGAAGGTCATCACAGCTAAC<br>ATCCTCCAGCTGCAGGTGAAGCCCTCGGCCAATGACCAGGAGCTGCTAGTCAAGATCCCCCTGGACATGGTGG<br>CTGGATTCAACACGCCCCTGGTCAAGACCATCGTGGAGTTCCACATGACGACTGAGGCCCAAGCCACCATCCG<br>CATGGACACCAGTGCAAGTGGCCCCACCCGCCTGGTCCTCAGTGACTGTGCCACCAGCCATGGGAGCCTGCGC<br>ATCCAACTGCTGCATAAGCTCTCCTTCCTGGTGAACGCCTTAGCTAAGCAGGTCATGAACCTCCTAGTGCCAT<br>CCCTGCCCAATCTAGTGAAAAACCAGCTGTGTCCCGTGATCGAGGCTTCCTTCAATGGCATGTATGCAGACCT<br>CCTGCAGCTGGTGAAGGTGCCCATTTCCCTCAGCATTGACCGTCTGGAGTTTGACCTTCTGTATCCTGCCATC<br>AAGGGTGACACCATTCAGCTCTACCTGGGGGCCAAGTTGTTGGACTCACAGGGAAAGGTGACCAAGTGGTTCA<br>ATAACTCTGCAGCTTCCCTGACAATGCCCACCCTGGACAACATCCCGTTCAGCCTCATCGTGAGTCAGGACGT<br>GGTGAAAGCTGCAGTGGCTGCTGTGCTCTCTCCAGAAGAATTCATGGTCCTGTTGGACTCTGTGCTTCCTGAG<br>AGTGCCCATCGGCTGAAGTCAAGCATCGGGCTGATCAATGAAAAGGCTGCAGATAAGCTGGGATCTACCCAGA<br>TCGTGAAGATCCTAACTCAGGACACTCCCGAGTTTTTTATAGACCAAGGCCATGCCAAGGTGGCCCAACTGAT<br>CGTGCTGGAAGTGTTTCCCTCCAGTGAAGCCCTCCGCCCTTTGTTCACCCTGGGCATCGAAGCCAGCTCGGAA<br>GCTCAGTTTTACACCAAAGGTGACCAACTTATACTCAACTTGAATAACATCAGCTCTGATCGGATCCAGCTGA<br>TGAACTCTGGGATTGGCTGGTTCCAACCTGATGTTCTGAAAAACATCATCACTGAGATCATCCACTCCATCCT<br>GCTGCCGAACCAGAATGGCAAATTAAGATCTGGGGTCCCAGTGTCATTGGTGAAGGCCTTGGGATTCGAGGCA<br>GCTGAGTCCTCACTGACCAAGGATGCCCTTGTGCTTACTCCAGCCTCCTTGTGGAAACCCAGCTCTCCTGTCT<br>CCCAGTGAAGACTTGGATGGCAGCCATCAGGGAAGGCTGGGTCCCAGCTGGGAGTATGGGTGTGAGCTCTATA<br>GACCATCCCTCTCTGCAATCAATAAACACTTGCCTGTGAT |
| #55 | GGAGTGGGGGAGAGAGAGGAGACCAGGACAGCTGCTGAGACCTCTAAGAAGTCCAGATACTAAGAGCAAAGAT<br>GTTTCAAACTGGGGGCCTCATTGTCTTCTACGGGCTGTTAGCCCAGACCATGGCCCAGTTTGGAGGCCTGCCC<br>GTGCCCCTGGACCAGACCCTGCCCTTGAATGTGAATCCAGCCCTGCCCTTGAGTCCCACAGGTCTTGCAGGAA<br>GCTTGACAAATGCCCTCAGCAATGGCCTGCTGTCTGGGGGCCTGTTGGGCATTCTGGAAAACCTTCCGCTCCT<br>GGACATCCTGAAGCCTGGAGGAGGTACTTCTGGTGGCCTCCTTGGGGGACTGCTTGGAAAAGTGACGTCAGTG<br>ATTCCTGGCCTGAACAACATCATTGACATAAAGGTCACTGACCCCCAGCTGCTGGAACTTGGCCTTGTGCAGA<br>GCCCTGATGGCCACCGTCTCTATGTCACCATCCCTCTCGGCATAAAGCTCCAAGTGAATACGCCCCTGGTCGG<br>TGCAAGTCTGTTGAGGCTGGCTGTGAAGCTGGACATCACTGCAGAAATCTTAGCTGTGAGAGATAAGCAGGAG<br>AGGATCCACCTGGTCCTTGGTGACTGCACCCATTCCCCTGGAAGCCTGCAAATTTCTCTGCTTGATGGACTTG<br>GCCCCCTCCCCATTCAAGGTCTTCTGGACAGCCTCACAGGGATCTTGAATAAAGTCCTGCCTGAGTTGGTTCA<br>GGGCAACGTGTGCCCTCTGGTCAATGAGGTTCTCAGAGGCTTGGACATCACCCTGGTGCATGACATTGTTAAC<br>ATGCTGATCCACGGACTACAGTTTGTCATCAAGGTCTAAGCCTTCCAGGAAGGGGCTGGCCTCTGCTGAGCTG<br>CTTCCCAGTGCTCACAGATGGCTGGCCCATGTGCTGGAAGATGACACAGTTGCCTTCTCTCCGAGGAACCTGC<br>CCCCTCTCCTTTCCCACCAGGCGTGTGTAACATCCCATGTGCCTCACCTAATAAAATGGCTCTTCTTCTGCAA<br>AAAAAAAAAAAAAAAAAAAAAAAAAA |

| | |
|---|---|
| #56 | GAGCAGAGCCCTTTCACACACCTCAGGAACACCTTTCGGCTGCCCGCTCCCCAGACACACCTGCAGCCCTGCC CAGCCGGCTTTGCTCACCCACTGCTTGTAAATGCCCCAGATATGAGCCAGCCCAGGCCCCGCTACGTGGTAGA CAGAGCCGCATACTCCCTTACCCTCTTCGACGATGAGTTTGAGAAGAAGGACCGGACATACCCAGTGGGAGAG AAACTTCGCAATGCCTTCAGATGTTCCTCAGCCAAGATCAAAGCTGTGGTGTTTGGGCTGCTGCCTGTGCTCT CCTGGCTCCCCAAGTACAAGATTAAAGACTACATCATTCCTGACCTGCTCGGTGGACTCAGCGGGGGATCCAT CCAGGTCCCACAAGGCATGGCATTTGCTCTGCTGGCCAACCTTCCTGCAGTCAATGGCCTCTACTCCTCCTTC TTCCCCCTCCTGACCTACTTCTTCCTGGGGGGTGTTCACCAGATGGTGCCAGGTACCTTTGCCGTTATCAGCA TCCTGGTGGGTAACATCTGTCTGCAGCTGGCCCCAGAGTCGAAATTCCAGGTCTTCAACAATGCCACCAATGA GAGCTATGTGGACACAGCAGCCATGGAGGCTGAGAGGCTGCACGTGTCAGCTACGCTAGCCTGCCTCACCGCC ATCATCCAGATGGGTCTGGGCTTCATGCAGTTTGGCTTTGTGGCCATCTACCTCTCCGAGTCCTTCATCCGGG GCTTCATGACGGCCGCCGGCCTGCAGATCCTGATTTCGGTGCTCAAGTACATCTTCGGACTGACCATCCCCTC CTACACAGGCCCAGGGTCCATCGTCTTTACCTTCATTGACATTTGCAAAAACCTCCCCCACACCAACATCGCC TCGCTCATCTTCGCTCTCATCAGCGGTGCCTTCCTGGTGCTGGTGAAGGAGCTCAATGCTCGCTACATGCACA AGATTCGCTTCCCCATCCCTACAGAGATGATTGTGGTGGTGGTGGCAACAGCTATCTCCGGGGGCTGTAAGAT GCCCAAAAAGTATCACATGCAGATCGTGGGAGAAATCCAACGCGGGTTCCCCACCCCGGTGTCGCCTGTGGTC TCACAGTGGAAGGACATGATAGGCACAGCCTTCTCCCTAGCCATCGTGAGCTACGTCATCAACCTGGCTATGG GCCGGACCCTGGCCAACAAGCACGGCTACGACGTGGATTCGAACCAGGAGATGATCGCTCTCGGCTGCAGCAA CTTCTTTGGCTCCTTCTTTAAAATTCATGTCATTTGCTGTGCGCTTTCTGTCACTCTGGCTGTGGATGGAGCT GGAGGAAAATCCCAGGTGGCCAGCCTGTGTGTGTCTCTGGTGGTGATGATCACCATCCTGGTCCTGGGGATCT ATCTGTATCCTCTCCCTAAGTCTGTGCTAGGAGCCCTGATCGCTGTCAATCTCAAGAACTCCCTCAAGCAACT CACCGACCCCTACTACCTGTGGAGGAAGAGCAAGCTGGACTGTTGCATCTGGGTAGTGAGCTTCCTCTCCTCC TTCTTCCTCAGCCTGCCCTATGGTGTGGCAGTGGGTGTCGCCTTCTCCGTCCTGGTCGTGGTCTTCCAGACTC AGTTTCGAAATGGCTATGCACTGGCCCAGGTCATGGACACTGACATTTATGTGAATCCCAAGACCTATAATAG GGCCCAGGATATCCAGGGGATTAAAATCATCACGTACTGCTCCCCTCTCTACTTTGCCAACTCAGAGATCTTC AGGCAAAAGGTCATCGCCAAGACAGGCATGGACCCCCAGAAAGTATTACTAGCCAAGCAAAAATACCTCAAGA AGCAGGAGAAGCGGAGAATGAGGCCCACACAACAGAGGAGGTCTCTATTCATGAAAACCAAGACTGTCTCCCT GCAGGAGCTGCAGCAGGACTTTGAGAATGCGCCCCCCACCGACCCCAACAACAACCAGACCCCGGCTAACGGC ACCAGCGTGTCCTATATCACCTTCAGCCCTGACAGCTCCTCACCTGCCCAGAGTGAGCCACCAGCCTCCGCTG AGGCCCCCGGCGAGCCCAGTGACATGCTGGCCAGCGTCCCACCCTTCGTCACCTTCCACACCCTCATCCTGGA CATGAGTGGAGTCAGCTTCGTGGACTTGATGGGCATCAAGGCCCTGGCCAAGCTGAGCTCCACCTATGGGAAG ATCGGCGTGAAGGTCTTCTTGGTGAACATCCATGCCCAGGTGTACAATGACATTAGCCATGGAGGCGTCTTTG AGGATGGGAGTCTAGAATGCAAGCACGTCTTTCCCAGCATACATGACGCAGTCCTCTTTGCCCAGGCAAATGC TAGAGACGTGACCCCAGGACACAACTTCCAAGGGGCTCCAGGGGATGCTGAGCTCTCCTTGTACGACTCAGAG GAGGACATTCGCAGCTACTGGGACTTAGAGCAGGAGATGTTCGGGAGCATGTTTCACGCAGAGACCCTGACCG CCCTGTGAGGGCTCAGCCAGTCCTCATGCTGCCTACAGAGTGCCTGGCACTTGGGACTTCCATAAAGGATGAG CCTGGGGTCACAGGGGGTGTCGGGCGGAGGAAAGTGCATCCCCCAGAGCTTGGGTTCCTCTCTCCTCTCCCCC TCTCTCCTCCCTTCCTTCCCTCCCCGCATCTCCAGAGAGAGCCTCTCAGCAGCAGGGGGGTGCTACCCTTACG GGAGTGAGAGTCTGGTGAGCCCACTCTTCACCCGTCAGGCCCTGGCCGCAATGGACAAGCCTCCTGCTCACTC CACCCCACCCACATCTGCCCTGTCCTTGGCAGCTGAAGGACACCTTGACTTCCAGCTTTTACGAGTGAGCCAA AAACAGAAGGACAAGTACAACTGTGCTGGCCTGCTGTACAAGCTTCAAAAAGTGTCCCAGAGCCCGCACGGCT CGGTGTCAGATGGTGTCAGGCTGTCACGGACATAGGGATAAACTTGGTTAGGACTCTGGCTTGCCTTCCCCAG CTGCCTCAACTCTGTCTCTGGCAGCTCTGCACCCAGGGACCATGTGCTCTCCACACCCAGGAGTCTAGGCCTT GGTAACTATGCGCCCCCCCTCCATCATCCCCAAGGCTGCCCAAACCACCACTGCTGTCAGCAAGCACATCAGA CTCTAGCCTGGACAGTGGCCAGGACCGTCGAGACCACCAGAGCTACCTCCCCGGGGACAGCCCACTAAGGTTC TGCCTCAGCCTCCTGAAACATCACTGCCCTCAGAGGCTGCTCCCTTCCCCTGGAGGCTGGCTAGAAACCCCAA AGAGGGGGATGGGTAGCTGGCAGAATCATCTGGCATCCTAGTAATAGATACCAGTTATTCTGCACAAAACTTT TGGGAATTCCTCTTTGCACCCAGAGACTCAGAGGGGAAGAGGGTGCTAGTACCAACACAGGGAAAACGGATGG GACCTGGGCCCAGACAGTCCCCCTTGACCCCAGGGCCCATCAGGGAAATGCCTCCCTTTGGTAAATCTGCCTT ATCCTTCTTTACCTGGCAAAGAGCCAATCATGTTAACTCTTCCTTATCAGCCTGTGGCCCAGAGACACAATGG GGTCCTTCTGTAGGCAAAGGTGGAAGTCCTCCAGGGATCCGCTACATCCCCTAACTGCATGCAGATGTGGAAA GGGGCTGATCCAGATTGGGTCTTCCTGCACAGGAAGACTCTTTAACACCCTTAGGACCTCAGGCCATCTTCTC CTATGAAGATGAAAATAGGGGTTAAGTTTTCCATATGTACAAGGAGGTATTGAGAGGAACCCTACTGTTGACT TGAAAATAAATAGGTTCCATGTGTAAGTGTTTTGTAAAATTTCAGTGGAAATGCACAGAAAATCTTCTGGCCT CTCATCACTGCTTTTCTCAAGCTTCTTCAGCTTAACAACCCCTTCCCTAACAGGTTGGGCTGGCCCAGCCTAG GAAAACATCCCCATTTCTAACTTCAGCCAGACCTGCGTTGTGTGTCTGTGTGTTGAGTGAGCTGGTCAGCTAA CAAGTCTTCTTAGAGTTAAAGGAGGGGGTGCTGGCCAAGAGCCAACACATTCTTGGCCCAGGAGCATTGCTTT TCTGTGAATTCATTATGCCATCTGGCTGCCAATGGAACTCAAAACTTGGAAGGCGAAGGACAATGTTATCTGG GATTCACCGTGCCCAGCACCCGAAGTGCCAAATTCCAGGAGGACAAGAGCCTTAGCCAATGACAACTCACTCT CCCCTACTCCACCTCCTTCCAAGTCCAGCTCAGGCCCAGGAGGTGGGAGAAGGTCACAGAGCCTCAGGAATTT CCAAGTCAGAGTCCCCTTTGAACCAAGTATCTAGATCCCCTGAGGACTTGATGAAGTGATCCTTAACCCCCAA GTAATCATTAACCCCCAGACCAGCCTCAGAACTGAAGGAGATTGTTGACCCAGTGACCTGGAGTTGAGGCTCA |

| | |
|---|---|
| | GGGAGAGATCTGCCACATGTCTGAGGGTTGCAGAGCCCGCTGTGGAGGTAAGATTGGAAACACATGAGGCAGA<br>GGGAAGACATTGAAGAAAACATCTCTGCTGGAATATTTGGAAAAGAACACTCTTCTGGACCTGGTTGAAGCAG<br>GAAAGATGGAGGCAAAGTAGTGAAATAATCCAGAATTTCAATGCTTTTGAATGTTCTTAGTGATACTGACCTG<br>TGATAATATAATTCCCAGGGAGGACTGGGAACCTTATCTCTTGAGATATTTGCATAATTTATTTAATTTAAGC<br>CTCATTCTCCTTTTGTTCATTTTGGTAATAAACTGGATTTGAATTGTGAACAAAAAAAAAAAAAAAAAAA |
| #57 | AATGCTCTAAGACCTCTCAGCACGGGCGGAAGAAACTCCCGGAGAGCTCACCCAAAAAACAAGGAGATCCCAT<br>CTAGATTTCTTCTTGCTTTTGACTCACAGCTGGAAGTTAGAAAAGCCTCGATTTCATCTTTGGAGAGGCCAAA<br>TGGTCTTAGCCTCAGTCTCTGTCTCTAAATATTCCACCATAAAACAGCTGAGTTATTTATGAATTAGAGGCTA<br>TAGCTCACATTTTCAATCCTCTATTTCTTTTTTTAAATATAACTTTCTACTCTGATGAGAGAATGTGGTTTTA<br>ATCTCTCTCTCACATTTTGATGATTTAGACAGACTCCCCCTCTTCCTCCTAGTCAATAAACCCATTGATGATC<br>TATTTCCCAGCTTATCCCCAAGAAAACTTTTGAAAGGAAAGAGTAGACCCAAAGATGTTATTTTCTGCTGTTT<br>GAATTTTGTCTCCCCACCCCCAACTTGGCTAGTAATAAACACTTACTGAAGAAGAAGCAATAAGAGAAAGATA<br>TTTGTAATCTCTCCAGCCCATGATCTCGGTTTTCTTACACTGTGATCTTAAAAGTTACCAAACCAAAGTCATT<br>TTCAGTTTGAGGCAACCAAACCTTTCTACTGCTGTTGACATCTTCTTATTACAGCAACACCATTCTAGGAGTT<br>TCCTGAGCTCTCCACTGGAGTCCTCTTTCTGTCGCGGGTCAGAAATTGTCCCTAGATGAATGAGAAAATTATT<br>TTTTTTAATTTAAGTCCTAAATATAGTTAAAATAAATAATGTTTTAGTAAAATGATACACTATCTCTGTGAAA<br>TAGCCTCACCCCTACATGTGGATAGAAGGAAATGAAAAAATAATTGCTTTGACATTGTCTATATGGTACTTTG<br>TAAAGTCATGCTTAAGTACAAATTCCATGAAAAGCTCACTGATCCTAATTCTTTCCCTTTGAGGTCTCTATGG<br>CTCTGATTGTACATGATAGTAAGTGTAAGCCATGTAAAAAGTAAATAATGTCTGGGCACAGTGGCTCACGCCT<br>GTAATCCTAGCACTTTGGGAGGCTGAGGAGGAAGGATCACTTGAGCCCAGAAGTTCGAGACTAGCCTGGGCAA<br>CATGGAGAAGCCCTGTCTCTACAAAATACAGAGAGAAAAAATCAGCCAGTCATGGTGGCATACACCTGTAGTC<br>CCAGCATTCCGGGAGGCTGAGGTGGGAGGATCACTTGAGCCCAGGGAGGTTGGGGCTGCAGTGAGCCATGATC<br>ACACCACTGCACTCCAGCCAGGTGACATAGCGAGATCCTGTCTAAAAAAATAAAAAATAAATAATGGAACACA<br>GCAAGTCCTAGGAAGTAGGTTAAAACTAATTCTTTAAAAAAAAAAAAAAGTTGAGCCTGAATTAAATGTAATG<br>TTTCCAAGTGACAGGTATCCACATTTGCATGGTTACAAGCCACTGCCAGTTGGCAGTAGCACTTTCCTGGCAC<br>TGTGGTCGGTTTTGTTTTGTTTTGCTTTGTTTAGAGACGGGGTCTCACTTTCCAGGCTGGCCTCAAACTCCTG<br>CACTCAAGCAATTCTTCTACCCTGGCCTCCCAAGTAGCTGGAATTACAGGTGTGCGCCATCACAACTAGCTGG<br>TGGTCAGTTTTGTTACTCTGAGAGCTGTTCACTTCTCTGAATTCACCTAGAGTGGTTGGACCATCAGATGTTT<br>GGGCAAAACTGAAAGCTCTTTGCAACCACACACCTTCCCTGAGCTTACATCACTGCCCTTTTGAGCAGAAAGT<br>CTAAATTCCTTCCAAGACAGTAGAATTCCATCCCAGTACCAAAGCCAGATAGGCCCCCTAGGAAACTGAGGTA<br>AGAGCAGTCTCTAAAAACTACCCACAGCAGCATTGGTGCAGGGGAACTTGGCCATTAGGTTATTATTTGAGAG<br>GAAAGTCCTCACATCAATAGTACATATGAAAGTGACCTCCAAGGGGATTGGTGAATACTCATAAGGATCTTCA<br>GGCTGAACAGACTATGTCTGGGGAAAGAACGGATTATGCCCCATTAAATAACAAGTTGTGTTCAAGAGTCAGA<br>GCAGTGAGCTCAGAGGCCCTTCTCACTGAGACAGCAACATTTAAACCAAACCAGAGGAAGTATTTGTGGAACT<br>CACTGCCTCAGTTTGGGTAAAGGATGAGCAGACAAGTCAACTAAAGAAAAAAGAAAAGCAAGGAGGAGGGTTG<br>AGCAATCTAGAGCATGGAGTTTGTTAAGTGCTCTCTGGATTTGAGTTGAAGAGCATCCATTTGAGTTGAAGGC<br>CACAGGGCACAATGAGCTCTCCCTTCTACCACCAGAAAGTCCCTGGTCAGGTCTCAGGTAGTGCGGTGTGGCT<br>CAGCTGGGTTTTTAATTAGCGCATTCTCTATCCAACATTTAATTGTTTGAAAGCCTCCATATAGTTAGATTGT<br>GCTTTGTAATTTTGTTGTTGTTGCTCTATCTTATTGTATATGCATTGAGTATTAACCTGAATGTTTTGTTACT<br>TAAATATTAAAAACACTGTTATCCTACAAAAAAACCCTCAAAGGCTGAAAATAAAGAAGGAAGATGGAGACAC<br>CCTCTGGGGGTCCTCTC |
| #58 | CTTTGCAGTGGATGCCCTTGGCAGGGTGAGCCCACAAGGAGCAATGGAGCAGGGCAGCGGCCGCTTGGAGGAC<br>TTCCCTGTCAATGTGTTCTCCGTCACTCCTTACACACCCAGCACCGCTGACATCCAGGTGTCCGATGATGACA<br>AGGCGGGGGCCACCTTGCTCTTCTCAGGCATCTTTCTGGGACTGGTGGGGATCACATTCACTGTCATGGGCTG<br>GATCAAATACCAAGGTGTCTCCCACTTTGAATGGACCCAGCTCCTTGGGCCCGTCCTGCTGTCAGTTGGGGTG<br>ACATTCATCCTGATTGCTGTGTGCAAGTTCAAAATGCTCTCCTGCCAGTTGTGCAAAGAAAGTGAGGAAAGGG<br>TCCCGGACTCGGAACAGACACCAGGAGGACCATCATTTGTTTTCACTGGCATCAACCAACCCATCACCTTCCA<br>TGGGGCCACTGTGGTGCAGTACATCCCTCCTCCTTATGGTTCTCCAGAGCCTATGGGGATAAATACCAGCTAC<br>CTGCAGTCTGTGGTGAGCCCCTGCGGCCTCATAACCTCTGGAGGGGCAGCAGCCGCCATGTCAAGTCCTCCTC<br>AATACTACACCATCTACCCTCAAGATAACTCTGCATTTGTGGTTGATGAGGGCTGCCTTTCTTTCACGGACGG<br>TGGAAATCACAGGCCCAATCCTGATGTTGACCAGCTAGAAGAGACACAGCTGGAAGAGGAGGCCTGTGCCTGC<br>TTCTCTCCTCCCCCTTATGAAGAAATATACTCTCTCCCTCGCTAGAGGCTATTCTGATATAATAACACAATGC<br>TCAGCTCAGGGAGCAAGTGTTTCCGTCATTGTTACCTGACAACCGTGGTGTTCTATGTTGTAACCTTCAGAAG<br>TTACAGCAGCGCCCAGGCAGCCTGACAGAGATCATTCAAGGGGGGAAAGGGGAAGTGGGAGGTGCAATTTCTC<br>AGATTGGTAAAAATTAGGCTGGGCTGGGGAAATTCTCCTCCGGAACAGTTTCAAATTCCCTCGGGTAAGAAAT<br>CTCCTGTATAAGGTTCAGGAGCAGGAATTTCACTTTTTCATCCACCACCCTCCCCCTTCTCTGTAGGAAGGCA<br>TTGGTGGCTCAATTTTAACCCCAGCAGCCAATGGAAAAATCACGACTTCTGAGACTTTGGGAGTTTCCACAGA<br>GGTGAGAGTCGGGTGGGAAGGAAGCAGGGAAGAGAAAGCAGGCCCAGCTGGAGATTTCCTGGTGGCTGTCCTT |

| | |
|---|---|
| | GGCCCCAAAGCAGACTCACTAATCCCAAACAACTCAGCTGCCATCTGGCCTCTCTGAGGACTCTGGGTACCTT AAAGACTATA |
| #59 | CAGGAAAGTTCGTGCTGCTAGGCAGAGGAACTGCAGCTTGTTGGCAGGTGAAGGGAGCCTGTTTAGCTGTGTC CAGCAACAACTTACGTGGTCCTGCTTGTGTTCCAGGTGAAGCGTCTGGCCGCCGAGCAGAGGAATCAAGACCT GCTCATTCTTTCCTCGGGGGATCCATCCAGCAATGACATCATCTCATGCTGCCACAAGGACCCCAAGTCTGGG CTGCTGGGGACCAGCCACGCTCCCCACTGCTCATTCCTTCATCCTAGAGACATTCTGACTCTCCTCCGACTGC GCTGTGCACAGGCGTGACAAGCTCTTTTACATCTCAGTCTGCACAACTTCAGGCACTTAGCAGATTGATATGC ATCCAACAAATATTGATTGAATATCTGCTAAATACCCAGTAATGTTTCATGAGTGATTGGGTGAATAAAGGAA TGCTGGTTCCTTCTGGCCATATTAACTCCTGCACAATACTAAGAAAAATAAATTGCACTAGCTGTGGAATAAT GTGAATCCCAATGTCATCTATTGAAATATTACCTGACTATTAAGAGGTATTTATTTTTGTATCTTTTCTAGCA AAGTAAATAAAATTCTTAATACAGCATATCCCCTTATTCACGGGGGGTATGTTCCAAGACCCCCGGTGGATGC CTGAAACTATGGATAATACCAGATCC |
| #60 | MGPFKSSVFILILHLLEGALSNSLIQLNNNGYEGIVVAIDPNVPEDETLIQQIKDMVTQASLYLFEATGKRFY FKNVAILIPETWKTKADYVRPKLETYKNADVLVAESTPPGNDEPYTEQMGNCGEKGERIHLTPDFIAGKKLAE YGPQGKAFVHEWAHLRWGVFDEYNNDEKFYLSNGRIQAVRCSAGITGTNVVKKCQGGSCYTKRCTFNKVTGLY EKGCEFVLQSRQTEKASIMFAQHVDSIVEFCTEQNHNKEAPNKQNQKCNLRSTWEVIRDSEDFKKTTPMTTQP PNPTFSLLQIGQRIVCLVLDKSGSMATGNRLNRLNQAGQLFLLQTVELGSWVGMVTFDSAAHVQSELIQINSG SDRDTLAKRLPAAASGGTSICSGLRSAFTVIRKKYPTDGSEIVLLTDGEDNTISGCFNEVKQSGAIIHTVALG PSAAQELEELSKMTGGLQTYASDQVQNNGLIDAFGALSSGNGAVSQRSIQLESKGLTLQNSQWMNGTVIVDST VGKDTLFLITWTTQPPQILLWDPSGQKQGGFVVDKNTKMAYLQIPGIAKVGTWKYSLQASSQTLTLTVTSRAS NATLPPITVTSKTNKDTSKFPSPLVVYANIRQGASPILRASVTALIESVNGKTVTLELLDNGAGADATKDDGV YSRYFTTYDTNGRYSVKVRALGGVN AARRRVIPQQSGALYIPGWIENDEIQWNPPRPEINKDDVQHKQVCFSRTSSGGSFVASDVPNAPIPDLFPPGQ ITDLKAEIHGGSLINLTWTAPGDDYDHGTAHKYIIRISTSILDLRDKFNESLQVNTTALIPKEANSEEVFLFK PENITFENGTDLFIAIQAVDKVDLKSEISNIARVSLFIPPQTPPETPSPDETSAPCPNIHINSTIPGIHILKI MWKWIGELQLSIA |
| #61 | MKKEGRKRWKRKEDKKRVVVSNLLFEGWSHKENPNRHHRGNQIKTSKYTVLSFVPKNIFEQLHRFANLYFVGI AVLNFIPVVNAFQPEVSMIPICVILAVTAIKDAWEDLRRYKSDKVINNRECLIYSRKEQTYVQKCWKDVRVGD FIQMKCNEIVPADILLLFSSDPNGICHLETASLDGETNLKQRRVVKGFSQQEVQFEPELFHNTIVCEKPNNHL NKFKGYMEHPDQTRTGFGCESLLLRGCTIRNTEMAVGIVIYAGHETKAMLNNSGPRYKRSKIERRMNIDIFFC IGILILMCLIGAVGHSIWNGTFEEHPPFDVPDANGSFLPSALGGFYMFLTMIILLQVLIPISLYVSIELVKLG QVFFLSNDLDLYDEETDLSIQCRALNIAEDLGQIQYIFSDKTGTLTENKMVFRRCTIMGSEYSHQENGIEAPK GSIPLSKRKYPALLRNEEIKDILLALLEAVWHFHKLLPVSLWSSLSQIRAVPITCKLSFVYKG |
| #62 | MGRRSPFKPRNKVFGFSYPWCRSYQPFPRKRAWPPSRVWLGACCASLASPPKGTIPSGEYYRPAPSSSGDSLR RESGALLQYLPSLASPCANHATRCSLLFPIYKIKMTLLYLTGLARTHCCCLADRCAEAVESAFYLVGSLCINA RGAAHLTD |
| #63 | MAGPWTFTLLCGLLAATLIQATLSPTAVLILGPKVIKEKLTQELKDHNATSILQQLPLLSAMREKPAGGIPVL GSLVNTVLKHIIWLKVITANILQLQVKPSANDQELLVKIPLDMVAGFNTPLVKTIVEFHMTTEAQATIRMDTS ASGPTRLVLSDCATSHGSLRIQLLHKLSFLVNALAKQVMNLLVPSLPNLVKNQLCPVIEASFNGMYADLLQLV KVPISLSIDRLEFDLLYPAIKGDTIQLYLGAKLLDSQGKVTKWFNNSAASLTMPTLDNIPFSLIVSQDVVKAA VAAVLSPEEFMVLLDSVLPESAHRLKSSIGLINEKAADKLGSTQIVKILTQDTPEFFIDQGHAKVAQLIVLEV FPSSEALRPLFTLGIEASSEAQFYTKGDQLILNLNNISSDRIQLMNSGIGWFQPDVLKNIITEIIHSILLPNQ NGKLRSGVPVSLVKALGFEAAESSLTKDALVLTPASLWKPSSPVSQ |
| #64 | MFQTGGLIVFYGLLAQTMAQFGGLPVPLDQTLPLNVNPALPLSPTGLAGSLTNALSNGLLSGGLLGILENLPL LDILKPGGGTSGGLLGGLLGKVTSVIPGLNNIIDIKVTDPQLLELGLVQSPDGHRLYVTIPLGIKLQVNTPLV GASLLRLAVKLDITAEILAVRDKQERIHLVLGDCTHSPGSLQISLLDGLGPLPIQGLLDSLTGILNKVLPELV QGNVCPLVNEVLRGLDITLVHDIVNMLIHGLQFVIKV |
| #65 | MSQPRPRYVVDRAAYSLTLFDDEFEKKDRTYPVGEKLRNAFRCSSAKIKAVVFGLLPVLSWLPKYKIKDYIIP DLLGGLSGGSIQVPQGMAFALLANLPAVNGLYSSFFPLLTYFFLGGVHQMVPGTFAVISILVGNICLQLAPES KFQVFNNATNESYVDTAAMEAERLHVSATLACLTAIIQMGLGFMQFGFVAIYLSESFIRGFMTAAGLQILISV |

| | |
|---|---|
| | LKYIFGLTIPSYTGPGSIVFTFIDICKNLPHTNIASLIFALISGAFLVLVKELNARYMHKIRFPIPTEMIVVV
VATAISGGCKMPKKYHMQIVGEIQRGFPTPVSPVVSQWKDMIGTAFSLAIVSYVINLAMGRTLANKHGYDVDS
NQEMIALGCSNFFGSFFKIHVICCALSVTLAVDGAGGKSQVASLCVSLVVMITMLVLGIYLYPLPKSVLGALI
AVNLKNSLKQLTDPYYLWRKSKLDCCIWVVSFLSSFFLSLPYGVAVGVAFSVLVVVFQTQFRNGYALAQVMDT
DIYVNPKTYNRAQDIQGIKIITYCSPLYFANSEIFRQKVIAKTGMDPQKVLLAKQKYLKKQEKRRMRPTQQRR
SLFMKTKTVSLQELQQDFENAPPTDPNNNQTPANGTSVSYITFSPDSSSPAQSEPPASAEAPGEPSDMLASVP
PFVTFHTLILDMSGVSFVDLMGIKA
LAKLSSTYGKIGVKVFLVNIHAQVYNDISHGGVFEDGSLECKHVFPSIHDAVLFAQANARDVTPGHNFQGAPG
DAELSLYDSEEDIRSYWDLEQEMFGSMFHAETLTAL |
| #66 | MEQGSGRLEDFPVNVFSVTPYTPSTADIQVSDDDKAGATLLFSGIFLGLVGITFTVMGWIKYQGVSHFEWTQL
LGPVLLSVGVTFILIAVCKFKMLSCQLCKESEERVPDSEQTPGGPSFVFTGINQPITFHGATVVQYIPPPYGS
PEPMGINTSYLQSVVSPCGLITSGGAAAAMSSPPQYYTIYPQDNSAFVVDEGCLSFTDGGNHRPNPDVDQLEE
TQLEEEACACFSPPPYEEIYSLPR |
| #67 | ACACGAATGGTAGATACAGTG |
| #68 | ATACTTGTGAGCTGTTCCATG |
| #69 | ACTGTTACCTTGCATGGACTG |
| #70 | CAATGAGAACACATGGACATG |
| #71 | CCATGAAAGCTCCATGTCTAC |
| #72 | AGAGATGGCACATATTCTGTC |
| #73 | ATCGGCTGAAGTCAAGCATCG |
| #74 | TGGTCAGTGAGGACTCAGCTG |
| #75 | TTTCTCTGCTTGATGCACTTG |
| #76 | GTGAGCACTGGGAAGCAGCTC |
| #77 | GGCAAATGCTAGAGACGTGAC |
| #78 | AGGTGTCCTTCAGCTGCCAAG |
| #79 | GTTAAGTGCTCTCTGGATTTG |
| #80 | ATCCTGATTGCTGTGTGCAAG |
| #81 | CTCTTCTAGCTGGTCAACATC |
| #82 | CCAGCAACAACTTACGTGGTC |
| #83 | CCTTTATTCACCCAATCACTC |
| #84 | agaacagcgcagtttgccctccgctcacgcagagcctctccgtggcctccgcaccttgag
cattaggccagttctcctcttctctctaatccatccgtcacctctcctgtcatccgtttc
catgccgtgaggtccattcacagaacacatccatggctctcatgctcagtttggttctga
gtctcctcaagctgggatcagggcagtggcaggtgtttgggccagacaagcctgtccagg
ccttggtgggggaggacgcagcattctcctgtttcctgtctcctaagaccaatgcagagg
ccatggaagtgcggttcttcaggggccagttctctagcgtggtccacctctacagggacg |

| | |
|---|---|
| | ggaaggaccagccatttatgcagatgccacagtatcaaggcaggacaaaactggtgaagg<br>attctattgcggaggggcgcatctctctgaggctggaaaacattactgtgttggatgctg<br>gcctctatgggtgcaggattagttcccagtcttactaccagaaggccatctgggagctac<br>aggtgtcagcactgggctcagttcctctcatttccatcacgggatatgttgatagagaca<br>tccagctactctgtcagtcctcgggctggttcccccggcccacagcgaagtggaaaggtc<br>cacaaggacaggatttgtccacagactccaggacaaacagagacatgcatggcctgtttg<br>atgtggagatctctctgaccgtccaagagaacgccgggagcatatcctgttccatgcggc<br>atgctcatctgagccgagaggtggaatccagggtacagataggagatacctttttcgagc<br>ctatatcgtggcacctggctaccaaagtactgggaatactctgctgtggcctatttttg<br>gcattgttggactgaagattttcttctccaaattccagtgtaagcgagagagagaagcat<br>gggccggtgccttattcatggttccagcagggacaggatcagagatgctcccacatccag<br>ctgcttctcttcttctagtcctagcctccagggcccaggcccaaaaaggaaaatccag<br>gcggaactggactggagaagaaagcacggacaggcagaattgagagacgcccggaaacac<br>gcagtggaggtgactctggatccagagacggctcacccgaagctctgcgtttctgatctg<br>aaaactgtaacccatagaaaagctccccaggaggtgcctcactctgagaagagatttaca<br>aggaagagtgtggtggcttctcagagtttccaagcagggaaacattactgggaggtggac<br>ggaggacacaataaaaggtggcgcgtgggagtgtgccgggatgatgtggacaggaggaag<br>gagtacgtgactttgtctcccgatcatgggtactgggtcctcagactgaatggagaacat<br>ttgtatttcacattaaatccccgttttatcagcgtcttccccaggaccccacctacaaaa<br>ataggggtcttcctggactatgagtgtgggaccatctccttcttcaacataaatgaccag<br>tcccttatttataccctgacatgtcggtttgaaggcttattgaggccctacattgagtat<br>ccgtcctataatgagcaaaatggaactcccatagtcatctgcccagtcacccaggaatca<br>gagaaagaggcctcttggcaaagggcctctgcaatcccagagacaagcaacagtgagtcc<br>tcctcacaggcaaccacgcccttcctccccaggggtgaaatgtaggatgaatcacatccc<br>acattcttctttagggatattaaggtctctctcccagatccaaagtcccgcagcagccgg<br>ccaaggtggcttccagatgaaggggactggcctgtccacatgggagtcaggtgtcatgg<br>ctgccctgagctgggagggaagaaggctgacattacatttagtttgctctcactccatct<br>ggctaagtgatcttgaaataccacctctcaggtgaagaaccgtcaggaattcccatctca<br>caggctgtggtgtagattaagtagacaaggaatgtgaataatgcttagatcttattgatg<br>acagagtgtatcctaatggtttgttcattatattacactttcagtaaaaaaaaaaaaaa<br>aaaaa |
| #85 | malmlslvlsllklgsgqwqvfgpdkpvqalvgedaafscflspktnaeamevrffrgqf<br>ssvvhlyrdgkdqpfmqmpqyqgrtklvkdsiaegrislrlenitvldaglygcrissqs<br>yyqkaiwelqvsalgsvplisitgyvdrdiqllcqssgwfprptakwkgpqgqdlstdsr<br>tnrdmhglfdveisltvqenagsiscsmrhahlsrevesrvqigdtffepiswhlatkvl<br>gilccglffgivglkiffskfqckrereawagalfmvpagtgsemlphpaaslllvlasr<br>gpgpkkenpggtglekkartgrierrpetrsggdsgsrdgspealrf |
| #86 | ATTCATGGTTCCAGCAGGGAC |
| #87 | GGGAGACAAAGTCACGTACTC |

| | |
|---|---|
| #88 | TCCTGGTGTTCGTGGTCTGCTT |
| #89 | GAGAGTCCTGGCTTTTGTGGGC |
| #90 | GSSDLTWPPAIKLGC |
| #91 | DRYVAVRHPLRARGLR |
| #92 | VAPRAKAHKSQDSLC |
| #93 | CFRSTRHNFNSMR |
| #94 | MNGTYNTCGSSDLTWPPAIKLG |
| #95 | RDTSDTPLCQLSQG |
| #96 | GIQEGGFCFRSTRHNFNSMRFP |
| #97 | AKEFQEASALAVAPRAKAHKSQDSLCVTLA |
| #98 | TCCTGCTCGTCGCTCTCCTGAT |
| #99 | TCGCTTTTTGTCGTATTTGC |
| #100 | HNGSYEISVLMMGNS |
| #101 | NLPTPPTVENQQRLA |

| | |
|---|---|
| #102 | RKYRKDYELRQKKWSHIPPENIFPLETNETNHVSLKIDDDKRRDTIQRLRQCKYDKKRVILKDLKHNDGN<br>FTEKQKIELNKLLQIDYYNLTKFYGTVKLDTMIFGVIEYCERGSLREVLNDTISYPDGTFMDWEFKISVL<br>YDIAKGMSYLHSSKTEVHGRLKSTNCVVDSRMVVKITDFGCNSILPPKKDLWTAPEHLRQANISQKGDVY<br>SYGIIAQEIILRKETFYTLSCRDRNEKIFRVENSNGMKPFRPDLFLETAEEKELEVYLLVKNCWEEDPEK<br>RPDFKKIETTLAKIFGLFHDQKNESYMDTLIRRLQLYSRNLEHLVEERTQLYKAERDRADRLNFMLLPRL<br>VVKSLKEKGFVEPELYEEVTIYFSDIVGFTTICKYSTPMEVVDMLNDIYKSFDHIVDHHDVYKVETIGDA<br>YMVASGLPKRNGNRHAIDIAKMALEILSFMGTFELEHLPGLPIWIRIGVHSGPCAAGVVGIKMPRYCLFG<br>DTVNTASRMESTGLPLRIHVSGSTIAILKRTECQFLYEVRGETYLKGRGNETTYWLTGMKDQKFNLPTPP<br>TVENQQRLQAEFSDMIANSLQKRQAAGIRSQKPRRVASYKKGTLEYLQLNTTDKESTYF |
| #103 | GCTGGTAACTATCTTCCTGC |
| #104 | GAAGAATGTTGTCCAGAGGT |
| #105 | LINKVPLPVDKLAPL |
| #106 | SEAVKKLLEALSHLV |
| #107 | TGTTTTCAACTACCAGGGGC |
| #108 | TGTTGGCTTTGGCAGAGTCC |
| #109 | GAGGCAGAGTTCAGGCTTCACCGA |
| #110 | TGTTGGCTTTGGCAGAGTCC |
| #111 | TGMDMWSTQDLYDNPVTSVFQYEGLWRSCVRQSSGFTECRPYFTILGLPAMLQAVR |
| #112 | DQWSTQDLYNNPVTAVFNYQGLWRSCVRESSGFTECRGYFTLL<br>GLPAMLQAVR |
| #113 | STQDLYNNPVTAVF |
| #114 | DMWSTQDLYDNP |
| #115 | CRPYFTILGLPA |
| #116 | TNFWMSTANMYTG |
| #117 | gccaggatca tgtccaccac cacatgccaa gtggtggcgt tcctcctgtc catcctgggg<br>ctggccggct gcatcgcggc caccgggatg gacatgtgga gcacccagga cctgtacgac<br>aaccccgtca cctccgtgtt ccagtacgaa gggctctgga ggagctgcgt gaggcagagt<br>tcaggcttca ccgaatgcag gccctatttc accatcctgg gacttccagc catgctgcag<br>gcagtgcgag ccctgatgat cgtaggcatc gtcctgggtg ccattggcct cctggtatcc<br>atctttgccc tgaaatgcat ccgcattggc agcatggagg actctgccaa agccaacatg<br>acactgacct ccgggatcat gttcattgtc tcaggtcttt gtgcaattgc tggagtgtct<br>gtgtttgcca acatgctggt gactaacttc tggatgtcca cagctaacat gtacaccggc<br>atgggtggga tggtgcagac tgttcagacc aggtacacat ttggtgcggc tctgttcgtg<br>ggctgggtcg ctggaggcct cacactaatt gggggtgtga tgatgtgcat cgcctgccgg<br>ggcctggcac cagaagaaac caactacaaa gccgtttctt atcatgcctc aggccacagt<br>gttgcctaca agcctggagg cttcaaggcc agcactggct ttgggtccaa caccaaaaac<br>aagaagatat acgatggagg tgcccgcaca gaggacgagg tacaatctta tccttccaag<br>cacgactatg tgtaatgctc taagacctct cagcac |
| #118 | MSTTTCQVVAFLLSILGLAGCIAATGMDMWSTQDLYDNPVTSVF<br>QYEGLWRSCVRQSSGFTECRPYFTILGLPAMLQAVRALMIVGIVLGAIGLLVSIFALK<br>CIRIGSMEDSAKANMTLTSGIMFIVSGLCAIAGVSVFANMLVTNFWMSTANMYTGMGG<br>MVQTVQTRYTFGAALFVGWVAGGLTLIGGVMMCIACRGLAPEETNYKAVSYHASGHSV<br>AYKPGGFKASTGFGSNTKNKKIYDGGARTEDEVQSYPSKHDYV |
| #119 | gccaggatca tgtccaccac cacatgccaa gtggtggcgt tcctcctgtc catcctgggg<br>ctggccggct gcatcgcggc caccgggatg gacatgtgga gcacccagga cctgtacgac<br>aaccccgtca cctccgtgtt ccagtacgaa gggctctgga ggagctgcgt gaggcagagt<br>tcaggcttca ccgaatgcag gccctatttc accatcctgg gacttcc |
| #120 | MSTTTCQVVAFLLSILGLAGCIAATGM**DMWSTQDLYDNP**VTSVFQYEGLWRSCVRQSSGFTE**CRPYFTI** |
| #121 | AATGAGAGGAAAGAGAAAAC |
| #122 | ATGGTAGAAGAGTAGGCAAT |
| #123 | EKWNLHKRIALKMVC |
| #124 | CLGFNFKEMFK |
| #125 | TAATGATGAACCCTACACTGAGC |

| | |
|---|---|
| #126 | ATGGACAAATGCCCTACCTT |
| #127 | AGTGCTGGAAGGATGTGCGTGT |
| #128 | TTGAGGTGGTTGTTGGGTTT |
| #129 | AGATGTGCTGAGGCTGTAGA |
| #130 | ATGAAGGTTGATTATTTGAG |
| #131 | AGCCGCATACTCCCTTACCCTCT |
| #132 | GCAGCAGCCCAAACACCACA |
| #133 | CTGAGCCGAGAGGTGGAATC |
| #134 | CTCTCTCGCTTACACTGGAA |
| #135 | QWQVFGPDKPVQAL |
| #136 | AKWKGPQGQDLSTDS |
| #137 | NMLVTNFWMSTANMYTGMGGMVQTVQTRYTFG |

SEQUENCE LISTING

```
<160> NUMBER OF SEQ ID NOS: 137

<210> SEQ ID NO 1
<211> LENGTH: 1875
<212> TYPE: DNA
<213> ORGANISM: Homo sapiens

<400> SEQUENCE: 1

caggccagag tcccagctgt cctggactct gctgtgggga agggctgatg caggtgtgga      60

gtcaaatgtg ggtgcctcct gcagccgggt gccaggaggg gtggaggggc caccctgggc     120

tttgtccggg agcctggtct tcccgtcctt gggctgacag gtgctgctgc ctctgagccc     180

tccctgctaa gagctgtgtg ctgggtaagg ctggtggccc tttgggctcc ctgtccagga     240

tttgtgctct ggagggtagg gcttgctggg ctggggactg gaggggaacg tggagctcct     300

tctgcctcct ttcctgcccc atgacagcag gcagatccca ggagagaaga gctcaggaga     360
```

-continued

```
tgggaagagg atctgtccag gggttagacc tcaagggtga cttggagttc tttacggcac    420
ccatgctttc tttgaggagt tttgtgtttg tgggtgtggg gtcggggctc acctcctccc    480
acatccctgc ccagaggtgg gcagagtggg ggcagtgcct tgctcccccct gctcgctctc    540
tgctgacctc cggctccctg tgctgcccca ggaccatgaa tggcacctac aacacctgtg    600
gctccagcga cctcacctgg cccccagcga tcaagctggg cttctacgcc tacttgggcg    660
tcctgctggt gctaggcctg ctgctcaaca gcctggcgct ctgggtgttc tgctgccgca    720
tgcagcagtg gacggagacc cgcatctaca tgaccaacct ggcggtggcc gacctctgcc    780
tgctgtgcac cttgcccttc gtgctgcact ccctgcgaga cacctcagac acgccgctgt    840
gccagctctc ccagggcatc tacctgacca acaggtacat gagcatcagc ctggtcacgg    900
ccatcgccgt ggaccgctat gtggccgtgc ggcacccgct gcgtgcccgc gggctgcggt    960
cccccaggca ggctgcggcc gtgtgcgcgg tcctctgggt gctggtcatc ggctccctgg   1020
tggctcgctg gctcctgggg attcaggagg gcggcttctg cttcaggagc acccggcaca   1080
atttcaactc catggcgttc ccgctgctgg gattctacct gcccctggcc gtggtggtct   1140
tctgctccct gaaggtggtg actgccctgg cccagaggcc acccaccgac gtggggcagg   1200
cagaggccac ccgcaaggct gcccgcatgg tctgggccaa cctcctggtg ttcgtggtct   1260
gcttcctgcc cctgcacgtg gggctgacag tgcgcctcgc agtgggctgg aacgcctgtg   1320
ccctcctgga gacgatccgt cgcgccctgt acataaccag caagctctca gatgccaact   1380
gctgcctgga cgccatctgc tactactaca tggccaagga gttccaggag gcgtctgcac   1440
tggccgtggc tcccagtgct aaggcccaca aaagccagga ctctctgtgc gtgaccctcg   1500
cctaagaggc gtgctgtggg cgctgtgggc caggtctcgg gggctccggg aggtgctgcc   1560
tgccagggga agctggaacc agtagcaagg agcccgggat cagccctgaa ctcactgtgt   1620
attctcttgg agccttgggt gggcagggac ggcccaggta cctgctctct tgggaagaga   1680
gagggacagg gacaagggca agaggactga ggccagagca aggccaatgt cagagacccc   1740
cgggatgggg cctcacactt gccacccccca gaaccagctc acctggccag agtgggttcc   1800
tgctggccag ggtgcagcct tgatgacacc tgccgctgcc cctcggggct ggaataaaac   1860
tccccaccca gagtc                                                    1875
```

<210> SEQ ID NO 2
<211> LENGTH: 3222
<212> TYPE: DNA
<213> ORGANISM: Homo sapiens

<400> SEQUENCE: 2

```
atgaagacgt tgctgttgga cttggctttg tggtcactgc tcttccagcc cgggtggctg     60
tcctttagtt cccaggtgag tcagaactgc cacaatggca gctatgaaat cagcgtcctg    120
atgatgggca actcagcctt tgcagagccc ctgaaaaact tggaagatgc ggtgaatgag    180
gggctggaaa tagtgagagg acgtctgcaa aatgctggcc taaatgtgac tgtgaacgct    240
actttcatgt attcggatgg tctgattcat aactcaggcg actgccggag tagcacctgt    300
gaaggcctcg acctactcag gaaaatttca aatgcacaac ggatgggctg tgtcctcata    360
gggccctcat gtacatactc caccttccag atgtaccttg acacagaatt gagctacccc    420
atgatctcag ctggaagttt tggattgtca tgtgactata aagaaacctt aaccaggctg    480
atgtctccag ctagaaagtt gatgtacttc ttggttaact tttggaaaac caacgatctg    540
cccttcaaaa cttattcctg gagcacttcg tatgtttaca agaatggtac agaaactgag    600
```

-continued

```
gactgtttct ggtaccttaa tgctctggag gctagcgttt cctatttctc ccacgaactc    660
ggctttaagg tggtgttaag acaagataag gagtttcagg atatcttaat ggaccacaac    720
aggaaaagca atgtgattat tatgtgtggt ggtccagagt tcctctacaa gctgaagggt    780
gaccgagcag tggctgaaga cattgtcatt attctagtgg atcttttcaa tgaccagtac    840
ttggaggaca atgtcacagc ccctgactat atgaaaaatg tccttgttct gacgctgtct    900
cctgggaatt cccttctaaa tagctctttc tccaggaatc tatcaccaac aaaacgagac    960
tttgctcttg cctatttgaa tggaatcctg ctctttggac atatgctgaa gatatttctt   1020
gaaaatggag aaaatattac cacccccaaa tttgctcatg ctttcaggaa tctcactttt   1080
gaagggtatg acggtccagt gaccttggat gactgggggg atgttgacag taccatggtg   1140
cttctgtata cctctgtgga caccaagaaa tacaaggttc ttttgaccta tgatacccac   1200
gtaaataaga cctatcctgt ggatatgagc cccacattca cttggaagaa ctctaaactt   1260
cctaatgata ttacaggccg ggccctcag atcctgatga ttgcagtctt caccctcact   1320
ggagctgtgg tgctgctcct gctcgtcgct ctcctgatgc tcagaaaata tagaaaagat   1380
tatgaacttc gtcagaaaaa atggtcccac attcctcctg aaaatatctt tcctctggag   1440
accaatgaga ccaatcatgt tagcctcaag atcgatgatg acaaaagacg agatacaatc   1500
cagagactac gacagtgcaa atacgacaaa aagcgagtga ttctcaaaga tctcaagcac   1560
aatgatggta atttcactga aaaacagaag atagaattga acaagttgct tcagattgac   1620
tattacaacc tgaccaagtt ctacggcaca gtgaaacttg ataccatgat cttcggggtg   1680
atagaatact gtgagagagg atccctccgg gaagttttaa atgacacaat ttcctaccct   1740
gatggcacat tcatggattg ggagtttaag atctctgtct tgtatgacat tgctaaggga   1800
atgtcatatc tgcactccag taagacagaa gtccatggtc gtctgaaatc taccaactgc   1860
gtagtggaca gtagaatggt ggtgaagatc actgattttg gctgcaattc cattttacct   1920
ccaaaaaagg acctgtggac agctccagag cacctccgcc aagccaacat ctctcagaaa   1980
ggagatgtgt acagctatgg gatcatcgca caggagatca ttctgcggaa agaaaccttc   2040
tacactttga gctgtcggga ccggaatgag aagattttca gagtggaaaa ttccaatgga   2100
atgaaaccct tccgcccaga tttattcttg gaaacagcag aggaaaaaga gctagaagtg   2160
tacctacttg taaaaaactg ttgggaggaa gatccagaaa agagaccaga tttcaaaaaa   2220
attgagacta cacttgccaa gatatttgga ctttttcatg accaaaaaaa tgaaagctat   2280
atggatacct tgatccgacg tctacagcta tattctcgaa acctggaaca tctggtagag   2340
gaaaggacac agctgtacaa ggcagagagg gacagggctg acagacttaa ctttatgttg   2400
cttccaaggc tagtggtaaa gtctctgaag gagaaaggct ttgtggagcc ggaactatat   2460
gaggaagtta caatctactt cagtgacatt gtaggtttca ctactatctg caaatacagc   2520
acccccatgg aagtggtgga catgcttaat gacatctata agagttttga ccacattgtt   2580
gatcatcatg atgtctacaa ggtggaaacc atcggtgatg cgtacatggt ggctagtggt   2640
ttgcctaaga gaaatggcaa tcggcatgca atagacattg ccaagatggc cttggaaatc   2700
ctcagcttca tggggacctt tgagctggag catcttcctg gcctcccaat atggattcgc   2760
attggagttc actctggtcc ctgtgctgct ggagttgtgg gaatcaagat gcctcgttat   2820
tgtctatttg gagatacggt caacacagcc tctaggatgg aatccactgg cctccctttg   2880
agaattcacg tgagtggctc caccatagcc atcctgaaga gaactgagtg ccagttcctt   2940
```

-continued

```
tatgaagtga gaggagaaac atacttaaag ggaagaggaa atgagactac ctactggctg   3000

actgggatga aggaccagaa attcaacctg ccaacccctc ctactgtgga gaatcaacag   3060

cgtttgcaag cagaattttc agacatgatt gccaactctt tacagaaaag acaggcagca   3120

gggataagaa gccaaaaacc cagacgggta gccagctata aaaaaggcac tctggaatac   3180

ttgcagctga ataccacaga caaggagagc acctattttt aa                      3222


<210> SEQ ID NO 3
<211> LENGTH: 336
<212> TYPE: DNA
<213> ORGANISM: Homo sapiens

<400> SEQUENCE: 3

atgaagacgt tgctgttgga cttggctttg tggtcactgc tcttccagcc cgggtggctg     60

tcctttagtt cccaggtgag tcagaactgc cacaatggca gctatgaaat cagcgtcctg    120

atgatgggca actcagcctt tgcagagccc ctgaaaaact tggaagatgc ggtgaatgag    180

gggctggaaa tagtgagagg acgtctgcaa aatgctggcc taaatgtgac tgtgaacgct    240

actttcatgt attcggatgg tctgattcat aactcaggcg actgccggag tagcacctgt    300

gaaggcctcg acctactcag gaaaatttca ccttga                              336


<210> SEQ ID NO 4
<211> LENGTH: 777
<212> TYPE: DNA
<213> ORGANISM: Homo sapiens

<400> SEQUENCE: 4

atgaagacgt tgctgttgga cttggctttg tggtcactgc tcttccagcc cgggtggctg     60

tcctttagtt cccaggtgag tcagaactgc cacaatggca gctatgaaat cagcgtcctg    120

atgatgggca actcagcctt tgcagagccc ctgaaaaact tggaagatgc ggtgaatgag    180

gggctggaaa tagtgagagg acgtctgcaa aatgctggcc taaatgtgac tgtgaacgct    240

actttcatgt attcggatgg tctgattcat aactcaggcg actgccggag tagcacctgt    300

gaaggcctcg acctactcag gaaaatttca aatgcacaac ggatgggctg tgtcctcata    360

gggccctcat gtacatactc caccttccag atgtaccttg acacagaatt gagctacccc    420

atgatctcag ctggaagttt tggattgtca tgtgactata aagaaacctt aaccaggctg    480

atgtctccag ctagaaagtt gatgtacttc ttggttaact tttggaaaac caacgatctg    540

cccttcaaaa cttattcctg gagcacttcg tatgtttaca agaatggtac agaaactgag    600

gactgtttct ggtaccttaa tgctctggag gctagcgttt cctatttctc ccacgaactc    660

ggctttaagg tggtgttaag acaagataag gagtttcagg atatcttaat ggaccacaac    720

aggaaaagca atgtgaccag tacttggagg acaatgtcac agcccctgac tatatga       777


<210> SEQ ID NO 5
<211> LENGTH: 3213
<212> TYPE: DNA
<213> ORGANISM: Homo sapiens

<400> SEQUENCE: 5

atgaagacgt tgctgttgga cttggctttg tggtcactgc tcttccagcc cgggtggctg     60

tcctttagtt cccaggtgag tcagaactgc cacaatggca gctatgaaat cagcgtcctg    120

atgatgggca actcagcctt tgcagagccc ctgaaaaact tggaagatgc ggtgaatgag    180

gggctggaaa tagtgagagg acgtctgcaa aatgctggcc taaatgtgac tgtgaacgct    240
```

-continued

```
actttcatgt attcggatgg tctgattcat aactcaggcg actgccggag tagcacctgt    300
gaaggcctcg acctactcag gaaaatttca aatgcacaac ggatgggctg tgtcctcata    360
gggccctcat gtacatactc caccttccag atgtaccttg acacagaatt gagctacccc    420
atgatctcag ctggaagttt tggattgtca tgtgactata aagaaacctt aaccaggctg    480
atgtctccag ctagaaagtt gatgtacttc ttggttaact tttggaaaac caacgatctg    540
cccttcaaaa cttattcctg gagcacttcg tatgtttaca agaatggtac agaaactgag    600
gactgtttct ggtaccttaa tgctctggag gctagcgttt cctatttctc ccacgaactc    660
ggctttaagg tggtgttaag acaagataag gagtttcagg atatcttaat ggaccacaac    720
aggaaaagca atgtgattat tatgtgtggt ggtccagagt tcctctacaa gctgaagggt    780
gaccgagcag tggctgaaga cattgtcatt attctagtgg atcttttcaa tgaccagtac    840
ttggaggaca atgtcacagc ccctgactat atgaaaaatg tccttgttct gacgctgtct    900
cctgggaatt cccttctaaa tagctctttc tccaggaatc tatcaccaac aaaacgagac    960
tttgctcttg cctatttgaa tggaatcctg ctctttggac atatgctgaa gatatttctt   1020
gaaaatggag aaaatattac cacccccaaa tttgctcatg ctttcaggaa tctcactttt   1080
gaagggtatg acggtccagt gaccttggat gactgggggg atgttgacag taccatggtg   1140
cttctgtata cctctgtgga caccaagaaa tacaaggttc ttttgaccta tgatacccac   1200
gtaaataaga cctatcctgt ggatatgagc cccacattca cttggaagaa ctctaaactt   1260
cctaatgata ttacaggccg ggccctcag atcctgatga ttgcagtctt caccctcact   1320
ggagctgtgg tgctgctcct gctcgtcgct ctcctgatgc tcagaaaata tagaaaagat   1380
tatgaacttc gtcagaaaaa atggtcccac attcctcctg aaaatatctt tcctctggag   1440
accaatgaga ccaatcatgt tagcctcaag atcgatgatg acaaaagacg agatacaatc   1500
cagagactac gacagtgcaa atacgacaaa aagcgagtga ttctcaaaga tctcaagcac   1560
aatgatggta atttcactga aaaacagaag atagaattga acaagattga ctattacaac   1620
ctgaccaagt tctacggcac agtgaaactt gataccatga tcttcggggt gatagaatac   1680
tgtgagagag gatccctccg ggaagtttta aatgacacaa tttcctaccc tgatggcaca   1740
ttcatggatt gggagtttaa gatctctgtc ttgtatgaca ttgctaaggg aatgtcatat   1800
ctgcactcca gtaagacaga agtccatggt cgtctgaaat ctaccaactg cgtagtggac   1860
agtagaatgg tggtgaagat cactgatttt ggctgcaatt ccattttacc tccaaaaaag   1920
gacctgtgga cagctccaga gcacctccgc caagccaaca tctctcagaa aggagatgtg   1980
tacagctatg ggatcatcgc acaggagatc attctgcgga aagaaacctt ctacactttg   2040
agctgtcggg accggaatga gaagattttc agagtggaaa attccaatgg aatgaaaccc   2100
ttccgcccag atttattctt ggaaacagca gaggaaaaag agctagaagt gtacctactt   2160
gtaaaaaact gttgggagga agatccagaa aagagaccag atttcaaaaa aattgagact   2220
acacttgcca agatatttgg actttttcat gaccaaaaaa atgaaagcta tatggatacc   2280
ttgatccgac gtctacagct atattctcga aacctggaac atctggtaga ggaaaggaca   2340
cagctgtaca aggcagagag ggacagggct gacagactta actttatgtt gcttccaagg   2400
ctagtggtaa agtctctgaa ggagaaaggc tttgtggagc cggaactata tgaggaagtt   2460
acaatctact tcagtgacat tgtaggtttc actactatct gcaaatacag cacccccatg   2520
gaagtggtgg acatgcttaa tgacatctat aagagttttg accacattgt tgatcatcat   2580
```

-continued

```
gatgtctaca aggtggaaac catcggtgat gcgtacatgg tggctagtgg tttgcctaag   2640

agaaatggca atcggcatgc aatagacatt gccaagatgg ccttggaaat cctcagcttc   2700

atggggacct ttgagctgga gcatcttcct ggcctcccaa tatggattcg cattggagtt   2760

cactctggtc cctgtgctgc tggagttgtg ggaatcaaga tgcctcgtta ttgtctattt   2820

ggagatacgg tcaacacagc ctctaggatg gaatccactg gcctcccttt gagaattcac   2880

gtgagtggct ccaccatagc catcctgaag agaactgagt gccagttcct ttatgaagtg   2940

agaggagaaa catacttaaa gggaagagga aatgagacta cctactggct gactgggatg   3000

aaggaccaga aattcaacct gccaacccct cctactgtgg agaatcaaca gcgtttgcaa   3060

gcagaatttt cagacatgat tgccaactct ttacagaaaa gacaggcagc agggataaga   3120

agccaaaaac ccagacgggt agccagctat aaaaaaggca ctctggaata cttgcagctg   3180

aataccacag acaaggagag cacctatttt taa                                3213
```

```
<210> SEQ ID NO 6
<211> LENGTH: 550
<212> TYPE: DNA
<213> ORGANISM: Homo sapiens

<400> SEQUENCE: 6

ggggacactt tgtatggcaa gtggaaccac tggcttggtg gattttgcta gatttttctg     60

atttttaaac tcctgaaaaa tatcccagat aactgtcatg aagctggtaa ctatcttcct    120

gctggtgacc atcagccttt gtagttactc tgctactgcc ttcctcatca acaaagtgcc    180

ccttcctgtt gacaagttgg cacctttacc tctggacaac attcttccct ttatggatcc    240

attaaagctt cttctgaaaa ctctgggcat ttctgttgag caccttgtgg aggggctaag    300

gaagtgtgta aatgagctgg gaccagaggc ttctgaagct gtgaagaaac tgctggaggc    360

gctatcacac ttggtgtgac atcaagataa agagcggagg tggatgggga tggaagatga    420

tgctcctatc ctccctgcct gaaacctgtt ctaccaatta tagatcaaat gccctaaaat    480

gtagtgaccc gtgaaaagga caaataaagc aatgaatact aaaaaaaaaa aaaaaaaaaa    540

aaaaaaaaaa                                                           550
```

```
<210> SEQ ID NO 7
<211> LENGTH: 786
<212> TYPE: DNA
<213> ORGANISM: Homo sapiens

<400> SEQUENCE: 7

atggccgtga ctgcctgtca gggcttgggg ttcgtggttt cactgattgg gattgcgggc     60

atcattgctg ccacctgcat ggaccagtgg agcacccaag acttgtacaa caaccccgta    120

acagctgttt tcaactacca ggggctgtgg cgctcctgtg tccgagagag ctctggcttc    180

accgagtgcc ggggctactt caccctgctg gggctgccag ccatgctgca ggcagtgcga    240

gccctgatga tcgtaggcat cgtcctgggt gccattggcc tcctggtatc catctttgcc    300

ctgaaatgca tccgcattgg cagcatggag gactctgcca aagccaacat gacactgacc    360

tccgggatca tgttcattgt ctcaggtctt tgtgcaattg ctggagtgtc tgtgtttgcc    420

aacatgctgg tgactaactt ctggatgtcc acagctaaca tgtacaccgg catgggtggg    480

atggtgcaga ctgttcagac caggtacaca tttggtgcgg ctctgttcgt gggctgggtc    540

gctggaggcc tcacactaat tgggggtgtg atgatgtgca tcgcctgccg gggcctggca    600

ccagaagaaa ccaactacaa agccgtttct tatcatgcct caggccacag tgttgcctac    660
```

-continued

```
aagcctggag gcttcaaggc cagcactggc tttgggtcca acaccaaaaa caagaagata    720

tacgatggag gtgcccgcac agaggacgag gtacaatctt atccttccaa gcacgactat    780

gtgtaa                                                               786
```

<210> SEQ ID NO 8
<211> LENGTH: 180
<212> TYPE: DNA
<213> ORGANISM: Homo sapiens

<400> SEQUENCE: 8

```
tgcgccacca tggccgtgac tgcctgtcag ggcttggggt tcgtggtttc actgattggg     60

attgcgggca tcattgctgc cacctgcatg gaccagtgga gcacccaaga cttgtacaac    120

aaccccgtaa cagctgtttt caactaccag gggctgtggc gctcctgtgt ccgagagagc    180
```

<210> SEQ ID NO 9
<211> LENGTH: 309
<212> TYPE: PRT
<213> ORGANISM: Homo sapiens

<400> SEQUENCE: 9

```
Met Asn Gly Thr Tyr Asn Thr Cys Gly Ser Ser Asp Leu Thr Trp Pro
1               5                   10                  15

Pro Ala Ile Lys Leu Gly Phe Tyr Ala Tyr Leu Gly Val Leu Leu Val
            20                  25                  30

Leu Gly Leu Leu Leu Asn Ser Leu Ala Leu Trp Val Phe Cys Cys Arg
        35                  40                  45

Met Gln Gln Trp Thr Glu Thr Arg Ile Tyr Met Thr Asn Leu Ala Val
    50                  55                  60

Ala Asp Leu Cys Leu Leu Cys Thr Leu Pro Phe Val Leu His Ser Leu
65                  70                  75                  80

Arg Asp Thr Ser Asp Thr Pro Leu Cys Gln Leu Ser Gln Gly Ile Tyr
                85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
        115                 120                 125

Ser Pro Arg Gln Ala Ala Ala Val Cys Ala Val Leu Trp Val Leu Val
    130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Arg Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
        195                 200                 205

Ala Glu Ala Thr Arg Lys Ala Ala Arg Met Val Trp Ala Asn Leu Leu
    210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270
```

-continued

```
Ala Ile Cys Tyr Tyr Tyr Met Ala Lys Glu Phe Gln Glu Ala Ser Ala
        275                 280                 285

Leu Ala Val Ala Pro Arg Ala Lys Ala His Lys Ser Gln Asp Ser Leu
    290                 295                 300

Cys Val Thr Leu Ala
305


<210> SEQ ID NO 10
<211> LENGTH: 394
<212> TYPE: PRT
<213> ORGANISM: Homo sapiens

<400> SEQUENCE: 10

Met Thr Ala Gly Arg Ser Gln Glu Arg Arg Ala Gln Glu Met Gly Arg
1               5                   10                  15

Gly Ser Val Gln Gly Leu Asp Leu Lys Gly Asp Leu Glu Phe Phe Thr
            20                  25                  30

Ala Pro Met Leu Ser Leu Arg Ser Phe Val Phe Val Gly Val Gly Ser
        35                  40                  45

Gly Leu Thr Ser Ser His Ile Pro Ala Gln Arg Trp Ala Glu Trp Gly
    50                  55                  60

Gln Cys Leu Ala Pro Pro Ala Arg Ser Leu Leu Thr Ser Gly Ser Leu
65                  70                  75                  80

Cys Cys Pro Arg Thr Met Asn Gly Thr Tyr Asn Thr Cys Gly Ser Ser
                85                  90                  95

Asp Leu Thr Trp Pro Pro Ala Ile Lys Leu Gly Phe Tyr Ala Tyr Leu
            100                 105                 110

Gly Val Leu Leu Val Leu Gly Leu Leu Leu Asn Ser Leu Ala Leu Trp
        115                 120                 125

Val Phe Cys Cys Arg Met Gln Gln Trp Thr Glu Thr Arg Ile Tyr Met
    130                 135                 140

Thr Asn Leu Ala Val Ala Asp Leu Cys Leu Leu Cys Thr Leu Pro Phe
145                 150                 155                 160

Val Leu His Ser Leu Arg Asp Thr Ser Asp Thr Pro Leu Cys Gln Leu
                165                 170                 175

Ser Gln Gly Ile Tyr Leu Thr Asn Arg Tyr Met Ser Ile Ser Leu Val
            180                 185                 190

Thr Ala Ile Ala Val Asp Arg Tyr Val Ala Val Arg His Pro Leu Arg
        195                 200                 205

Ala Arg Gly Leu Arg Ser Pro Arg Gln Ala Ala Ala Val Cys Ala Val
    210                 215                 220

Leu Trp Val Leu Val Ile Gly Ser Leu Val Ala Arg Trp Leu Leu Gly
225                 230                 235                 240

Ile Gln Glu Gly Gly Phe Cys Phe Arg Ser Thr Arg His Asn Phe Asn
                245                 250                 255

Ser Met Ala Phe Pro Leu Leu Gly Phe Tyr Leu Pro Leu Ala Val Val
            260                 265                 270

Val Phe Cys Ser Leu Lys Val Val Thr Ala Leu Ala Gln Arg Pro Pro
        275                 280                 285

Thr Asp Val Gly Gln Ala Glu Ala Thr Arg Lys Ala Ala Arg Met Val
    290                 295                 300

Trp Ala Asn Leu Leu Val Phe Val Val Cys Phe Leu Pro Leu His Val
305                 310                 315                 320

Gly Leu Thr Val Arg Leu Ala Val Gly Trp Asn Ala Cys Ala Leu Leu
```

-continued

```
                325                 330                 335

Glu Thr Ile Arg Arg Ala Leu Tyr Ile Thr Ser Lys Leu Ser Asp Ala
            340                 345                 350

Asn Cys Cys Leu Asp Ala Ile Cys Tyr Tyr Tyr Met Ala Lys Glu Phe
        355                 360                 365

Gln Glu Ala Ser Ala Leu Ala Val Ala Pro Ser Ala Lys Ala His Lys
    370                 375                 380

Ser Gln Asp Ser Leu Cys Val Thr Leu Ala
385                 390


<210> SEQ ID NO 11
<211> LENGTH: 1073
<212> TYPE: PRT
<213> ORGANISM: Homo sapiens

<400> SEQUENCE: 11

Met Lys Thr Leu Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Glu Gly Leu Glu Ile
    50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Leu Glu Asp Asn Val Thr Ala Pro
        275                 280                 285

Asp Tyr Met Lys Asn Val Leu Val Leu Thr Leu Ser Pro Gly Asn Ser
    290                 295                 300
```

-continued

```
Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
            340                 345                 350

His Ala Phe Arg Asn Leu Thr Phe Glu Gly Tyr Asp Gly Pro Val Thr
        355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Gln Ile Leu
            420                 425                 430

Met Ile Ala Val Phe Thr Leu Thr Gly Ala Val Val Leu Leu Leu Leu
        435                 440                 445

Val Ala Leu Leu Met Leu Arg Lys Tyr Arg Lys Asp Tyr Glu Leu Arg
    450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
                485                 490                 495

Arg Asp Thr Ile Gln Arg Leu Arg Gln Cys Lys Tyr Asp Lys Lys Arg
            500                 505                 510

Val Ile Leu Lys Asp Leu Lys His Asn Asp Gly Asn Phe Thr Glu Lys
        515                 520                 525

Gln Lys Ile Glu Leu Asn Lys Leu Leu Gln Ile Asp Tyr Tyr Asn Leu
    530                 535                 540

Thr Lys Phe Tyr Gly Thr Val Lys Leu Asp Thr Met Ile Phe Gly Val
545                 550                 555                 560

Ile Glu Tyr Cys Glu Arg Gly Ser Leu Arg Glu Val Leu Asn Asp Thr
                565                 570                 575

Ile Ser Tyr Pro Asp Gly Thr Phe Met Asp Trp Glu Phe Lys Ile Ser
            580                 585                 590

Val Leu Tyr Asp Ile Ala Lys Gly Met Ser Tyr Leu His Ser Ser Lys
        595                 600                 605

Thr Glu Val His Gly Arg Leu Lys Ser Thr Asn Cys Val Val Asp Ser
    610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
                645                 650                 655

Ile Ser Gln Lys Gly Asp Val Tyr Ser Tyr Gly Ile Ile Ala Gln Glu
            660                 665                 670

Ile Ile Leu Arg Lys Glu Thr Phe Tyr Thr Leu Ser Cys Arg Asp Arg
        675                 680                 685

Asn Glu Lys Ile Phe Arg Val Glu Asn Ser Asn Gly Met Lys Pro Phe
    690                 695                 700

Arg Pro Asp Leu Phe Leu Glu Thr Ala Glu Glu Lys Glu Leu Glu Val
705                 710                 715                 720

Tyr Leu Leu Val Lys Asn Cys Trp Glu Glu Asp Pro Glu Lys Arg Pro
```

-continued

```
                725                 730                 735

Asp Phe Lys Lys Ile Glu Thr Thr Leu Ala Lys Ile Phe Gly Leu Phe
            740                 745                 750

His Asp Gln Lys Asn Glu Ser Tyr Met Asp Thr Leu Ile Arg Arg Leu
        755                 760                 765

Gln Leu Tyr Ser Arg Asn Leu Glu His Leu Val Glu Glu Arg Thr Gln
    770                 775                 780

Leu Tyr Lys Ala Glu Arg Asp Arg Ala Asp Arg Leu Asn Phe Met Leu
785                 790                 795                 800

Leu Pro Arg Leu Val Val Lys Ser Leu Lys Glu Lys Gly Phe Val Glu
                805                 810                 815

Pro Glu Leu Tyr Glu Glu Val Thr Ile Tyr Phe Ser Asp Ile Val Gly
            820                 825                 830

Phe Thr Thr Ile Cys Lys Tyr Ser Thr Pro Met Glu Val Val Asp Met
        835                 840                 845

Leu Asn Asp Ile Tyr Lys Ser Phe Asp His Ile Val Asp His His Asp
    850                 855                 860

Val Tyr Lys Val Glu Thr Ile Gly Asp Ala Tyr Met Val Ala Ser Gly
865                 870                 875                 880

Leu Pro Lys Arg Asn Gly Asn Arg His Ala Ile Asp Ile Ala Lys Met
                885                 890                 895

Ala Leu Glu Ile Leu Ser Phe Met Gly Thr Phe Glu Leu Glu His Leu
            900                 905                 910

Pro Gly Leu Pro Ile Trp Ile Arg Ile Gly Val His Ser Gly Pro Cys
        915                 920                 925

Ala Ala Gly Val Val Gly Ile Lys Met Pro Arg Tyr Cys Leu Phe Gly
    930                 935                 940

Asp Thr Val Asn Thr Ala Ser Arg Met Glu Ser Thr Gly Leu Pro Leu
945                 950                 955                 960

Arg Ile His Val Ser Gly Ser Thr Ile Ala Ile Leu Lys Arg Thr Glu
                965                 970                 975

Cys Gln Phe Leu Tyr Glu Val Arg Gly Glu Thr Tyr Leu Lys Gly Arg
            980                 985                 990

Gly Asn Glu Thr Thr Tyr Trp Leu  Thr Gly Met Lys Asp  Gln Lys Phe
        995                 1000                1005

Asn Leu  Pro Thr Pro Pro Thr  Val Glu Asn Gln Gln  Arg Leu Gln
    1010                1015                1020

Ala Glu  Phe Ser Asp Met Ile  Ala Asn Ser Leu Gln  Lys Arg Gln
    1025                1030                1035

Ala Ala  Gly Ile Arg Ser Gln  Lys Pro Arg Arg Val  Ala Ser Tyr
    1040                1045                1050

Lys Lys  Gly Thr Leu Glu Tyr  Leu Gln Leu Asn Thr  Thr Asp Lys
    1055                1060                1065

Glu Ser  Thr Tyr Phe
    1070


<210> SEQ ID NO 12
<211> LENGTH: 111
<212> TYPE: PRT
<213> ORGANISM: Homo sapiens

<400> SEQUENCE: 12

Met Lys Thr Leu Leu Leu Asp Leu Ala Leu Trp Ser Leu Leu Phe Gln
1               5                   10                  15
```

-continued

```
Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Glu Gly Leu Glu Ile
    50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Pro
            100                 105                 110


<210> SEQ ID NO 13
<211> LENGTH: 258
<212> TYPE: PRT
<213> ORGANISM: Homo sapiens

<400> SEQUENCE: 13

Met Lys Thr Leu Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Glu Gly Leu Glu Ile
    50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Thr Ser Thr Trp Arg Thr Met Ser Gln Pro Leu
                245                 250                 255

Thr Ile


<210> SEQ ID NO 14
<211> LENGTH: 1070
```

-continued

<212> TYPE: PRT
<213> ORGANISM: Homo sapiens

<400> SEQUENCE: 14

```
Met Lys Thr Leu Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Glu Gly Leu Glu Ile
    50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Leu Glu Asp Asn Val Thr Ala Pro
        275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
            340                 345                 350

His Ala Phe Arg Asn Leu Thr Phe Glu Gly Tyr Asp Gly Pro Val Thr
        355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400
```

-continued

```
Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Gln Ile Leu
            420                 425                 430

Met Ile Ala Val Phe Thr Leu Thr Gly Ala Val Val Leu Leu Leu Leu
        435                 440                 445

Val Ala Leu Leu Met Leu Arg Lys Tyr Arg Lys Asp Tyr Glu Leu Arg
    450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
                485                 490                 495

Arg Asp Thr Ile Gln Arg Leu Arg Gln Cys Lys Tyr Asp Lys Lys Arg
            500                 505                 510

Val Ile Leu Lys Asp Leu Lys His Asn Asp Gly Asn Phe Thr Glu Lys
        515                 520                 525

Gln Lys Ile Glu Leu Asn Lys Ile Asp Tyr Tyr Asn Leu Thr Lys Phe
    530                 535                 540

Tyr Gly Thr Val Lys Leu Asp Thr Met Ile Phe Gly Val Ile Glu Tyr
545                 550                 555                 560

Cys Glu Arg Gly Ser Leu Arg Glu Val Leu Asn Asp Thr Ile Ser Tyr
                565                 570                 575

Pro Asp Gly Thr Phe Met Asp Trp Glu Phe Lys Ile Ser Val Leu Tyr
            580                 585                 590

Asp Ile Ala Lys Gly Met Ser Tyr Leu His Ser Ser Lys Thr Glu Val
        595                 600                 605

His Gly Arg Leu Lys Ser Thr Asn Cys Val Val Asp Ser Arg Met Val
    610                 615                 620

Val Lys Ile Thr Asp Phe Gly Cys Asn Ser Ile Leu Pro Pro Lys Lys
625                 630                 635                 640

Asp Leu Trp Thr Ala Pro Glu His Leu Arg Gln Ala Asn Ile Ser Gln
                645                 650                 655

Lys Gly Asp Val Tyr Ser Tyr Gly Ile Ile Ala Gln Glu Ile Ile Leu
            660                 665                 670

Arg Lys Glu Thr Phe Tyr Thr Leu Ser Cys Arg Asp Arg Asn Glu Lys
        675                 680                 685

Ile Phe Arg Val Glu Asn Ser Asn Gly Met Lys Pro Phe Arg Pro Asp
    690                 695                 700

Leu Phe Leu Glu Thr Ala Glu Glu Lys Glu Leu Glu Val Tyr Leu Leu
705                 710                 715                 720

Val Lys Asn Cys Trp Glu Glu Asp Pro Glu Lys Arg Pro Asp Phe Lys
                725                 730                 735

Lys Ile Glu Thr Thr Leu Ala Lys Ile Phe Gly Leu Phe His Asp Gln
            740                 745                 750

Lys Asn Glu Ser Tyr Met Asp Thr Leu Ile Arg Arg Leu Gln Leu Tyr
        755                 760                 765

Ser Arg Asn Leu Glu His Leu Val Glu Glu Arg Thr Gln Leu Tyr Lys
    770                 775                 780

Ala Glu Arg Asp Arg Ala Asp Arg Leu Asn Phe Met Leu Leu Pro Arg
785                 790                 795                 800

Leu Val Val Lys Ser Leu Lys Glu Lys Gly Phe Val Glu Pro Glu Leu
                805                 810                 815
```

-continued

```
Tyr Glu Glu Val Thr Ile Tyr Phe Ser Asp Ile Val Gly Phe Thr Thr
            820                 825                 830

Ile Cys Lys Tyr Ser Thr Pro Met Glu Val Val Asp Met Leu Asn Asp
        835                 840                 845

Ile Tyr Lys Ser Phe Asp His Ile Val Asp His His Asp Val Tyr Lys
    850                 855                 860

Val Glu Thr Ile Gly Asp Ala Tyr Met Val Ala Ser Gly Leu Pro Lys
865                 870                 875                 880

Arg Asn Gly Asn Arg His Ala Ile Asp Ile Ala Lys Met Ala Leu Glu
                885                 890                 895

Ile Leu Ser Phe Met Gly Thr Phe Glu Leu Glu His Leu Pro Gly Leu
            900                 905                 910

Pro Ile Trp Ile Arg Ile Gly Val His Ser Gly Pro Cys Ala Ala Gly
        915                 920                 925

Val Val Gly Ile Lys Met Pro Arg Tyr Cys Leu Phe Gly Asp Thr Val
    930                 935                 940

Asn Thr Ala Ser Arg Met Glu Ser Thr Gly Leu Pro Leu Arg Ile His
945                 950                 955                 960

Val Ser Gly Ser Thr Ile Ala Ile Leu Lys Arg Thr Glu Cys Gln Phe
                965                 970                 975

Leu Tyr Glu Val Arg Gly Glu Thr Tyr Leu Lys Gly Arg Gly Asn Glu
            980                 985                 990

Thr Thr Tyr Trp Leu Thr Gly Met  Lys Asp Gln Lys Phe  Asn Leu Pro
        995                 1000                 1005

Thr Pro  Pro Thr Val Glu Asn  Gln Gln Arg Leu Gln  Ala Glu Phe
    1010                 1015                 1020

Ser Asp  Met Ile Ala Asn Ser  Leu Gln Lys Arg Gln  Ala Ala Gly
    1025                 1030                 1035

Ile Arg  Ser Gln Lys Pro Arg  Arg Val Ala Ser Tyr  Lys Lys Gly
    1040                 1045                 1050

Thr Leu  Glu Tyr Leu Gln Leu  Asn Thr Thr Asp Lys  Glu Ser Thr
    1055                 1060                 1065

Tyr Phe
    1070


<210> SEQ ID NO 15
<211> LENGTH: 93
<212> TYPE: PRT
<213> ORGANISM: Homo sapiens

<400> SEQUENCE: 15

Met Lys Leu Val Thr Ile Phe Leu Leu Val Thr Ile Ser Leu Cys Ser
1               5                   10                  15

Tyr Ser Ala Thr Ala Lys Leu Ile Asn Lys Cys Pro Leu Pro Val Asp
            20                  25                  30

Lys Leu Ala Pro Leu Pro Leu Asp Asn Ile Leu Pro Phe Met Asp Pro
        35                  40                  45

Leu Lys Leu Leu Leu Lys Thr Leu Gly Ile Ser Val Glu His Leu Val
    50                  55                  60

Glu Gly Leu Arg Lys Cys Val Asn Glu Leu Gly Pro Glu Ala Ser Glu
65                  70                  75                  80

Ala Val Lys Lys Leu Leu Glu Ala Leu Ser His Leu Val
                85                  90


<210> SEQ ID NO 16
```

-continued

<211> LENGTH: 261
<212> TYPE: PRT
<213> ORGANISM: Homo sapiens

<400> SEQUENCE: 16

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 17
<211> LENGTH: 10
<212> TYPE: PRT
<213> ORGANISM: Homo sapiens

<400> SEQUENCE: 17

```
Asp Gln Trp Ser Thr Gln Asp Leu Tyr Asn
1               5                   10
```

<210> SEQ ID NO 18
<211> LENGTH: 11
<212> TYPE: PRT
<213> ORGANISM: Homo sapiens

<400> SEQUENCE: 18

```
Asn Asn Pro Val Thr Ala Val Phe Asn Tyr Gln
1               5                   10
```

-continued

<210> SEQ ID NO 19
<211> LENGTH: 47
<212> TYPE: PRT
<213> ORGANISM: Homo sapiens

<400> SEQUENCE: 19

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln
        35                  40                  45
```

<210> SEQ ID NO 20
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 20
aggtacatga gcatcagcct g 21

<210> SEQ ID NO 21
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 21
gcagcagttg gcatctgaga g 21

<210> SEQ ID NO 22
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 22
gcaatagaca ttgccaagat g 21

<210> SEQ ID NO 23
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 23
aacgctgttg attctccaca g 21

<210> SEQ ID NO 24
<211> LENGTH: 33
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 24

-continued

```
ggatcctcct ttagttccca ggtgagtcag aac                              33


<210> SEQ ID NO 25
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 25

tgctctggag gctagcgttt c                                           21


<210> SEQ ID NO 26
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 26

accaatcatg ttagcctcaa g                                           21


<210> SEQ ID NO 27
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 27

agctatggga tcatcgcaca g                                           21


<210> SEQ ID NO 28
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 28

cctttgagct ggagcatctt c                                           21


<210> SEQ ID NO 29
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 29

ctttctagct ggagacatca g                                           21


<210> SEQ ID NO 30
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 30
```

-continued

```
caccatggta ctgtcaacat c                                              21


<210> SEQ ID NO 31
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 31

atgtcataca agacagagat c                                              21


<210> SEQ ID NO 32
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 32

tctgccttgt acagctgtgt c                                              21


<210> SEQ ID NO 33
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 33

tctgtggtat tcagctgcaa g                                              21


<210> SEQ ID NO 34
<211> LENGTH: 22
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 34

tactcaggaa aatttcacct tg                                             22


<210> SEQ ID NO 35
<211> LENGTH: 27
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 35

gaccacaaca ggaaaagcaa tgtgacc                                        27


<210> SEQ ID NO 36
<211> LENGTH: 22
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 36

gatagaattg aacaagattg ac                                             22
```

-continued

<210> SEQ ID NO 37
<211> LENGTH: 21
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 37
cagcctttgt agttactctg c 21

<210> SEQ ID NO 38
<211> LENGTH: 21
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 38
tgtcacacca agtgtgatag c 21

<210> SEQ ID NO 39
<211> LENGTH: 28
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 39
ggttcgtggt ttcactgatt gggattgc 28

<210> SEQ ID NO 40
<211> LENGTH: 27
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 40
cggctttgta gttggtttct tctggtg 27

<210> SEQ ID NO 41
<211> LENGTH: 3814
<212> TYPE: DNA
<213> ORGANISM: Homo sapiens

<400> SEQUENCE: 41
ctattgaagc cacctgctca ggacaatgaa attcttcagt tacattctgg tttatcgccg 60
atttctcttc gtggttttca ctgtgttggt tttactacct ctgcccatcg tcctccacac 120
caaggaagca gaatgtgcct acacactctt tgtggtcgcc acattttggc tcacagaagc 180
attgcctctg tcggtaacag ctttgctacc tagtttaatg ttacccatgt ttgggatcat 240
gccttctaag aaggtggcat ctgcttattt caaggatttt cacttactgc taattggagt 300
tatctgttta gcaacatcca tagaaaaatg gaatttgcac aagagaattg ctctgaaaat 360
ggtgatgatg gttggtgtaa atcctgcatg gctgacgctg gggttcatga gcagcactgc 420
ctttttgtct atgtggctca gcaacacctc gacggctgcc atggtgatgc ccattgcgga 480
ggctgtagtg cagcagatca tcaatgcaga agcagaggtc gaggccactc agatgactta 540

-continued

```
cttcaacgga tcaaccaacc acggactaga aattgatgaa agtgttaatg gacatgaaat    600
aaatgagagg aaagagaaaa caaaaccagt tccaggatac aataatgata cagggaaaat    660
ttcaagcaag gtggagttgg aaaagaactc aggcatgaga accaaatatc gaacaaagaa    720
gggccacgtg acacgtaaac ttacgtgttt gtgcattgcc tactcttcta ccattggtgg    780
actgacaaca atcactggta cctccaccaa cttgatcttt gcagagtatt tcaatacacg    840
ctatcctgac tgtcgttgcc tcaactttgg atcatggttt acgttttcct tcccagctgc    900
ccttatcatt ctactcttat cctggatctg gcttcagtgg cttttcctag gattcaattt    960
taaggagatg ttcaaatgtg gcaaaaccaa aacagtccaa caaaaagctt gtgctgaggt   1020
gattaagcaa gaataccaaa agcttgggcc aataaggtat caagaaattg tgaccttggt   1080
cctcttcatt ataatggctc tgctatggtt tagtcgagac cccggatttg ttcctggttg   1140
gtctgcactt ttttcagagt accctggttt tgctacagat tcaactgttg ctttacttat   1200
agggctgcta ttctttctta tcccagctaa gacactgact aaaactacac ctacaggaga   1260
aattgttgct tttgattact ctccactgat tacttggaaa gaattccagt cattcatgcc   1320
ctgggatata gccattcttg ttggtggagg gtttgccctg gcagatggtt gtgaggagtc   1380
tggattatct aagtggatag gaaataaatt atctcctctg ggttcattac cagcatggct   1440
aataattctg atatcttctt tgatggtgac atctttaact gaggtagcca gcaatccagc   1500
taccattaca ctctttctcc caatattatc tccattggcc gaagccattc atgtgaaccc   1560
tctttatatt ctgatacctt ctactctgtg tacttcattt gcattcctcc taccagtagc   1620
aaatccaccc aatgctattg tcttttcata tggtcatctg aaagtcattg acatggttaa   1680
agctggactt ggtgtcaaca ttgttggtgt tgctgtggtt atgcttggca tatgtacttg   1740
gattgtaccc atgtttgacc tctacactta cccttcgtgg gctcctgcta tgagtaatga   1800
gaccatgcca taataagcac aaaatttctg actatcttgc ggtaatttct ggaagacatt   1860
aatgattgac tgtaaaatgt ggctctaaat aactaatgac acacatttaa atcagttatg   1920
gtgtagctgc tgcaattccc gtgaataccc gaaacctgct ggtataactc agagtccata   1980
tttgttattg cagtgcaact aaagagcatc tatgtgcctt catcaagaag cccatgtttt   2040
gagattttgc tcatgaacca tctgcaactt gcttcatcat aagaataatt tataacttga   2100
ccttcaaaga gattagagca tttgtttcat cttacagttg gagttcaatg taacatttta   2160
aatgcaattt attatttcag aaatttccca tgaaactaaa aatagaaaat aagatataca   2220
agttaattcg gtacttggat aaatcatttc tgcattgttg ttccagagaa tttgctgaga   2280
aatcaaagcc atggtcatct ggtgatgaag agaaaaggtt aatctaaatg atatgtgcat   2340
ttcctcattt aaaaaatcca attggattat tcttaatata tacatgtaat atgaaaattg   2400
agattgaagc actaattcca aaattatggc tgaatatact aaataacaga aaagttacag   2460
ataagaattt atttctactg aactctatag ttagtgtaat ataattcata tttttatgat   2520
attggcacac tgagaaattc attttgtaga gctatggata aggcttgcta tgatttgcac   2580
tattagtaca gtatagttag aaaggaaagc tgaacactat aaaactatta acatattttc   2640
gtatatgagt aacaactttg cttaagtgtt tatcttagtt cagaaataca taatgtcata   2700
tgttaaaaat aaagagatgt agaaatctaa atgaattatc actgtgtata cagacagaaa   2760
aatcacataa ctctggtgtg ttaacattgc aatgaaaaaa tgaaaaaaag aaggaaaaaa   2820
gaataagaat gaaaactgct gacgtattac aaaacagaaa aataaatgat ttaaaatcaa   2880
atcaaaaaga aaaaaactaa acatttaaac aaaaatggga taagaatagt cttctagaag   2940
```

-continued

```
tgaggatgcg taaaagaatg agtttccaat taccctgatg tgacaattac acattgtaga   3000

caggtagcaa aatatcacat acacccccaa aatatgtaca aatattatat atcaataaat   3060

aaatttttaa agagtaagtg ctattggcat tccaaaattc agctaaagga aaaatgatca   3120

aaaacaaagt aaggtgcaca gttagcaaaa gatgcagatg ttatatcaca gcaattctca   3180

tgctaaaaat acaacaaaag acaaagcaaa aaataaacct ttgctttttt tttttttttt   3240

tttttttttt gagacggagt ctcgctctgt cgcccaggct ggagtgcagt ggcgggatct   3300

cggctcactg caagctccgc ctcccaggtt cacgccattc tcctgcctca gccaaacctt   3360

tgctattttt aatcttcgtt ggcactttcc agctgttact gaccttgtca tttttgttc    3420

aaataagatt atttacaaac ttattcttga aactaaatat agtaaagagg gtttttaaaa   3480

taatatttaa catacgaatt attaattggc catgttcatt atttatctat gtttattaat   3540

gggccaatgc aaaaaatcat tttttcaaag aaaaatttgt ccatgtaaag cttaaattat   3600

aatattgctg ctttgtataa ctcttctatg tttattctat tcatttgttc ctttccctac   3660

catattttac acatgtattt ataatctgta gtatttatta catttctgct tttttctagt   3720

cattcaattt atcactgctg aattgcatca gatcatggat gcatttttat tatgaaaaaa   3780

taaaatgact tttcaaatta aaaaaaaaaa aaaa                               3814
```

<210> SEQ ID NO 42
<211> LENGTH: 734
<212> TYPE: DNA
<213> ORGANISM: Homo sapiens

<400> SEQUENCE: 42

```
caggacaatg aaattcttca gttacattct ggtttatcgc cgatttctct tcgtggtttt     60

cactgtgttg gttttactac ctctgcccat cgtcctccac accaaggaag cagaatgtgc    120

ctacacactc tttgtggtcg ccacattttg gctcacagaa gcattgcctc tgtcggtaac    180

agctttgcta cctagtttaa tgttacccat gtttgggatc atgccttcta agaaggtggc    240

atctgcttat ttcaaggatt ttcacttact gctaattgga gttatctgtt tagcaacatc    300

catagaaaaa tggaatttgc acaagagaat tgctctgaaa atggtgatga tggttggtgt    360

aaatcctgca tggctgacgc tggggttcat gagcagcact gcctttttgt ctatgtggct    420

cagcaacacc tcgacggctg ccatggtgat gcccattgcg gaggctgtag tgcagcagat    480

catcaatgca gaagcagagg tcgaggccac tcagatgact tacttcaacg gatcaaccaa    540

ccacggacta gaaattgatg aaagtgttaa tggacatgaa ataaatgaga ggaaagagaa    600

aacaaaacca gttccaggat acaataatga tacagggaaa atttcaagca aggtggagtt    660

ggaaaagact gtttaactac tgaaatgaag ctattctcct gactaaacat aactgaaaaa    720

ccattcatta aatg                                                      734
```

<210> SEQ ID NO 43
<211> LENGTH: 539
<212> TYPE: DNA
<213> ORGANISM: Homo sapiens

<400> SEQUENCE: 43

```
gccactcaga tgacttactt caacggatca accaaccacg gactagaaat tgatgaaagt     60

gttaatggac atgaaataaa tgagaggaaa gagaaaacaa aaccagttcc aggatacaat    120

aatgatacag ggaaaatttc aagcaaggtg gagttggaaa agcactggaa acttgcagtt    180
```

-continued

```
caagatggct ccccatctcc ctctgtccat tctgtatcgc agctagctgc tcaaggaaag    240

gagaaagtgg aaggcatatg tacttagaaa ttattctatt actttcctgg atttaagagt    300

attcagattt tctatttcaa catcaaacaa ttgcattttt aaaaagaaat ttatgtgttc    360

catgtcaaat ttagtagtgt gtggttgttt ataatatttt cttatatcta cttaatttct    420

atagtattta tagttatatg tctttatttc taacattttt cttgtgcttt taaagattat    480

ttaaagatta tttttaaata atctttattt catttaaata aaatatttta tttaagtct     539


<210> SEQ ID NO 44
<211> LENGTH: 556
<212> TYPE: DNA
<213> ORGANISM: Homo sapiens

<400> SEQUENCE: 44

cacggactag aaattgatga aagtgttaat ggacatgaaa taaatgagag gaaagagaaa     60

acaaaaccag ttccaggata caataatgat acagggaaaa tttcaagcaa ggtggagttg    120

gaaaagaact caggcatgag aaccaaatat cgaacaaaga agggccacgt gacacgtaaa    180

cttacgtgtt tgtgcattgc ctactcttct accattggtg gactgacaac aatcactggt    240

acctccacca acttgatctt tgcagagtat ttcaatacat tccatccaca cagaagagga    300

gatcgtacaa ggcatgtaca ccaggaggca gaaatttgag gcatatcttg gaactctgtc    360

taccacatcc tgaacatcac acagtttcca ctcttgttgc cttcaatcct gagaatgcat    420

ccaggagcca ttctgtttta tgtcaattac taattagatc atgtcacgtt actaacttac    480

tacgttccaa ttagtcctta ttgcatttgt aataaaatcc gcatactttc ggactggcta    540

caaggttata catgat                                                    556


<210> SEQ ID NO 45
<211> LENGTH: 595
<212> TYPE: PRT
<213> ORGANISM: Homo sapiens

<400> SEQUENCE: 45

Met Lys Phe Phe Ser Tyr Ile Leu Val Tyr Arg Arg Phe Leu Phe Val
1               5                   10                  15

Val Phe Thr Val Leu Val Leu Leu Pro Leu Pro Ile Val Leu His Thr
            20                  25                  30

Lys Glu Ala Glu Cys Ala Tyr Thr Leu Phe Val Val Ala Thr Phe Trp
        35                  40                  45

Leu Thr Glu Ala Leu Pro Leu Ser Val Thr Ala Leu Leu Pro Ser Leu
    50                  55                  60

Met Leu Pro Met Phe Gly Ile Met Pro Ser Lys Lys Val Ala Ser Ala
65                  70                  75                  80

Tyr Phe Lys Asp Phe His Leu Leu Leu Ile Gly Val Ile Cys Leu Ala
                85                  90                  95

Thr Ser Ile Glu Lys Trp Asn Leu His Lys Arg Ile Ala Leu Lys Met
            100                 105                 110

Val Met Met Val Gly Val Asn Pro Ala Trp Leu Thr Leu Gly Phe Met
        115                 120                 125

Ser Ser Thr Ala Phe Leu Ser Met Trp Leu Ser Asn Thr Ser Thr Ala
    130                 135                 140

Ala Met Val Met Pro Ile Ala Glu Ala Val Val Gln Gln Ile Ile Asn
145                 150                 155                 160

Ala Glu Ala Glu Val Glu Ala Thr Gln Met Thr Tyr Phe Asn Gly Ser
```

-continued

```
                165                 170                 175

Thr Asn His Gly Leu Glu Ile Asp Glu Ser Val Asn Gly His Glu Ile
            180                 185                 190

Asn Glu Arg Lys Glu Lys Thr Lys Pro Val Pro Gly Tyr Asn Asn Asp
        195                 200                 205

Thr Gly Lys Ile Ser Ser Lys Val Glu Leu Glu Lys Asn Ser Gly Met
    210                 215                 220

Arg Thr Lys Tyr Arg Thr Lys Lys Gly His Val Thr Arg Lys Leu Thr
225                 230                 235                 240

Cys Leu Cys Ile Ala Tyr Ser Ser Thr Ile Gly Gly Leu Thr Thr Ile
                245                 250                 255

Thr Gly Thr Ser Thr Asn Leu Ile Phe Ala Glu Tyr Phe Asn Thr Arg
            260                 265                 270

Tyr Pro Asp Cys Arg Cys Leu Asn Phe Gly Ser Trp Phe Thr Phe Ser
        275                 280                 285

Phe Pro Ala Ala Leu Ile Ile Leu Leu Leu Ser Trp Ile Trp Leu Gln
    290                 295                 300

Trp Leu Phe Leu Gly Phe Asn Phe Lys Glu Met Phe Lys Cys Gly Lys
305                 310                 315                 320

Thr Lys Thr Val Gln Gln Lys Ala Cys Ala Glu Val Ile Lys Gln Glu
                325                 330                 335

Tyr Gln Lys Leu Gly Pro Ile Arg Tyr Gln Glu Ile Val Thr Leu Val
            340                 345                 350

Leu Phe Ile Ile Met Ala Leu Leu Trp Phe Ser Arg Asp Pro Gly Phe
        355                 360                 365

Val Pro Gly Trp Ser Ala Leu Phe Ser Glu Tyr Pro Gly Phe Ala Thr
    370                 375                 380

Asp Ser Thr Val Ala Leu Leu Ile Gly Leu Leu Phe Phe Leu Ile Pro
385                 390                 395                 400

Ala Lys Thr Leu Thr Lys Thr Thr Pro Thr Gly Glu Ile Val Ala Phe
                405                 410                 415

Asp Tyr Ser Pro Leu Ile Thr Trp Lys Glu Phe Gln Ser Phe Met Pro
            420                 425                 430

Trp Asp Ile Ala Ile Leu Val Gly Gly Gly Phe Ala Leu Ala Asp Gly
        435                 440                 445

Cys Glu Glu Ser Gly Leu Ser Lys Trp Ile Gly Asn Lys Leu Ser Pro
    450                 455                 460

Leu Gly Ser Leu Pro Ala Trp Leu Ile Ile Leu Ile Ser Ser Leu Met
465                 470                 475                 480

Val Thr Ser Leu Thr Glu Val Ala Ser Asn Pro Ala Thr Ile Thr Leu
                485                 490                 495

Phe Leu Pro Ile Leu Ser Pro Leu Ala Glu Ala Ile His Val Asn Pro
            500                 505                 510

Leu Tyr Ile Leu Ile Pro Ser Thr Leu Cys Thr Ser Phe Ala Phe Leu
        515                 520                 525

Leu Pro Val Ala Asn Pro Pro Asn Ala Ile Val Phe Ser Tyr Gly His
    530                 535                 540

Leu Lys Val Ile Asp Met Val Lys Ala Gly Leu Gly Val Asn Ile Val
545                 550                 555                 560

Gly Val Ala Val Val Met Leu Gly Ile Cys Thr Trp Ile Val Pro Met
                565                 570                 575

Phe Asp Leu Tyr Thr Tyr Pro Ser Trp Ala Pro Ala Met Ser Asn Glu
            580                 585                 590
```

```
Thr Met Pro
        595


<210> SEQ ID NO 46
<211> LENGTH: 224
<212> TYPE: PRT
<213> ORGANISM: Homo sapiens

<400> SEQUENCE: 46

Arg Thr Met Lys Phe Phe Ser Tyr Ile Leu Val Tyr Arg Arg Phe Leu
1               5                   10                  15

Phe Val Val Phe Thr Val Leu Val Leu Leu Pro Leu Pro Ile Val Leu
            20                  25                  30

His Thr Lys Glu Ala Glu Cys Ala Tyr Thr Leu Phe Val Val Ala Thr
        35                  40                  45

Phe Trp Leu Thr Glu Ala Leu Pro Leu Ser Val Thr Ala Leu Leu Pro
    50                  55                  60

Ser Leu Met Leu Pro Met Phe Gly Ile Met Pro Ser Lys Lys Val Ala
65                  70                  75                  80

Ser Ala Tyr Phe Lys Asp Phe His Leu Leu Leu Ile Gly Val Ile Cys
                85                  90                  95

Leu Ala Thr Ser Ile Glu Lys Trp Asn Leu His Lys Arg Ile Ala Leu
            100                 105                 110

Lys Met Val Met Met Val Gly Val Asn Pro Ala Trp Leu Thr Leu Gly
        115                 120                 125

Phe Met Ser Ser Thr Ala Phe Leu Ser Met Trp Leu Ser Asn Thr Ser
    130                 135                 140

Thr Ala Ala Met Val Met Pro Ile Ala Glu Ala Val Val Gln Gln Ile
145                 150                 155                 160

Ile Asn Ala Glu Ala Glu Val Glu Ala Thr Gln Met Thr Tyr Phe Asn
                165                 170                 175

Gly Ser Thr Asn His Gly Leu Glu Ile Asp Glu Ser Val Asn Gly His
            180                 185                 190

Glu Ile Asn Glu Arg Lys Glu Lys Thr Lys Pro Val Pro Gly Tyr Asn
        195                 200                 205

Asn Asp Thr Gly Lys Ile Ser Ser Lys Val Glu Leu Glu Lys Thr Val
    210                 215                 220


<210> SEQ ID NO 47
<211> LENGTH: 88
<212> TYPE: PRT
<213> ORGANISM: Homo sapiens

<400> SEQUENCE: 47

Ala Thr Gln Met Thr Tyr Phe Asn Gly Ser Thr Asn His Gly Leu Glu
1               5                   10                  15

Ile Asp Glu Ser Val Asn Gly His Glu Ile Asn Glu Arg Lys Glu Lys
            20                  25                  30

Thr Lys Pro Val Pro Gly Tyr Asn Asn Asp Thr Gly Lys Ile Ser Ser
        35                  40                  45

Lys Val Glu Leu Glu Lys His Trp Lys Leu Ala Val Gln Asp Gly Ser
    50                  55                  60

Pro Ser Pro Ser Val His Ser Val Ser Gln Leu Ala Ala Gln Gly Lys
65                  70                  75                  80

Glu Lys Val Glu Gly Ile Cys Thr
                85
```

-continued

<210> SEQ ID NO 48
<211> LENGTH: 112
<212> TYPE: PRT
<213> ORGANISM: Homo sapiens

<400> SEQUENCE: 48

```
His Gly Leu Glu Ile Asp Glu Ser Val Asn Gly His Glu Ile Asn Glu
1               5                   10                  15

Arg Lys Glu Lys Thr Lys Pro Val Pro Gly Tyr Asn Asn Asp Thr Gly
            20                  25                  30

Lys Ile Ser Ser Lys Val Glu Leu Glu Lys Asn Ser Gly Met Arg Thr
        35                  40                  45

Lys Tyr Arg Thr Lys Lys Gly His Val Thr Arg Lys Leu Thr Cys Leu
    50                  55                  60

Cys Ile Ala Tyr Ser Ser Thr Ile Gly Gly Leu Thr Thr Ile Thr Gly
65                  70                  75                  80

Thr Ser Thr Asn Leu Ile Phe Ala Glu Tyr Phe Asn Thr Phe His Pro
                85                  90                  95

His Arg Arg Gly Asp Arg Thr Arg His Val His Gln Glu Ala Glu Ile
            100                 105                 110
```

<210> SEQ ID NO 49
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 49
ccagctttaa ccatgtcaat g 21

<210> SEQ ID NO 50
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 50
cagatggttg tgaggagtct g 21

<210> SEQ ID NO 51
<211> LENGTH: 3311
<212> TYPE: DNA
<213> ORGANISM: Homo sapiens

<400> SEQUENCE: 51

```
tgctaatgct tttggtacaa atggatgtgg aatataattg aatattttct tgtttaaggg     60

gagcatgaag aggtgttgag gttatgtcaa gcatctggca cagctgaagg cagatggaaa    120

tatttacaag tacgcaattt gagactaaga tattgttatc attctcctat tgaagacaag    180

agcaatagta aaacacatca ggtcaggggg ttaaagacct gtgataaacc acttccgata    240

agttggaaac gtgtgtctat attttcatat ctgtatatat ataatggtaa agaaagacac    300

cttcgtaacc cgcattttcc aaagagagga atcacaggga gatgtacagc aatggggcca    360

tttaagagtt ctgtgttcat cttgattctt caccttctag aaggggccct gagtaattca    420

ctcattcagc tgaacaacaa tggctatgaa ggcattgtcg ttgcaatcga ccccaatgtg    480
```

-continued

```
ccagaagatg aaacactcat tcaacaaata aaggacatgg tgacccaggc atctctgtat    540
ctgtttgaag ctacaggaaa gcgattttat ttcaaaaatg ttgccatttt gattcctgaa    600
acatggaaga caaaggctga ctatgtgaga ccaaaacttg agacctacaa aaatgctgat    660
gttctggttg ctgagtctac tcctccaggt aatgatgaac cctacactga gcagatgggc    720
aactgtggag agaagggtga aaggatccac ctcactcctg atttcattgc aggaaaaaag    780
ttagctgaat atggaccaca aggtaaggca tttgtccatg agtgggctca tctacgatgg    840
ggagtatttg acgagtacaa taatgatgag aaattctact tatccaatgg aagaatacaa    900
gcagtaagat gttcagcagg tattactggt acaaatgtag taaagaagtg tcagggaggc    960
agctgttaca ccaaaagatg cacattcaat aaagttacag gactctatga aaaaggatgt   1020
gagtttgttc tccaatcccg ccagacggag aaggcttcta taatgtttgc acaacatgtt   1080
gattctatag ttgaattctg tacagaacaa aaccacaaca aagaagctcc aaacaagcaa   1140
aatcaaaaat gcaatctccg aagcacatgg gaagtgatcc gtgattctga ggactttaag   1200
aaaaccactc ctatgacaac acagccacca aatcccacct tctcattgct gcagattgga   1260
caaagaattg tgtgtttagt ccttgacaaa tctggaagca tggcgactgg taaccgcctc   1320
aatcgactga atcaagcagg ccagcttttc ctgctgcaga cagttgagct ggggtcctgg   1380
gttgggatgg tgacatttga cagtgctgcc catgtacaaa gtgaactcat acagataaac   1440
agtggcagtg acagggacac actcgccaaa agattacctg cagcagcttc aggagggacg   1500
tccatctgca gcgggcttcg atcggcattt actgtgatta ggaagaaata tccaactgat   1560
ggatctgaaa ttgtgctgct gacggatggg gaagacaaca ctataagtgg gtgctttaac   1620
gaggtcaaac aaagtggtgc catcatccac acagtcgctt tggggccctc tgcagctcaa   1680
gaactagagg agctgtccaa aatgacagga ggtttacaga catatgcttc agatcaagtt   1740
cagaacaatg gcctcattga tgcttttggg gccctttcat caggaaatgg agctgtctct   1800
cagcgctcca tccagcttga gagtaaggga ttaaccctcc agaacagcca gtggatgaat   1860
ggcacagtga tcgtggacag caccgtggga aaggacactt tgtttcttat cacctggaca   1920
acgcagcctc cccaaatcct tctctgggat cccagtggac agaagcaagg tggctttgta   1980
gtggacaaaa acaccaaaat ggcctacctc caaatcccag gcattgctaa ggttggcact   2040
tggaaataca gtctgcaagc aagctcacaa accttgaccc tgactgtcac gtcccgtgcg   2100
tccaatgcta ccctgcctcc aattacagtg acttccaaaa cgaacaagga caccagcaaa   2160
ttccccagcc ctctggtagt ttatgcaaat attcgccaag gagcctcccc aattctcagg   2220
gccagtgtca cagccctgat tgaatcagtg aatggaaaaa cagttacctt ggaactactg   2280
gataatggag caggtgctga tgctactaag gatgacggtg tctactcaag gtatttcaca   2340
acttatgaca cgaatggtag atacagtgta aaagtgcggg ctctgggagg agttaacgca   2400
gccagacgga gagtgatacc ccagcagagt ggagcactgt acatacctgg ctggattgag   2460
aatgatgaaa tacaatggaa tccaccaaga cctgaaatta ataaggatga tgttcaacac   2520
aagcaagtgt gtttcagcag aacatcctcg ggaggctcat ttgtggcttc tgatgtccca   2580
aatgctccca tacctgatct cttcccacct ggccaaatca ccgacctgaa ggcggaaatt   2640
cacgggggca gtctcattaa tctgacttgg acagctcctg gggatgatta tgaccatgga   2700
acagctcaca agtatatcat tcgaataagt acaagtattc ttgatctcag agacaagttc   2760
aatgaatctc ttcaagtgaa tactactgct ctcatcccaa aggaagccaa ctctgaggaa   2820
```

-continued

```
gtctttttgt ttaaaccaga aaacattact tttgaaaatg gcacagatct tttcattgct   2880

attcaggctg ttgataaggt cgatctgaaa tcagaaatat ccaacattgc acgagtatct   2940

ttgtttattc ctccacagac tccgccagag acacctagtc ctgatgaaac gtctgctcct   3000

tgtcctaata ttcatatcaa cagcaccatt cctggcattc acattttaaa aattatgtgg   3060

aagtggatag gagaactgca gctgtcaata gcctagggct gaatttttgt cagataaata   3120

aaataaatca ttcatccttt ttttgattat aaaattttct aaaatgtatt ttagacttcc   3180

tgtagggggc gatatactaa atgtatatag tacatttata ctaaatgtat tcctgtaggg   3240

ggcgatatac taaatgtatt ttagacttcc tgtagggggc gataaaataa aatgctaaac   3300

aactgggtaa a                                                        3311
```

<210> SEQ ID NO 52
<211> LENGTH: 3067
<212> TYPE: DNA
<213> ORGANISM: Homo sapiens

<400> SEQUENCE: 52

```
aattaaatta tgagaattaa aaagacaaca ttgagcagag atgaaaaagg aagggaggaa     60

aaggtggaaa agaaaagaag acaagaagcg agtagtggtc tctaacttgc tctttgaagg    120

atggtctcac aaagagaacc ccaacagaca tcatcgtggg aatcaaatca agaccagcaa    180

gtacaccgtg ttgtccttcg tccccaaaaa catttttgag cagctacacc ggtttgccaa    240

tctctatttt gtgggcattg cggttctgaa ttttatccct gtggtcaatg ctttccagcc    300

tgaggtgagc atgataccaa tctgtgttat cctggcagtc actgccatca aggacgcttg    360

ggaagacctc cggaggtaca aatcggataa agtcatcaat aaccgagagt gcctcatcta    420

cagcagaaaa gagcagacct atgtgcagaa gtgctggaag gatgtgcgtg tgggagactt    480

catccaaatg aaatgcaatg agattgtccc agcagacata ctcctccttt tttcctctga    540

ccccaatggg atatgccatc tggaaactgc cagcttggat ggagagacaa acctcaagca    600

aagacgtgtc gtgaagggct tctcacagca ggaggtacag ttcgaaccag agcttttcca    660

caataccatc gtgtgtgaga aacccaacaa ccacctcaac aaatttaagg gttatatgga    720

gcatcctgac cagaccagga ctggctttgg ctgtgagagt cttctgcttc gaggctgcac    780

catcagaaac accgagatgg ctgttggcat tgtcatctat gcaggccatg agacgaaagc    840

catgctgaac aacagtggcc cccggtacaa acgcagcaag attgagcggc gcatgaatat    900

agacatcttc ttctgcattg ggatcctcat cctcatgtgc cttattggag ctgtaggtca    960

cagcatctgg aatgggacct ttgaagaaca ccctcccttc gatgtgccag atgccaatgg   1020

cagcttcctt cccagtgccc ttgggggctt ctacatgttc ctcacaatga tcatcctgct   1080

ccaggtgctg atccccatct ctttgtatgt ctccattgag ctggtgaagc tcgggcaagt   1140

gttcttcttg agcaatgacc ttgacctgta tgatgaagag accgatttat ccattcaatg   1200

tcgagccctc aacatcgcag aggacttggg ccagatccag tacatcttct ccgataagac   1260

ggggaccctg acagagaaca agatggtgtt ccgacgttgc accatcatgg gcagcgagta   1320

ttctcaccaa gaaaatggta tagaagctcc caagggctcc atccctcttt ctaaaaggaa   1380

ataccctgct ctcctaagaa acgaggagat aaaagacatt ctcctggctc tcttagaggc   1440

tgtgtggcat ttccacaagt tgcttcctgt atccctgtgg tcttccttgt cacagatcag   1500

ggctgttcca attacttgta aactttcatt tgtttacaaa ggttagaagt tatcccatat   1560

gtggttcccc ttcagctgat ctttgtctgg tgccagacaa agcactttat gagacgagtt   1620
```

-continued

```
ttttatctgt cagcaatgga ttggagacat ttcccaattg tgtgccagtc acacaaccaa   1680
ggcttaggaa tttctcaggc caccttacct gacatgtcag ggcaggtctg tgtctaggtg   1740
catggtcaga tttaatacat ccagaagatg tcttctattc taacagatct cttagcttgt   1800
cactgaggca aagttttgat ttaggagata gggctataaa atgcctggac tgttaccttg   1860
catggactga atatgactca taaaactgat ctgattcctt cagccatcat ctgcccaact   1920
tggttcccct ccccaccccc ccacaacaca cacacacact ttctaagaaa agaaaagaaa   1980
ttcttttttt tcaatacttt aagttctggg atacatgtgc agaatgtgca ggtttgttac   2040
ataggtatac atgtgtcatg gtggtttgca gcacccacca acccatcatc taccttaggt   2100
atttctccta atgctatccc tcccctagcc cccaaccccc cgatgggctc cagtgtgtga   2160
tgttcccctc catgtccatg tgttctcatt gttcaattcc cacttatgag tgagaacatg   2220
cagtatttgg ttttctgttc ttgtgttagt ttgctgatgg tttcctgttc atccgtgtcc   2280
ctgcaaagga catgaactca tcctttttta tggctgcata atattccatg gtgtatatgt   2340
gccacatttt ctttatccag tctatcgctg atgggcactg ggttggttc caagtctttg    2400
ctattgtgaa cagtgctgca ataaacttac atgtgcatgt gtctttagta gaatgattta   2460
taatcctttg ggtatatacc cagtaatggg attgctggtc aaatggtatt tctggttcta   2520
gatccttgag gaatctttgt cttccacaat ggttgaacta atttgtactc ccaccaacag   2580
tgtaaaagta ttcctgtttc tctacatcct cttcagcatc tgttgtgtcc tgacatttta   2640
atgatcacta ttctcactgg cgtgagatgt tatctcattg tggttttgat ttgcatttct   2700
ctaatgacca gtaatgatga gctttttttc atatgtttgt tggctgcata aatgtcttct   2760
tttgagaagt gtctgttcat atccttcacc catttttgga agaaaacaaa ctcttaagag   2820
agcagtattc attcttttga gtgtgaggga tggagaaaga gaaagatgga gagagtatta   2880
taagcagctg tatccccttt gccatggtga tagcagacca ttcacatggg agcttctggt   2940
ctctttgtaa taataataag agccacatta ccagtactta gagtatgcta gttattttaa   3000
cacattgtat cattaaatct tcaaaacatc cctatgagtt agaaacctaa aaaaaaaaaa   3060
aaaaaaa                                                              3067
```

<210> SEQ ID NO 53
<211> LENGTH: 2778
<212> TYPE: DNA
<213> ORGANISM: Homo sapiens

<400> SEQUENCE: 53

```
ctcattttga tgtctagaat caggggatcc aggatcatca ccaaggtcat tttcccaggt     60
atggaggggt ctttctgctt ctttcttgtc atgcacagct gctgaggaag gggctgggag    120
taaagacagt gaaatgggga ggaggagtcc attcaaaccg agaaacaaag tgtttggttt    180
ttcttacccc tggtgtagaa gctaccaacc ttttccaaga aagagggcct ggcccccttc    240
tcgggtctgg ctgggtgcct gctgtgcctc tctggcctcc cctccgaagg gcaccattcc    300
ctcgggtgag tactaccggc ctgcaccgtc ttccagtggg gacagcctga gaagagagtc    360
tggggcctta cttcagtacc ttccttcact ggcctcaccc tgtgcaaatc atgccacacg    420
ctgcagcctc cttttcccta tctataaaat aaaaatgacc ctgctctatc tcactgggct    480
ggcaagaaca cactgttgtt gccttgcaga cagatgtgct gaggctgtag aaagtgcttt    540
ttatttggtt gggagcttgt gcataaatgc gagaggggct gcacatctga cggactagag    600
```

-continued

```
gtgactcatg gctgaaccgg aacaggacat cggggagaag ccagcagcca tgctgaactc    660
tccacagggc cctgtgaaaa gctcttcacc tcctctgccc tctggatcta gtgaagccta    720
ttcatccttc agatgtcagc tcaaataatc aaccttcatg gaggcctccc ttgaccccta    780
acatgctttc aaagtactgt gtatttcaca ttcatcatgc cccgacaact gtgatttccc    840
atttattaat atctgtctct tctgctggcc tgcaaactcc aggagcacag agacatcttt    900
gggatttttg aacatgattt ccccagggct tagcccagtg cctggtgcaa agcaggcttt    960
caacatgttc agtggatatt gtaagaaaga aagaaataca caaaaggcct ggcatatgca   1020
aagcactcta aatattcact cctttccctt ccctctgggt gagaaaattt ctccttataa   1080
agacaccctc ctaactgtat ctctgctaga gaactgaaga cataaagcac tctgtgccaa   1140
aaatatttaa gtaaaaactt gagctaagca cagagattat aaatatttct tccccagatt   1200
acgcaccatt taaaaatact gtctcagctc cttttcatga tttgggtggt gattaaagaa   1260
aattactctt caagactgaa agtcattact gcccttttcc tgacttgcct tttcccttga   1320
gaaggggagg ataagctgca gggcaggaag tggaagtggg gcatccttgt cctttgtctg   1380
gcagacagcc aactggtcag gtactgctcc ttctcaactc tttcctgatt cccaggtgaa   1440
tataaacaag aaggcacaaa tccacacttg ccaacaacgg acccaagtga taacaagaaa   1500
cccagtgaca cctgtctagg tgaagactca gcccctatgt gaccaggttg caaagccaaa   1560
ctgaccatct gctttccatt tggactttta gttcatactg tatcttctca ggacagttaa   1620
gttggaatac aatgccactg tcctgaaaga tggtagaatt atcctatttc tggaggagtg   1680
ggggtggtgg gtaggaatct caagagcgat ttgctcctct gcacaatagc ttctttaagg   1740
acaccagggc ccccagggct atacatttcc ctgaagcttt ccagataagc aacaaggtat   1800
gagcacctgc tatgtattgc ccaagggtga tgtgtttaaa tatccattgc atattttaaa   1860
tccttggctg gcttaaagct gcaagctttc tgtcttcagt ggatataatg gggcataca    1920
tcccagagct tgcccaacac tccaagaaaa gaaccctcag ctaatgcaaa gtgtgtatgt   1980
gcccatgaaa gctccatgtc tacttaacat tcagttttta ggattattta tgctgtaata   2040
atagatatga aaatctctga caggtatttt gtttccttta caaactgtat ttgaatttat   2100
gggtgattta gagcttgtgt ttaaagtcag aattcagaac cccaaagaaa atgacttcat   2160
tgaaattgaa ctgaagagac aagaactgag ttaccaaaac ctactaaacg tgagttgctg   2220
tgaactgggg attaaaccag aacgagtgga gaagatcaga aagctaccaa acacactgct   2280
cagaaaggac aaagacattc gaagactgcg ggactttcag gaagtggaac tcattttaat   2340
gaaaaatgga agctccagat tgacagaata tgtgccatct ctgacagaaa ggccctgcta   2400
tgatagcaaa gctgcaaaaa tgacttatta aatactccca ggaatggccg cgcatggtgg   2460
ctcacccccct gtaatcccag cactttggga agccaaggtg ggcggatcac ctgaggtcag   2520
gagttctaga ccagcctggc caacatatag tgaaacccag tctctactaa aaaaaataca   2580
aaaattagct aggtgtggtg gcgcacacct gtagtagtcc cagctacatg ggaagctgag   2640
gcaggagaat cacctgaacc caggaggcag aggttgcagt gagctgagat tgcgccactg   2700
cactccagcc tggcgacaga gcaagactct gtctctcaaa ataaataaat aaataaataa   2760
ataaataaat aaataatc                                                 2778
```

<210> SEQ ID NO 54
<211> LENGTH: 1646
<212> TYPE: DNA
<213> ORGANISM: Homo sapiens -continued

<400> SEQUENCE: 54

```
gcccgggaga ggagaggagc gggccgagga ctccagcgtg cccaggtctg gcatcctgca     60
cttgctgccc tctgacacct gggaagatgg ccggcccgtg gaccttcacc cttctctgtg    120
gtttgctggc agccaccttg atccaagcca ccctcagtcc cactgcagtt ctcatcctcg    180
gcccaaaagt catcaaagaa aagctgacac aggagctgaa ggaccacaac gccaccagca    240
tcctgcagca gctgccgctg ctcagtgcca tgcgggaaaa gccagccgga ggcatccctg    300
tgctgggcag cctggtgaac accgtcctga agcacatcat ctggctgaag gtcatcacag    360
ctaacatcct ccagctgcag gtgaagccct cggccaatga ccaggagctg ctagtcaaga    420
tccccctgga catggtggct ggattcaaca cgcccctggt caagaccatc gtggagttcc    480
acatgacgac tgaggcccaa gccaccatcc gcatggacac cagtgcaagt ggccccaccc    540
gcctggtcct cagtgactgt gccaccagcc atgggagcct gcgcatccaa ctgctgcata    600
agctctcctt cctggtgaac gccttagcta agcaggtcat gaacctccta gtgccatccc    660
tgcccaatct agtgaaaaac cagctgtgtc ccgtgatcga ggcttccttc aatggcatgt    720
atgcagacct cctgcagctg gtgaaggtgc ccatttccct cagcattgac cgtctggagt    780
ttgaccttct gtatcctgcc atcaagggtg acaccattca gctctacctg gggggccaagt    840
tgttggactc acagggaaag gtgaccaagt ggttcaataa ctctgcagct tccctgacaa    900
tgcccaccct ggacaacatc ccgttcagcc tcatcgtgag tcaggacgtg gtgaaagctg    960
cagtggctgc tgtgctctct ccagaagaat tcatggtcct gttggactct gtgcttcctg   1020
agagtgccca tcggctgaag tcaagcatcg ggctgatcaa tgaaaaggct gcagataagc   1080
tgggatctac ccagatcgtg aagatcctaa ctcaggacac tcccgagttt tttatagacc   1140
aaggccatgc caaggtggcc caactgatcg tgctggaagt gtttccctcc agtgaagccc   1200
tccgcccttt gttcaccctg ggcatcgaag ccagctcgga agctcagttt tacaccaaag   1260
gtgaccaact tatactcaac ttgaataaca tcagctctga tcggatccag ctgatgaact   1320
ctgggattgg ctggttccaa cctgatgttc tgaaaaacat catcactgag atcatccact   1380
ccatcctgct gccgaaccag aatggcaaat taagatctgg ggtcccagtg tcattggtga   1440
aggccttggg attcgaggca gctgagtcct cactgaccaa ggatgccctt gtgcttactc   1500
cagcctcctt gtggaaaccc agctctcctg tctcccagtg aagacttgga tggcagccat   1560
cagggaaggc tgggtcccag ctgggagtat gggtgtgagc tctatagacc atccctctct   1620
gcaatcaata aacacttgcc tgtgat                                        1646
```

<210> SEQ ID NO 55
<211> LENGTH: 1049
<212> TYPE: DNA
<213> ORGANISM: Homo sapiens

<400> SEQUENCE: 55

```
ggagtggggg agagagagga gaccaggaca gctgctgaga cctctaagaa gtccagatac     60
taagagcaaa gatgtttcaa actgggggcc tcattgtctt ctacgggctg ttagcccaga    120
ccatggccca gtttggaggc ctgcccgtgc ccctggacca gaccctgccc ttgaatgtga    180
atccagccct gcccttgagt cccacaggtc ttgcaggaag cttgacaaat gccctcagca    240
atggcctgct gtctgggggc ctgttgggca ttctggaaaa ccttccgctc ctggacatcc    300
tgaagcctgg aggaggtact tctggtggcc tccttggggg actgcttgga aaagtgacgt    360
```

-continued

```
cagtgattcc tggcctgaac aacatcattg acataaaggt cactgacccc cagctgctgg    420

aacttggcct tgtgcagagc cctgatggcc accgtctcta tgtcaccatc cctctcggca    480

taaagctcca agtgaatacg cccctggtcg gtgcaagtct gttgaggctg gctgtgaagc    540

tggacatcac tgcagaaatc ttagctgtga gagataagca ggagaggatc cacctggtcc    600

ttggtgactg cacccattcc cctggaagcc tgcaaatttc tctgcttgat ggacttggcc    660

ccctccccat tcaaggtctt ctggacagcc tcacagggat cttgaataaa gtcctgcctg    720

agttggttca gggcaacgtg tgccctctgg tcaatgaggt tctcagaggc ttggacatca    780

ccctggtgca tgacattgtt aacatgctga tccacggact acagtttgtc atcaaggtct    840

aagccttcca ggaaggggct ggcctctgct gagctgcttc ccagtgctca cagatggctg    900

gcccatgtgc tggaagatga cacagttgcc ttctctccga ggaacctgcc ccctctcctt    960

tcccaccagg cgtgtgtaac atcccatgtg cctcacctaa taaaatggct cttcttctgc   1020

aaaaaaaaaa aaaaaaaaaa aaaaaaaaa                                     1049


<210> SEQ ID NO 56
<211> LENGTH: 4815
<212> TYPE: DNA
<213> ORGANISM: Homo sapiens

<400> SEQUENCE: 56

gagcagagcc ctttcacaca cctcaggaac acctttcggc tgcccgctcc ccagacacac     60

ctgcagccct gcccagccgg ctttgctcac ccactgcttg taaatgcccc agatatgagc    120

cagcccaggc cccgctacgt ggtagacaga gccgcatact ccccttaccct cttcgacgat    180

gagtttgaga agaaggaccg gacataccca gtgggagaga aacttcgcaa tgccttcaga    240

tgttcctcag ccaagatcaa agctgtggtg tttgggctgc tgcctgtgct ctcctggctc    300

cccaagtaca agattaaaga ctacatcatt cctgacctgc tcggtggact cagcgggggga    360

tccatccagg tcccacaagg catggcattt gctctgctgg ccaaccttcc tgcagtcaat    420

ggcctctact cctccttctt ccccctcctg acctacttct tcctgggggg tgttcaccag    480

atggtgccag gtacctttgc cgttatcagc atcctggtgg gtaacatctg tctgcagctg    540

gccccagagt cgaaattcca ggtcttcaac aatgccacca atgagagcta tgtggacaca    600

gcagccatgg aggctgagag gctgcacgtg tcagctacgc tagcctgcct caccgccatc    660

atccagatgg gtctgggctt catgcagttt ggctttgtgg ccatctacct ctccgagtcc    720

ttcatccggg gcttcatgac ggccgccggc ctgcagatcc tgatttcggt gctcaagtac    780

atcttcggac tgaccatccc ctcctacaca ggcccagggt ccatcgtctt taccttcatt    840

gacatttgca aaaacctccc ccacaccaac atcgcctcgc tcatcttcgc tctcatcagc    900

ggtgccttcc tggtgctggt gaaggagctc aatgctcgct acatgcacaa gattcgcttc    960

cccatcccta cagagatgat tgtggtggtg gtggcaacag ctatctccgg gggctgtaag   1020

atgcccaaaa agtatcacat gcagatcgtg ggagaaatcc aacgcgggtt ccccaccccg   1080

gtgtcgcctg tggtctcaca gtggaaggac atgataggca cagccttctc cctagccatc   1140

gtgagctacg tcatcaacct ggctatgggc cggaccctgg ccaacaagca cggctacgac   1200

gtggattcga accaggagat gatcgctctc ggctgcagca acttctttgg ctccttcttt   1260

aaaattcatg tcatttgctg tgcgctttct gtcactctgg ctgtggatgg agctggagga   1320

aaatcccagg tggccagcct gtgtgtgtct ctggtggtga tgatcaccat gctggtcctg   1380

gggatctatc tgtatcctct ccctaagtct gtgctaggag ccctgatcgc tgtcaatctc   1440
```

-continued

```
aagaactccc tcaagcaact caccgacccc tactacctgt ggaggaagag caagctggac   1500
tgttgcatct gggtagtgag cttcctctcc tccttcttcc tcagcctgcc ctatggtgtg   1560
gcagtgggtg tcgccttctc cgtcctggtc gtggtcttcc agactcagtt tcgaaatggc   1620
tatgcactgg cccaggtcat ggacactgac atttatgtga atcccaagac ctataatagg   1680
gcccaggata tccaggggat taaaatcatc acgtactgct cccctctcta ctttgccaac   1740
tcagagatct tcaggcaaaa ggtcatcgcc aagacaggca tggacccccca gaaagtatta   1800
ctagccaagc aaaaatacct caagaagcag gagaagcgga gaatgaggcc cacacaacag   1860
aggaggtctc tattcatgaa aaccaagact gtctccctgc aggagctgca gcaggacttt   1920
gagaatgcgc cccccaccga ccccaacaac aaccagaccc cggctaacgg caccagcgtg   1980
tcctatatca ccttcagccc tgacagctcc tcacctgccc agagtgagcc accagcctcc   2040
gctgaggccc ccggcgagcc cagtgacatg ctggccagcg tcccaccctt cgtcaccttc   2100
cacaccctca tcctggacat gagtggagtc agcttcgtgg acttgatggg catcaaggcc   2160
ctggccaagc tgagctccac ctatgggaag atcggcgtga aggtcttctt ggtgaacatc   2220
catgcccagg tgtacaatga cattagccat ggaggcgtct ttgaggatgg gagtctagaa   2280
tgcaagcacg tctttcccag catacatgac gcagtcctct ttgcccaggc aaatgctaga   2340
gacgtgaccc caggacacaa cttccaaggg gctccagggg atgctgagct ctccttgtac   2400
gactcagagg aggacattcg cagctactgg gacttagagc aggagatgtt cgggagcatg   2460
tttcacgcag agaccctgac cgccctgtga gggctcagcc agtcctcatg ctgcctacag   2520
agtgcctggc acttgggact tccataaagg atgagcctgg ggtcacaggg ggtgtcgggc   2580
ggaggaaagt gcatcccccca gagcttgggt tcctctctcc tctccccctc tctcctccct   2640
tccttccctc cccgcatctc cagagagagc ctctcagcag cagggggggtg ctacccttac   2700
gggagtgaga gtctggtgag cccactcttc acccgtcagg ccctggccgc aatggacaag   2760
cctcctgctc actccacccc acccacatct gccctgtcct tggcagctga aggacacctt   2820
gacttccagc ttttacgagt gagccaaaaa cagaaggaca agtacaactg tgctggcctg   2880
ctgtacaagc ttcaaaaagt gtcccagagc ccgcacggct cggtgtcaga tggtgtcagg   2940
ctgtcacgga catagggata aacttggtta ggactctggc ttgccttccc cagctgcctc   3000
aactctgtct ctggcagctc tgcacccagg gaccatgtgc tctccacacc caggagtcta   3060
ggccttggta actatgcgcc ccccctccat catccccaag gctgcccaaa ccaccactgc   3120
tgtcagcaag cacatcagac tctagcctgg acagtggcca ggaccgtcga gaccaccaga   3180
gctacctccc cggggacagc ccactaaggt tctgcctcag cctcctgaaa catcactgcc   3240
ctcagaggct gctcccttcc cctggaggct ggctagaaac cccaaagagg gggatgggta   3300
gctggcagaa tcatctggca tcctagtaat agataccagt tattctgcac aaaacttttg   3360
ggaattcctc tttgcaccca gagactcaga ggggaagagg gtgctagtac caacacaggg   3420
aaaacggatg ggacctgggc ccagacagtc cccccttgacc ccagggccca tcagggaaat   3480
gcctcccttt ggtaaatctg ccttatcctt ctttacctgg caaagagcca atcatgttaa   3540
ctcttcctta tcagcctgtg gcccagagac acaatggggt ccttctgtag gcaaaggtgg   3600
aagtcctcca gggatccgct acatccccta actgcatgca gatgtggaaa ggggctgatc   3660
cagattgggt cttcctgcac aggaagactc tttaacaccc ttaggacctc aggccatctt   3720
ctcctatgaa gatgaaaata ggggttaagt tttccatatg tacaaggagg tattgagagg   3780
```

-continued

```
aaccctactg ttgacttgaa aataaatagg ttccatgtgt aagtgttttg taaaatttca   3840

gtggaaatgc acagaaaatc ttctggcctc tcatcactgc ttttctcaag cttcttcagc   3900

ttaacaaccc cttccctaac aggttgggct ggcccagcct aggaaaacat ccccatttct   3960

aacttcagcc agacctgcgt tgtgtgtctg tgtgttgagt gagctggtca gctaacaagt   4020

cttcttagag ttaaaggagg gggtgctggc caagagccaa cacattcttg gcccaggagc   4080

attgcttttc tgtgaattca ttatgccatc tggctgccaa tggaactcaa aacttggaag   4140

gcgaaggaca atgttatctg ggattcaccg tgcccagcac ccgaagtgcc aaattccagg   4200

aggacaagag ccttagccaa tgacaactca ctctccccta ctccacctcc ttccaagtcc   4260

agctcaggcc caggaggtgg gagaaggtca cagagcctca ggaatttcca agtcagagtc   4320

ccctttgaac caagtatcta gatcccctga ggacttgatg aagtgatcct taacccccaa   4380

gtaatcatta acccccagac cagcctcaga actgaaggag attgttgacc cagtgacctg   4440

gagttgaggc tcagggagag atctgccaca tgtctgaggg ttgcagagcc cgctgtggag   4500

gtaagattgg aaacacatga ggcagaggga agacattgaa gaaaacatct ctgctggaat   4560

atttggaaaa gaacactctt ctggacctgg ttgaagcagg aaagatggag gcaaagtagt   4620

gaaataatcc agaatttcaa tgcttttgaa tgttcttagt gatactgacc tgtgataata   4680

taattcccag ggaggactgg gaaccttatc tcttgagata tttgcataat ttatttaatt   4740

taagcctcat tctcctttg ttcattttgg taataaactg gatttgaatt gtgaacaaaa   4800

aaaaaaaaaa aaaaa                                                     4815
```

<210> SEQ ID NO 57
<211> LENGTH: 2572
<212> TYPE: DNA
<213> ORGANISM: Homo sapiens

<400> SEQUENCE: 57

```
aatgctctaa gacctctcag cacgggcgga agaaactccc ggagagctca cccaaaaaac     60

aaggagatcc catctagatt tcttcttgct tttgactcac agctggaagt tagaaaagcc    120

tcgatttcat ctttggagag gccaaatggt cttagcctca gtctctgtct ctaaatattc    180

caccataaaa cagctgagtt atttatgaat tagaggctat agctcacatt ttcaatcctc    240

tatttctttt tttaaatata actttctact ctgatgagag aatgtggttt taatctctct    300

ctcacatttt gatgatttag acagactccc cctcttcctc ctagtcaata aacccattga    360

tgatctattt cccagcttat ccccaagaaa actttttgaaa ggaaagagta gacccaaaga    420

tgttattttc tgctgtttga attttgtctc cccaccccca acttggctag taataaacac    480

ttactgaaga agaagcaata agagaaagat atttgtaatc tctccagccc atgatctcgg    540

ttttcttaca ctgtgatctt aaaagttacc aaaccaaagt cattttcagt ttgaggcaac    600

caaacctttc tactgctgtt gacatcttct tattacagca acaccattct aggagtttcc    660

tgagctctcc actggagtcc tctttctgtc gcgggtcaga aattgtccct agatgaatga    720

gaaaattatt ttttttaatt taagtcctaa atatagttaa aataaataat gttttagtaa    780

aatgatacac tatctctgtg aaatagcctc acccctacat gtggatagaa ggaaatgaaa    840

aaataattgc tttgacattg tctatatggt actttgtaaa gtcatgctta agtacaaatt    900

ccatgaaaag ctcactgatc ctaattcttt ccctttgagg tctctatggc tctgattgta    960

catgatagta agtgtaagcc atgtaaaaag taaataatgt ctgggcacag tggctcacgc   1020

ctgtaatcct agcactttgg gaggctgagg aggaaggatc acttgagccc agaagttcga   1080
```

-continued

```
gactagcctg ggcaacatgg agaagccctg tctctacaaa atacagagag aaaaaatcag   1140
ccagtcatgg tggcatacac ctgtagtccc agcattccgg gaggctgagg tgggaggatc   1200
acttgagccc agggaggttg gggctgcagt gagccatgat cacaccactg cactccagcc   1260
aggtgacata gcgagatcct gtctaaaaaa ataaaaaata aataatggaa cacagcaagt   1320
cctaggaagt aggttaaaac taattcttta aaaaaaaaaa aaagttgagc ctgaattaaa   1380
tgtaatgttt ccaagtgaca ggtatccaca tttgcatggt tacaagccac tgccagttgg   1440
cagtagcact ttcctggcac tgtggtcggt tttgttttgt tttgctttgt ttagagacgg   1500
ggtctcactt tccaggctgg cctcaaactc ctgcactcaa gcaattcttc taccctggcc   1560
tcccaagtag ctggaattac aggtgtgcgc catcacaact agctggtggt cagttttgtt   1620
actctgagag ctgttcactt ctctgaattc acctagagtg gttggaccat cagatgtttg   1680
ggcaaaactg aaagctcttt gcaaccacac accttccctg agcttacatc actgcccttt   1740
tgagcagaaa gtctaaattc cttccaagac agtagaattc catcccagta ccaaagccag   1800
ataggccccc taggaaactg aggtaagagc agtctctaaa aactacccac agcagcattg   1860
gtgcagggga acttggccat taggttatta tttgagagga aagtcctcac atcaatagta   1920
catatgaaag tgacctccaa ggggattggt gaatactcat aaggatcttc aggctgaaca   1980
gactatgtct ggggaaagaa cggattatgc cccattaaat aacaagttgt gttcaagagt   2040
cagagcagtg agctcagagg cccttctcac tgagacagca acatttaaac caaaccagag   2100
gaagtatttg tggaactcac tgcctcagtt tgggtaaagg atgagcagac aagtcaacta   2160
aagaaaaaag aaaagcaagg aggagggttg agcaatctag agcatggagt ttgttaagtg   2220
ctctctggat ttgagttgaa gagcatccat ttgagttgaa ggccacaggg cacaatgagc   2280
tctcccttct accaccagaa agtccctggt caggtctcag gtagtgcggt gtggctcagc   2340
tgggttttta attagcgcat tctctatcca acatttaatt gtttgaaagc ctccatatag   2400
ttagattgtg ctttgtaatt ttgttgttgt tgctctatct tattgtatat gcattgagta   2460
ttaacctgaa tgttttgtta cttaaatatt aaaaacactg ttatcctaca aaaaaaccct   2520
caaaggctga aaataaagaa ggaagatgga gacaccctct gggggtcctc tc           2572
```

<210> SEQ ID NO 58
<211> LENGTH: 1324
<212> TYPE: DNA
<213> ORGANISM: Homo sapiens

<400> SEQUENCE: 58

```
ctttgcagtg gatgcccttg gcagggtgag cccacaagga gcaatggagc agggcagcgg     60
ccgcttggag gacttccctg tcaatgtgtt ctccgtcact ccttacacac ccagcaccgc    120
tgacatccag gtgtccgatg atgacaaggc gggggccacc ttgctcttct caggcatctt    180
tctgggactg gtggggatca cattcactgt catgggctgg atcaaatacc aaggtgtctc    240
ccactttgaa tggacccagc tccttgggcc cgtcctgctg tcagttgggg tgacattcat    300
cctgattgct gtgtgcaagt tcaaaatgct ctcctgccag ttgtgcaaag aaagtgagga    360
aagggtcccg gactcggaac agacaccagg aggaccatca tttgttttca ctggcatcaa    420
ccaacccatc accttccatg ggccactgt ggtgcagtac atccctcctc cttatggttc    480
tccagagcct atggggataa ataccagcta cctgcagtct gtggtgagcc cctgcggcct    540
cataacctct ggaggggcag cagccgccat gtcaagtcct cctcaatact acaccatcta    600
```

-continued

```
ccctcaagat aactctgcat ttgtggttga tgagggctgc ctttctttca cggacggtgg     660

aaatcacagg cccaatcctg atgttgacca gctagaagag acacagctgg aagaggaggc     720

ctgtgcctgc ttctctcctc ccccttatga agaaatatac tctctccctc gctagaggct     780

attctgatat aataacacaa tgctcagctc agggagcaag tgtttccgtc attgttacct     840

gacaaccgtg gtgttctatg ttgtaacctt cagaagttac agcagcgccc aggcagcctg     900

acagagatca ttcaaggggg gaaaggggaa gtgggaggtg caatttctca gattggtaaa     960

aattaggctg ggctggggaa attctcctcc ggaacagttt caaattccct cgggtaagaa    1020

atctcctgta taaggttcag gagcaggaat ttcacttttt catccaccac cctcccccctt    1080

ctctgtagga aggcattggt ggctcaattt taaccccagc agccaatgga aaaatcacga    1140

cttctgagac tttgggagtt tccacagagg tgagagtcgg gtgggaagga agcagggaag    1200

agaaagcagg cccagctgga gatttcctgg tggctgtcct tggccccaaa gcagactcac    1260

taatcccaaa caactcagct gccatctggc ctctctgagg actctgggta ccttaaagac    1320

tata                                                                 1324


<210> SEQ ID NO 59
<211> LENGTH: 683
<212> TYPE: DNA
<213> ORGANISM: Homo sapiens

<400> SEQUENCE: 59

caggaaagtt cgtgctgcta ggcagaggaa ctgcagcttg ttggcaggtg aagggagcct      60

gtttagctgt gtccagcaac aacttacgtg gtcctgcttg tgttccaggt gaagcgtctg     120

gccgccgagc agaggaatca agacctgctc attctttcct cgggggatcc atccagcaat     180

gacatcatct catgctgcca caaggacccc aagtctgggc tgctggggac cagccacgct     240

ccccactgct cattccttca tcctagagac attctgactc tcctccgact gcgctgtgca     300

caggcgtgac aagctctttt acatctcagt ctgcacaact tcaggcactt agcagattga     360

tatgcatcca acaaatattg attgaatatc tgctaaatac ccagtaatgt ttcatgagtg     420

attgggtgaa taaaggaatg ctggttcctt ctggccatat taactcctgc acaatactaa     480

gaaaaataaa ttgcactagc tgtggaataa tgtgaatccc aatgtcatct attgaaatat     540

tacctgacta ttaagaggta tttatttttg tatcttttct agcaaagtaa ataaaattct     600

taatacagca tatcccctta ttcacggggg gtatgttcca agacccccgg tggatgcctg     660

aaactatgga taataccaga tcc                                             683


<210> SEQ ID NO 60
<211> LENGTH: 914
<212> TYPE: PRT
<213> ORGANISM: Homo sapiens

<400> SEQUENCE: 60

Met Gly Pro Phe Lys Ser Ser Val Phe Ile Leu Ile Leu His Leu Leu
1               5                   10                  15

Glu Gly Ala Leu Ser Asn Ser Leu Ile Gln Leu Asn Asn Asn Gly Tyr
            20                  25                  30

Glu Gly Ile Val Val Ala Ile Asp Pro Asn Val Pro Glu Asp Glu Thr
        35                  40                  45

Leu Ile Gln Gln Ile Lys Asp Met Val Thr Gln Ala Ser Leu Tyr Leu
    50                  55                  60

Phe Glu Ala Thr Gly Lys Arg Phe Tyr Phe Lys Asn Val Ala Ile Leu
```

-continued

```
65                  70                  75                  80

Ile Pro Glu Thr Trp Lys Thr Lys Ala Asp Tyr Val Arg Pro Lys Leu
                85                  90                  95

Glu Thr Tyr Lys Asn Ala Asp Val Leu Val Ala Glu Ser Thr Pro Pro
            100                 105                 110

Gly Asn Asp Glu Pro Tyr Thr Glu Gln Met Gly Asn Cys Gly Glu Lys
        115                 120                 125

Gly Glu Arg Ile His Leu Thr Pro Asp Phe Ile Ala Gly Lys Lys Leu
    130                 135                 140

Ala Glu Tyr Gly Pro Gln Gly Lys Ala Phe Val His Glu Trp Ala His
145                 150                 155                 160

Leu Arg Trp Gly Val Phe Asp Glu Tyr Asn Asn Asp Glu Lys Phe Tyr
                165                 170                 175

Leu Ser Asn Gly Arg Ile Gln Ala Val Arg Cys Ser Ala Gly Ile Thr
            180                 185                 190

Gly Thr Asn Val Val Lys Lys Cys Gln Gly Gly Ser Cys Tyr Thr Lys
        195                 200                 205

Arg Cys Thr Phe Asn Lys Val Thr Gly Leu Tyr Glu Lys Gly Cys Glu
    210                 215                 220

Phe Val Leu Gln Ser Arg Gln Thr Glu Lys Ala Ser Ile Met Phe Ala
225                 230                 235                 240

Gln His Val Asp Ser Ile Val Glu Phe Cys Thr Glu Gln Asn His Asn
                245                 250                 255

Lys Glu Ala Pro Asn Lys Gln Asn Gln Lys Cys Asn Leu Arg Ser Thr
            260                 265                 270

Trp Glu Val Ile Arg Asp Ser Glu Asp Phe Lys Lys Thr Thr Pro Met
        275                 280                 285

Thr Thr Gln Pro Pro Asn Pro Thr Phe Ser Leu Leu Gln Ile Gly Gln
    290                 295                 300

Arg Ile Val Cys Leu Val Leu Asp Lys Ser Gly Ser Met Ala Thr Gly
305                 310                 315                 320

Asn Arg Leu Asn Arg Leu Asn Gln Ala Gly Gln Leu Phe Leu Leu Gln
                325                 330                 335

Thr Val Glu Leu Gly Ser Trp Val Gly Met Val Thr Phe Asp Ser Ala
            340                 345                 350

Ala His Val Gln Ser Glu Leu Ile Gln Ile Asn Ser Gly Ser Asp Arg
        355                 360                 365

Asp Thr Leu Ala Lys Arg Leu Pro Ala Ala Ala Ser Gly Gly Thr Ser
    370                 375                 380

Ile Cys Ser Gly Leu Arg Ser Ala Phe Thr Val Ile Arg Lys Lys Tyr
385                 390                 395                 400

Pro Thr Asp Gly Ser Glu Ile Val Leu Leu Thr Asp Gly Glu Asp Asn
                405                 410                 415

Thr Ile Ser Gly Cys Phe Asn Glu Val Lys Gln Ser Gly Ala Ile Ile
            420                 425                 430

His Thr Val Ala Leu Gly Pro Ser Ala Ala Gln Glu Leu Glu Glu Leu
        435                 440                 445

Ser Lys Met Thr Gly Gly Leu Gln Thr Tyr Ala Ser Asp Gln Val Gln
    450                 455                 460

Asn Asn Gly Leu Ile Asp Ala Phe Gly Ala Leu Ser Ser Gly Asn Gly
465                 470                 475                 480

Ala Val Ser Gln Arg Ser Ile Gln Leu Glu Ser Lys Gly Leu Thr Leu
                485                 490                 495
```

-continued

```
Gln Asn Ser Gln Trp Met Asn Gly Thr Val Ile Val Asp Ser Thr Val
            500                 505                 510

Gly Lys Asp Thr Leu Phe Leu Ile Thr Trp Thr Thr Gln Pro Pro Gln
        515                 520                 525

Ile Leu Leu Trp Asp Pro Ser Gly Gln Lys Gln Gly Gly Phe Val Val
    530                 535                 540

Asp Lys Asn Thr Lys Met Ala Tyr Leu Gln Ile Pro Gly Ile Ala Lys
545                 550                 555                 560

Val Gly Thr Trp Lys Tyr Ser Leu Gln Ala Ser Ser Gln Thr Leu Thr
                565                 570                 575

Leu Thr Val Thr Ser Arg Ala Ser Asn Ala Thr Leu Pro Pro Ile Thr
            580                 585                 590

Val Thr Ser Lys Thr Asn Lys Asp Thr Ser Lys Phe Pro Ser Pro Leu
        595                 600                 605

Val Val Tyr Ala Asn Ile Arg Gln Gly Ala Ser Pro Ile Leu Arg Ala
    610                 615                 620

Ser Val Thr Ala Leu Ile Glu Ser Val Asn Gly Lys Thr Val Thr Leu
625                 630                 635                 640

Glu Leu Leu Asp Asn Gly Ala Gly Ala Asp Ala Thr Lys Asp Asp Gly
                645                 650                 655

Val Tyr Ser Arg Tyr Phe Thr Thr Tyr Asp Thr Asn Gly Arg Tyr Ser
            660                 665                 670

Val Lys Val Arg Ala Leu Gly Gly Val Asn Ala Ala Arg Arg Arg Val
        675                 680                 685

Ile Pro Gln Gln Ser Gly Ala Leu Tyr Ile Pro Gly Trp Ile Glu Asn
    690                 695                 700

Asp Glu Ile Gln Trp Asn Pro Pro Arg Pro Glu Ile Asn Lys Asp Asp
705                 710                 715                 720

Val Gln His Lys Gln Val Cys Phe Ser Arg Thr Ser Ser Gly Gly Ser
                725                 730                 735

Phe Val Ala Ser Asp Val Pro Asn Ala Pro Ile Pro Asp Leu Phe Pro
            740                 745                 750

Pro Gly Gln Ile Thr Asp Leu Lys Ala Glu Ile His Gly Gly Ser Leu
        755                 760                 765

Ile Asn Leu Thr Trp Thr Ala Pro Gly Asp Asp Tyr Asp His Gly Thr
    770                 775                 780

Ala His Lys Tyr Ile Ile Arg Ile Ser Thr Ser Ile Leu Asp Leu Arg
785                 790                 795                 800

Asp Lys Phe Asn Glu Ser Leu Gln Val Asn Thr Thr Ala Leu Ile Pro
                805                 810                 815

Lys Glu Ala Asn Ser Glu Glu Val Phe Leu Phe Lys Pro Glu Asn Ile
            820                 825                 830

Thr Phe Glu Asn Gly Thr Asp Leu Phe Ile Ala Ile Gln Ala Val Asp
        835                 840                 845

Lys Val Asp Leu Lys Ser Glu Ile Ser Asn Ile Ala Arg Val Ser Leu
    850                 855                 860

Phe Ile Pro Pro Gln Thr Pro Pro Glu Thr Pro Ser Pro Asp Glu Thr
865                 870                 875                 880

Ser Ala Pro Cys Pro Asn Ile His Ile Asn Ser Thr Ile Pro Gly Ile
                885                 890                 895

His Ile Leu Lys Ile Met Trp Lys Trp Ile Gly Glu Leu Gln Leu Ser
            900                 905                 910
```

-continued

```
Ile Ala


<210> SEQ ID NO 61
<211> LENGTH: 501
<212> TYPE: PRT
<213> ORGANISM: Homo sapiens

<400> SEQUENCE: 61

Met Lys Lys Glu Gly Arg Lys Arg Trp Lys Arg Lys Glu Asp Lys Lys
1               5                   10                  15

Arg Val Val Val Ser Asn Leu Leu Phe Glu Gly Trp Ser His Lys Glu
            20                  25                  30

Asn Pro Asn Arg His His Arg Gly Asn Gln Ile Lys Thr Ser Lys Tyr
        35                  40                  45

Thr Val Leu Ser Phe Val Pro Lys Asn Ile Phe Glu Gln Leu His Arg
    50                  55                  60

Phe Ala Asn Leu Tyr Phe Val Gly Ile Ala Val Leu Asn Phe Ile Pro
65                  70                  75                  80

Val Val Asn Ala Phe Gln Pro Glu Val Ser Met Ile Pro Ile Cys Val
                85                  90                  95

Ile Leu Ala Val Thr Ala Ile Lys Asp Ala Trp Glu Asp Leu Arg Arg
            100                 105                 110

Tyr Lys Ser Asp Lys Val Ile Asn Asn Arg Glu Cys Leu Ile Tyr Ser
        115                 120                 125

Arg Lys Glu Gln Thr Tyr Val Gln Lys Cys Trp Lys Asp Val Arg Val
    130                 135                 140

Gly Asp Phe Ile Gln Met Lys Cys Asn Glu Ile Val Pro Ala Asp Ile
145                 150                 155                 160

Leu Leu Leu Phe Ser Ser Asp Pro Asn Gly Ile Cys His Leu Glu Thr
                165                 170                 175

Ala Ser Leu Asp Gly Glu Thr Asn Leu Lys Gln Arg Arg Val Val Lys
            180                 185                 190

Gly Phe Ser Gln Gln Glu Val Gln Phe Glu Pro Glu Leu Phe His Asn
        195                 200                 205

Thr Ile Val Cys Glu Lys Pro Asn Asn His Leu Asn Lys Phe Lys Gly
    210                 215                 220

Tyr Met Glu His Pro Asp Gln Thr Arg Thr Gly Phe Gly Cys Glu Ser
225                 230                 235                 240

Leu Leu Leu Arg Gly Cys Thr Ile Arg Asn Thr Glu Met Ala Val Gly
                245                 250                 255

Ile Val Ile Tyr Ala Gly His Glu Thr Lys Ala Met Leu Asn Asn Ser
            260                 265                 270

Gly Pro Arg Tyr Lys Arg Ser Lys Ile Glu Arg Arg Met Asn Ile Asp
        275                 280                 285

Ile Phe Phe Cys Ile Gly Ile Leu Ile Leu Met Cys Leu Ile Gly Ala
    290                 295                 300

Val Gly His Ser Ile Trp Asn Gly Thr Phe Glu Glu His Pro Pro Phe
305                 310                 315                 320

Asp Val Pro Asp Ala Asn Gly Ser Phe Leu Pro Ser Ala Leu Gly Gly
                325                 330                 335

Phe Tyr Met Phe Leu Thr Met Ile Ile Leu Leu Gln Val Leu Ile Pro
            340                 345                 350

Ile Ser Leu Tyr Val Ser Ile Glu Leu Val Lys Leu Gly Gln Val Phe
        355                 360                 365
```

-continued

```
Phe Leu Ser Asn Asp Leu Asp Leu Tyr Asp Glu Glu Thr Asp Leu Ser
    370                 375                 380

Ile Gln Cys Arg Ala Leu Asn Ile Ala Glu Asp Leu Gly Gln Ile Gln
385                 390                 395                 400

Tyr Ile Phe Ser Asp Lys Thr Gly Thr Leu Thr Glu Asn Lys Met Val
                405                 410                 415

Phe Arg Arg Cys Thr Ile Met Gly Ser Glu Tyr Ser His Gln Glu Asn
            420                 425                 430

Gly Ile Glu Ala Pro Lys Gly Ser Ile Pro Leu Ser Lys Arg Lys Tyr
        435                 440                 445

Pro Ala Leu Leu Arg Asn Glu Glu Ile Lys Asp Ile Leu Leu Ala Leu
    450                 455                 460

Leu Glu Ala Val Trp His Phe His Lys Leu Leu Pro Val Ser Leu Trp
465                 470                 475                 480

Ser Ser Leu Ser Gln Ile Arg Ala Val Pro Ile Thr Cys Lys Leu Ser
                485                 490                 495

Phe Val Tyr Lys Gly
            500


<210> SEQ ID NO 62
<211> LENGTH: 154
<212> TYPE: PRT
<213> ORGANISM: Homo sapiens

<400> SEQUENCE: 62

Met Gly Arg Arg Ser Pro Phe Lys Pro Arg Asn Lys Val Phe Gly Phe
1               5                   10                  15

Ser Tyr Pro Trp Cys Arg Ser Tyr Gln Pro Phe Pro Arg Lys Arg Ala
            20                  25                  30

Trp Pro Pro Ser Arg Val Trp Leu Gly Ala Cys Cys Ala Ser Leu Ala
        35                  40                  45

Ser Pro Pro Lys Gly Thr Ile Pro Ser Gly Glu Tyr Tyr Arg Pro Ala
    50                  55                  60

Pro Ser Ser Ser Gly Asp Ser Leu Arg Arg Glu Ser Gly Ala Leu Leu
65                  70                  75                  80

Gln Tyr Leu Pro Ser Leu Ala Ser Pro Cys Ala Asn His Ala Thr Arg
                85                  90                  95

Cys Ser Leu Leu Phe Pro Ile Tyr Lys Ile Lys Met Thr Leu Leu Tyr
            100                 105                 110

Leu Thr Gly Leu Ala Arg Thr His Cys Cys Cys Leu Ala Asp Arg Cys
        115                 120                 125

Ala Glu Ala Val Glu Ser Ala Phe Tyr Leu Val Gly Ser Leu Cys Ile
    130                 135                 140

Asn Ala Arg Gly Ala Ala His Leu Thr Asp
145                 150


<210> SEQ ID NO 63
<211> LENGTH: 484
<212> TYPE: PRT
<213> ORGANISM: Homo sapiens

<400> SEQUENCE: 63

Met Ala Gly Pro Trp Thr Phe Thr Leu Leu Cys Gly Leu Leu Ala Ala
1               5                   10                  15

Thr Leu Ile Gln Ala Thr Leu Ser Pro Thr Ala Val Leu Ile Leu Gly
            20                  25                  30
```

-continued

```
Pro Lys Val Ile Lys Glu Lys Leu Thr Gln Glu Leu Lys Asp His Asn
        35                  40                  45

Ala Thr Ser Ile Leu Gln Gln Leu Pro Leu Leu Ser Ala Met Arg Glu
    50                  55                  60

Lys Pro Ala Gly Gly Ile Pro Val Leu Gly Ser Leu Val Asn Thr Val
65                  70                  75                  80

Leu Lys His Ile Ile Trp Leu Lys Val Ile Thr Ala Asn Ile Leu Gln
                85                  90                  95

Leu Gln Val Lys Pro Ser Ala Asn Asp Gln Glu Leu Leu Val Lys Ile
            100                 105                 110

Pro Leu Asp Met Val Ala Gly Phe Asn Thr Pro Leu Val Lys Thr Ile
        115                 120                 125

Val Glu Phe His Met Thr Thr Glu Ala Gln Ala Thr Ile Arg Met Asp
    130                 135                 140

Thr Ser Ala Ser Gly Pro Thr Arg Leu Val Leu Ser Asp Cys Ala Thr
145                 150                 155                 160

Ser His Gly Ser Leu Arg Ile Gln Leu Leu His Lys Leu Ser Phe Leu
                165                 170                 175

Val Asn Ala Leu Ala Lys Gln Val Met Asn Leu Leu Val Pro Ser Leu
            180                 185                 190

Pro Asn Leu Val Lys Asn Gln Leu Cys Pro Val Ile Glu Ala Ser Phe
        195                 200                 205

Asn Gly Met Tyr Ala Asp Leu Leu Gln Leu Val Lys Val Pro Ile Ser
    210                 215                 220

Leu Ser Ile Asp Arg Leu Glu Phe Asp Leu Leu Tyr Pro Ala Ile Lys
225                 230                 235                 240

Gly Asp Thr Ile Gln Leu Tyr Leu Gly Ala Lys Leu Leu Asp Ser Gln
                245                 250                 255

Gly Lys Val Thr Lys Trp Phe Asn Asn Ser Ala Ala Ser Leu Thr Met
            260                 265                 270

Pro Thr Leu Asp Asn Ile Pro Phe Ser Leu Ile Val Ser Gln Asp Val
        275                 280                 285

Val Lys Ala Ala Val Ala Ala Val Leu Ser Pro Glu Glu Phe Met Val
    290                 295                 300

Leu Leu Asp Ser Val Leu Pro Glu Ser Ala His Arg Leu Lys Ser Ser
305                 310                 315                 320

Ile Gly Leu Ile Asn Glu Lys Ala Ala Asp Lys Leu Gly Ser Thr Gln
                325                 330                 335

Ile Val Lys Ile Leu Thr Gln Asp Thr Pro Glu Phe Phe Ile Asp Gln
            340                 345                 350

Gly His Ala Lys Val Ala Gln Leu Ile Val Leu Glu Val Phe Pro Ser
        355                 360                 365

Ser Glu Ala Leu Arg Pro Leu Phe Thr Leu Gly Ile Glu Ala Ser Ser
    370                 375                 380

Glu Ala Gln Phe Tyr Thr Lys Gly Asp Gln Leu Ile Leu Asn Leu Asn
385                 390                 395                 400

Asn Ile Ser Ser Asp Arg Ile Gln Leu Met Asn Ser Gly Ile Gly Trp
                405                 410                 415

Phe Gln Pro Asp Val Leu Lys Asn Ile Ile Thr Glu Ile Ile His Ser
            420                 425                 430

Ile Leu Leu Pro Asn Gln Asn Gly Lys Leu Arg Ser Gly Val Pro Val
        435                 440                 445

Ser Leu Val Lys Ala Leu Gly Phe Glu Ala Ala Glu Ser Ser Leu Thr
```

-continued

```
    450                 455                 460

Lys Asp Ala Leu Val Leu Thr Pro Ala Ser Leu Trp Lys Pro Ser Ser
465                 470                 475                 480

Pro Val Ser Gln


<210> SEQ ID NO 64
<211> LENGTH: 256
<212> TYPE: PRT
<213> ORGANISM: Homo sapiens

<400> SEQUENCE: 64

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
    50                  55                  60

Leu Gly Ile Leu Glu Asn Leu Pro Leu Leu Asp Ile Leu Lys Pro Gly
65                  70                  75                  80

Gly Gly Thr Ser Gly Gly Leu Leu Gly Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
        115                 120                 125

Leu Tyr Val Thr Ile Pro Leu Gly Ile Lys Leu Gln Val Asn Thr Pro
    130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
        195                 200                 205

Gly Ile Leu Asn Lys Val Leu Pro Glu Leu Val Gln Gly Asn Val Cys
    210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255


<210> SEQ ID NO 65
<211> LENGTH: 791
<212> TYPE: PRT
<213> ORGANISM: Homo sapiens

<400> SEQUENCE: 65

Met Ser Gln Pro Arg Pro Arg Tyr Val Val Asp Arg Ala Ala Tyr Ser
1               5                   10                  15

Leu Thr Leu Phe Asp Asp Glu Phe Glu Lys Lys Asp Arg Thr Tyr Pro
            20                  25                  30

Val Gly Glu Lys Leu Arg Asn Ala Phe Arg Cys Ser Ser Ala Lys Ile
        35                  40                  45
```

-continued

```
Lys Ala Val Val Phe Gly Leu Leu Pro Val Leu Ser Trp Leu Pro Lys
    50                  55                  60

Tyr Lys Ile Lys Asp Tyr Ile Ile Pro Asp Leu Leu Gly Gly Leu Ser
65                  70                  75                  80

Gly Gly Ser Ile Gln Val Pro Gln Gly Met Ala Phe Ala Leu Leu Ala
                85                  90                  95

Asn Leu Pro Ala Val Asn Gly Leu Tyr Ser Ser Phe Phe Pro Leu Leu
            100                 105                 110

Thr Tyr Phe Phe Leu Gly Gly Val His Gln Met Val Pro Gly Thr Phe
        115                 120                 125

Ala Val Ile Ser Ile Leu Val Gly Asn Ile Cys Leu Gln Leu Ala Pro
    130                 135                 140

Glu Ser Lys Phe Gln Val Phe Asn Asn Ala Thr Asn Glu Ser Tyr Val
145                 150                 155                 160

Asp Thr Ala Ala Met Glu Ala Glu Arg Leu His Val Ser Ala Thr Leu
                165                 170                 175

Ala Cys Leu Thr Ala Ile Ile Gln Met Gly Leu Gly Phe Met Gln Phe
            180                 185                 190

Gly Phe Val Ala Ile Tyr Leu Ser Glu Ser Phe Ile Arg Gly Phe Met
        195                 200                 205

Thr Ala Ala Gly Leu Gln Ile Leu Ile Ser Val Leu Lys Tyr Ile Phe
    210                 215                 220

Gly Leu Thr Ile Pro Ser Tyr Thr Gly Pro Gly Ser Ile Val Phe Thr
225                 230                 235                 240

Phe Ile Asp Ile Cys Lys Asn Leu Pro His Thr Asn Ile Ala Ser Leu
                245                 250                 255

Ile Phe Ala Leu Ile Ser Gly Ala Phe Leu Val Leu Val Lys Glu Leu
            260                 265                 270

Asn Ala Arg Tyr Met His Lys Ile Arg Phe Pro Ile Pro Thr Glu Met
        275                 280                 285

Ile Val Val Val Val Ala Thr Ala Ile Ser Gly Gly Cys Lys Met Pro
    290                 295                 300

Lys Lys Tyr His Met Gln Ile Val Gly Glu Ile Gln Arg Gly Phe Pro
305                 310                 315                 320

Thr Pro Val Ser Pro Val Val Ser Gln Trp Lys Asp Met Ile Gly Thr
                325                 330                 335

Ala Phe Ser Leu Ala Ile Val Ser Tyr Val Ile Asn Leu Ala Met Gly
            340                 345                 350

Arg Thr Leu Ala Asn Lys His Gly Tyr Asp Val Asp Ser Asn Gln Glu
        355                 360                 365

Met Ile Ala Leu Gly Cys Ser Asn Phe Phe Gly Ser Phe Phe Lys Ile
    370                 375                 380

His Val Ile Cys Cys Ala Leu Ser Val Thr Leu Ala Val Asp Gly Ala
385                 390                 395                 400

Gly Gly Lys Ser Gln Val Ala Ser Leu Cys Val Ser Leu Val Val Met
                405                 410                 415

Ile Thr Met Leu Val Leu Gly Ile Tyr Leu Tyr Pro Leu Pro Lys Ser
            420                 425                 430

Val Leu Gly Ala Leu Ile Ala Val Asn Leu Lys Asn Ser Leu Lys Gln
        435                 440                 445

Leu Thr Asp Pro Tyr Tyr Leu Trp Arg Lys Ser Lys Leu Asp Cys Cys
    450                 455                 460
```

-continued

```
Ile Trp Val Val Ser Phe Leu Ser Ser Phe Phe Leu Ser Leu Pro Tyr
465                 470                 475                 480

Gly Val Ala Val Gly Val Ala Phe Ser Val Leu Val Val Val Phe Gln
                485                 490                 495

Thr Gln Phe Arg Asn Gly Tyr Ala Leu Ala Gln Val Met Asp Thr Asp
            500                 505                 510

Ile Tyr Val Asn Pro Lys Thr Tyr Asn Arg Ala Gln Asp Ile Gln Gly
        515                 520                 525

Ile Lys Ile Ile Thr Tyr Cys Ser Pro Leu Tyr Phe Ala Asn Ser Glu
    530                 535                 540

Ile Phe Arg Gln Lys Val Ile Ala Lys Thr Gly Met Asp Pro Gln Lys
545                 550                 555                 560

Val Leu Leu Ala Lys Gln Lys Tyr Leu Lys Lys Gln Glu Lys Arg Arg
                565                 570                 575

Met Arg Pro Thr Gln Gln Arg Arg Ser Leu Phe Met Lys Thr Lys Thr
            580                 585                 590

Val Ser Leu Gln Glu Leu Gln Gln Asp Phe Glu Asn Ala Pro Pro Thr
        595                 600                 605

Asp Pro Asn Asn Asn Gln Thr Pro Ala Asn Gly Thr Ser Val Ser Tyr
    610                 615                 620

Ile Thr Phe Ser Pro Asp Ser Ser Ser Pro Ala Gln Ser Glu Pro Pro
625                 630                 635                 640

Ala Ser Ala Glu Ala Pro Gly Glu Pro Ser Asp Met Leu Ala Ser Val
                645                 650                 655

Pro Pro Phe Val Thr Phe His Thr Leu Ile Leu Asp Met Ser Gly Val
            660                 665                 670

Ser Phe Val Asp Leu Met Gly Ile Lys Ala Leu Ala Lys Leu Ser Ser
        675                 680                 685

Thr Tyr Gly Lys Ile Gly Val Lys Val Phe Leu Val Asn Ile His Ala
    690                 695                 700

Gln Val Tyr Asn Asp Ile Ser His Gly Gly Val Phe Glu Asp Gly Ser
705                 710                 715                 720

Leu Glu Cys Lys His Val Phe Pro Ser Ile His Asp Ala Val Leu Phe
                725                 730                 735

Ala Gln Ala Asn Ala Arg Asp Val Thr Pro Gly His Asn Phe Gln Gly
            740                 745                 750

Ala Pro Gly Asp Ala Glu Leu Ser Leu Tyr Asp Ser Glu Glu Asp Ile
        755                 760                 765

Arg Ser Tyr Trp Asp Leu Glu Gln Glu Met Phe Gly Ser Met Phe His
    770                 775                 780

Ala Glu Thr Leu Thr Ala Leu
785                 790


<210> SEQ ID NO 66
<211> LENGTH: 243
<212> TYPE: PRT
<213> ORGANISM: Homo sapiens

<400> SEQUENCE: 66

Met Glu Gln Gly Ser Gly Arg Leu Glu Asp Phe Pro Val Asn Val Phe
1               5                   10                  15

Ser Val Thr Pro Tyr Thr Pro Ser Thr Ala Asp Ile Gln Val Ser Asp
            20                  25                  30

Asp Asp Lys Ala Gly Ala Thr Leu Leu Phe Ser Gly Ile Phe Leu Gly
        35                  40                  45
```

-continued

```
Leu Val Gly Ile Thr Phe Thr Val Met Gly Trp Ile Lys Tyr Gln Gly
    50                  55                  60

Val Ser His Phe Glu Trp Thr Gln Leu Leu Gly Pro Val Leu Leu Ser
65                  70                  75                  80

Val Gly Val Thr Phe Ile Leu Ile Ala Val Cys Lys Phe Lys Met Leu
            85                  90                  95

Ser Cys Gln Leu Cys Lys Glu Ser Glu Glu Arg Val Pro Asp Ser Glu
            100                 105                 110

Gln Thr Pro Gly Gly Pro Ser Phe Val Phe Thr Gly Ile Asn Gln Pro
        115                 120                 125

Ile Thr Phe His Gly Ala Thr Val Val Gln Tyr Ile Pro Pro Pro Tyr
    130                 135                 140

Gly Ser Pro Glu Pro Met Gly Ile Asn Thr Ser Tyr Leu Gln Ser Val
145                 150                 155                 160

Val Ser Pro Cys Gly Leu Ile Thr Ser Gly Gly Ala Ala Ala Ala Met
            165                 170                 175

Ser Ser Pro Pro Gln Tyr Tyr Thr Ile Tyr Pro Gln Asp Asn Ser Ala
            180                 185                 190

Phe Val Val Asp Glu Gly Cys Leu Ser Phe Thr Asp Gly Gly Asn His
        195                 200                 205

Arg Pro Asn Pro Asp Val Asp Gln Leu Glu Glu Thr Gln Leu Glu Glu
    210                 215                 220

Glu Ala Cys Ala Cys Phe Ser Pro Pro Pro Tyr Glu Glu Ile Tyr Ser
225                 230                 235                 240

Leu Pro Arg
```

```
<210> SEQ ID NO 67
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 67

acacgaatgg tagatacagt g                                            21


<210> SEQ ID NO 68
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 68

atacttgtga gctgttccat g                                            21


<210> SEQ ID NO 69
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 69

actgttacct tgcatggact g                                            21
```

-continued

<210> SEQ ID NO 70
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 70
caatgagaac acatggacat g 21

<210> SEQ ID NO 71
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 71
ccatgaaagc tccatgtcta c 21

<210> SEQ ID NO 72
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 72
agagatggca catattctgt c 21

<210> SEQ ID NO 73
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 73
atcggctgaa gtcaagcatc g 21

<210> SEQ ID NO 74
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 74
tggtcagtga ggactcagct g 21

<210> SEQ ID NO 75
<211> LENGTH: 21
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 75
tttctctgct tgatgcactt g 21

<210> SEQ ID NO 76

-continued

<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 76
gtgagcactg ggaagcagct c 21

<210> SEQ ID NO 77
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 77
ggcaaatgct agagacgtga c 21

<210> SEQ ID NO 78
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 78
aggtgtcctt cagctgccaa g 21

<210> SEQ ID NO 79
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 79
gttaagtgct ctctggattt g 21

<210> SEQ ID NO 80
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 80
atcctgattg ctgtgtgcaa g 21

<210> SEQ ID NO 81
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 81
ctcttctagc tggtcaacat c 21

<210> SEQ ID NO 82
<211> LENGTH: 21

-continued

<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 82
ccagcaacaa cttacgtggt c 21

<210> SEQ ID NO 83
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 83
cctttattca cccaatcact c 21

<210> SEQ ID NO 84
<211> LENGTH: 2165
<212> TYPE: DNA
<213> ORGANISM: Homo sapiens

<400> SEQUENCE: 84
agaacagcgc agtttgccct ccgctcacgc agagcctctc cgtggcctcc gcaccttgag 60
cattaggcca gttctcctct tctctctaat ccatccgtca cctctcctgt catccgtttc 120
catgccgtga ggtccattca cagaacacat ccatggctct catgctcagt ttggttctga 180
gtctcctcaa gctgggatca gggcagtggc aggtgtttgg gccagacaag cctgtccagg 240
ccttggtggg ggaggacgca gcattctcct gtttcctgtc tcctaagacc aatgcagagg 300
ccatggaagt gcggttcttc aggggccagt tctctagcgt ggtccacctc tacagggacg 360
ggaaggacca gccatttatg cagatgccac agtatcaagg caggacaaaa ctggtgaagg 420
attctattgc ggaggggcgc atctctctga ggctggaaaa cattactgtg ttggatgctg 480
gcctctatgg gtgcaggatt agttcccagt cttactacca gaaggccatc tgggagctac 540
aggtgtcagc actgggctca gttcctctca tttccatcac gggatatgtt gatagagaca 600
tccagctact ctgtcagtcc tcgggctggt tcccccggcc cacagcgaag tggaaaggtc 660
cacaaggaca ggatttgtcc acagactcca ggacaaacag agacatgcat ggcctgtttg 720
atgtggagat ctctctgacc gtccaagaga acgccgggag catatcctgt tccatgcggc 780
atgctcatct gagccgagag gtggaatcca gggtacagat aggagatacc tttttcgagc 840
ctatatcgtg gcacctggct accaaagtac tgggaatact ctgctgtggc ctattttttg 900
gcattgttgg actgaagatt ttcttctcca aattccagtg taagcgagag agagaagcat 960
gggccggtgc cttattcatg gttccagcag ggacaggatc agagatgctc ccacatccag 1020
ctgcttctct tcttctagtc ctagcctcca ggggcccagg cccaaaaaag gaaaatccag 1080
gcggaactgg actggagaag aaagcacgga caggcagaat tgagagacgc ccggaaacac 1140
gcagtggagg tgactctgga tccagagacg gctcacccga agctctgcgt ttctgatctg 1200
aaaactgtaa cccatagaaa agctccccag gaggtgcctc actctgagaa gagatttaca 1260
aggaagagtg tggtggcttc tcagagtttc caagcaggga aacattactg ggaggtggac 1320
ggaggacaca ataaaaggtg gcgcgtggga gtgtgccggg atgatgtgga caggaggaag 1380
gagtacgtga ctttgtctcc cgatcatggg tactgggtcc tcagactgaa tggagaacat 1440

-continued

```
ttgtatttca cattaaatcc ccgttttatc agcgtcttcc ccaggacccc acctacaaaa   1500

ataggggtct tcctggacta tgagtgtggg accatctcct tcttcaacat aaatgaccag   1560

tcccttattt ataccctgac atgtcggttt gaaggcttat tgaggcccta cattgagtat   1620

ccgtcctata atgagcaaaa tggaactccc atagtcatct gcccagtcac ccaggaatca   1680

gagaaagagg cctcttggca aagggcctct gcaatcccag agacaagcaa cagtgagtcc   1740

tcctcacagg caaccacgcc cttcctcccc aggggtgaaa tgtaggatga atcacatccc   1800

acattcttct ttagggatat taaggtctct ctcccagatc caaagtcccg cagcagccgg   1860

ccaaggtggc ttccagatga agggggactg gcctgtccac atgggagtca ggtgtcatgg   1920

ctgccctgag ctgggaggga agaaggctga cattacattt agtttgctct cactccatct   1980

ggctaagtga tcttgaaata ccacctctca ggtgaagaac cgtcaggaat tcccatctca   2040

caggctgtgg tgtagattaa gtagacaagg aatgtgaata atgcttagat cttattgatg   2100

acagagtgta tcctaatggt ttgttcatta tattacactt tcagtaaaaa aaaaaaaaaa   2160

aaaaa                                                               2165


<210> SEQ ID NO 85
<211> LENGTH: 347
<212> TYPE: PRT
<213> ORGANISM: Homo sapiens

<400> SEQUENCE: 85

Met Ala Leu Met Leu Ser Leu Val Leu Ser Leu Leu Lys Leu Gly Ser
1               5                   10                  15

Gly Gln Trp Gln Val Phe Gly Pro Asp Lys Pro Val Gln Ala Leu Val
            20                  25                  30

Gly Glu Asp Ala Ala Phe Ser Cys Phe Leu Ser Pro Lys Thr Asn Ala
        35                  40                  45

Glu Ala Met Glu Val Arg Phe Phe Arg Gly Gln Phe Ser Ser Val Val
    50                  55                  60

His Leu Tyr Arg Asp Gly Lys Asp Gln Pro Phe Met Gln Met Pro Gln
65                  70                  75                  80

Tyr Gln Gly Arg Thr Lys Leu Val Lys Asp Ser Ile Ala Glu Gly Arg
                85                  90                  95

Ile Ser Leu Arg Leu Glu Asn Ile Thr Val Leu Asp Ala Gly Leu Tyr
            100                 105                 110

Gly Cys Arg Ile Ser Ser Gln Ser Tyr Tyr Gln Lys Ala Ile Trp Glu
        115                 120                 125

Leu Gln Val Ser Ala Leu Gly Ser Val Pro Leu Ile Ser Ile Thr Gly
    130                 135                 140

Tyr Val Asp Arg Asp Ile Gln Leu Leu Cys Gln Ser Ser Gly Trp Phe
145                 150                 155                 160

Pro Arg Pro Thr Ala Lys Trp Lys Gly Pro Gln Gly Gln Asp Leu Ser
                165                 170                 175

Thr Asp Ser Arg Thr Asn Arg Asp Met His Gly Leu Phe Asp Val Glu
            180                 185                 190

Ile Ser Leu Thr Val Gln Glu Asn Ala Gly Ser Ile Ser Cys Ser Met
        195                 200                 205

Arg His Ala His Leu Ser Arg Glu Val Glu Ser Arg Val Gln Ile Gly
    210                 215                 220

Asp Thr Phe Phe Glu Pro Ile Ser Trp His Leu Ala Thr Lys Val Leu
225                 230                 235                 240
```

-continued

```
Gly Ile Leu Cys Cys Gly Leu Phe Phe Gly Ile Val Gly Leu Lys Ile
                245                 250                 255

Phe Phe Ser Lys Phe Gln Cys Lys Arg Glu Arg Glu Ala Trp Ala Gly
            260                 265                 270

Ala Leu Phe Met Val Pro Ala Gly Thr Gly Ser Glu Met Leu Pro His
        275                 280                 285

Pro Ala Ala Ser Leu Leu Leu Val Leu Ala Ser Arg Gly Pro Gly Pro
    290                 295                 300

Lys Lys Glu Asn Pro Gly Gly Thr Gly Leu Glu Lys Lys Ala Arg Thr
305                 310                 315                 320

Gly Arg Ile Glu Arg Arg Pro Glu Thr Arg Ser Gly Gly Asp Ser Gly
                325                 330                 335

Ser Arg Asp Gly Ser Pro Glu Ala Leu Arg Phe
            340                 345


<210> SEQ ID NO 86
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 86

attcatggtt ccagcaggga c                                              21


<210> SEQ ID NO 87
<211> LENGTH: 21
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 87

gggagacaaa gtcacgtact c                                              21


<210> SEQ ID NO 88
<211> LENGTH: 22
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 88

tcctggtgtt cgtggtctgc tt                                             22


<210> SEQ ID NO 89
<211> LENGTH: 22
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 89

gagagtcctg gcttttgtgg gc                                             22


<210> SEQ ID NO 90
<211> LENGTH: 15
<212> TYPE: PRT
<213> ORGANISM: Homo sapiens
```

-continued

<400> SEQUENCE: 90

Gly Ser Ser Asp Leu Thr Trp Pro Pro Ala Ile Lys Leu Gly Cys
1 5 10 15

<210> SEQ ID NO 91
<211> LENGTH: 16
<212> TYPE: PRT
<213> ORGANISM: Homo sapiens

<400> SEQUENCE: 91

Asp Arg Tyr Val Ala Val Arg His Pro Leu Arg Ala Arg Gly Leu Arg
1 5 10 15

<210> SEQ ID NO 92
<211> LENGTH: 15
<212> TYPE: PRT
<213> ORGANISM: Homo sapiens

<400> SEQUENCE: 92

Val Ala Pro Arg Ala Lys Ala His Lys Ser Gln Asp Ser Leu Cys
1 5 10 15

<210> SEQ ID NO 93
<211> LENGTH: 13
<212> TYPE: PRT
<213> ORGANISM: Homo sapiens

<400> SEQUENCE: 93

Cys Phe Arg Ser Thr Arg His Asn Phe Asn Ser Met Arg
1 5 10

<210> SEQ ID NO 94
<211> LENGTH: 22
<212> TYPE: PRT
<213> ORGANISM: Homo sapiens

<400> SEQUENCE: 94

Met Asn Gly Thr Tyr Asn Thr Cys Gly Ser Ser Asp Leu Thr Trp Pro
1 5 10 15

Pro Ala Ile Lys Leu Gly
20

<210> SEQ ID NO 95
<211> LENGTH: 14
<212> TYPE: PRT
<213> ORGANISM: Homo sapiens

<400> SEQUENCE: 95

Arg Asp Thr Ser Asp Thr Pro Leu Cys Gln Leu Ser Gln Gly
1 5 10

<210> SEQ ID NO 96
<211> LENGTH: 22
<212> TYPE: PRT
<213> ORGANISM: Homo sapiens

<400> SEQUENCE: 96

Gly Ile Gln Glu Gly Gly Phe Cys Phe Arg Ser Thr Arg His Asn Phe
1 5 10 15

Asn Ser Met Arg Phe Pro
20

<210> SEQ ID NO 97

-continued

<211> LENGTH: 30
<212> TYPE: PRT
<213> ORGANISM: Homo sapiens

<400> SEQUENCE: 97

Ala Lys Glu Phe Gln Glu Ala Ser Ala Leu Ala Val Ala Pro Arg Ala
1 5 10 15

Lys Ala His Lys Ser Gln Asp Ser Leu Cys Val Thr Leu Ala
20 25 30

<210> SEQ ID NO 98
<211> LENGTH: 22
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 98
tcctgctcgt cgctctcctg at 22

<210> SEQ ID NO 99
<211> LENGTH: 20
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 99 tcgcttttg tcgtatttgc 20

<210> SEQ ID NO 100
<211> LENGTH: 15
<212> TYPE: PRT
<213> ORGANISM: Homo sapiens

<400> SEQUENCE: 100

His Asn Gly Ser Tyr Glu Ile Ser Val Leu Met Met Gly Asn Ser
1 5 10 15

<210> SEQ ID NO 101
<211> LENGTH: 15
<212> TYPE: PRT
<213> ORGANISM: Homo sapiens

<400> SEQUENCE: 101

Asn Leu Pro Thr Pro Pro Thr Val Glu Asn Gln Gln Arg Leu Ala
1 5 10 15

<210> SEQ ID NO 102
<211> LENGTH: 619
<212> TYPE: PRT
<213> ORGANISM: Homo sapiens

<400> SEQUENCE: 102

Arg Lys Tyr Arg Lys Asp Tyr Glu Leu Arg Gln Lys Lys Trp Ser His
1 5 10 15

Ile Pro Pro Glu Asn Ile Phe Pro Leu Glu Thr Asn Glu Thr Asn His
20 25 30

Val Ser Leu Lys Ile Asp Asp Asp Lys Arg Arg Asp Thr Ile Gln Arg
35 40 45

Leu Arg Gln Cys Lys Tyr Asp Lys Lys Arg Val Ile Leu Lys Asp Leu
50 55 60

-continued

```
Lys His Asn Asp Gly Asn Phe Thr Glu Lys Gln Lys Ile Glu Leu Asn
65                  70                  75                  80

Lys Leu Leu Gln Ile Asp Tyr Tyr Asn Leu Thr Lys Phe Tyr Gly Thr
                85                  90                  95

Val Lys Leu Asp Thr Met Ile Phe Gly Val Ile Glu Tyr Cys Glu Arg
            100                 105                 110

Gly Ser Leu Arg Glu Val Leu Asn Asp Thr Ile Ser Tyr Pro Asp Gly
        115                 120                 125

Thr Phe Met Asp Trp Glu Phe Lys Ile Ser Val Leu Tyr Asp Ile Ala
    130                 135                 140

Lys Gly Met Ser Tyr Leu His Ser Ser Lys Thr Glu Val His Gly Arg
145                 150                 155                 160

Leu Lys Ser Thr Asn Cys Val Val Asp Ser Arg Met Val Val Lys Ile
                165                 170                 175

Thr Asp Phe Gly Cys Asn Ser Ile Leu Pro Pro Lys Lys Asp Leu Trp
            180                 185                 190

Thr Ala Pro Glu His Leu Arg Gln Ala Asn Ile Ser Gln Lys Gly Asp
        195                 200                 205

Val Tyr Ser Tyr Gly Ile Ile Ala Gln Glu Ile Ile Leu Arg Lys Glu
    210                 215                 220

Thr Phe Tyr Thr Leu Ser Cys Arg Asp Arg Asn Glu Lys Ile Phe Arg
225                 230                 235                 240

Val Glu Asn Ser Asn Gly Met Lys Pro Phe Arg Pro Asp Leu Phe Leu
                245                 250                 255

Glu Thr Ala Glu Glu Lys Glu Leu Glu Val Tyr Leu Leu Val Lys Asn
            260                 265                 270

Cys Trp Glu Glu Asp Pro Glu Lys Arg Pro Asp Phe Lys Lys Ile Glu
        275                 280                 285

Thr Thr Leu Ala Lys Ile Phe Gly Leu Phe His Asp Gln Lys Asn Glu
    290                 295                 300

Ser Tyr Met Asp Thr Leu Ile Arg Arg Leu Gln Leu Tyr Ser Arg Asn
305                 310                 315                 320

Leu Glu His Leu Val Glu Glu Arg Thr Gln Leu Tyr Lys Ala Glu Arg
                325                 330                 335

Asp Arg Ala Asp Arg Leu Asn Phe Met Leu Leu Pro Arg Leu Val Val
            340                 345                 350

Lys Ser Leu Lys Glu Lys Gly Phe Val Glu Pro Glu Leu Tyr Glu Glu
        355                 360                 365

Val Thr Ile Tyr Phe Ser Asp Ile Val Gly Phe Thr Thr Ile Cys Lys
    370                 375                 380

Tyr Ser Thr Pro Met Glu Val Val Asp Met Leu Asn Asp Ile Tyr Lys
385                 390                 395                 400

Ser Phe Asp His Ile Val Asp His His Asp Val Tyr Lys Val Glu Thr
                405                 410                 415

Ile Gly Asp Ala Tyr Met Val Ala Ser Gly Leu Pro Lys Arg Asn Gly
            420                 425                 430

Asn Arg His Ala Ile Asp Ile Ala Lys Met Ala Leu Glu Ile Leu Ser
        435                 440                 445

Phe Met Gly Thr Phe Glu Leu Glu His Leu Pro Gly Leu Pro Ile Trp
    450                 455                 460

Ile Arg Ile Gly Val His Ser Gly Pro Cys Ala Ala Gly Val Val Gly
465                 470                 475                 480
```

-continued

```
Ile Lys Met Pro Arg Tyr Cys Leu Phe Gly Asp Thr Val Asn Thr Ala
                485                 490                 495

Ser Arg Met Glu Ser Thr Gly Leu Pro Leu Arg Ile His Val Ser Gly
            500                 505                 510

Ser Thr Ile Ala Ile Leu Lys Arg Thr Glu Cys Gln Phe Leu Tyr Glu
        515                 520                 525

Val Arg Gly Glu Thr Tyr Leu Lys Gly Arg Gly Asn Glu Thr Thr Tyr
    530                 535                 540

Trp Leu Thr Gly Met Lys Asp Gln Lys Phe Asn Leu Pro Thr Pro Pro
545                 550                 555                 560

Thr Val Glu Asn Gln Gln Arg Leu Gln Ala Glu Phe Ser Asp Met Ile
                565                 570                 575

Ala Asn Ser Leu Gln Lys Arg Gln Ala Ala Gly Ile Arg Ser Gln Lys
            580                 585                 590

Pro Arg Arg Val Ala Ser Tyr Lys Lys Gly Thr Leu Glu Tyr Leu Gln
        595                 600                 605

Leu Asn Thr Thr Asp Lys Glu Ser Thr Tyr Phe
    610                 615


<210> SEQ ID NO 103
<211> LENGTH: 20
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 103

gctggtaact atcttcctgc                                                20


<210> SEQ ID NO 104
<211> LENGTH: 20
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 104

gaagaatgtt gtccagaggt                                                20


<210> SEQ ID NO 105
<211> LENGTH: 15
<212> TYPE: PRT
<213> ORGANISM: Homo sapiens

<400> SEQUENCE: 105

Leu Ile Asn Lys Val Pro Leu Pro Val Asp Lys Leu Ala Pro Leu
1               5                   10                  15


<210> SEQ ID NO 106
<211> LENGTH: 15
<212> TYPE: PRT
<213> ORGANISM: Homo sapiens

<400> SEQUENCE: 106

Ser Glu Ala Val Lys Lys Leu Leu Glu Ala Leu Ser His Leu Val
1               5                   10                  15


<210> SEQ ID NO 107
<211> LENGTH: 20
<212> TYPE: DNA
```

-continued

<213> ORGANISM: Artificial Sequence
<220> FEATURE:
<223> OTHER INFORMATION: Description of the Artificial Sequence: Oligonucleotide

<400> SEQUENCE: 107
tgttttcaac taccaggggc 20

<210> SEQ ID NO 108
<211> LENGTH: 20
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 108
tgttggcttt ggcagagtcc 20

<210> SEQ ID NO 109
<211> LENGTH: 24
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 109
gaggcagagt tcaggcttca ccga 24

<210> SEQ ID NO 110
<211> LENGTH: 20
<212> TYPE: DNA
<213> ORGANISM: Artificial Sequence
<220> FEATURE:
<223> OTHER INFORMATION: Description of the Artificial Sequence: Oligonucleotide

<400> SEQUENCE: 110
tgttggcttt ggcagagtcc 20

<210> SEQ ID NO 111
<211> LENGTH: 56
<212> TYPE: PRT
<213> ORGANISM: Homo sapiens

<400> SEQUENCE: 111

```
Thr Gly Met Asp Met Trp Ser Thr Gln Asp Leu Tyr Asp Asn Pro Val
1               5                   10                  15

Thr Ser Val Phe Gln Tyr Glu Gly Leu Trp Arg Ser Cys Val Arg Gln
            20                  25                  30

Ser Ser Gly Phe Thr Glu Cys Arg Pro Tyr Phe Thr Ile Leu Gly Leu
        35                  40                  45

Pro Ala Met Leu Gln Ala Val Arg
    50                  55
```

<210> SEQ ID NO 112
<211> LENGTH: 53
<212> TYPE: PRT
<213> ORGANISM: Homo sapiens

<400> SEQUENCE: 112

```
Asp Gln Trp Ser Thr Gln Asp Leu Tyr Asn Asn Pro Val Thr Ala Val
1               5                   10                  15
```

-continued

```
Phe Asn Tyr Gln Gly Leu Trp Arg Ser Cys Val Arg Glu Ser Ser Gly
            20                  25                  30

Phe Thr Glu Cys Arg Gly Tyr Phe Thr Leu Leu Gly Leu Pro Ala Met
        35                  40                  45

Leu Gln Ala Val Arg
    50


<210> SEQ ID NO 113
<211> LENGTH: 14
<212> TYPE: PRT
<213> ORGANISM: Homo sapiens

<400> SEQUENCE: 113

Ser Thr Gln Asp Leu Tyr Asn Asn Pro Val Thr Ala Val Phe
1               5                   10


<210> SEQ ID NO 114
<211> LENGTH: 12
<212> TYPE: PRT
<213> ORGANISM: Homo sapiens

<400> SEQUENCE: 114

Asp Met Trp Ser Thr Gln Asp Leu Tyr Asp Asn Pro
1               5                   10


<210> SEQ ID NO 115
<211> LENGTH: 12
<212> TYPE: PRT
<213> ORGANISM: Homo sapiens

<400> SEQUENCE: 115

Cys Arg Pro Tyr Phe Thr Ile Leu Gly Leu Pro Ala
1               5                   10


<210> SEQ ID NO 116
<211> LENGTH: 13
<212> TYPE: PRT
<213> ORGANISM: Homo sapiens

<400> SEQUENCE: 116

Thr Asn Phe Trp Met Ser Thr Ala Asn Met Tyr Thr Gly
1               5                   10


<210> SEQ ID NO 117
<211> LENGTH: 816
<212> TYPE: DNA
<213> ORGANISM: Homo sapiens

<400> SEQUENCE: 117

gccaggatca tgtccaccac cacatgccaa gtggtggcgt tcctcctgtc catcctgggg      60

ctggccggct gcatcgcggc caccgggatg gacatgtgga gcacccagga cctgtacgac     120

aaccccgtca cctccgtgtt ccagtacgaa gggctctgga ggagctgcgt gaggcagagt     180

tcaggcttca ccgaatgcag gccctatttc accatcctgg gacttccagc catgctgcag     240

gcagtgcgag ccctgatgat cgtaggcatc gtcctgggtg ccattggcct cctggtatcc     300

atctttgccc tgaaatgcat ccgcattggc agcatggagg actctgccaa agccaacatg     360

acactgacct ccgggatcat gttcattgtc tcaggtcttt gtgcaattgc tggagtgtct     420

gtgtttgcca acatgctggt gactaacttc tggatgtcca cagctaacat gtacaccggc     480

atgggtggga tggtgcagac tgttcagacc aggtacacat ttggtgcggc tctgttcgtg     540
```

-continued

```
ggctgggtcg ctggaggcct cacactaatt gggggtgtga tgatgtgcat cgcctgccgg    600

ggcctggcac cagaagaaac caactacaaa gccgtttctt atcatgcctc aggccacagt    660

gttgcctaca agcctggagg cttcaaggcc agcactggct ttgggtccaa caccaaaaac    720

aagaagatat acgatggagg tgcccgcaca gaggacgagg tacaatctta tccttccaag    780

cacgactatg tgtaatgctc taagacctct cagcac                              816
```

<210> SEQ ID NO 118
<211> LENGTH: 261
<212> TYPE: PRT
<213> ORGANISM: Homo sapiens

<400> SEQUENCE: 118

```
Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 119
<211> LENGTH: 227
<212> TYPE: DNA
<213> ORGANISM: Homo sapiens

<400> SEQUENCE: 119

```
gccaggatca tgtccaccac cacatgccaa gtggtggcgt tcctcctgtc catcctgggg     60
```

-continued

```
ctggccggct gcatcgcggc caccgggatg gacatgtgga gcacccagga cctgtacgac    120

aaccccgtca cctccgtgtt ccagtacgaa gggctctgga ggagctgcgt gaggcagagt    180

tcaggcttca ccgaatgcag gccctatttc accatcctgg gacttcc                  227


<210> SEQ ID NO 120
<211> LENGTH: 69
<212> TYPE: PRT
<213> ORGANISM: Homo sapiens

<400> SEQUENCE: 120

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile
65


<210> SEQ ID NO 121
<211> LENGTH: 20
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 121

aatgagagga aagagaaaac                                                 20


<210> SEQ ID NO 122
<211> LENGTH: 20
<212> TYPE: DNA
<213> ORGANISM: Artificial Sequence
<220> FEATURE:
<223> OTHER INFORMATION: Description of the Artificial Sequence:
      Oligonucleotide

<400> SEQUENCE: 122

atggtagaag agtaggcaat                                                 20


<210> SEQ ID NO 123
<211> LENGTH: 15
<212> TYPE: PRT
<213> ORGANISM: Homo sapiens

<400> SEQUENCE: 123

Glu Lys Trp Asn Leu His Lys Arg Ile Ala Leu Lys Met Val Cys
1               5                   10                  15


<210> SEQ ID NO 124
<211> LENGTH: 11
<212> TYPE: PRT
<213> ORGANISM: Homo sapiens

<400> SEQUENCE: 124

Cys Leu Gly Phe Asn Phe Lys Glu Met Phe Lys
1               5                   10


<210> SEQ ID NO 125
```

-continued

<211> LENGTH: 23
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 125
taatgatgaa ccctacactg agc 23

<210> SEQ ID NO 126
<211> LENGTH: 20
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 126
atggacaaat gccctacctt 20

<210> SEQ ID NO 127
<211> LENGTH: 22
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 127
agtgctggaa ggatgtgcgt gt 22

<210> SEQ ID NO 128
<211> LENGTH: 20
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 128
ttgaggtggt tgttgggttt 20

<210> SEQ ID NO 129
<211> LENGTH: 20
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 129
agatgtgctg aggctgtaga 20

<210> SEQ ID NO 130
<211> LENGTH: 20
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 130
atgaaggttg attatttgag 20

<210> SEQ ID NO 131
<211> LENGTH: 23

-continued

<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 131
agccgcatac tcccttaccc tct 23

<210> SEQ ID NO 132
<211> LENGTH: 20
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 132
gcagcagccc aaacaccaca 20

<210> SEQ ID NO 133
<211> LENGTH: 20
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 133
ctgagccgag aggtggaatc 20

<210> SEQ ID NO 134
<211> LENGTH: 20
<212> TYPE: DNA
<213> ORGANISM: Artificial Sequence
<220> FEATURE:
<223> OTHER INFORMATION: Description of the Artificial Sequence:
Oligonucleotide

<400> SEQUENCE: 134
ctctctcgct tacactggaa 20

<210> SEQ ID NO 135
<211> LENGTH: 14
<212> TYPE: PRT
<213> ORGANISM: Homo sapiens

<400> SEQUENCE: 135

Gln Trp Gln Val Phe Gly Pro Asp Lys Pro Val Gln Ala Leu
1 5 10

<210> SEQ ID NO 136
<211> LENGTH: 15
<212> TYPE: PRT
<213> ORGANISM: Homo sapiens

<400> SEQUENCE: 136

Ala Lys Trp Lys Gly Pro Gln Gly Gln Asp Leu Ser Thr Asp Ser
1 5 10 15

<210> SEQ ID NO 137
<211> LENGTH: 32
<212> TYPE: PRT
<213> ORGANISM: Homo sapiens

<400> SEQUENCE: 137

-continued

```
Asn Met Leu Val Thr Asn Phe Trp Met Ser Thr Ala Asn Met Tyr Thr
1               5                   10                  15

Gly Met Gly Gly Met Val Gln Thr Val Gln Thr Arg Tyr Thr Phe Gly
            20                  25                  30
```

GENETIC PRODUCTS DIFFERENTIALLY EXPRESSED IN TUMORS AND THE USE THEREOF

This application is a United States national stage filing under 35 U.S.C. §371 of international (PCT) application No. PCT/EP2003/013091, filed Nov. 21, 2003, and designating the US, which claims priority to German application no. 102 54 601.0 filed Nov. 22, 2002.

BACKGROUND OF THE INVENTION

Despite interdisciplinary approaches and exhaustive use of classical therapeutic procedures, cancers are still among the leading causes of death. More recent therapeutic concepts aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced. Tumor cells biologically differ substantially from their nonmalignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens. The specific recognition of tumor-associated antigens involves cellular and humoral mechanisms which are two functionally interconnected units: $CD4^+$ and $CD8^+$ T lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, *Nat. Med.* 4:525-31, 1998). Accordingly, a central aim of tumor immunology is to molecularly define these structures. The molecular nature of these antigens has been enigmatic for a long time. Only after development of appropriate cloning techniques has it been possible to screen cDNA expression libraries of tumors systematically for tumor-associated antigens by analyzing the target structures of cytotoxic T lymphocytes (CTL) (van der Bruggen et al., *Science* 254:1643-7, 1991) or by using circulating autoantibodies (Sahin et al., *Curr. Opin. Immunol.* 9:709-16, 1997) as probes. To this end, cDNA expression libraries were prepared from fresh tumor tissue and recombinantly expressed as proteins in suitable systems. Immunoeffectors isolated from patients, namely CTL clones with tumor-specific lysis patterns, or circulating autoantibodies were utilized for cloning the respective antigens.

In recent years a multiplicity of antigens have been defined in various neoplasias by these approaches. However, the probes utilized for antigen identification in the classical methods illustrated above are immunoeffectors (circulating autoantibodies or CTL clones) from patients usually having already advanced cancer. A number of data indicate that tumors can lead, for example, to tolerization and anergization of T cells and that, during the course of the disease, especially those specificities which could cause effective immune recognition are lost from the immunoeffector repertoire. Current patient studies have not yet produced any solid evidence of a real action of the previously found and utilized tumor-associated antigens. Accordingly, it cannot be ruled out that proteins evoking spontaneous immune responses are the wrong target structures.

BRIEF SUMMARY OF THE INVENTION

It was the object of the present invention to provide target structures for a diagnosis and therapy of cancers.

According to the invention, this object is achieved by the subject matter of the claims.

According to the invention, a strategy for identifying and providing antigens expressed in association with a tumor and the nucleic acids coding therefor was pursued. This strategy is based on the fact that particular genes which are expressed in an organ specific manner, e.g. exclusively in colon, lung or kidney tissue, are reactivated also in tumor cells of the respective organs and moreover in tumor cells of other tissues in an ectopic and forbidden manner. First, data mining produces a list as complete as possible of all known organ-specific genes which are then evaluated for their aberrant activation in different tumors by expression analyses by means of specific RT-PCR. Data mining is a known method of identifying tumor-associated genes. In the conventional strategies, however, transcriptoms of normal tissue libraries are usually subtracted electronically from tumor tissue libraries, with the assumption that the remaining genes are tumor-specific (Schmitt et al., *Nucleic Acids Res.* 27:4251-60, 1999; Vasmatzis et al., *Proc. Natl. Acad. Sci. USA.* 95:300-4, 1998; Scheurle et al., *Cancer Res.* 60:4037-43, 2000).

The concept of the invention, which has proved much more successful, however, is based on utilizing data mining for electronically extracting all organ-specific genes and then evaluating said genes for expression in tumors.

The invention thus relates in one aspect to a strategy for identifying tissue-specific genes differentially expressed in tumors. Said strategy combines data mining of public sequence libraries ("in silico") with subsequent evaluating laboratory-experimental ("wet bench") studies.

According to the invention, a combined strategy based on two different bioinformatic scripts enabled new tumor genes to be identified. These have previously been classified as being purely organ-specific. The finding that these genes are aberrantly activated in tumor cells allows them to be assigned a substantially new quality with functional implications. According to the invention, these tumor-associated genes and the genetic products encoded thereby were identified and provided independently of an immunogenic action.

The tumor-associated antigens identified according to the invention have an amino acid sequence encoded by a nucleic acid which is selected from the group consisting of (a) a nucleic acid which comprises a nucleic acid sequence selected from the group consisting of SEQ ID NOs: 1-8, 41-44, 51-59, 84, 117, and 119, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, a tumor-associated antigen identified according to the invention has an amino acid sequence encoded by a nucleic acid which is selected from the group consisting of SEQ ID NOs: 1-8, 41-44, 51-59, 84, 117, and 119. In a further preferred embodiment, a tumor-associated antigen identified according to the invention comprises an amino acid sequence selected from the group consisting of SEQ ID NOs: 9-19, 45-48, 60-66, 85, 90-97, 100-102, 105, 106, 111-116, 118, 120, 123, 124, and 135-137, a part or derivative thereof.

The present invention generally relates to the use of tumor-associated antigens identified according to the invention or of parts or derivatives thereof, of nucleic acids coding therefor or of nucleic acids directed against said coding nucleic acids or of antibodies directed against the tumor-associated antigens identified according to the invention or parts or derivatives thereof for therapy and diagnosis. This utilization may relate to individual but also to combinations of two or more of these antigens, functional fragments, nucleic acids, antibodies, etc., in one embodiment also in combination with other tumor-associated genes and antigens for diagnosis, therapy and progress control.

Preferred diseases for a therapy and/or diagnosis are those in which one or more of the tumor-associated antigens identified according to the invention are selectively expressed or abnormally expressed.

The invention also relates to nucleic acids and genetic products which are expressed in association with a tumor cell.

Furthermore, the invention relates to genetic products, i.e. nucleic acids and proteins or peptides, which are produced by altered splicing (splice variants) of known genes or altered translation using alternative open reading frames. In this aspect the invention relates to nucleic acids which comprise a nucleic acid sequence selected from the group consisting of sequences according to SEQ ID NOs: 3-5 of the sequence listing. Moreover, in this aspect, the invetion relates to proteins or peptides which comprise an amino acid sequence selected from the group consisting of the sequences according to SEQ ID NOs: 10 and 12-14 of the sequence listing. The splice variants of the invention can be used according to the invention as targets for diagnosis and therapy of tumor diseases.

In particular, the invention relates to the amino acid sequence according to SEQ ID NO: 10 of the sequence listing which is encoded by an alternative open reading frame identified according to the invention and differs from the previously described protein sequence (SEQ ID NO: 9) in additional 85 amino acids at the N terminus of the protein.

Very different mechanisms may cause splice variants to be produced, for example

- utilization of variable transcription initiation sites
- utilization of additional exons
- complete or incomplete splicing out of single or two or more exons,
- splice regulator sequences altered via mutation (deletion or generation of new donor/acceptor sequences),
- incomplete elimination of intron sequences.

Altered splicing of a gene results in an altered transcript sequence (splice variant). Translation of a splice variant in the region of its altered sequence results in an altered protein which may be distinctly different in the structure and function from the original protein. Tumor-associated splice variants may produce tumor-associated transcripts and tumor-associated proteins/antigens. These may be utilized as molecular markers both for detecting tumor cells and for therapeutic targeting of tumors. Detection of tumor cells, for example in blood, serum, bone marrow, sputum, bronchial lavage, bodily secretions and tissue biopsies, may be carried out according to the invention, for example, after extraction of nucleic acids by PCR amplification with splice variant-specific oligonucleotides. In particular, pairs of primers are suitable as oligonucleotides at least one of which binds to the region of the splice variant which is tumor-associated under stringent conditions. According to the invention, oligonucleotides described for this purpose in the examples are suitable, in particular oligonucleotides which have or comprise a sequence selected from SEQ ID NOs: 34-36, 39, 40, and 107-110 of the sequence listing. According to the invention, all sequence-dependent detection systems are suitable for detection. These are, apart from PCR, for example gene chip/microarray systems, Northern blot, RNAse protection assays (RDA) and others. All detection systems have in common that detection is based on a specific hybridization with at least one splice variant-specific nucleic acid sequence. However, tumor cells may also be detected according to the invention by antibodies which recognize a specific epitope encoded by the splice variant. Said antibodies may be prepared by using for immunization peptides which are specific for said splice variant. In this aspect, the invention relates, in particular, to peptides which have or comprise a sequence selected from SEQ ID NOs: 17-19, 111-115, 120, and 137 of the sequence listing and specific antibodies which are directed thereto. Suitable for immunization are particularly the amino acids whose epitopes are distinctly different from the variant(s) of the genetic product, which is (are) preferably produced in healthy cells. Detection of the tumor cells with antibodies may be carried out here on a sample isolated from the patient or as imaging with intravenously administered antibodies. In addition to diagnostic usability, splice variants having new or altered epitopes are attractive targets for immunotherapy. The epitopes of the invention may be utilized for targeting therapeutically active monoclonal antibodies or T lymphocytes. In passive immunotherapy, antibodies or T lymphocytes which recognize splice variant-specific epitopes are adaptively transferred here. As in the case of other antigens, antibodies may be generated also by using standard technologies (immunization of animals, panning strategies for isolation of recombinant antibodies) with utilization of polypeptides which include these epitopes. Alternatively, it is possible to utilize for immunization nucleic acids coding for oligo- or polypeptides which contain said epitopes. Various techniques for in vitro or in vivo generation of epitope-specific T lymphocytes are known and have been described in detail (for example Kessler J H, et al. 2001, Sahin et al., 1997) and are likewise based on utilizing oligo- or polypeptides which contain the splice variant-specific epitopes or nucleic acids coding for said oligo- or polypeptides. Oligo- or polypeptides which contain the splice variant-specific epitopes or nucleic acids coding for said polypeptides may also be used as pharmaceutically active substances in active immunotherapy (vaccination, vaccine therapy).

The present invention also describes proteins which differ in nature and degree of their secondary modifications in normal and tumor tissue (for example Durand & Seta, 2000; Clin. Chem. 46: 795-805; Hakomori, 1996; Cancer Res. 56: 5309-18).

The analysis of protein modifications can be done in Western blots. In particular, glycosylations which as a rule have a size of several kDa result in a higher overall mass of the target protein which can be separated in an SDS-PAGE. For the detection of specific O- and N-glycosidic bonds protein lysates are incubated with O- or N-glycosylases (according to the instructions of the respective manufactures, for example, PNgase, endoglycosidase F, endoglycosidase H, Roche Diagnostics) prior to denaturation using SDS. Thereafter, a Western blot is performed. If the size of target protein is reduced a specific glycosylation can be detected in this manner following incubation with a glycosidase and thus, also the tumor specificity of a modification can be analyzed. Protein regions which are differentially glycosylated in tumor cells and healthy cells are of particular interest. Such differences in glycosylation, however, have hitherto only been described for a few cell surface proteins (for example, Muc1).

According to the invention, it was possible to detect a differential glycosylation for Claudin-18 in tumors. Gastrointestinal carcinomas, pancreas carcinomas, esophagus tumors, prostate tumors as well as lung tumors have a form of Claudin-18 which is glycosylated at a lower level. Glycosylation in healthy tissues masks protein epitopes of Claudin-18 which are not covered on tumor cells due to lacking glycosylation. Correspondingly it is possible according to the invention to select ligands and antibodies which bind to these domains. Such ligands and antibodies according to the invention do not bind to Claudin-18 on healthy cells since here the epitops are covered due to glycosylation.

As has been described above for protein epitopes which are derived from tumor-associated splice variants it is thus possible to use the differential glycosylation to distinguish normal cells and tumor cells with diagnostic as well as therapeutic intention.

In one aspect, the invention relates to a pharmaceutical composition comprising an agent which recognizes the tumor-associated antigen identified according to the invention and which is preferably selective for cells which have expression or abnormal expression of a tumor-associated antigen identified according to the invention. In particular embodiments, said agent may cause induction of cell death, reduction in cell growth, damage to the cell membrane or secretion of cytokines and preferably have a tumor-inhibiting activity. In one embodiment, the agent is an antisense nucleic acid which hybridizes selectively with the nucleic acid coding for the tumor-associated antigen. In a further embodiment, the agent is an antibody which binds selectively to the tumor-associated antigen, in particular a complement-activated or toxin conjugated antibody which binds selectively to the tumor-associated antigen. In a further embodiment, the agent comprises two or more agents which each selectively recognize different tumor-associated antigens, at least one of which is a tumor-associated antigen identified according to the invention. Recognition needs not be accompanied directly with inhibition of activity or expression of the antigen. In this aspect of the invention, the antigen selectively limited to tumors preferably serves as a label for recruiting effector mechanisms to this specific location. In a preferred embodiment, the agent is a cytotoxic T lymphocyte which recognizes the antigen on an HLA molecule and lyses the cells labeled in this way. In a further embodiment, the agent is an antibody which binds selectively to the tumor-associated antigen and thus recruits natural or artificial effector mechanisms to said cell. In a further embodiment, the agent is a T helper lymphocyte which enhances effector functions of other cells specifically recognizing said antigen.

In one aspect, the invention relates to a pharmaceutical composition comprising an agent which inhibits expression or activity of a tumor-associated antigen identified according to the invention. In a preferred embodiment, the agent is an antisense nucleic acid which hybridizes selectively with the nucleic acid coding for the tumor-associated antigen. In a further embodiment, the agent is an antibody which binds selectively to the tumor-associated antigen. In a further embodiment, the agent comprises two or more agents which each selectively inhibit expression or activity of different tumor-associated antigens, at least one of which is a tumor-associated antigen identified according to the invention.

The invention furthermore relates to a pharmaceutical composition which comprises an agent which, when administered, selectively increases the amount of complexes between an HLA molecule and a peptide epitope from the tumor-associated antigen identified according to the invention. In one embodiment, the agent comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule. In one embodiment, the agent comprises two or more agents which each selectively increase the amount of complexes between MHC molecules and peptide epitopes of different tumor-associated antigens, at least one of which is a tumor-associated antigen identified according to the invention.

The invention furthermore relates to a pharmaceutical composition which comprises one or more components selected from the group consisting of (i) a tumor-associated antigen identified according to the invention or a part thereof, (ii) a nucleic acid which codes for a tumor-associated antigen identified according to the invention or for a part thereof, (iii) an antibody which binds to a tumor-associated antigen identified according to the invention or to a part thereof, (iv) an antisense nucleic acid which hybridizes specifically with a nucleic acid coding for a tumor-associated antigen identified according to the invention, (v) a host cell which expresses a tumor-associated antigen identified according to the invention or a part thereof, and (vi) isolated complexes between a tumor-associated antigen identified according to the invention or a part thereof and an HLA molecule.

A nucleic acid coding for a tumor-associated antigen identified according to the invention or for a part thereof may be present in the pharmaceutical composition in an expression vector and functionally linked to a promoter.

A host cell present in a pharmaceutical composition of the invention may secrete the tumor-associated antigen or the part thereof, express it on the surface or may additionally express an HLA molecule which binds to said tumor-associated antigen or said part thereof. In one embodiment, the host cell expresses the HLA molecule endogenously. In a further embodiment, the host cell expresses the HLA molecule and/or the tumor-associated antigen or the part thereof in a recombinant manner. The host cell is preferably nonproliferative. In a preferred embodiment, the host cell is an antigen-presenting cell, in particular a dendritic cell, a monocyte or a macrophage.

An antibody present in a pharmaceutical composition of the invention may be a monoclonal antibody. In further embodiments, the antibody is a chimeric or humanized antibody, a fragment of a natural antibody or a synthetic antibody, all of which may be produced by combinatory techniques. The antibody may be coupled to a therapeutically or diagnostically useful agent.

An antisense nucleic acid present in a pharmaceutical composition of the invention may comprise a sequence of 6-50, in particular 10-30, 15-30 and 20-30, contiguous nucleotides of the nucleic acid coding for the tumor-associated antigen identified according to the invention.

In further embodiments, a tumor-associated antigen, provided by a pharmaceutical composition of the invention either directly or via expression of a nucleic acid, or a part thereof binds to MHC molecules on the surface of cells, said binding preferably causing a cytolytic response and/or inducing cytokine release.

A pharmaceutical composition of the invention may comprise a pharmaceutically compatible carrier and/or an adjuvant. The adjuvant may be selected from saponin, GM-CSF, CpG nucleotides, RNA, a cytokine or a chemokine. A pharmaceutical composition of the invention is preferably used for the treatment of a disease characterized by selective expression or abnormal expression of a tumor-associated antigen. In a preferred embodiment, the disease is cancer.

The invention furthermore relates to methods of treating or diagnosing a disease characterized by expression or abnormal expression of one of more tumor-associated antigens. In one embodiment, the treatment comprises administering a pharmaceutical composition of the invention.

In one aspect, the invention relates to a method of diagnosing a disease characterized by expression or abnormal expression of a tumor-associated antigen identified according to the invention. The method comprises detection of (i) a nucleic acid which codes for the tumor-associated antigen or of a part thereof and/or (ii) detection of the tumor-associated antigen or of a part thereof, and/or (iii) detection of an antibody to the tumor-associated antigen or to a part thereof and/or (iv) detection of cytotoxic or T helper lymphocytes which are specific for the tumor-associated antigen or for a part thereof in a biological sample isolated from a patient. In particular embodiments, detection comprises (i) contacting the biological sample with an agent which binds specifically to the nucleic acid coding for the tumor-associated antigen or to the part thereof, to said tumor-associated antigen or said part thereof, to the antibody or to cytotoxic or T helper lymphocytes specific for the tumor-associated antigen or parts thereof, and (ii) detecting the formation of a complex between the agent and the nucleic acid or the part thereof, the tumor-associated antigen or the part thereof, the antibody or the cytotoxic or T helper lymphocytes. In one embodiment, the disease is characterized by expression or abnormal expression of two or more different tumor-associated antigens and detection comprises detection of two or more nucleic acids coding for said two or more different tumor-associated antigens or of parts thereof, detection of two or more different tumor-associated antigens or of parts thereof, detection of two or more antibodies binding to said two or more different tumor-associated antigens or to parts thereof or detection of two or more cytotoxic or T helper lymphocytes specific for said two or more different tumor-associated antigens. In a further embodiment, the biological sample isolated from the patient is compared to a comparable normal biological sample.

In a further aspect, the invention relates to a method for determining regression, course or onset of a disease characterized by expression or abnormal expression of a tumor-associated antigen identified according to the invention, which method comprises monitoring a sample from a patient who has said disease or is suspected of falling ill with said disease, with respect to one or more parameters selected from the group consisting of (i) the amount of nucleic acid which codes for the tumor-associated antigen or of a part thereof, (ii) the amount of the tumor-associated antigen or a part thereof, (iii) the amount of antibodies which bind to the tumor-associated antigen or to a part thereof, and (iv) the amount of cytolytic T cells or T helper cells which are specific for a complex between the tumor-associated antigen or a part thereof and an MHC molecule. The method preferably comprises determining the parameter(s) in a first sample at a first point in time and in a further sample at a second point in time and in which the course of the disease is determined by comparing the two samples. In particular embodiments, the disease is characterized by expression or abnormal expression of two or more different tumor-associated antigens and monitoring comprises monitoring (i) the amount of two or more nucleic acids which code for said two or more different tumor-associated antigens or of parts thereof, and/or (ii) the amount of said two or more different tumor-associated antigens or of parts thereof, and/or (iii) the amount of two or more antibodies which bind to said two or more different tumor-associated antigens or to parts thereof, and/or (iv) the amount of two or more cytolytic T cells or of T helper cells which are specific for complexes between said two or more different tumor-associated antigens or of parts thereof and MHC molecules.

According to the invention, detection of a nucleic acid or of a part thereof or monitoring the amount of a nucleic acid or of a part thereof may be carried out using a polynucleotide probe which hybridizes specifically to said nucleic acid or said part thereof or may be carried out by selective amplification of said nucleic acid or said part thereof. In one embodiment, the polynucleotide probe comprises a sequence of 6-50, in particular 10-30, 15-30 and 20-30, contiguous nucleotides of said nucleic acid.

In particular embodiments, the tumor-associated antigen to be detected or the part thereof is present intracellularly or on the cell surface. According to the invention, detection of a tumor-associated antigen or of a part thereof or monitoring the amount of a tumor-associated antigen or of a part thereof may be carried out using an antibody binding specifically to said tumor-associated antigen or said part thereof.

In further embodiments, the tumor-associated antigen to be detected or the part thereof is present in a complex with an MHC molecule, in particular an HLA molecule.

According to the invention, detection of an antibody or monitoring the amount of antibodies may be carried out using a protein or peptide binding specifically to said antibody.

According to the invention, detection of cytolytic T cells or of T helper cells or monitoring the amount of cytolytic T cells or of T helper cells which are specific for complexes between an antigen or a part thereof and MHC molecules may be carried out using a cell presenting the complex between said antigen or said part thereof and an MHC molecule.

The polynucleotide probe, the antibody, the protein or peptide or the cell, which is used for detection or monitoring, is preferably labeled in a detectable manner. In particular embodiments, the detectable marker is a radioactive marker or an enzymic marker. T lymphocytes may additionally be detected by detecting their proliferation, their cytokine production, and their cytotoxic activity triggered by specific stimulation with the complex of MHC and tumor-associated antigen or parts thereof. T lymphocytes may also be detected via a recombinant MHC molecule or else a complex of two or more MHC molecules which are loaded with the particular immunogenic fragment of one or more of the tumor-associated antigens and which can identify the specific T lymphocytes by contacting the specific T cell receptor.

In a further aspect, the invention relates to a method of treating, diagnosing or monitoring a disease characterized by expression or abnormal expression of a tumor-associated antigen identified according to the invention, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of a natural antibody.

The invention also relates to a method of treating a patient having a disease characterized by expression or abnormal expression of a tumor-associated antigen identified according to the invention, which method comprises (i) removing a sample containing immunoreactive cells from said patient, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. The invention likewise relates to cloning the T cell receptor of cytolytic T cells against the tumor-associated antigen. Said receptor may be transferred to other T cells which thus receive the desired specificity and, as under (iii), may be introduced into the patient.

In one embodiment, the host cell endogenously expresses an HLA molecule. In a further embodiment, the host cell recombinantly expresses an HLA molecule and/or the tumor-associated antigen or the part thereof. The host cell is preferably nonproliferative. In a preferred embodiment, the host cell is an antigen-presenting cell, in particular a dendritic cell, a monocyte or a macrophage.

In a further aspect, the invention relates to a method of treating a patient having a disease characterized by expression or abnormal expression of a tumor-associated antigen, which method comprises (i) identifying a nucleic acid which codes for a tumor-associated antigen identified according to the invention and which is expressed by cells associated with said disease, (ii) transfecting a host cell with said nucleic acid or a part thereof, (iii) culturing the transfected host cell for expression of said nucleic acid (this is not obligatory when a high rate of transfection is obtained), and (iv) introducing the host cells or an extract thereof into the patient in an amount suitable for increasing the immune response to the patient's cells associated with the disease. The method may further comprise identifying an MHC molecule presenting the tumor-associated antigen or a part thereof, with the host cell expressing the identified MHC molecule and presenting said tumor-associated antigen or a part thereof. The immune response may comprise a B cell response or a T cell response. Furthermore, a T cell response may comprise production of cytolytic T cells and/or T helper cells which are specific for the host cells presenting the tumor-associated antigen or a part thereof or specific for cells of the patient which express said tumor-associated antigen or a part thereof.

The invention also relates to a method of treating a disease characterized by expression or abnormal expression of a tumor-associated antigen identified according to the invention, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

Preferably, the host cells used according to the invention are nonproliferative or are rendered nonproliferative. A disease characterized by expression or abnormal expression of a tumor-associated antigen is in particular cancer.

The present invention furthermore relates to a nucleic acid selected from the group consisting of (a) a nucleic acid which comprises a nucleic acid sequence selected from the group consisting of SEQ ID NOs: 3-5, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The invention furthermore relates to a nucleic acid, which codes for a protein or polypeptide comprising an amino acid sequence selected from the group consisting of SEQ ID NOs: 10 and 12-14, a part or derivative thereof.

In a further aspect, the invention relates to promoter sequences of nucleic acids of the invention. These sequences may be functionally linked to another gene, preferably in an expression vector, and thus ensure selective expression of said gene in appropriate cells.

In a further aspect, the invention relates to a recombinant nucleic acid molecule, in particular DNA or RNA molecule, which comprises a nucleic acid of the invention.

The invention also relates to host cells which contain a nucleic acid of the invention or a recombinant nucleic acid molecule comprising a nucleic acid of the invention.

The host cell may also comprise a nucleic acid coding for a HLA molecule. In one embodiment, the host cell endogenously expresses the HLA molecule. In a further embodiment, the host cell recombinantly expresses the HLA molecule and/or the nucleic acid of the invention or a part thereof. Preferably, the host cell is nonproliferative. In a preferred embodiment, the host cell is an antigen-presenting cell, in particular a dendritic cell, a monocyte or a macrophage.

In a further embodiment, the invention relates to oligonucleotides which hybridize with a nucleic acid identified according to the invention and which may be used as genetic probes or as "antisense" molecules. Nucleic acid molecules in the form of oligonucleotide primers or competent samples, which hybridize with a nucleic acid identified according to the invention or parts thereof, may be used for finding nucleic acids which are homologous to said nucleic acid identified according to the invention. PCR amplification, Southern and Northern hybridization may be employed for finding homologous nucleic acids. Hybridization may be carried out under low stringency, more preferably under medium stringency and most preferably under high stringency conditions. The term "stringent conditions" according to the invention refers to conditions which allow specific hybridization between polynucleotides.

In a further aspect, the invention relates to a protein, polypeptide or peptide which is encoded by a nucleic acid selected from the group consisting of (a) a nucleic acid which comprises a nucleic acid sequence selected from the group consisting of SEQ ID NOs: 3-5, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the invention relates to a protein or polypeptide or peptide which comprises an amino acid sequence selected from the group consisting of SEQ ID NOs: 10 and 12-14, a part or derivative thereof.

In a further aspect, the invention relates to an immunogenic fragment of a tumor-associated antigen identified according to the invention. Said fragment preferably binds to a human HLA receptor or to a human antibody. A fragment of the invention preferably comprises a sequence of at least 6, in particular at least 8, at least 10, at least 12, at least 15, at least 20, at least 30 or at least 50, amino acids.

In this aspect the invention relates, in particular, to a peptide which has or comprises a sequence selected from the group consisting of SEQ ID NOs: 17-19, 90-97, 100-102, 105, 106, 111-116, 120, 123, 124, and 135-137, a part or derivative thereof.

In a further aspect, the invention relates to an agent which binds to a tumor-associated antigen identified according to the invention or to a part thereof. In a preferred embodiment, the agent is an antibody. In further embodiments, the antibody is a chimeric, a humanized antibody or an antibody produced by combinatory techniques or is a fragment of an antibody. Furthermore, the invention relates to an antibody which binds selectively to a complex of (i) a tumor-associated antigen identified according to the invention or a part thereof and (ii)

an MHC molecule to which said tumor-associated antigen identified according to the invention or said part thereof binds, with said antibody not binding to (i) or (ii) alone. An antibody of the invention may be a monoclonal antibody. In further embodiments, the antibody is a chimeric or humanized antibody or a fragment of a natural antibody.

In particular, the invention relates to such an agent, in particular an antibody, which specifically binds to a peptide which has or comprises a sequence selected from the group consisting of SEQ ID NOs: 17-19, 90-97, 100-102, 105, 106, 111-116, 120, 123, 124, and 135-137, a part or derivative thereof.

The invention furthermore relates to a conjugate between an agent of the invention which binds to a tumor-associated antigen identified according to the invention or to a part thereof or an antibody of the invention and a therapeutic or diagnostic agent. In one embodiment, the therapeutic or diagnostic agent is a toxin.

In a further aspect, the invention relates to a kit for detecting expression or abnormal expression of a tumor-associated antigen identified according to the invention, which kit comprises agents for detection (i) of the nucleic acid which codes for the tumor-associated antigen or of a part thereof, (ii) of the tumor-associated antigen or of a part thereof, (iii) of antibodies which bind to the tumor-associated antigen or to a part thereof, and/or (iv) of T cells which are specific for a complex between the tumor-associated antigen or a part thereof and an MHC molecule. In one embodiment, the agents for detection of the nucleic acid or the part thereof are nucleic acid molecules for selective amplification of said nucleic acid, which comprise, in particular a sequence of 6-50, in particular 10-30, 15-30 and 20-30, contiguous nucleotides of said nucleic acid.

DETAILED DESCRIPTION OF THE INVENTION

According to the invention, genes are described which are expressed in tumor cells selectively or aberrantly and which are tumor-associated antigens.

According to the invention, these genes and/or their genetic products and/or their derivatives and/or parts are preferred target structures for therapeutic approaches. Conceptionally, said therapeutic approaches may aim at inhibiting the activity of the selectively expressed tumor-associated genetic product. This is useful, if said aberrant respective selective expression is functionally important in tumor pathogenecity and if its ligation is accompanied by selective damage of the corresponding cells. Other therapeutic concepts contemplate tumor-associated antigens as labels which recruit effector mechanisms having cell-damaging potential selectively to tumor cells. Here, the function of the target molecule itself and its role in tumor development are totally irrelevant.

"Derivative" of a nucleic acid means according to the invention that single or multiple nucleotide substitutions, deletions and/or additions are present in said nucleic acid. Furthermore, the term "derivative" also comprises chemical derivatization of a nucleic acid on a nucleotide base, on the sugar or on the phosphate. The term "derivative" also comprises nucleic acids which contain nucleotides and nucleotide analogs not occurring naturally.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

According to the invention, complementary nucleic acids have at least 40%, in particular at least 50%, at least 60%, at least 70%, at least 80%, at least 90% and preferably at least 95%, at least 98% or at least 99%, identical nucleotides.

Nucleic acids coding for tumor-associated antigens may, according to the invention, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

Thus, on the one hand, the tumor-associated antigens illustrated herein may be combined with any expression control sequences and promoters. On the other hand, however, the promoters of the tumor-associated genetic products illustrated herein may, according to the invention, be combined with any other genes. This allows the selective activity of these promoters to be utilized.

According to the invention, a nucleic acid may furthermore be present in combination with another nucleic acid which codes for a polypeptide controlling secretion of the protein or polypeptide encoded by said nucleic acid from a host cell. According to the invention, a nucleic acid may also be present in combination with another nucleic acid which codes for a polypeptide causing the encoded protein or polypeptide to be anchored on the cell membrane of the host cell or compartmentalized into particular organelles of said cell. Similarly, a combination with a nucleic acid is possible which represents a reporter gene or any “tag”.

In a preferred embodiment, a recombinant DNA molecule is according to the invention a vector, where appropriate with a promoter, which controls expression of a nucleic acid, for example a nucleic acid coding for a tumor-associated antigen of the invention. The term “vector” is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids or viral genomes.

The nucleic acids coding for a tumor-associated antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

According to the invention, the term “host cell” relates to any cell which can be transformed or transfected with an exogenous nucleic acid. The term “host cells” comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines.

Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the invention, the term “expression” is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selectable marker such as a gene imparting resistance to G418 (and thus enabling stably transfected cell lines to be selected) and the enhancer-promoter sequences of cytomegalovirus (CMV).

In those cases of the invention in which an HLA molecule presents a tumor-associated antigen or a part thereof, an expression vector may also comprise a nucleic acid sequence coding for said HLA molecule. The nucleic acid sequence coding for the HLA molecule may be present on the same expression vector as the nucleic acid coding for the tumor-associated antigen or the part thereof, or both nucleic acids may be present on different expression vectors. In the latter case, the two expression vectors may be cotransfected into a cell. If a host cell expresses neither the tumor-associated antigen or the part thereof nor the HLA molecule, both nucleic acids coding therefor are transfected into the cell either on the same expression vector or on different expression vectors. If the cell already expresses the HLA molecule, only the nucleic acid sequence coding for the tumor-associated antigen or the part thereof can be transfected into the cell.

The invention also comprises kits for amplification of a nucleic acid coding for a tumor-associated antigen. Such kits comprise, for example, a pair of amplification primers which hybridize to the nucleic acid coding for the tumor-associated antigen. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid coding for the tumor-associated antigen, and the other primer will hybridize to the complementary strand in an arrangement which allows amplification of the nucleic acid coding for the tumor-associated antigen.

“Antisense” molecules or “antisense” nucleic acids may be used for regulating, in particular reducing, expression of a nucleic acid. The term “antisense molecule” or “antisense nucleic acid” refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, an “antisense molecule” also comprises a construct which contains a nucleic acid or a part thereof in reverse orientation with respect to its natural promoter. An antisense transcript of a nucleic acid or of a part thereof may form a duplex with the naturally occurring mRNA specifying the enzyme and thus prevent accumulation of or translation of the mRNA into the active enzyme.

Another possibility is the use of ribozymes for inactivating a nucleic acid. Antisense oligonucleotides preferred according to the invention have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a “modified” oligonucleotide. Here, the oligonucleotide may be modified in very different ways, without impairing its ability to bind its target, in order to increase, for example, its stability or therapeutic efficacy. According to the invention, the term “modified oligonucleotide” means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term “modified oligonucleotide” also comprises oligonucleotides having a covalently modified base and/or sugar. “Modified oligonucleotides” comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

Preferably, the proteins and polypeptides described according to the invention have been isolated. The terms “isolated protein” or “isolated polypeptide” mean that the protein or polypeptide has been separated from its natural environment. An isolated protein or polypeptide may be in an essentially purified state. The term “essentially purified” means that the protein or polypeptide is essentially free of other substances with which it is associated in nature or in vivo.

Such proteins and polypeptides may be used, for example, in producing antibodies and in an immunological or diagnostic assay or as therapeutics. Proteins and polypeptides described according to the invention may be isolated from biological samples such as tissue or cell homogenates and may also be expressed recombinantly in a multiplicity of pro- or eukaryotic expression systems.

For the purposes of the present invention, “derivatives” of a protein or polypeptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid deletion variants are characterized by the removal of one or more amino acids from the sequence. Amino acid substitution variants are characterized by at least one residue in the sequence being removed and another residue being inserted in its place. Preference is given to the modifications being in positions in the amino acid sequence which are not conserved between homologous proteins or polypeptides. Preference is given to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:

1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

The amino acid variants described above may be readily prepared with the aid of known peptide synthesis techniques such as, for example, by solid phase synthesis (Merrifield, 1964) and similar methods or by recombinant DNA manipulation. Techniques for introducing substitution mutations at predetermined sites into DNA which has a known or partially known sequence are well known and comprise M13 mutagenesis, for example. The manipulation of DNA sequences for preparing proteins having substitutions, insertions or deletions, is described in detail in Sambrook et al. (1989), for example.

According to the invention, “derivatives” of proteins, polypeptides or peptides also comprise single or multiple substitutions, deletions and/or additions of any molecules associated with the enzyme, such as carbohydrates, lipids and/or proteins, polypeptides or peptides. The term “derivative” also extends to all functional chemical equivalents of said proteins, polypeptides or peptides.

According to the invention, a part or fragment of a tumor-associated antigen has a functional property of the polypeptide from which it has been derived. Such functional properties comprise the interaction with antibodies, the interaction with other polypeptides or proteins, the selective binding of nucleic acids and an enzymatic activity. A particular property is the ability to form a complex with HLA and, where appropriate, generate an immune response. This immune response may be based on stimulating cytotoxic or T helper cells. A part or fragment of a tumor-associated antigen of the invention preferably comprises a sequence of at least 6, in particular at least 8, at least 10, at least 12, at least 15, at least 20, at least 30 or at least 50, consecutive amino acids of the tumor-associated antigen.

A part or a fragment of a nucleic acid coding for a tumor-associated antigen relates according to the invention to the part of the nucleic acid, which codes at least for the tumor-associated antigen and/or for a part or a fragment of said tumor-associated antigen, as defined above.

The isolation and identification of genes coding for tumor-associated antigens also make possible the diagnosis of a disease characterized by expression of one or more tumor-associated antigens. These methods comprise determining one or more nucleic acids which code for a tumor-associated antigen and/or determining the encoded tumor-associated antigens and/or peptides derived therefrom. The nucleic acids may be determined in the conventional manner, including by polymerase chain reaction or hybridization with a labeled probe. Tumor-associated antigens or peptides derived therefrom may be determined by screening patient antisera with respect to recognizing the antigen and/or the peptides. They may also be determined by screening T cells of the patient for specificities for the corresponding tumor-associated antigen.

The present invention also enables proteins binding to tumor-associated antigens described herein to be isolated, including antibodies and cellular binding partners of said tumor-associated antigens.

According to the invention, particular embodiments ought to involve providing “dominant negative” polypeptides derived from tumor-associated antigens. A dominant negative polypeptide is an inactive protein variant which, by way of interacting with the cellular machinery, displaces an active protein from its interaction with the cellular machinery or which competes with the active protein, thereby reducing the effect of said active protein. For example, a dominant negative receptor which binds to a ligand but does not generate any signal as response to binding to the ligand can reduce the biological effect of said ligand. Similarly, a dominant negative catalytically inactive kinase which usually interacts with target proteins but does not phosphorylate said target proteins may reduce phosphorylation of said target proteins as response to a cellular signal. Similarly, a dominant negative transcription factor which binds to a promoter site in the control region of a gene but does not increase transcription of said gene may reduce the effect of a normal transcription factor by occupying promoter binding sites, without increasing transcription.

The result of expression of a dominant negative polypeptide in a cell is a reduction in the function of active proteins. The skilled worker may prepare dominant negative variants of a protein, for example, by conventional mutagenesis methods and by evaluating the dominant negative effect of the variant polypeptide.

The invention also comprises substances such as polypeptides which bind to tumor-associated antigens. Such binding substances may be used, for example, in screening assays for detecting tumor-associated antigens and complexes of tumor-associated antigens with their binding partners and in the purification of said tumor-associated antigens and of complexes thereof with their binding partners. Such substances may also be used for inhibiting the activity of tumor-associated antigens, for example by binding to such antigens.

The invention therefore comprises binding substances such as, for example, antibodies or antibody fragments, which are capable of selectively binding to tumor-associated antigens. Antibodies comprise polyclonal and monoclonal antibodies which are produced in the conventional manner.

Such antibodies can recognize proteins in the native and/or denaturated state (Anderson et al., J. Immunol. 143: 1899-1904, 1989; Gardsvoll, J. Immunol. Methods 234: 107-116, 2000; Kayyem et al., Eur. J. Biochem. 208: 1-8, 1992; Spiller et al., J. Immunol. Methods 224: 51-60, 1999).

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual: Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol. Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology,* 7th Edition, Blackwell Scientific Publications, Oxford). The pFc' and Fc regions are, for example, effectors of the complement cascade but are not involved in antigen binding. An antibody from which the pfc' region has been enzymatically removed or which has been produced without the pFc' region, referred to as $F(ab')_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

This is utilized in the so called "SLAM" technology, wherein B cells from whole blood are isolated and the cells are monocloned. Then, the supernatant of the single B cells is analyzed with respect to its antibody specificity. In contrast to the hybridoma technology the variable region of the antibody gene is amplified using single cell PCR and cloned into a suitable vector. In this way, the provision of monoclonal antibodies is accelerated (de Wildt et al., J. Immunol. Methods 207: 61-67, 1997).

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

The invention also provides $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The invention also comprises "single-chain" antibodies.

The invention also comprises polypeptides which bind specifically to tumor-associated antigens. Polypeptide binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Phage display may be particularly effective in identifying binding peptides of the invention. In this connection, for example, a phage library is prepared (using, for example, the M13, fd or lambda phages) which presents inserts of from 4 to about 80 amino acid residues in length. Phages are then selected which carry inserts which bind to the tumor-associated antigen. This process may be repeated via two or more cycles of a reselection of phages binding to the tumor-associated antigen. Repeated rounds result in a concentration of phages carrying particular sequences. An analysis of DNA sequences may be carried out in order to identify the sequences of the expressed polypeptides. The smallest linear portion of the sequence binding to the tumor-associated antigen may be determined. The "two-hybrid system" of yeast may also be used for identifying polypeptides which bind to a tumor-associated antigen. Tumor-associated antigens described according to the invention or fragments thereof may be used for screening peptide libraries, including phage-display libraries, in order to identify and select peptide binding partners of the tumor-associated antigens. Such molecules may be used, for example, for screening assays, purification protocols, for interference with the function of the tumor-associated antigen and for other purposes known to the skilled worker.

The antibodies described above and other binding molecules may be used, for example, for identifying tissue which expresses a tumor-associated antigen. Antibodies may also be coupled to specific diagnostic substances for displaying cells and tissues expressing tumor-associated antigens. They may also be coupled to therapeutically useful substances. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium. According to the invention, the term "therapeutically useful substance" means any therapeutic molecule which, as desired, is selectively guided to a cell which expresses one or more tumor-associated antigens, including anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

According to the invention, the term "disease" refers to any pathological state in which tumor-associated antigens are expressed or abnormally expressed. "Abnormal expression" means according to the invention that expression is altered, preferably increased, compared to the state in a healthy individual. An increase in expression refers to an increase by at least 10%, in particular at least 20%, at least 50% or at least 100%. In one embodiment, the tumor-associated antigen is expressed only in tissue of a diseased individual, while expression in a healthy individual is repressed. One example of such a disease is cancer, wherein the term "cancer" according to the invention comprises leukemias, seminomas, melanomas, teratomas, gliomas, kidney cancer, adrenal cancer, thyroid cancer, intestinal cancer, liver cancer, colon cancer, stomach cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the matastases thereof.

According to the invention, a biological sample may be a tissue sample and/or a cellular sample and may be obtained in the conventional manner such as by tissue biopsy, including punch biopsy, and by taking blood, bronchial aspirate, sputum, urine, feces or other body fluids, for use in the various methods described herein.

According to the invention, the term "immunoreactive cell" means a cell which can mature into an immune cell (such as B cell, T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

Some therapeutic methods are based on a reaction of the immune system of a patient, which results in a lysis of antigen-presenting cells such as cancer cells which present one or more tumor-associated antigens. In this connection, for example autologous cytotoxic T lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for detecting specific clones of cytotoxic T lymphocytes (Altman et al., *Science* 274:94-96, 1996; Dunbar et al., *Curr. Biol.* 8:413-416, 1998). Soluble MHC class I molecules are folded in vitro in the presence of $\beta_2$ microglobulin and a peptide antigen binding to said class I molecule. The MHC/peptide complexes are purified and then labeled with biotin. Tetramers are formed by mixing the biotinylated peptide-MHC complexes with labeled avidin (e.g. phycoerythrin) in a molar ratio of 4:1. Tetramers are then contacted with cytotoxic T lymphocytes such as peripheral blood or lymph nodes. The tetramers bind to cytotoxic T lymphocytes which recognize the peptide antigen/MHC class I complex. Cells which are bound to the tetramers may be sorted by fluorescence-controlled cell sorting to isolate reactive cytotoxic T lymphocytes. The isolated cytotoxic T lymphocytes may then be propagated in vitro.

In a therapeutic method referred to as adoptive transfer (Greenberg, *J. Immunol.* 136(5):1917, 1986; Riddel et al., *Science* 257:238, 1992; Lynch et al., *Eur. J. Immunol.* 21:1403-1410, 1991; Kast et al., *Cell* 59:603-614, 1989), cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Often, of the T cell repertoire of a patient, only T cells with low affinity for a specific complex of this kind can be propagated, since those with high affinity have been extinguished due to development of tolerance. An alternative here may be a transfer of the T cell receptor itself. For this too, cells presenting the desired complex (e.g. dendritic cells) are combined with cytotoxic T lymphocytes of healthy individuals or another species (e.g. mouse). This results in propagation of specific cytotoxic T lymphocytes with high affinity if the T lymphocytes are derived from a donor organism which had no previous contact with the specific complex. The high affinity T cell receptor of these propagated specific T lymphocytes is cloned. If the high affinity T cell receptors have been cloned from another species they can be humanized to a different extent. Such T cell receptors are then transduced via gene transfer, for example using retroviral vectors, into T cells of patients, as desired. Adoptive transfer is then carried out using these genetically altered T lymphocytes (Stanislawski et al., Nat Immunol. 2:962-70, 2001; Kessels et al., Nat Immunol. 2:957-61, 2001).

The therapeutic aspects above start out from the fact that at least some of the abnormal cells of the patient present a complex of a tumor-associated antigen and an HLA molecule. Such cells may be identified in a manner known per se. As soon as cells presenting the complex have been identified, they may be combined with a sample from the patient, which contains cytotoxic T lymphocytes. If the cytotoxic T lymphocytes lyse the cells presenting the complex, it can be assumed that a tumor-associated antigen is presented.

Adoptive transfer is not the only form of therapy which can be applied according to the invention. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting HLA molecule). Various cell types may be used. Furthermore, it is possible to use vectors which carry one or both of the genes of interest. Particular preference is given to viral or bacterial vectors. For example, nucleic acids coding for a tumor-associated antigen or for a part thereof may be functionally linked to promoter and enhancer sequences which control expression of said tumor-associated antigen or a fragment thereof in particular tissues or cell types. The nucleic acid may be incorporated into an expression vector. Expression vectors may be nonmodified extrachromosomal nucleic acids, plasmids or viral genomes into which exogenous nucleic acids may be inserted. Nucleic acids coding for a tumor-associated antigen may also be inserted into a retroviral genome, thereby enabling the nucleic acid to be integrated into the genome of the target tissue or target cell. In these systems, a microorganism such as vaccinia virus, pox virus, Herpes simplex virus, retrovirus or adenovirus carries the gene of interest and de facto “infects” host cells. Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen-presenting cells in vivo possible. The tumor-associated antigen or a fragment thereof may be represented as protein, as DNA (e.g. within a vector) or as RNA. The tumor-associated antigen is processed to produce a peptide partner for the HLA molecule, while a fragment thereof may be presented without the need for further processing. The latter is the case in particular, if these can bind to HLA molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor-associated antigen to a patient by intradermal injection, for example. However, injection may also be carried out intranodally into a lymph node (Maloy et al., *Proc Natl Acad Sci USA* 98:3299-303, 2001). It may also be carried out in combination with reagents which facilitate uptake into dendritic cells. Preferred tumor-associated antigens comprise those which react with allogenic cancer antisera or with T cells of many cancer patients. Of particular interest, however, are those against which no spontaneous immune responses pre-exist. Evidently, it is possible to induce against these immune responses which can lyse tumors (Keogh et al., *J. Immunol.* 167:787-96,. 2001; Appella et al., *Biomed Pept Proteins Nucleic Acids* 1:177-84, 1995; Wentworth et al., *Mol Immunol.* 32:603-12, 1995).

The pharmaceutical compositions described according to the invention may also be used as vaccines for immunization. According to the invention, the terms “immunization” or “vaccination” mean an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization, one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and/or stimulating particular lymphocytes. Adjuvants are known and comprise in a nonlimiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., Mol. Cells 7:178-186, 1997), incomplete Freund's adjuvant, complete Freund's adjuvant, vitamin E, montanide, alum, CpG oligonucleotides (cf. Kreig et al., Nature 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 μg to about 100 μg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids. Examples of such costimulating molecules are B7-1 and B7-2 (CD80 and CD86, respectively) which are expressed on dendritic cells (DC) and interact with the CD28 molecule expressed on the T cells. This interaction provides a costimulation (signal 2) for an antigen/MHC/TCR-stimulated (signal 1) T cell, thereby enhancing propagation of said T cell and the effector function. B7 also interacts with CTLA4 (CD152) on T cells, and studies involving CTLA4 and B7 ligands demonstrate that B7-CTLA4 interaction can enhance antitumor immunity and CTL propagation (Zheng, P. et al., *Proc. Natl. Acad. Sci. USA* 95(11):6284-6289 (1998)).

B7 is typically not expressed on tumor cells so that these are no effective antigen-presenting cells (APCs) for T cells. Induction of B7 expression would enable tumor cells to stimulate more effectively propagation of cytotoxic T lymphocytes and an effector function. Costimulation by a combination of B7/IL-6/IL-12 revealed induction of IFN-gamma and Th1-cytokine profile in a T cell population, resulting in further enhanced T cell activity (Gajewski et al., *J. Immunol.* 154:5637-5648 (1995)).

A complete activation of cytotoxic T lymphocytes and a complete effector function require an involvement of T helper cells via interaction between the CD40 ligand on said T helper cells and the CD40 molecule expressed by dendritic cells (Ridge et al., *Nature* 393:474 (1998), Bennett et al., *Nature* 393:478 (1998), Schönberger et al., *Nature* 393:480 (1998)). The mechanism of this costimulating signal probably relates to the increase in B7 production and associated IL-6/IL-12 production by said dendritic cells (antigen-presenting cells). CD40-CD40L interaction thus complements the interaction of signal 1 (antigen/MHC-TCR) and signal 2 (B7-CD28).

The use of anti-CD40 antibodies for stimulating dendritic cells would be expected to directly enhance a response to tumor antigens which are usually outside the range of an inflammatory response or which are presented by nonprofessional antigen-presenting cells (tumor cells). In these situations, T helper and B7-costimulating signals are not provided. This mechanism could be used in connection with therapies based on antigen-pulsed dendritic cells.

The invention also provides for administration of nucleic acids, polypeptides or peptides. Polypeptides and peptides may be administered in a manner known per se. In one embodiment, nucleic acids are administered by ex vivo methods, i.e. by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The invention also provides for administering nucleic acids in vivo by using vectors such as viruses and target-controlled liposomes.

In a preferred embodiment, a viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Various methods may be used in order to introduce according to the invention nucleic acids into cells in vitro or in vivo. Methods of this kind comprise transfection of nucleic acid $CaPO_4$ precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants, CpG and cytokines and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of a particular condition characterized by expression of one or more tumor-associated antigens, the desired reaction relates to inhibition of the course of the disease. This comprises slowing down the progress of the disease and, in particular, interrupting the progress of the disease. The desired reaction in a treatment of a disease or of a condition may also be delay of the onset or a prevention of the onset of said disease or said condition.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 μg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, suspensions, syrups, elixir or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting.

Owing to the description and the examples, further embodiments which are likewise included in the invention are accessible to the skilled worker.

RT-PCR investigations with DNA-free RNA show GPR35 expression in most of the colon carcinoma biopsies. By contrast, there is no detectable expression in normal tissues. (1-Breast, 2-lung, 3-lymph nodes, 4-thymus, 5-colon, 6-15 colon carcinoma, 16-neg. control).

Figure 2:
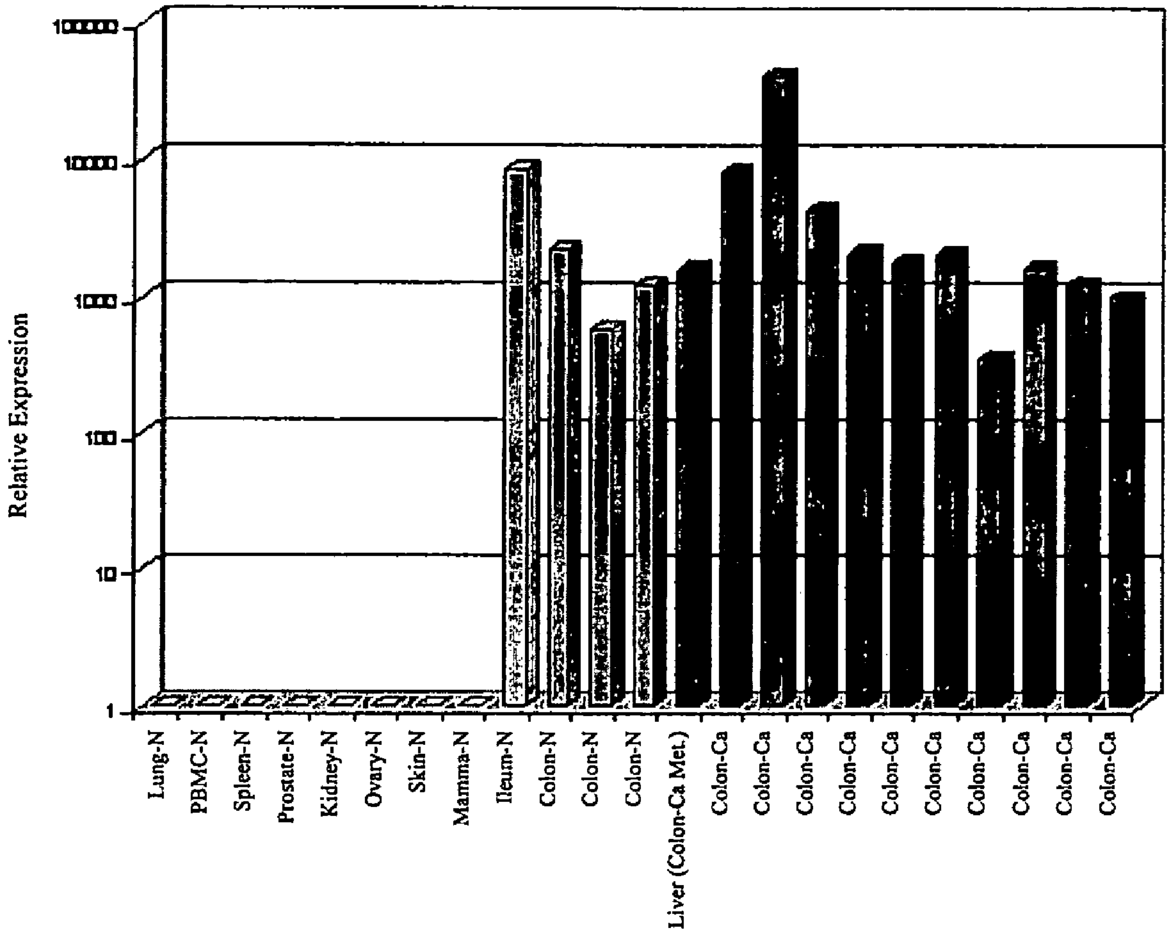

FIG. 2. Quantitative PCR analysis of GUCY2C mRNA expression in normal and tumor tissues Real-time PCR investigation with GUCY2C-specific primers (SEQ ID NO: 22-23) shows selective mRNA expression in normal ileum, colon, and in all colon carcinoma biopsies. Distinct quanities of GUCY2C transcripts were also detected in a colon carcinoma metastasis in the liver.

Figure 3:
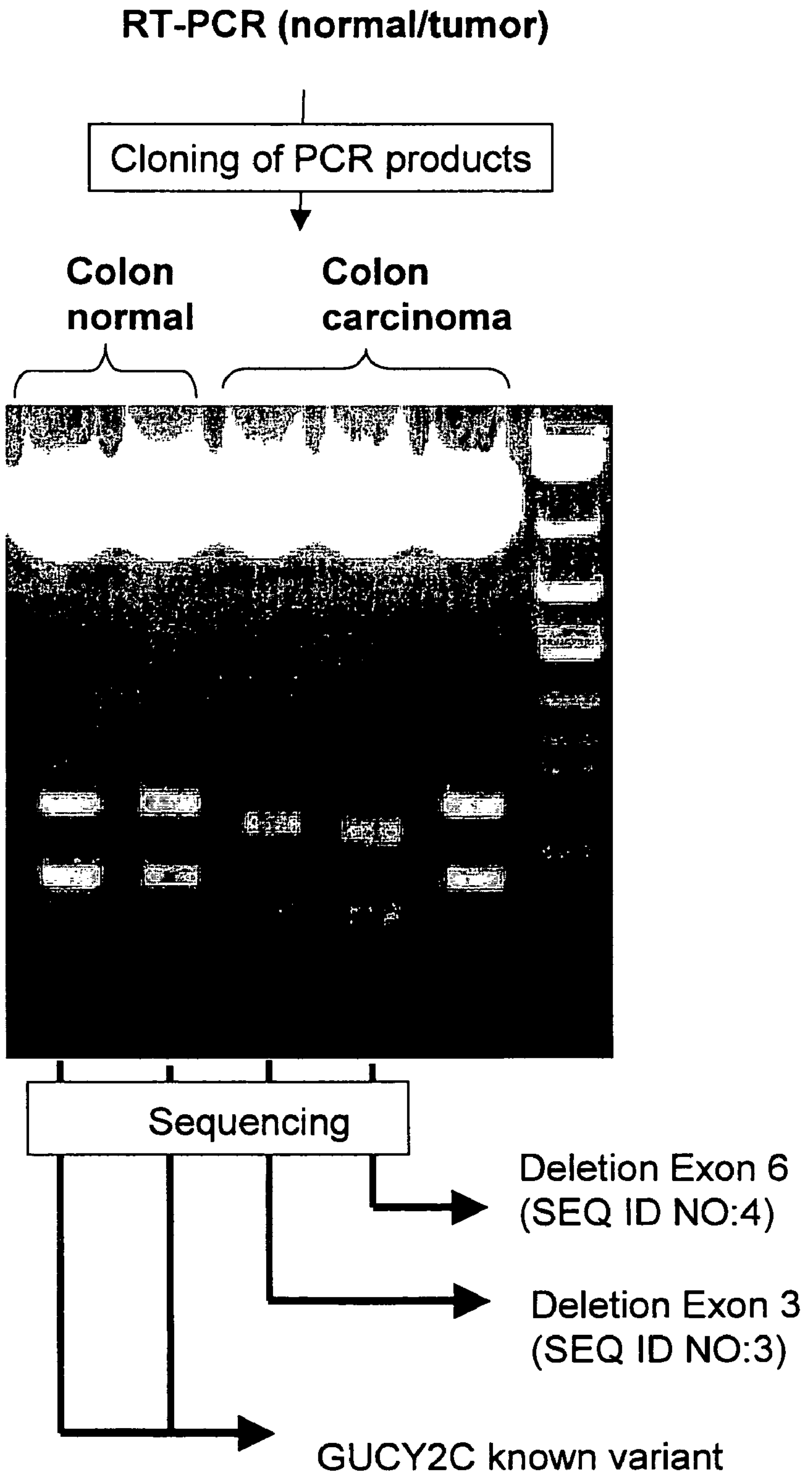

FIG. 3. Identification of tumor-specific GUCY2C splice variants

PCR products from normal colon tissues and colon carcinomas were cloned, and clones from both groups were checked by restriction analysis (EcoR I) and sequenced.

Figure 4:
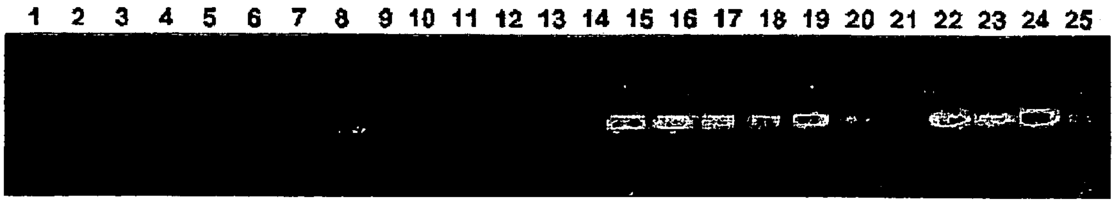

FIG. 4. Selective SCGB3A expression in normal lung and lung carcinoma

RT-PCR analysis with gene-specific SCGB3A2 primers (SEQ ID NO: 37, 38) shows cDNA amplification exclusively in normal lung (lane 8, 14-15) and in lung carcinoma biopsies (lane 16-24). (1-Liver-N, 2-PBMC-N, 3-lymph node-N, 4-stomach-N, 5-testis-N, 6-breast-N, 7-kidney-N, 8-lung-N, 9-thymus-N, 10-ovary-N, 11-adrenal-N, 12-spleen-N, 14-15-lung-N, 16-24-lung carcinoma, 25-negative control).

Figure 5:
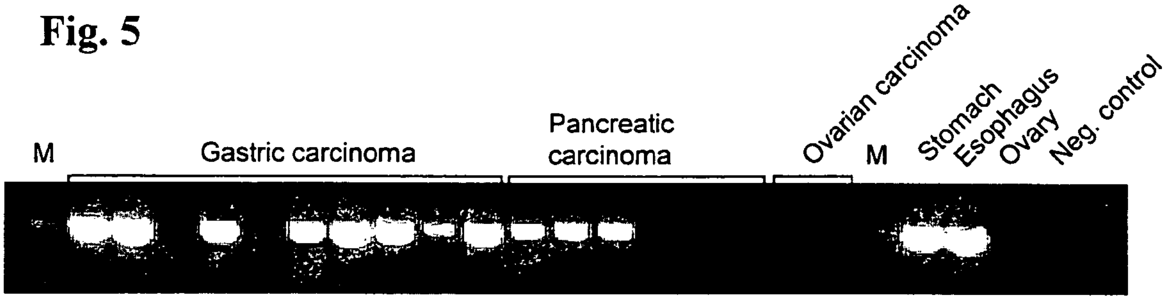

FIG. 5. Claudin-18A2.1 expression in stomach, esophagus, stomach carcinoma and pancreatic carcinoma RT-PCR analysis with claudin-18A2.1-specific primers (SEQ ID NO: 39, 40) showed according to the invention pronounced claudin-18A2.1 expression in 8/10 stomach carcinoma biopsies and in 3/6 pancreatic carcinoma biopsies. Distinct expression was also detected in stomach and normal esophageal tissue. In contrast thereto, no expression was detected in the ovary and in ovarian carcinoma.

Figure 6:
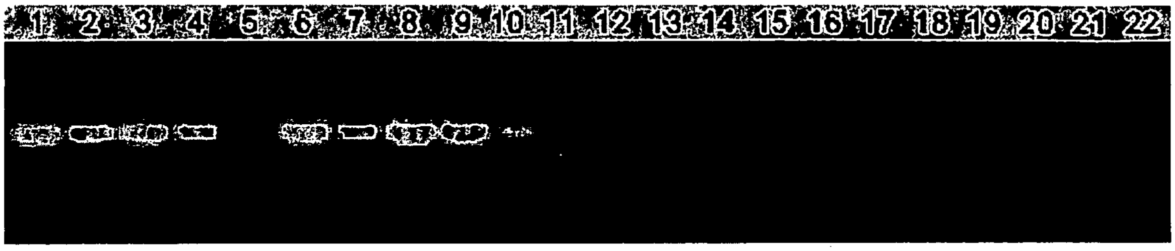

FIG. 6. SLC13A1 expression in the kidney and renal cell carcinoma

RT-PCR analysis with SLC13A1-specific primers (SEQ ID NO: 49, 50) showed expression in 7/8 renal cell carcinoma samples. Otherwise, transcripts within normal tissues were detected exclusively in the kidney. (1-2-kidney, 3-10-renal cell carcinoma, 11-breast, 12-lung, 13-liver, 14-colon, 15-lymph nodes, 16-spleen, 17-esophagus, 18-thymus, 19-thyroid, 20-PBMCs, 21-ovary, 22-testis).

Figure 7:
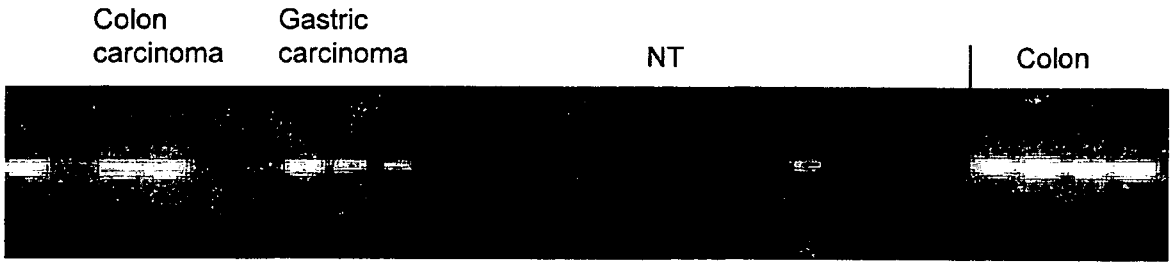

FIG. 7. CLCA1 expression in colon, colon carcinoma and stomach carcinoma

RT-PCR investigations with CLCA1-specific primers. (SEQ ID NO: 67, 68) confirmed selective expression in the colon and showed high expression in (3/7) investigated colon carcinoma and (1/3) investigated stomach carcinoma samples. The other normal tissues (NT) showed no or only very weak expression.

Figure 8:

FIG. 8. FLJ21477 expression in the colon and colon carcinoma

RT-PCR investigations with FLJ21477-specific primers (SEQ ID NO: 69, 70) showed selective expression in the colon and additionally various levels of expression in (7/12) investigated colon carcinoma samples. The other normal tissues (NT) showed no expression.

Figure 9:
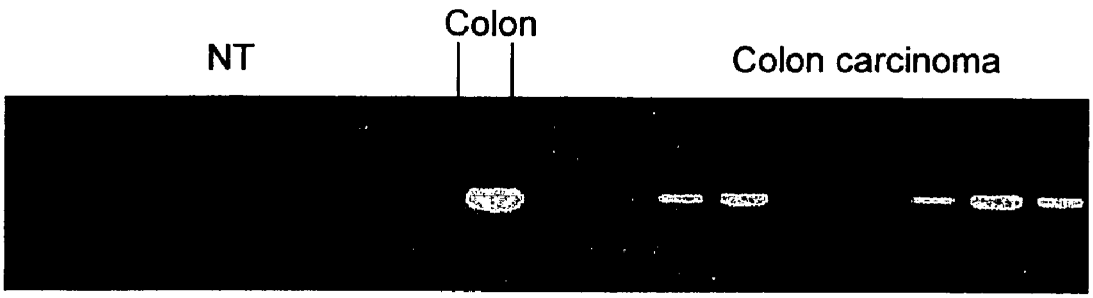

FIG. 9. FLJ20694 expression in the colon and colon carcinoma

RT-PCR investigations with FLJ20694-specific primers (SEQ ID NO: 71, 72) showed selective expression in the colon and additionally various levels of expression in (5/9) investigated colon carcinoma samples. The other normal tissues (NT) showed no expression.

Figure 10:
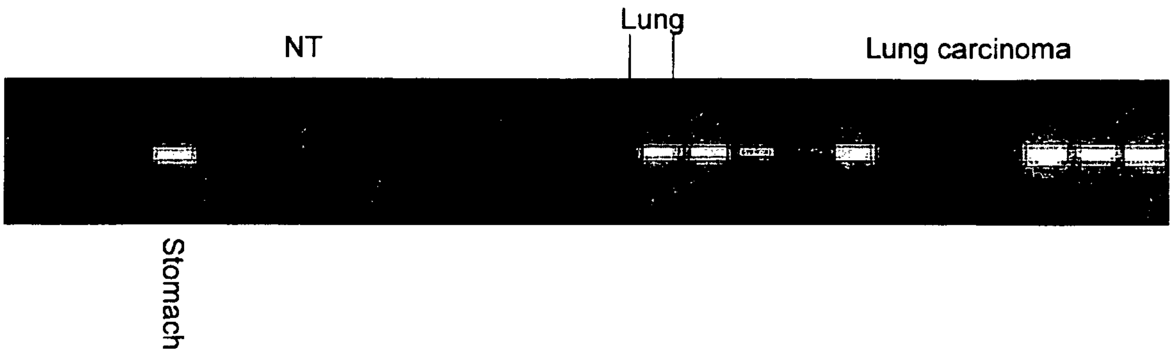

FIG. 10. von Ebner expression in stomach, lung and lung carcinoma

RT-PCR investigations with von Ebner-specific primers (SEQ ID NO: 73, 74) showed selective expression in the stomach, in the lung and in (5/10) investigated lung carcinoma samples. The other normal tissues (NT) showed no expression.

Figure 11:
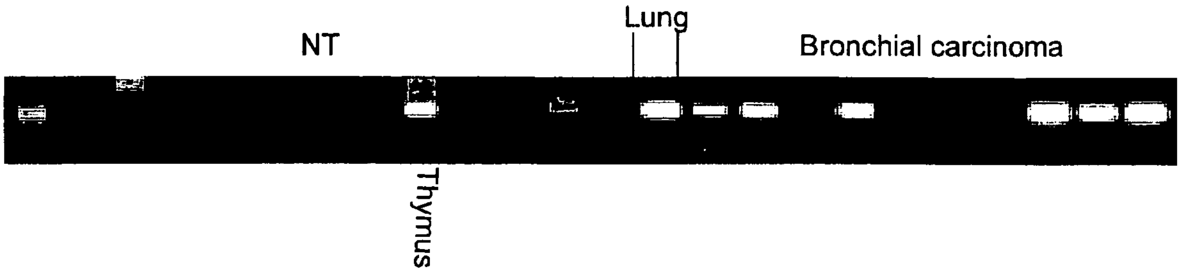

FIG. 11. Plunc expression in thymus, lung and lung carcinoma

RT-PCR investigations with Plunc-specific primers (SEQ ID NO: 75, 76) showed selective expression in the thymus, in the lung and in (6/10) investigated lung carcinoma samples. The other normal tissues showed no expression.

Figure 12:
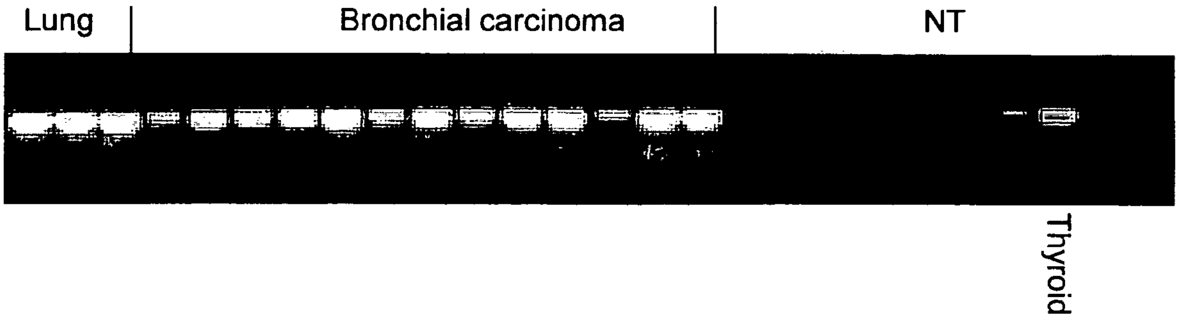

FIG. 12. SLC26A9 expression in lung, lung carcinoma and thyroid

RT-PCR investigations with SLC26A9-specific primers (SEQ ID NO: 77, 78) showed selective expression in the lung and in all (13/13) investigated lung carcinoma samples. The other normal tissues (NT) showed no expression with the exception of the thyroid.

Figure 13:
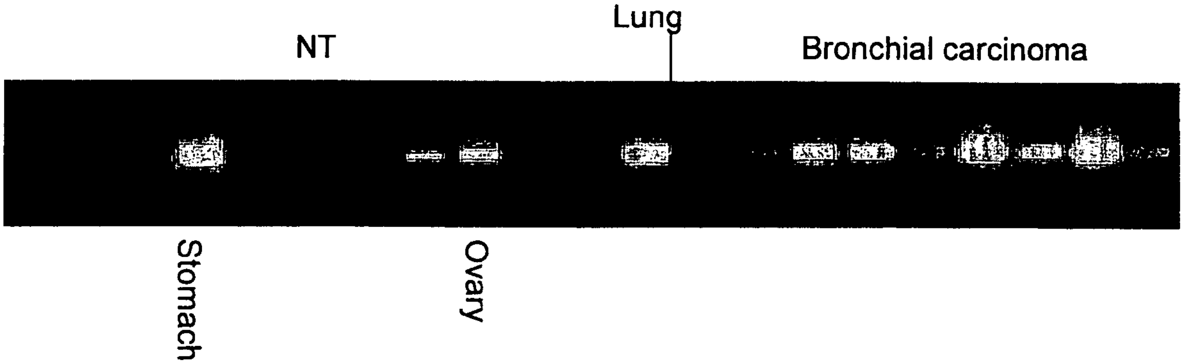

FIG. 13. THC1005163 expression in stomach, ovary, lung and lung carcinoma

RT-PCR investigations with a THC1005163-specific primer (SEQ ID NO: 79) and a nonspecific oligo dT tag primer showed expression in stomach, ovary, lung and in (5/9) lung carcinoma biopsies. The other normal tissues (NT) showed no expression.

Figure 14:
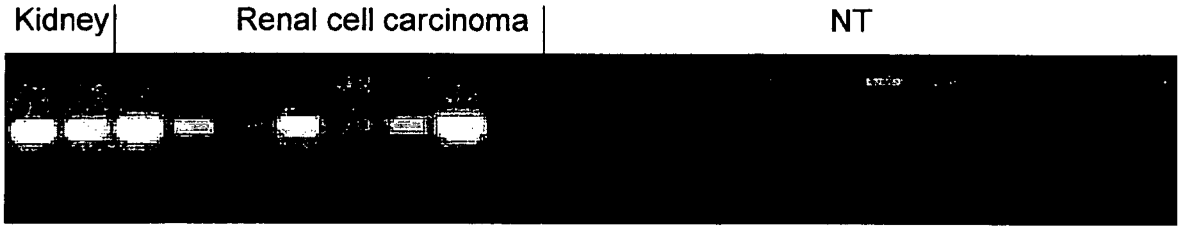

FIG. 14. LOC134288 expression in kidney and renal cell carcinoma

RT-PCR investigations with LOC134288-specific primers (SEQ ID NO: 80, 81) showed selective expression in the kidney and in (5/8) investigated renal cell carcinoma biopsies.

Figure 15:
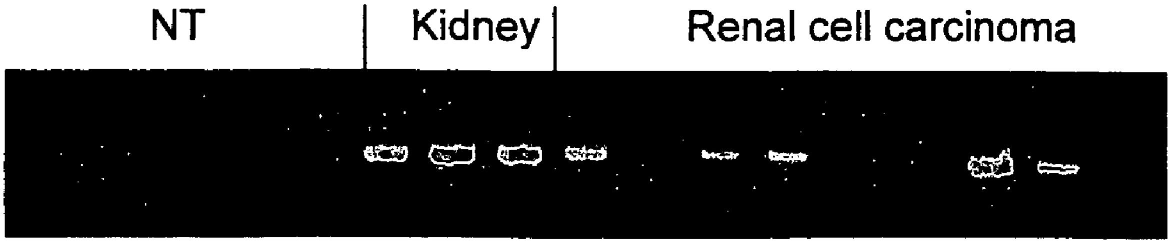

FIG. 15. THC943866 expression in kidney and renal cell carcinoma

RT-PCR investigations with THC943866-specific primers (SEQ ID NO: 82, 83) showed selective expression in the kidney and in (4/8) investigated renal cell carcinoma biopsies.

Figure 16:
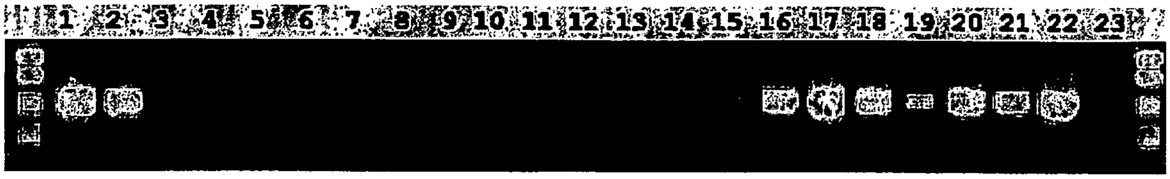

FIG. 16. FLJ21458 expression in colon and colon carcinoma

RT-PCR investigations with FLJ21458-specific primers (SEQ ID NO: 86, 87) showed selective expression in the colon and in (7/10) investigated colon carcinoma biopsies. (1-2-colon, 3-liver, 4-PBMCs, 5-spleen, 6-prostate, 7-kidney, 8-ovary, 9-skin, 10-ileum, 11-lung, 12-testis, 13-22 colon carcinoma, 23-neg. control).

Figure 17:

FIG. 17. Cellular localization of GPR35

Immunofluorescence for detecting the cellular localization of GPR35 after transfection of a plasmid that expresses a GPR35-GFP fusion protein. The arrows identify the membrane-associated fluorescence of the fluorescent GFP.

Figure 18:
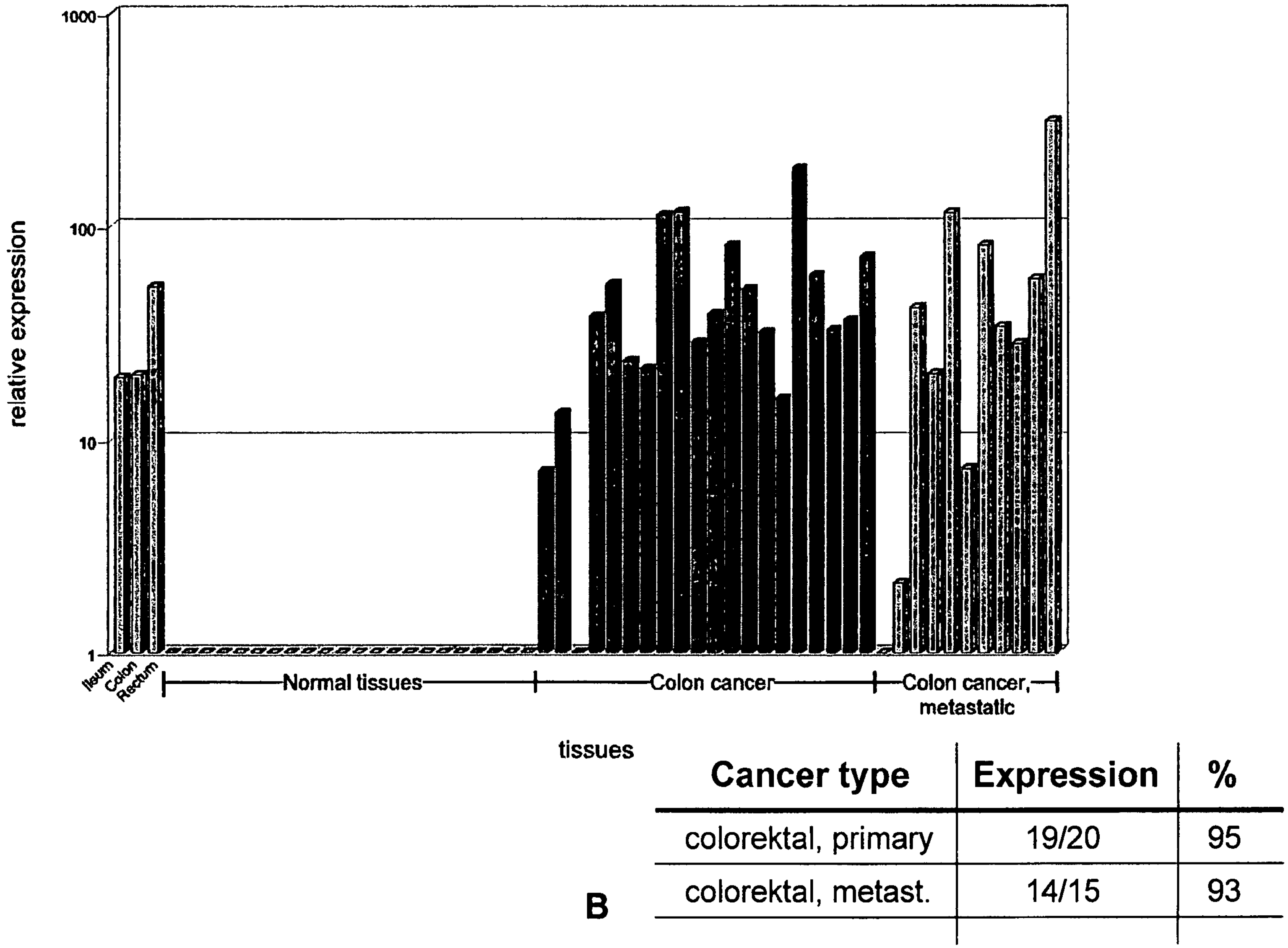

FIG. 18. Quantitative expression of GPR35

A. Quantitative RT-PCR with GPR35-specific primers (SEQ ID NO: 88, 89) show selective expression in the intestine, in colon tumor samples and in metastases from intestinal tumors. The following normal tissues were analyzed: liver, lung, lymph nodes, stomach, spleen, adrenal, kidney, esophagus, ovary, testis, thymus, skin, breast, pancreas, lymphocytes, activated lymphocytes, prostate, thyroid, fallopian tube, endometrium, cerebellum, brain.

B. Prevalence of GPR35 in colon tumors and metastases thereof. GPR35 is expressed both in the tumor and in metastases in more than 90% of the cases.

Figure 19:
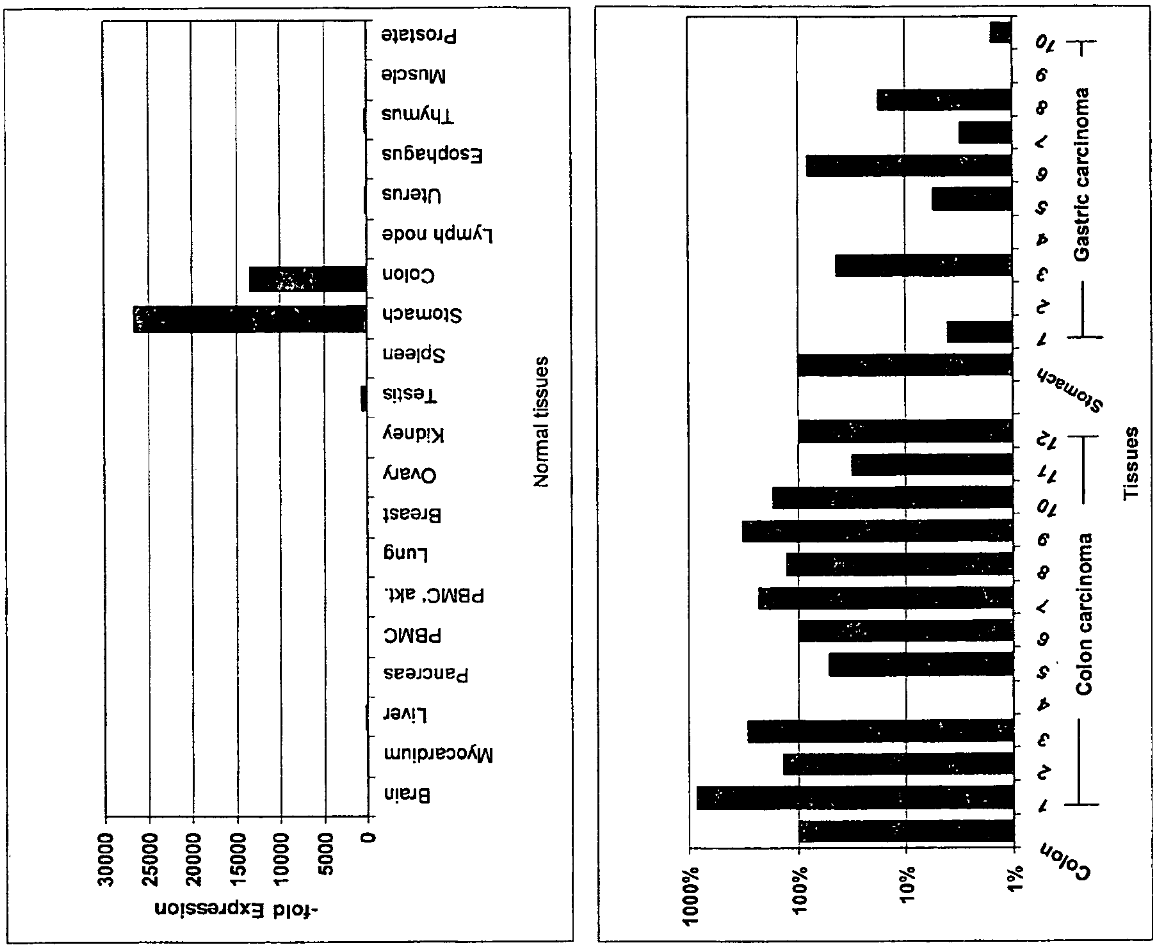

FIG. 19. Quantitative expression of GUCY2C

Quantitative RT-PCR with GUCY2C-specific primers (SEQ ID NO: 98, 99) show high and selective expression in normal colonic and gastric tissue (A) and GUCY2C-specific expression in colonic and gastric tumor samples (B). GUCY2C is detectable in 11/12 colon carcinomas and in 7/10 stomach carcinomas.

Figure 20:
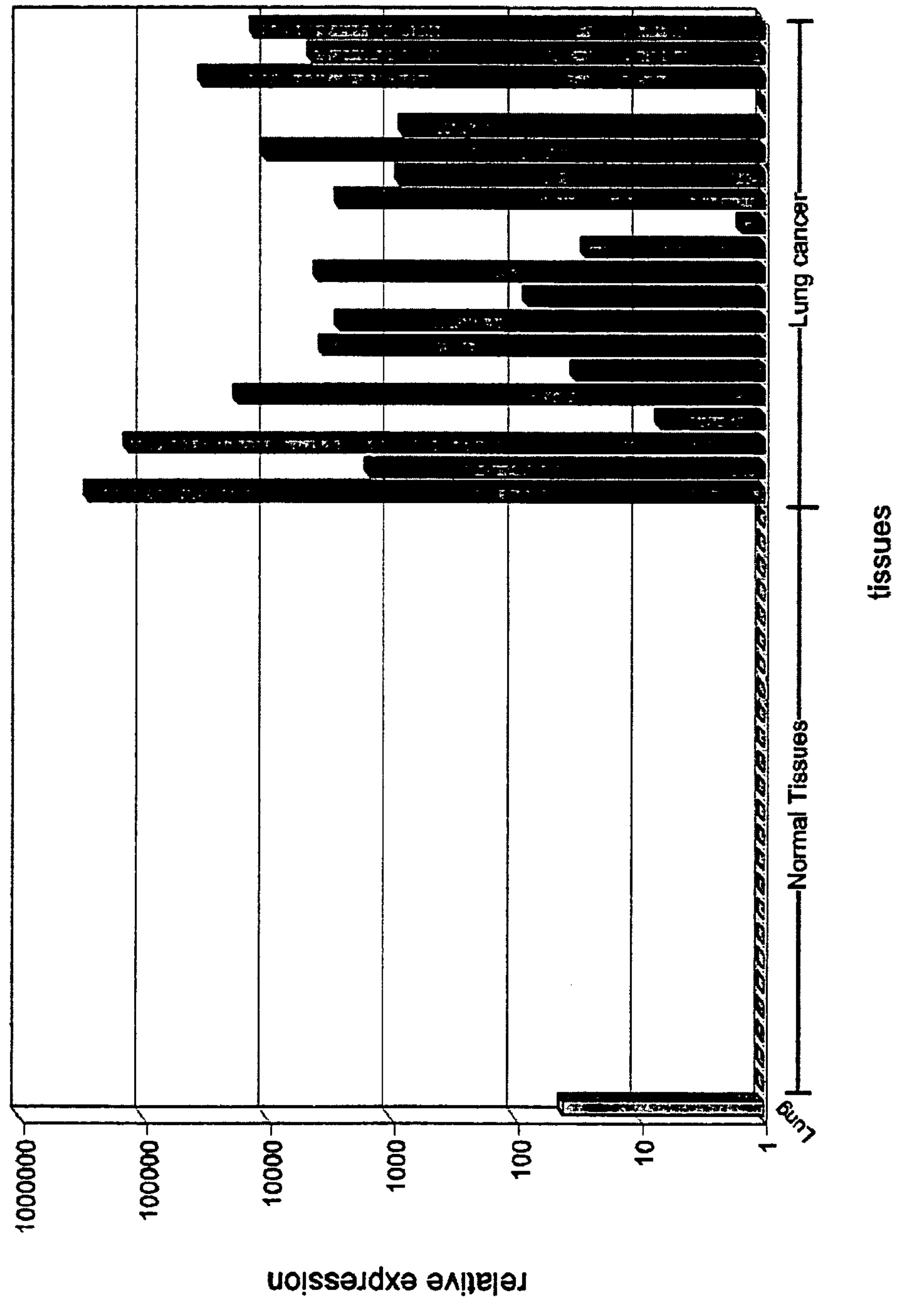

FIG. 20. Quantitative expression of SCGB3A2

Quantitative RT-PCR with SCGB3A2-specific primers (SEQ ID NO: 103, 104) show selective expression in lung samples and lung tumor samples. 19/20 lung tumor samples are SCGB3A2-positive, and SCGB3A2 is over-expressed by a factor of at least 10 in more than 50% of the samples. The following normal tissues were analyzed: liver, lung, lymph nodes, stomach, spleen, adrenal, kidney, esophagus, ovary, testis, thymus, skin, breast, pancreas, lymphocytes, activated lymphocytes, prostate, thyroid, fallopian tube, endometrium, cerebellum, brain.

Figure 21:
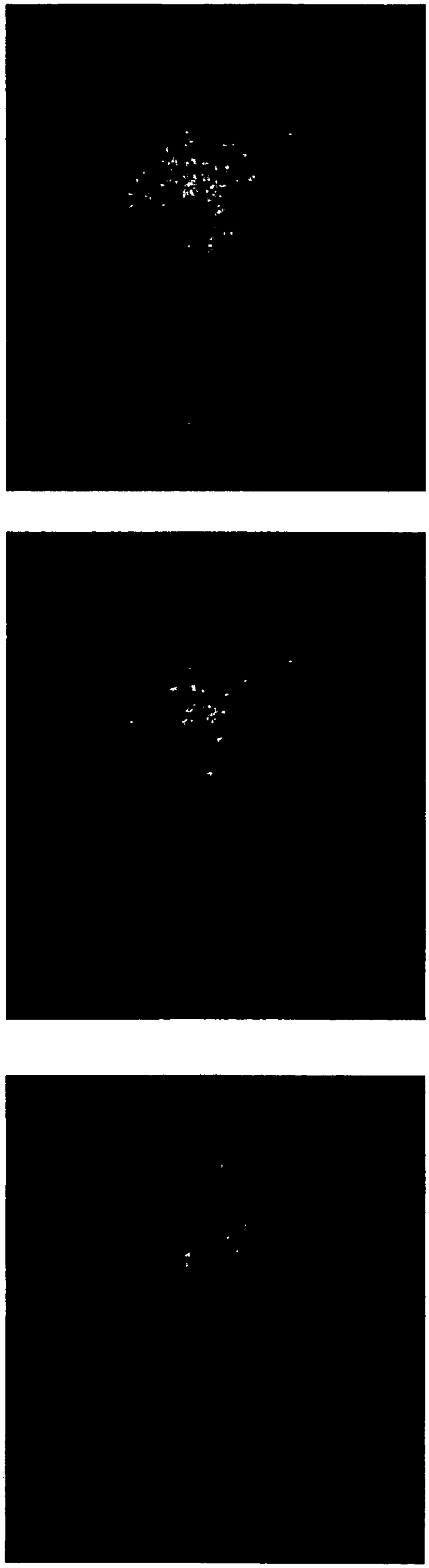

FIG. 21. Immunofluorescence with SCGB3A2-specific anti-bodies

COS7 cells were transfected with a plasmid which codes for an SCGB3A2-GFP fusion protein. A. Detection of the transfected fusion protein with an SCGB3A2-specific rabbit antiserum (immunization with SEQ ID NO: 105). B. Detection of the transfected fusion protein by GFP fluorescence. C. Superimposition of the two fluorescences from A and B. The yellow color is produced at the points where the two fluorescences are superimposed and thus demonstrates the specificity of the SCGB3A2 antiserum.

FIG. 22. Diagrammatic depiction of claudin-18 splice variants

The two claudin-18 splice variants A1 and A2 differ in the N terminus and show different potential glycosylation sites.

Figure 23:
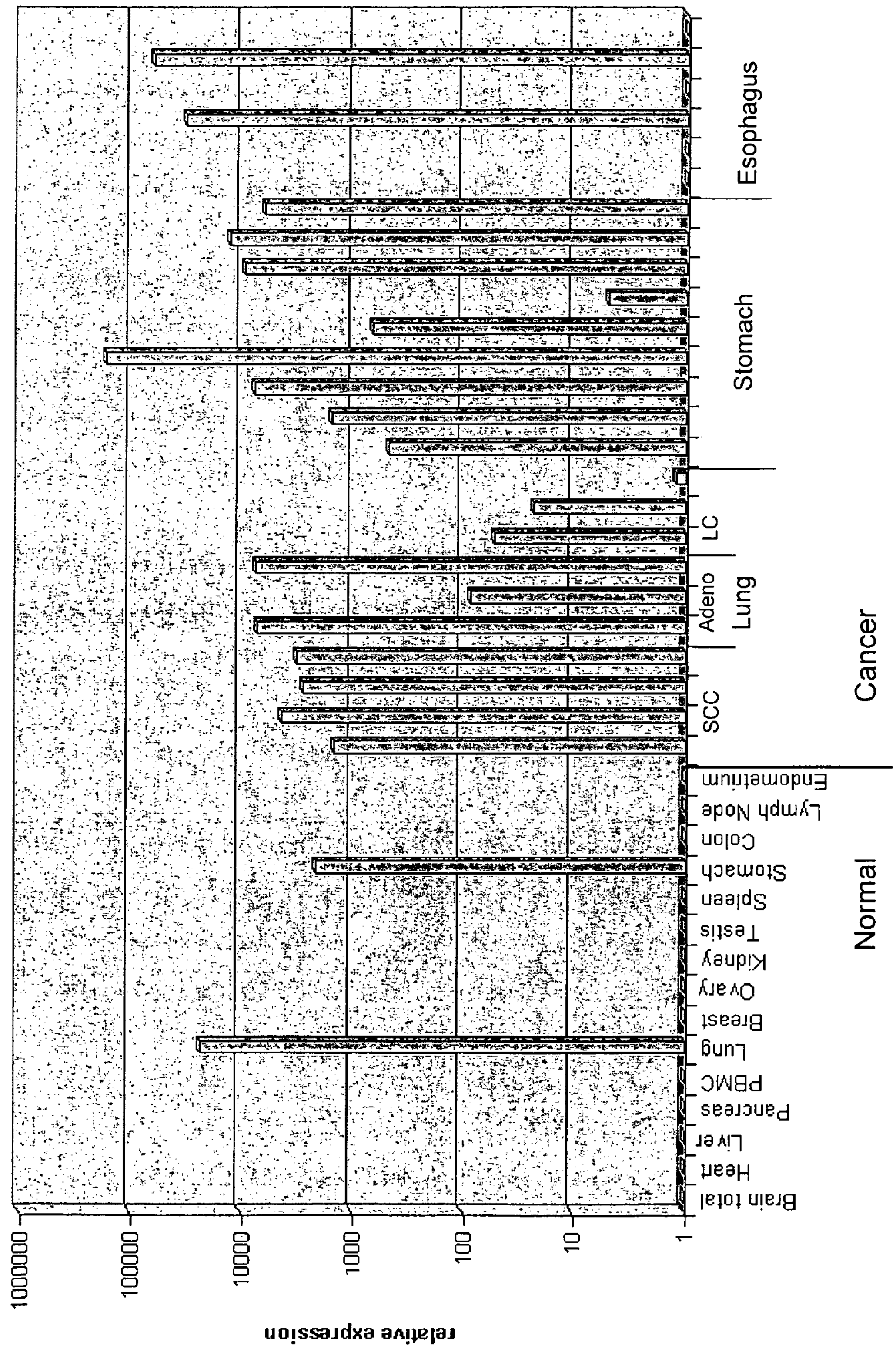

FIG. 23. Quantitative expression of claudin-18, variant A1

Claudin-A1 is highly activated in a large number of tumor tissues. Particularly strong expression is found in gastric tumors, lung tumors, pancreatic carcinomas and esophageal carcinomas.

Figure 24:
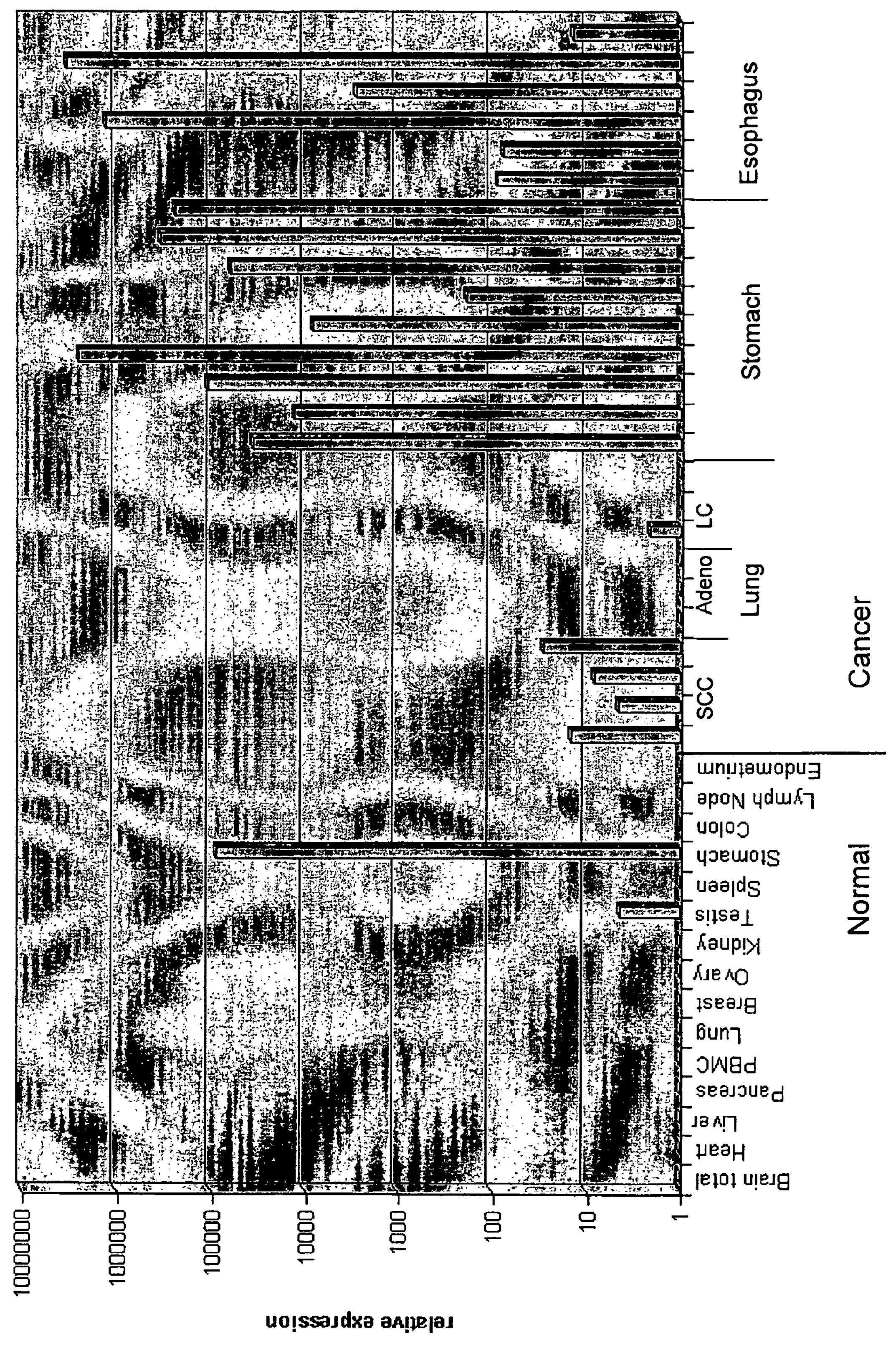

FIG. 24. Quantitative expression of claudin-18, variant A2

Variant A2 is, like variant A1, activated in many tumors.

Figure 25:
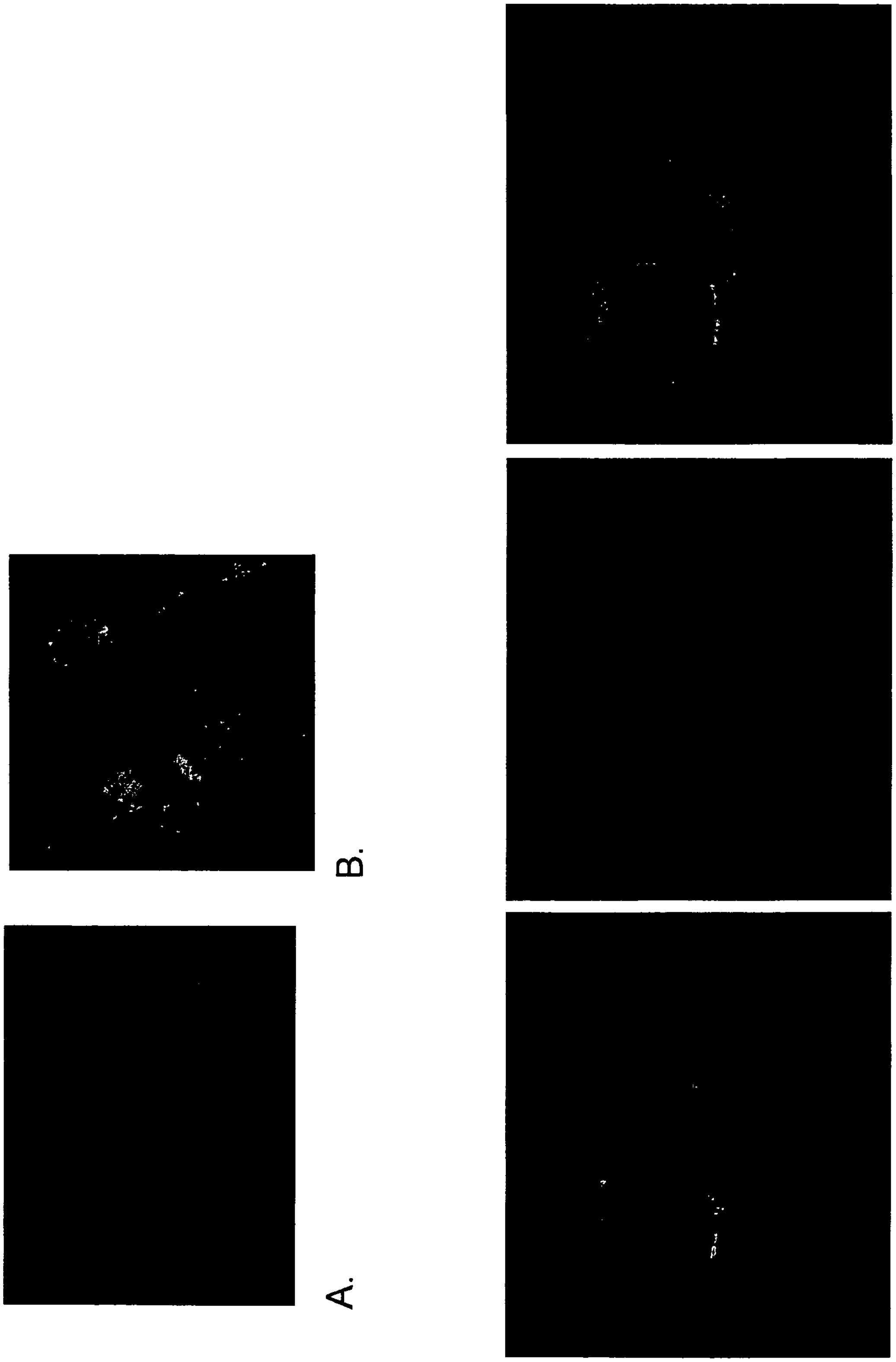

FIG. 25. Use of claudin-18A2-specific antibodies (extracellular domain)

(Top) Staining of claudin-18A2-positive gastric carcinoma cells (SNU-16) with an antibody which was produced by immunization with a peptide (SEQ ID NO: 17). Membrane staining appears particularly strongly in the cell/cell interaction regions. A-preimmune, MeOH; B-immune serum MeOH, 5 μg/ml; (Below) Demonstration of the specificity of the antibody by colocalization analysis in claudin-18A2-GFP-transfected 293 T cells. A-Claudin-18A2 GFP; B-anti-claudin-A2; C-superimposition.

Figure 26:
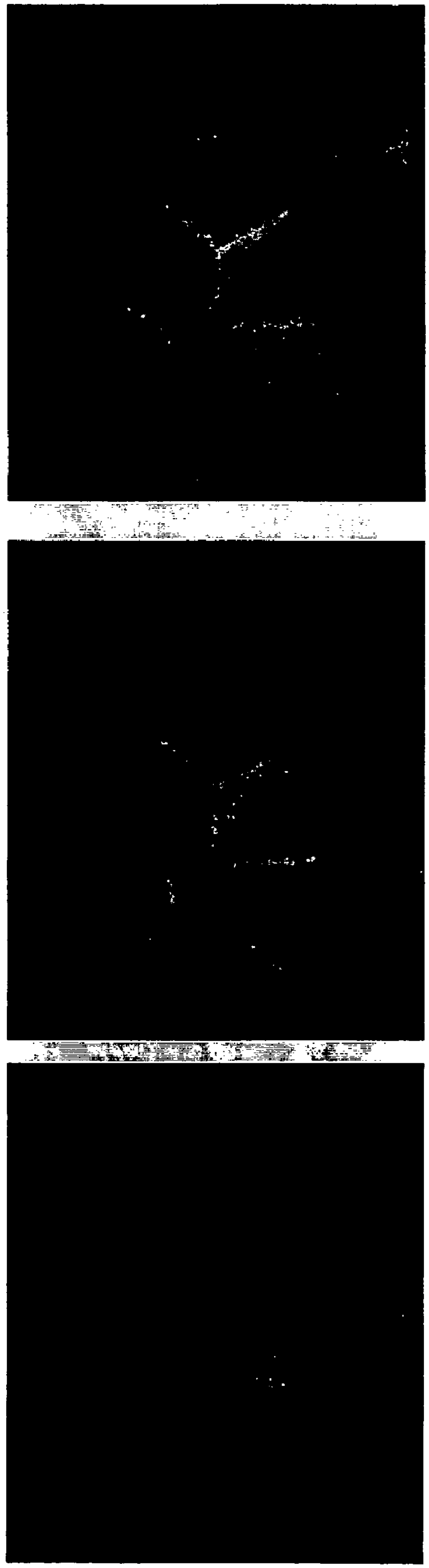

FIG. 26. Use of claudin-18A2-specific antibodies (extracellular domain)

Membrane staining of claudin-18A2-positive gastric carcinoma cells (SNU-16) with an antibody which was produced by immunization with a peptide (SEQ ID NO: 113, N-terminally located extracellular domain). A monoclonal antibody which is directed against E-cadherin was used for counter-staining. A-antibody; B-counterstaining; C-superimposition.

Figure 27:
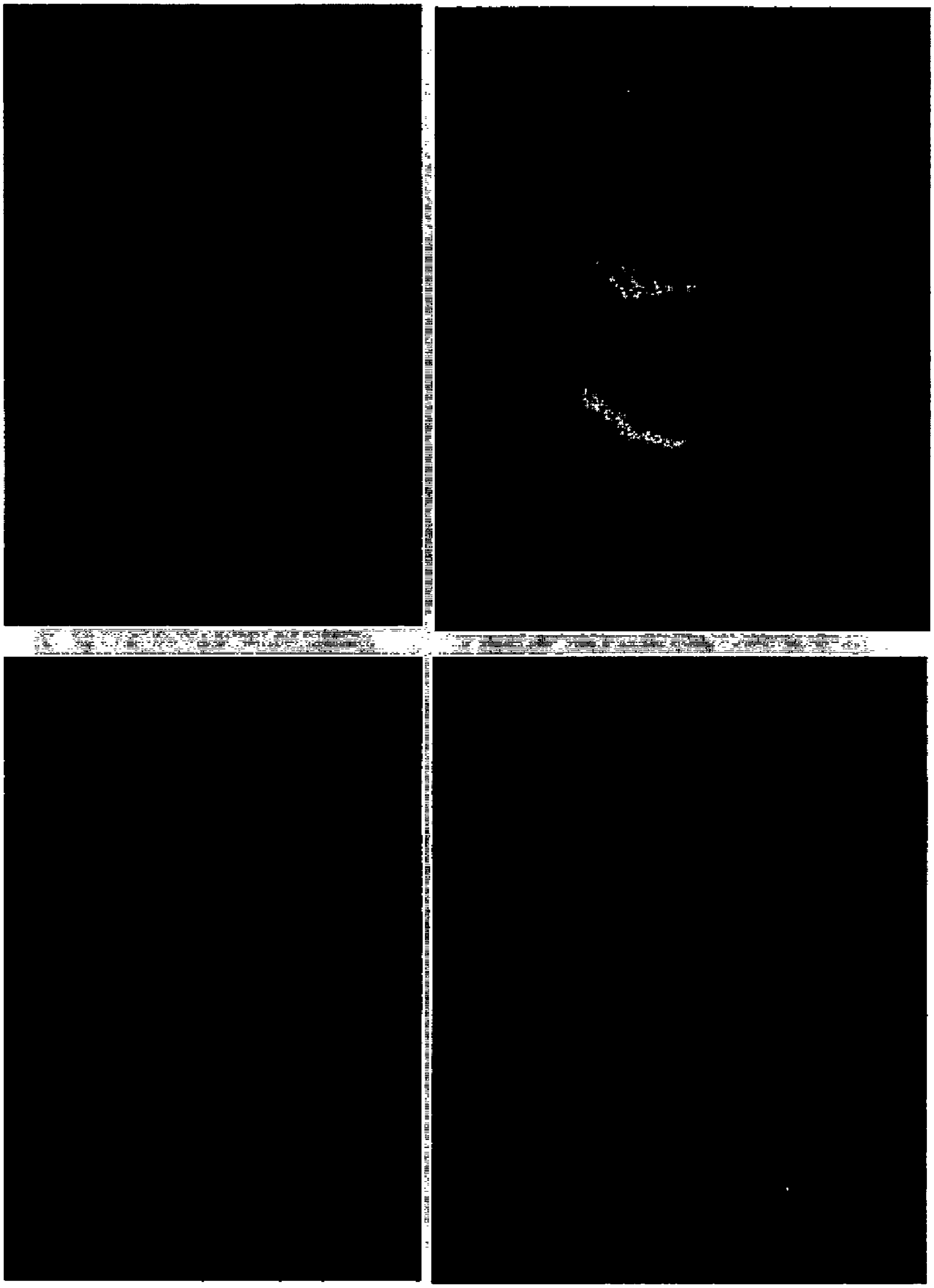

FIG. 27. Use of antibodies against the C-terminal extracellular domain of claudin-18

(Left, top and below) Membrane staining of claudin-18A2-positive gastric carcinoma cells (SNU-16) with an antibody which was produced by immunization with a peptide (SEQ ID NO: 116, C-terminally located extra-cellular domain). A monoclonal antibody which is directed against E-cadherin was used for counter-staining (right top, below).

Figure 28:
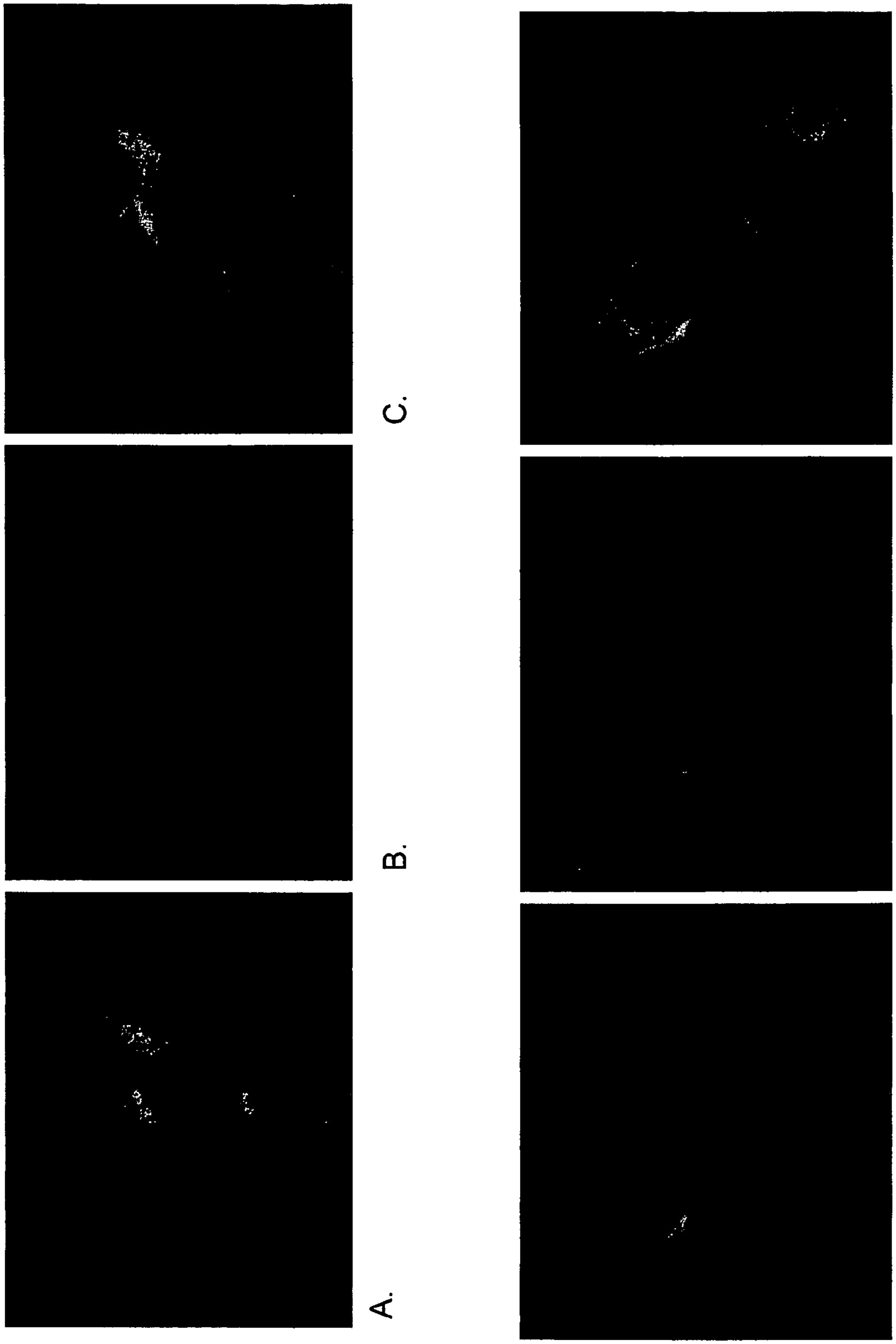

FIG. 28. Use of claudin-18A1-specific antibodies (Top) Weak to absent staining of gastric carcinoma cells (SNU-16; claudin18A2 positive) with an antibody which was produced by immunization with a claudin-18A1-specific peptide (SEQ ID NO: 115). A-anti-E-cadherin; B-anti-claudin-18A1; C-superimposition. (Below) Demonstration of the specificity of the antibody by colocalization analysis in claudin-18A1-GFP-transfected 293T cells. A-GFP-claudin-18A1; B-anti-claudin-18A1; C-superimposition.

Figure 29:
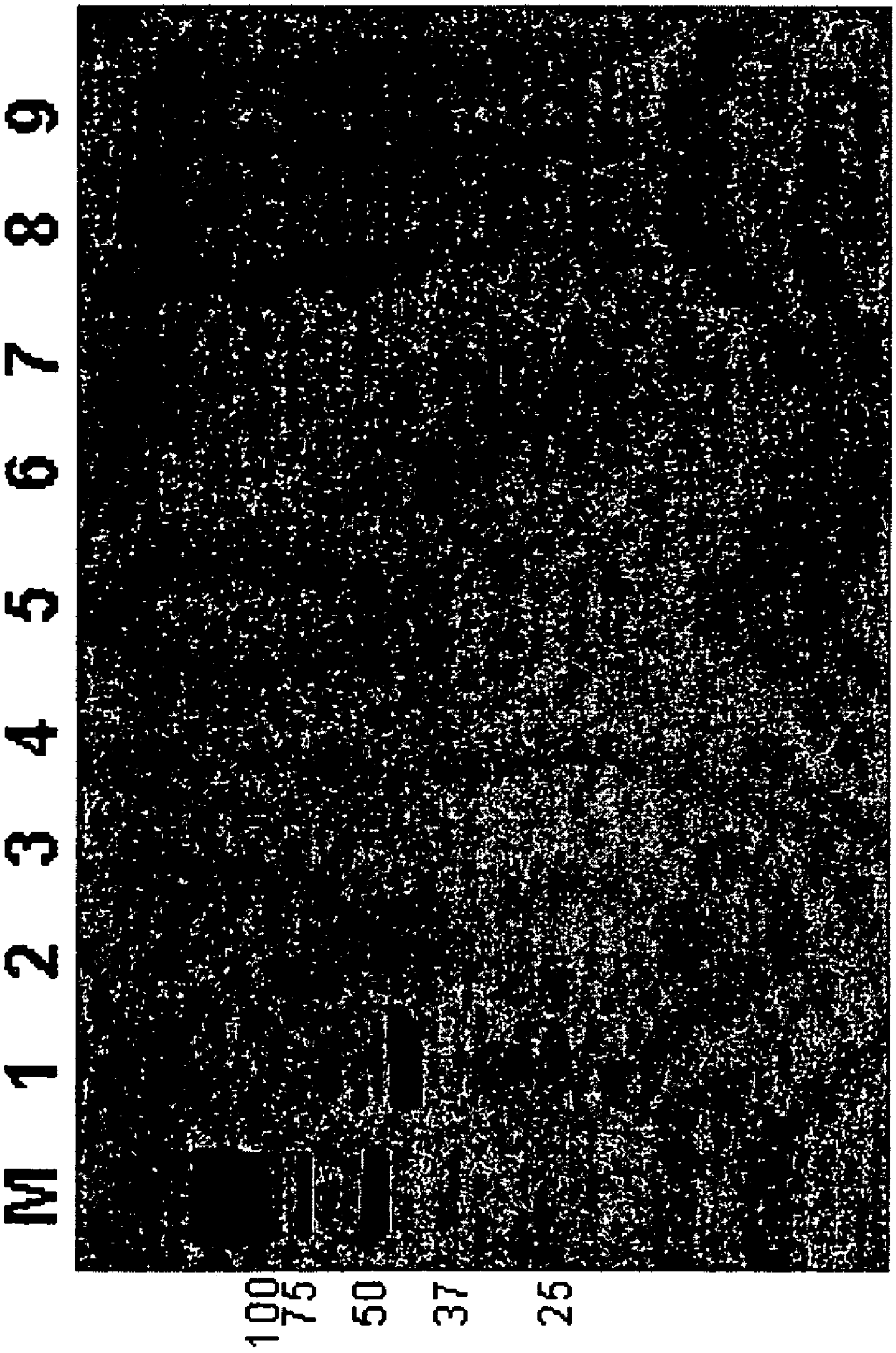

FIG. 29. Detection of claudin-18A2 in a Western blot.

Western blotting with lysates from various healthy tissues with a claudin-18A2-specific antibody directed against the epitope with SEQ ID NO: 17. 1-Stomach; 2-testis; 3-skin; 4-breast; 5-liver; 6-colon; 7-lung; 8-kidney; 9-lymph nodes.

FIG. 30. Claudin-18A2 Western blotting with samples from stomach and stomach tumors Lysates from stomach and stomach tumors were blotted and tested using a claudin-18A2-specific antibody against the epitope having SEQ ID NO: 17. Stomach tumors show a less glycosylated form of claudin-18A2. PNGase F treatment of stomach lysates leads to the formation of the low-glycosylated form.

Left: 1-stomach No #A; 2-stomach Tu #A; 3-stomach No #B; 4-stomach Tu #B

Figure 31:
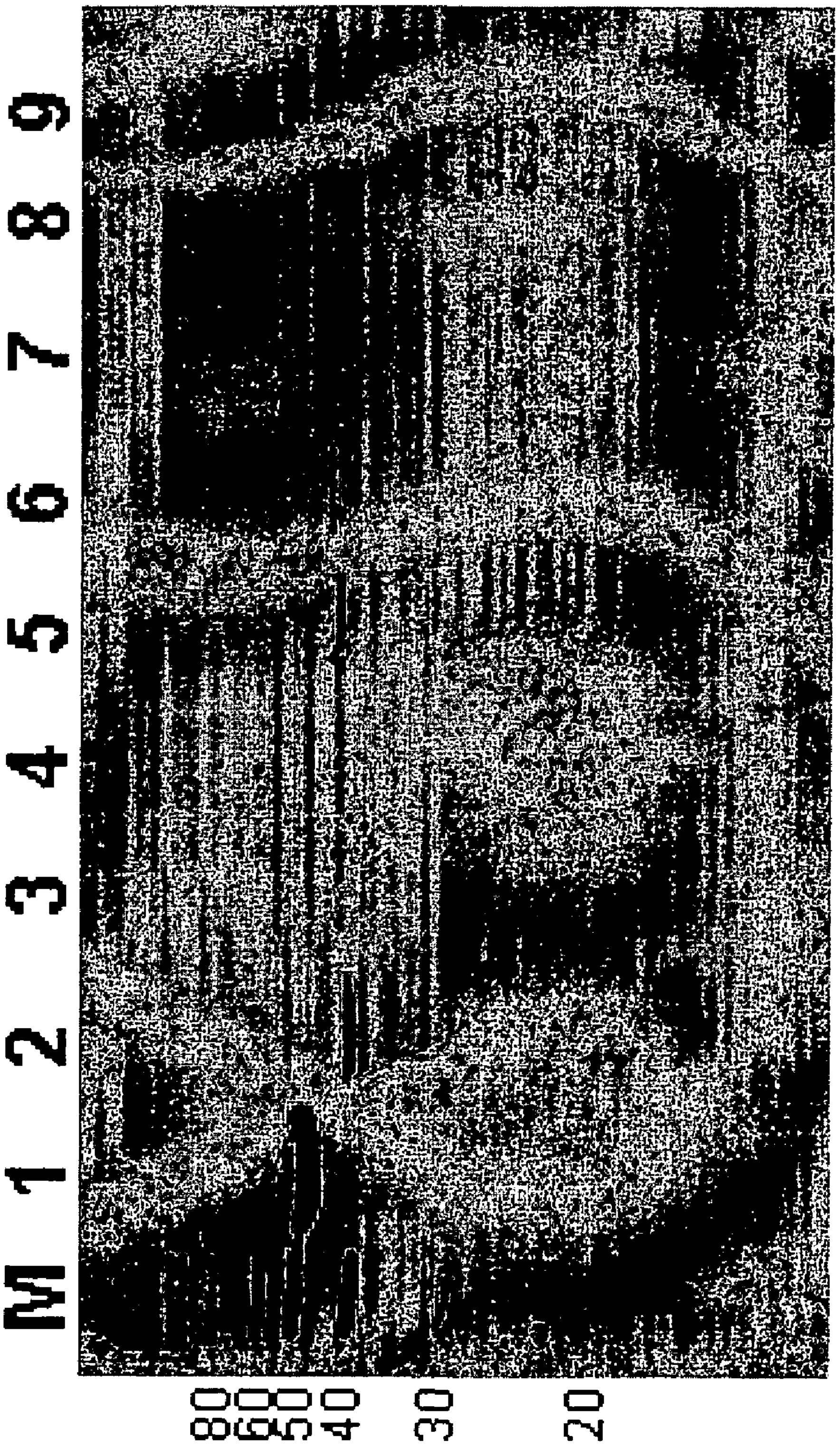

Right: 1-stomach No #A; 2-stomach No #B; 3-stomach No #B+PNGase F; 4-stomach Tu #C; 5-stomach Tu #D; 6-stomach Tu #D+PNGase F FIG. 31. Expression of claudin-18 in lung tumors Low-glycosylated claudin-18A2 variants were detected in lung tumors in accordance with FIG. 30. 1-Stomach No; 2-stomach Tu; 3-9-lung Tu.

Figure 32:

FIG. 32. Immunohistochemical analysis of claudin-18 using claudin-18A2-specific antibodies in stomach tumor tissue FIG. 33. Indirect immunofluorescence of stomach-specific Snu16 cells with a claudin-18-specific polyclonal antiserum A. Staining with a preimmune serum generated before the immunization; B. Staining with the claudin-18-specific serum.

Figure 34:
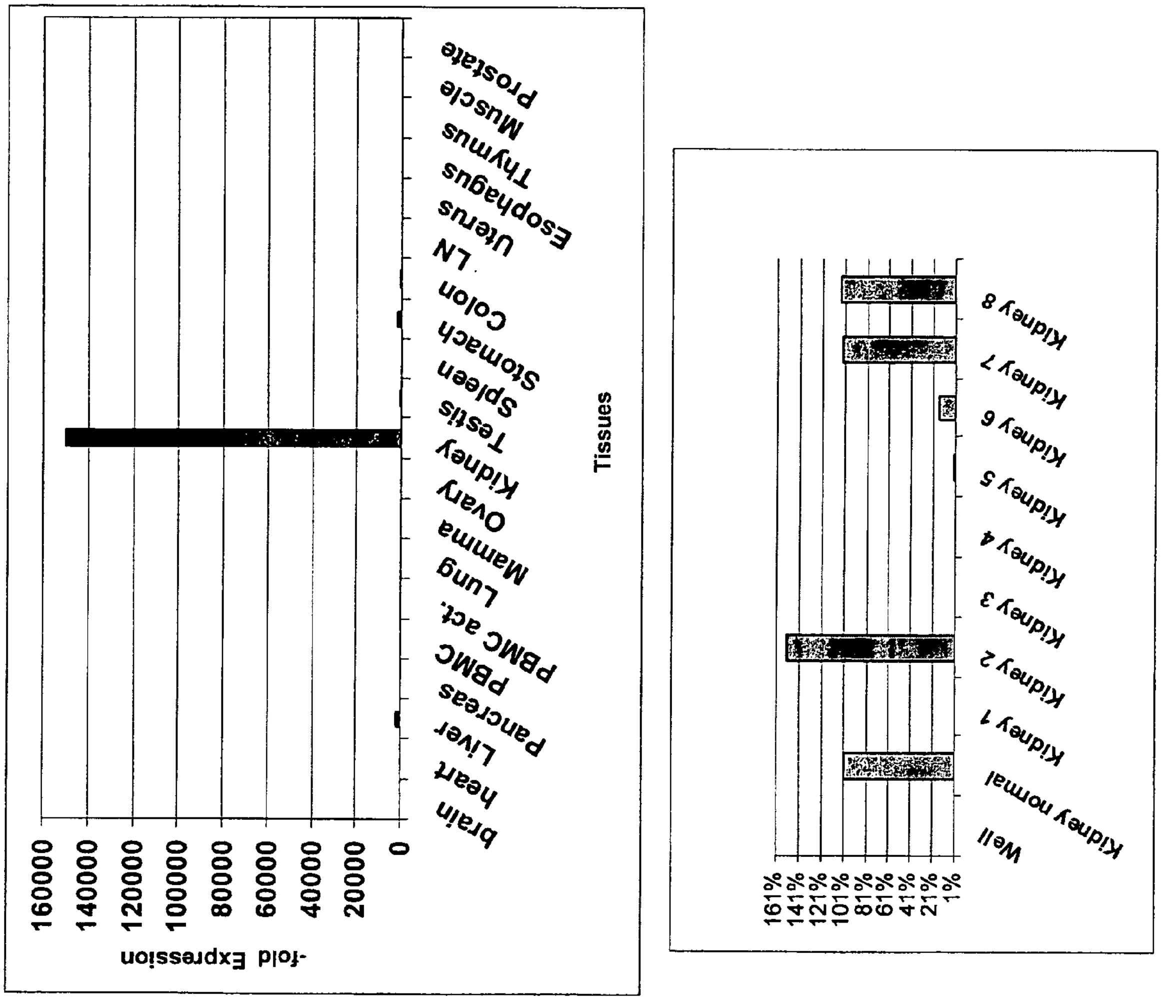

FIG. 34. Quantitative expression of SLC13A1

Quantitative RT-PCR with SLC13A1-specific primers (SEQ ID NO: 121, 122) show high and selective expression in normal kidney tissue (A) and SLC13A1-specific expression in renal cell carcinomas (B). SLC13A1 transcription is detectable in 5/8 renal cell carcinomas.

Figure 35:
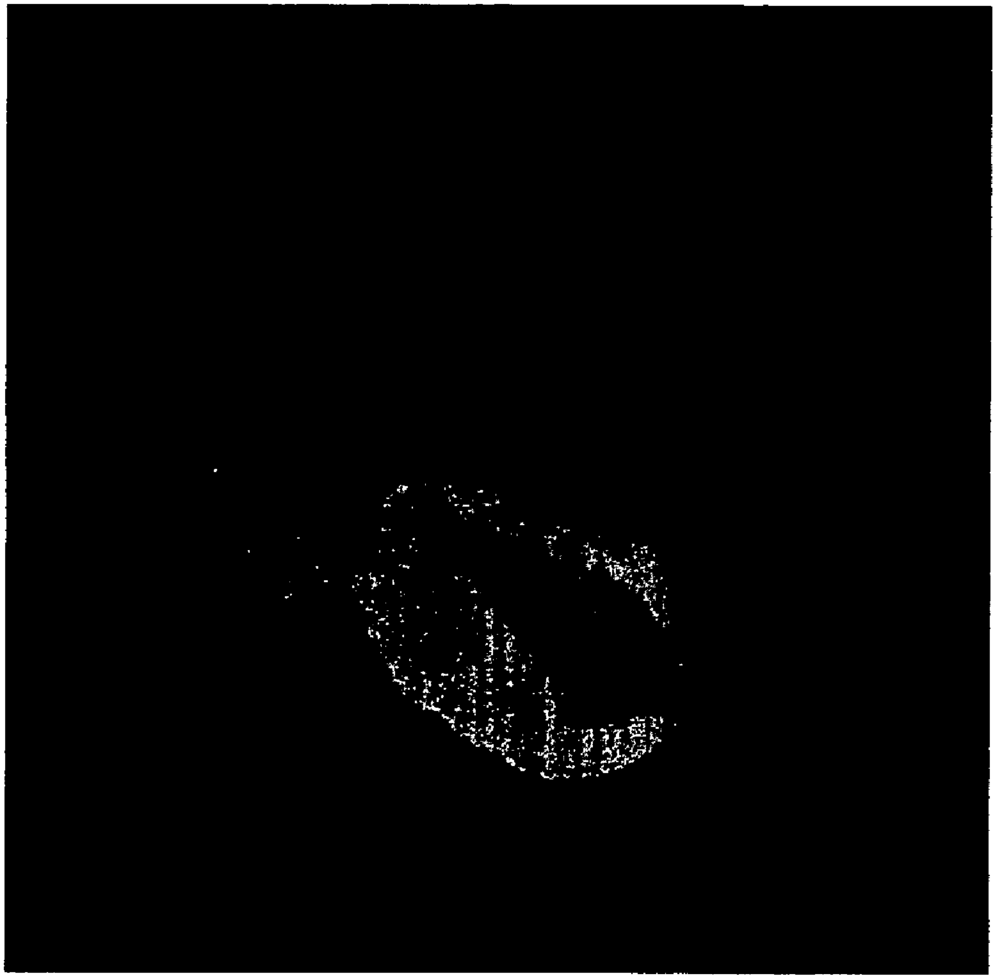

FIG. 35. Cellular localization of SLC13A1

Immunofluorescence to demonstrate the cellular localization of SLC13A1 after transfection of a plasmid which provides an SLC13A1-GFP fusion protein. The membrane-associated fluorescence of the SLC13A1 fusion protein is to be seen clearly (as ring around the transfected cell).

Figure 36:
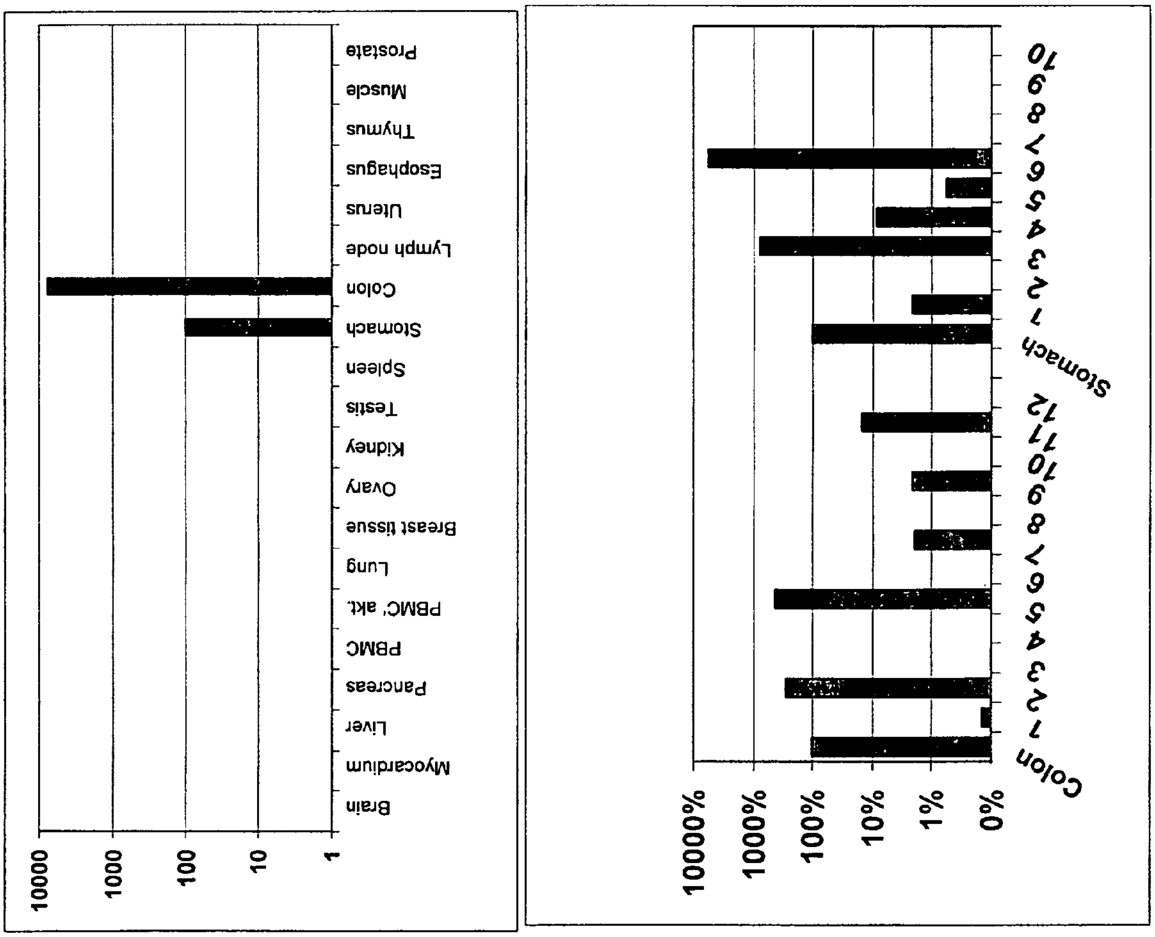

FIG. 36. Quantitative expression of CLCA1

Quantitative RT-PCR with CLCA1-specific primers (SEQ ID NO: 125, 126) show high and selective expression in normal colonic tissue and stomach tissue (A) and CLCA1-specific expression in colonic and gastric tumor samples (B). CLCA1 is detectable in 6/12 colon carcinomas and in 7/10 stomach carcinomas.

Figure 37:
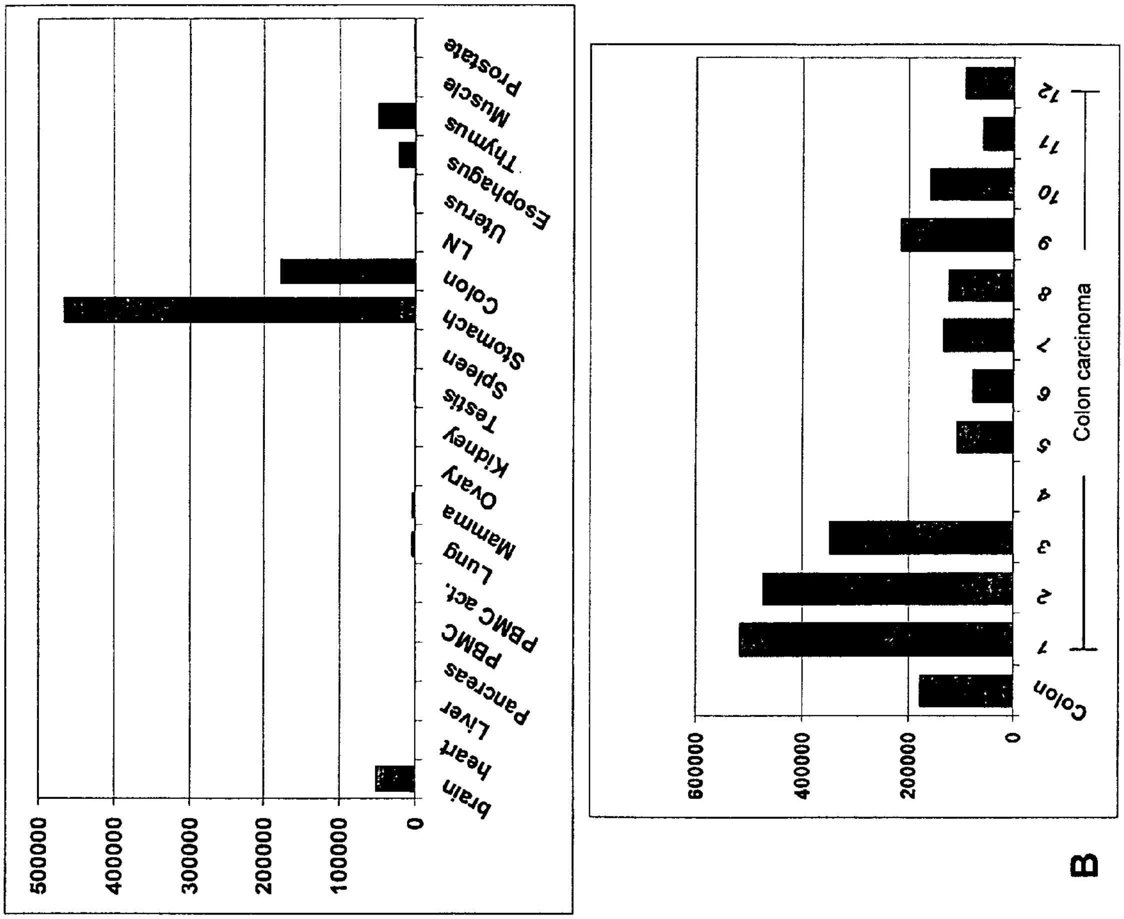

FIG. 37. Quantitative expression of FLJ21477

Quantitative RT-PCR with FLJ21477-specific primers (SEQ ID NO: 127, 128) show high and selective expression in normal colonic and gastric tissue and weak expression in thymus, esophagus and brain (A) and the FLJ21477-specific expression in colonic tumor samples (B). FLJ21477 is detectable in 11/12 colon carcinomas.

Figure 38:
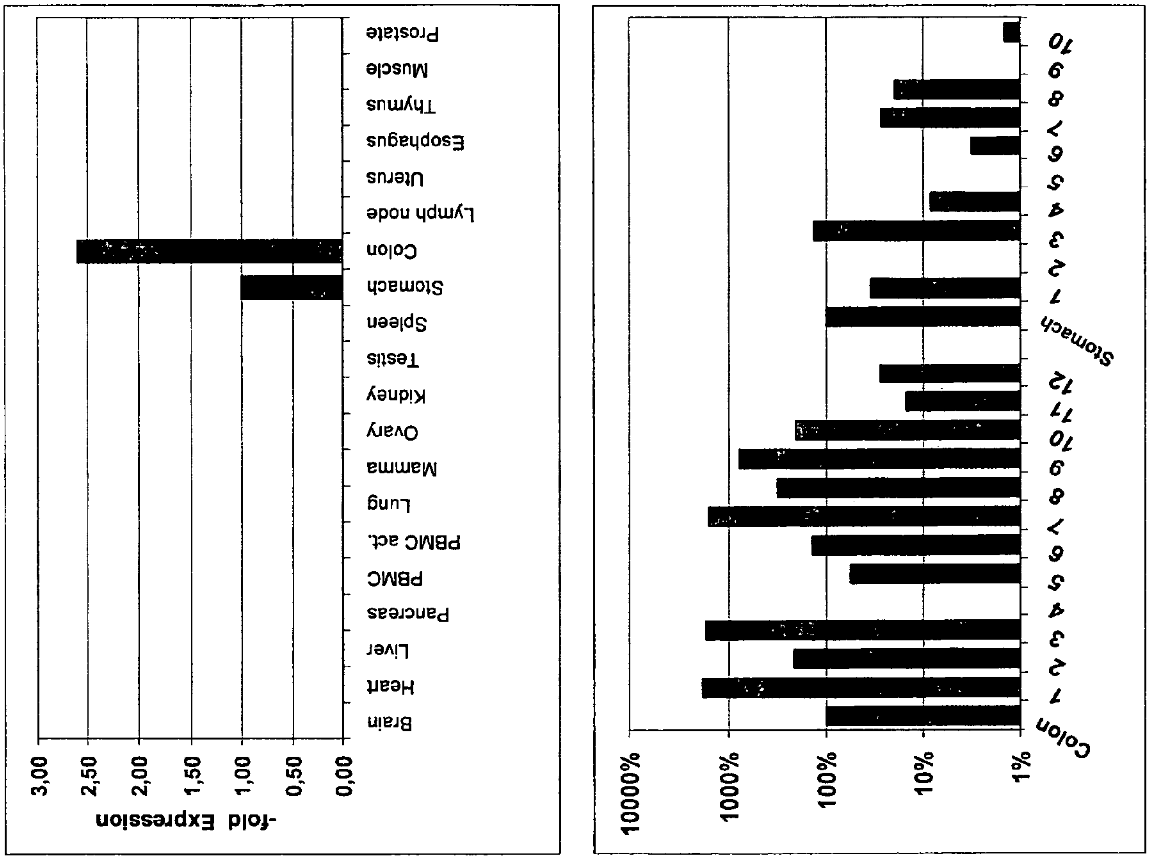

FIG. 38. Quantitative expression of FLJ20694

Quantitative RT-PCR with FLJ20694-specific primers (SEQ ID NO: 129, 130) show high and selective expression in normal colonic and gastric tissue (A) and FLJ20694-specific overexpression in colonic and gastric tumor samples (B). FLJ20694 is detectable in 11/12 colon carcinomas and in 7/10 stomach carcinomas.

Figure 39:
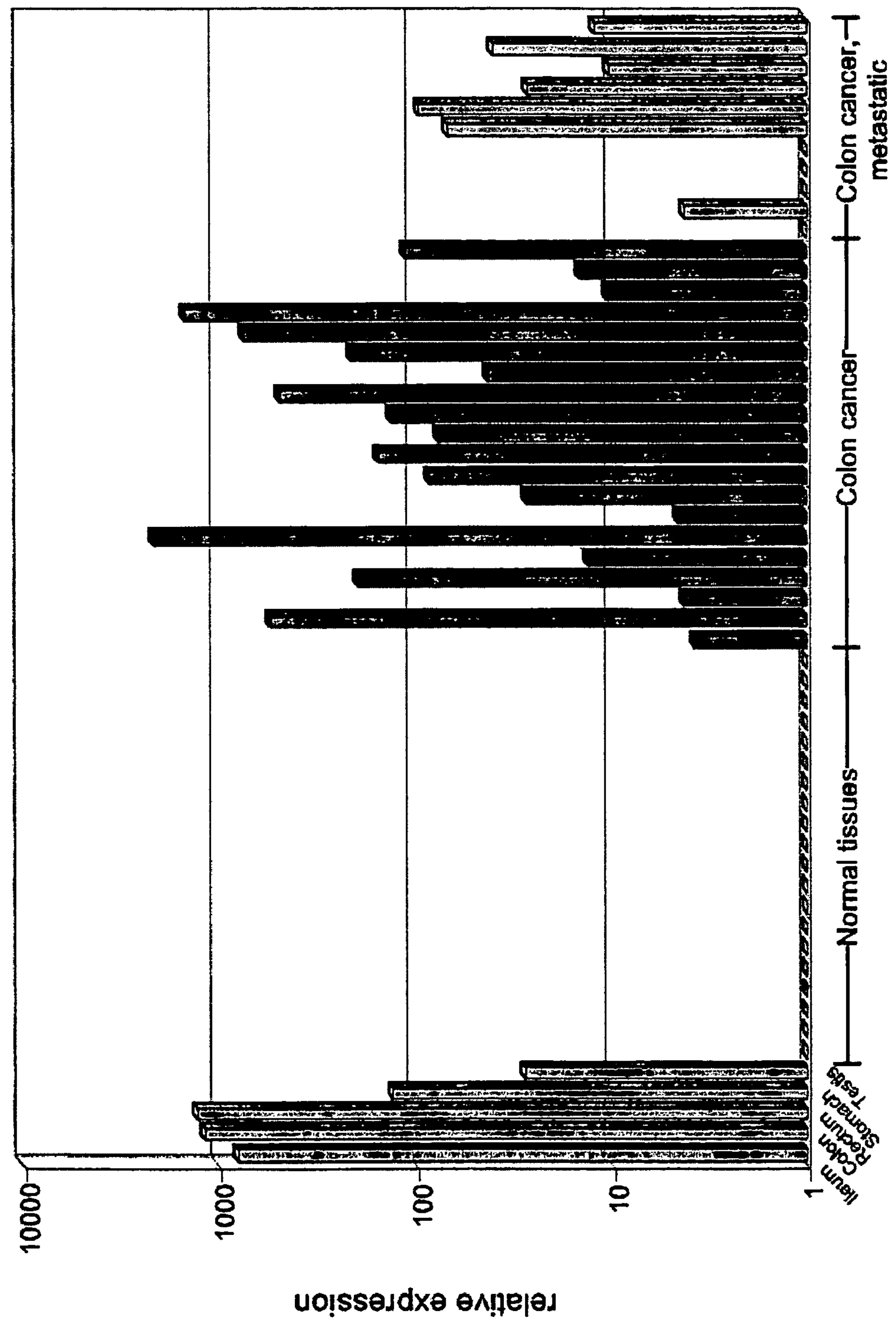

FIG. 39. Quantitative expression of FLJ21458

Quantitative RT-PCR with FLJ21458-specific primers (SEQ ID NO: 133, 134) show selective expression in testis, gastric and intestinal tissue. In addition, FLJ21458-specific transcripts were detectable in 20/20 colonic tumors and in 7/11 colonic metastases. The following normal tissues were analyzed: liver, lung, lymph nodes, spleen, adrenal, kidney, esophagus, ovary, testis, thymus, skin, breast, pancreas, lymphocytes, activated lymphocytes, prostate, thyroid, fallopian tube, endometrium, cerebellum, brain.

Figure 40:
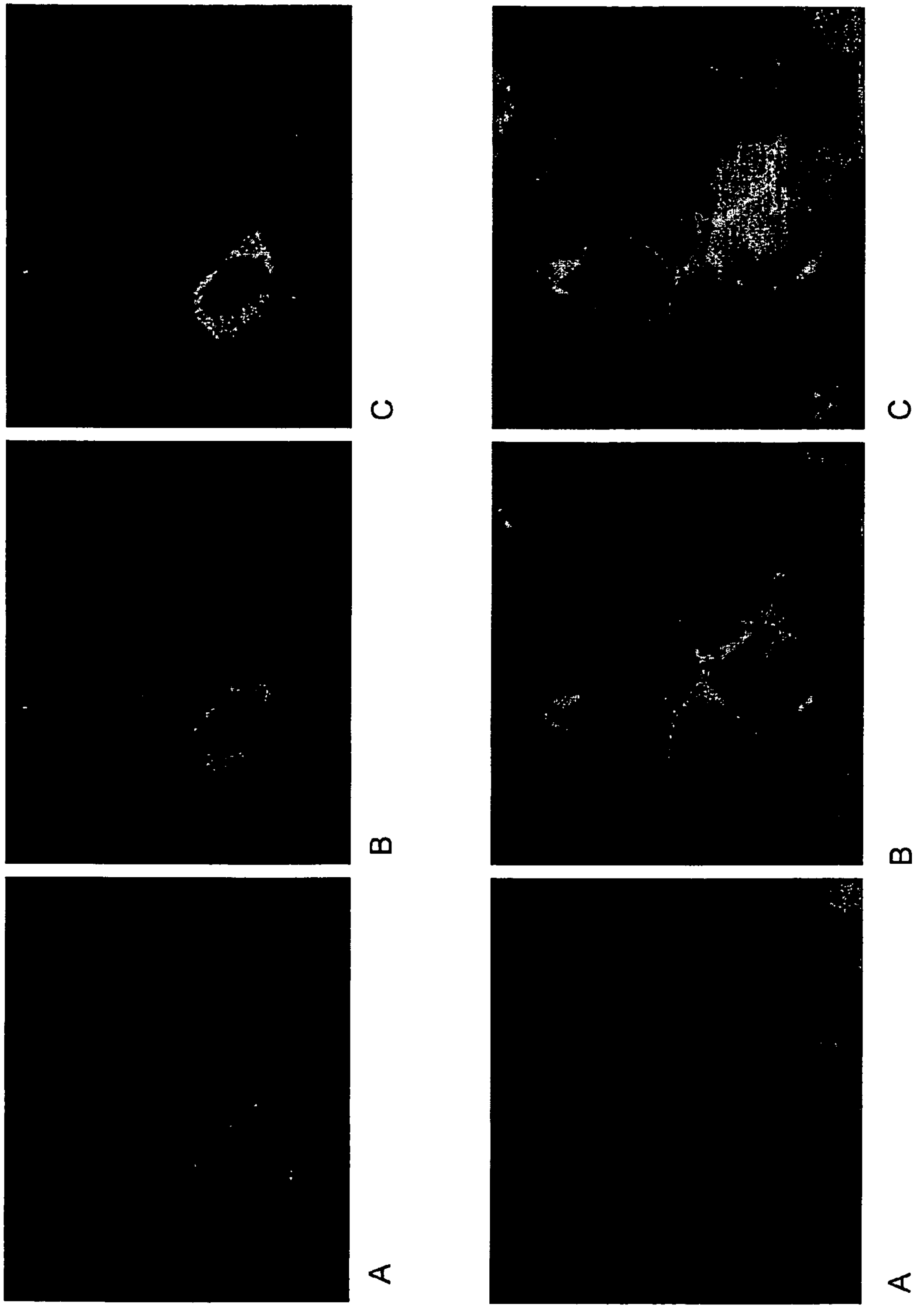

FIG. 40. Immunofluorescence with FLJ21458-specific antibodies (Top) 293 cells were transfected with a plasmid which codes for an FLJ21458-GFP fusion protein. A: detection of the transfected fusion protein with an FLJ21458-specific rabbit antiserum (immunization with SEQ ID NO: 136). B: detection of the transfected fusion protein by GFP fluorescence. C: superimposition of the two fluorescences from A and B. The yellow color is produced at the points where the two fluorescences are superimposed and thus demonstrates the specificity of the FLJ21458 antiserum.

(Below) Analysis of Snu16 cells which endogenously synthesize FLJ21458. A: protein detection using an FLJ21458-specific rabbit antiserum (immunization with SEQ ID NO: 136). B: detection of the membrane protein E-cadherin. C: superimposition of the two fluorescences from A and B. The yellow color is produced at the points where the two fluorescences are superimposed, and demonstrates the membrane localization of FLJ21458.

FIG. 41. Sequences

The sequences to which reference is made herein are shown.

EXAMPLES

Material and Methods

The terms "in silico", "electronic" and "virtual cloning" refer solely to the utilization of methods based on databases, which may also be used to simulate laboratory experimental processes.

Unless expressly defined otherwise, all other terms and expressions are used so as to be understood by the skilled worker. The techniques and methods mentioned are carried out in a manner known per se and are described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information.

Datamining-based Strategy for Determining New Tumor-associated Genes

Two in silico strategies, namely GenBank keyword search and the cDNAxProfiler, were combined. Utilizing the NCBI ENTREZ Search and Retrieval System (http://www.ncbi.nlm.nih.gov/Entrez), a GenBank search was carried out for candidate genes annotated as being specifically expressed in specific tissues (Wheeler et al., *Nucleic Acids Research* 28:10-14, 2000).

Carrying out queries with keywords such as "colon-specific gene", "stomach-specific gene" or "kidney-specific gene", candidate genes (GOI, genes of interest) were extracted from the databases. The search was restricted to part of the total information of these databases by using the limits "*homo sapiens*", for the organism, and "mRNA", for the type of molecule.

The list of the GOI found was curated by determining different names for the same sequence and eliminating such redundancies.

All candidate genes obtained by the keyword search were in turn studied with respect to their tissue distribution by the "electronic Northern" (eNorthen) method. The eNorthern is based on aligning the sequence of a GOI with an EST (expressed sequence tag) database (Adams et al., *Science* 252:1651, 1991) (http://www.ncbi.nlm.nih.gov/BLAST). The tissue origin of each EST which is found to be homologous to the inserted GOI can be determined and in this way the sum of all ESTs produces a preliminary assessment of the tissue distribution of the GOI. Further studies were carried out only with those GOI which had no homologies to EST from non organ-specific normal tissues. This evaluation also took into account that the public domain contains wrongly annotated cDNA libraries (Scheurle et al., *Cancer Res.* 60:4037-4043, 2000) (www.fau.edu/cmbb/publications/cancergenes6.htm).

The second datamining method utilized was the cDNA xprofiler of the NCBI Cancer Genome Anatomy Project (http://cgap.nci.nih.gov/Tissues/xProfiler) (Hillier et al., *Genome Research* 6:807-828, 1996; Pennisi, *Science* 276:1023-1024, 1997). This allows pools of transcriptomes deposited in databases to be related to one another by logical operators. We have defined a pool A to which all expression libraries prepared for example from colon were assigned, excluding mixed libraries. All cDNA libraries prepared from normal tissues other than colon were assigned to pool B. Generally, all cDNA libraries were utilized independently of underlying preparation methods, but only those with a size>1000 were admitted. Pool B was digitally subtracted from pool A by means of the BUT NOT operator. The set of GOI found in this manner was also subjected to eNorthern studies and validated by a literature research.

This combined datamining includes all of the about 13,000 full-length genes in the public domain and predicts out of these genes having potential organ-specific expression.

All other genes were first evaluated in normal tissues by means of specific RT-PCR. All GOI which had proved to be expressed in non-organ specific normal tissues had to be regarded as false-positives and were excluded from further studies. The remaining ones were studied in a large panel of a wide variety of tumor tissues. The antigens depicted below proved here to be activated in tumor cells.

RNA Extraction, Preparation of poly-d(T) Primed cDNA and Conventional RT-PCR Analysis Total RNA was extracted from native tissue material by using guanidium isothiocyanate as chaotropic agent (Chomczynski & Sacchi, *Anal. Biochem.* 162:156-9, 1987). After extraction with acidic phenol and precipitation with isopropanol, said RNA was dissolved in DEPC-treated water.

First strand cDNA synthesis from 2-4 μg of total RNA was carried out in a 20 μl reaction mixture by means of Superscript II (Invitrogen), according to the manufacturer's information. The primer used was a dT(18) oligonucleotide. Integrity and quality of the cDNA were checked by amplification of p53 in a 30 cycle PGR (sense CGTGAGCGCTTCGAGATGTTCCG (SEQ ID NO. 138), antisense CCTAACCAGCTGCCCAACTGTAG (SEQ ID NO. 139), hybridization temperature 67 ° C.).

An archive of first strand cDNA was prepared from a number of normal tissues and tumor entities. For expression studies, 0.5 μl of these cDNAs was amplified in a 30 μl reaction mixture, using GOI-specific primers (see below) and 1 U of HotStarTaq DNA polymerase (Qiagen). Each reaction mixture contained 0.3 mM dNTPs, 0.3 μM of each primer and 3 μl of 10× reaction buffer. The primers were selected so as to be located in two different exons, and elimination of the interference by contaminating genomic DNA as the reason for false-positive results was confirmed by testing nonreverse-transcribed DNA as template. After 15 minutes at 95° C. to activate the HotStarTaq DNA polymerase, 35 cycles of PCR were carried out (1 min at 94° C., 1 min at the particular hybridization temperature, 2 min at 72° C. and final elongation at 72° C. for 6 min). 20 μl of this reaction were fractionated and analyzed on an ethidium bromide-stained agarose gel.

The following primers were used for expression analysis of the corresponding antigens at the hybridization temperature indicated.

```
GPR35 (65° C.)
Sense:        5'-AGGTACATGAGCATCAGCCTG-3'     (SEQ ID NO. 20)
Antisense:    5'-GCAGCAGTTGGCATCTGAGAG-3'     (SEQ ID NO. 21)
```

-continued

| | | |
|---|---|---|
| GUCY2C (62° C.) | | |
| Sense: | 5'-GCAATAGACATTGCCAAGATG-3' | (SEQ ID NO. 22) |
| Antisense: | 5'-AACGCTGTTGATTCTCCACAG-3' | (SEQ ID NO. 23) |
| SCGB3A2 (66° C.) | | |
| Sense: | 5'-CAGCCTTTGTAGTTACTCTGC-3' | (SEQ ID NO. 37) |
| Antisense: | 5'-TGTCACACCAAGTGTGATAGC-3' | (SEQ ID NO. 38) |
| Claudin18A2 (68° C.) | | |
| Sense1: | 5'-GGTTCGTGGTTTCACTGATTGGGATTGC-3' | (SEQ ID NO. 39) |
| Antisense1: | 5'-CGGCTTTGTAGTTGGTTTCTTCTGGTG-3' | (SEQ ID NO. 40) |
| Sense2: | 5'-TGTTTTCAACTACCAGGGGC-3' | (SEQ ID NO. 107) |
| Antisense2: | 5'-TGTTGGCTTTGGCAGAGTCC-3' | (SEQ ID NO. 108) |
| Claudin18A1 (64° C.) | | |
| Sense: | 5'-GAGGCAGAGTTCAGGCTTCACCGA-3' | (SEQ ID NO. 109) |
| Antisense: | 5'-TGTTGGCTTTGGCAGAGTCC-3' | (SEQ ID NO. 110) |
| SLCI3A1 (64° C.) | | |
| Sense: | 5'-CAGATGGTTGTGAGGAGTCTG-3' | (SEQ ID NO. 50) |
| Antisense: | 5'-CCAGCTTTAACCATGTCAATG-3' | (SEQ ID NO. 49) |
| CLCA1 (62° C.) | | |
| Sense: | 5'-ACACGAATGGTAGATACAGTG-3' | (SEQ ID NO. 67) |
| Antisense: | 5'-ATACTTGTGAGCTGTTCCATG-3' | (SEQ ID NO. 68) |
| FLJ21477 (68° C.) | | |
| Sense: | 5'-ACTGTTACCTTGCATGGACTG-3' | (SEQ ID NO. 69) |
| Antisense: | 5'-CAATGAGAACACATGGACATG-3' | (SEQ ID NO. 70) |
| FLJ20694 (64° C.) | | |
| Sense: | 5'-CCATGAAAGCTCCATGTCTA-3' | (SEQ ID NO. 140) |
| Antisense: | 5'-AGAGATGGCACATATTCTGTC | (SEQ ID NO. 72) |
| Ebner (70° C.) | | |
| Sense: | 5'-ATCGGCTGAAGTCAAGCATCG-3' | (SEQ ID NO. 73) |
| Antisense: | 5'-TGGTCAGTGAGGACTCAGCTC-3' | (SEQ ID NO. 74) |
| Plunc (55° C.) | | |
| Sense: | 5'-TTTCTCTGCTTGATGCACTTG-3' | (SEQ ID NO. 75) |
| Antisense: | 5'-GTGAGCACTGGGAAGCAGCTC-3' | (SEQ ID NO. 76) |
| SLC26A9 (67° C.) | | |
| Sense: | 5'-GGCAAATGCTAGAGACGTGA-3' | (SEQ ID NO. 141) |
| Antisense: | 5'-AGGTGTCCTTCAGCTGCCAAG-3' | (SEQ ID NO. 78) |
| THC1005163 (60° C.) | | |
| Sense: | 5'-GTTAAGTGCTCTCTGGATTTG-3' | (SEQ ID NO. 79) |
| LOC134288 (64° C.) | | |
| Sense: | 5'-ATCCTGATTGCTGTGTGCAAG-3' | (SEQ ID NO. 80) |
| Antisense: | 5'-CTCTTCTAGCTGGTCAACATC-3' | (SEQ ID NO. 81) |
| THC943866 (59° C.) | | |
| Sense: | 5'-CCAGCAACAACTTACGTGGTC-3' | (SEQ ID NO. 82) |
| Antisense: | 5'-CCTTTATTCACCCAATCACTC-3' | (SEQ ID NO. 83) |
| FLJ21458 (62° C.) | | |
| Sense: | 5'-ATTCATGGTTCCAGCAGGGAC-3' | (SEQ ID NO. 86) |
| Antisense: | 5'-GGGAGACAAAGTCACGTACTC-3' | (SEQ ID NO. 87) |

Preparation of Random Hexamer-primed cDNA and Quantitative Real-time PCR

The expression of several genes was quantified by real-time PCR. The PCR products were detected using SYBR Green as intercalating reporter dye. The reporter fluorescence of SYBR Green is suppressed in solution and the dye is active only after binding to double-stranded DNA fragments. The increase in the SYBR Green fluorescence as a result of the specific amplification using GOI-specific primers after each PCR cycle is utilized for quantification. Expression of the target gene is quantified absolutely or relative to the expression of a control gene with constant expression in the tissues to be investigated. Expression was measured after standardization of the samples against 18 s RNA as so-called housekeeping gene using the $\Delta\Delta$-$C_t$ method (PE Biosystems, USA). The reactions were carried out in duplicates and determined in triplicates. The QuantiTect SYBR Green PCR kit (Qiagen, Hilden) was used in accordance with the manufacturer's instructions. The cDNA was synthesized using the high capacity cDNA Archive Kit (PE Biosystems, USA) with use of hexamer primers in accordance with the manufacturer's instructions. Each 5 μl portions of the diluted cDNA were employed in a total volume of 25 μl for the PCR: sense primer 300 nM, antisense primer 300 nM; initial denaturation 95° C. for 15 min; 95° C. for 30 sec; annealing for 30 sec; 72° C. for 30 sec; 40 cycles. The sequences of the primers used are indicated in the respective examples.

Cloning and Sequence Analysis

Cloning of full-lengths and gene fragments took place by conventional methods. To ascertain the sequence, corresponding antigenes were amplified using the proofreading polymerase pfu (Stratagene). After completion of the PCR, adenosine was ligated by means of HotStarTaq DNA polymerase to the ends of the amplicon in order to clone the fragments in accordance with the manufacturer's instructions into the TOPO-TA vector. The sequencing was carried out by a commercial service. The sequences were analysed using conventional prediction programs and algorithms.

Western Blotting

Cells from cell culture (endogenous expression of the target gene or synthesis of the target protein after transfection of an expression vector which encodes the target protein) or tissue samples which might contain the target protein are lysed in a 1% SDS solution. The SDS denatures the proteins present in the lysate. The lysates of an experimental mixture are fractionated according to size by electrophoresis on 8-15% denaturing polyacrylamide gels (containing 1% SDS) depending on the expected protein size (SDS polyacrylamide gel electrophoresis, SDS-PAGE). The proteins are then transferred by the semi-dry electroblotting method (Biorad) to nitrocellulose membrane (Schleicher & Schüll) on which the desired protein can be detected. For this purpose, the membrane is initially blocked (e.g. with milk powder) and then incubated with the specific antibody in a dilution of 1:20-1:200 (depending on the specificity of the antibody) for 60 minutes. After a washing step, the membrane is incubated with a second antibody coupled to a marker (e.g. enzymes such as peroxidase or alkaline phosphatase) which recognizes the first antibody. After a further washing step, subsequently the target protein is visualized in a color or chemiluminescence reaction on the membrane by means of an enzyme reaction (e.g. ECL, Amersham Bioscience). The result is documented by photographing with a suitable camera.

Analysis of protein modifications usually takes place by Western blotting. Glycosilations, which usually have a size of several kDa, lead to a larger total mass of the target protein, which can be fractionated in the SDS-PAGE. To detect specific O- and N-glycosidic linkages, protein lysates from tissues or cells are incubated before denaturation by SDS with O- or N-glycosidases (in accordance with their respective manufacturer's instructions, e.g. PNgase, endoglycosidase F, endoglycosidase H, Roche Diagnostics). This is followed by Western blotting as described above. Thus, if there is a reduction in the size of a target protein after incubation with a glycosidase it is possible to detect a specific glycosilation and, in this way, also analyse the tumor specificity of a modification. The exact position of the glycosilated amino acid can be predicted with algorithms and prediction programs.

Immunofluorescence

Cells of established cell lines which either synthesize the target protein endogenously (detection of the RNA in RT-PCR or of the protein by Western blotting) or else have been transfected with plasmid DNA before the IF are used. A wide variety of methods (e.g. electroporation, liposome-based transfection, calcium phosphate precipitation) are well established for transfecting cell lines with DNA (e.g. Lemoine et al. Methods Mol. Biol. 1997; 75: 441-7). The transfected plasmid may in the immunofluorescence encode the unmodified protein or else couple various amino acid markers to the target protein. The most important markers are, for example, the fluorescing "green fluorescent protein" (GFP) in its various differentially fluorescing forms and short peptide sequences of 6-12 amino acids for which high-affinity and specific antibodies are available. Cells which synthesize the target protein are fixed with paraformaldehyde, saponin or methanol. The cells can then if required be permeabilized by incubation with detergents (e.g. 0.2% Triton X-100). After the fixation/permeabilization, the cells are incubated with a primary antibody which is directed against the target protein or against one of the coupled markers. After a washing step, the mixture is incubated with a second antibody coupled to a fluorescent marker (e.g. fluorescin, Texas Red, Dako) which binds to the first antibody. The cells labeled in this way are then covered with a layer of glycerol and analysed with the aid of a fluorescence microscope according to the manufacturer's instructions. Specific fluorescence emissions are achieved in this case by specific excitation depending on the substances employed. The analysis normally allows reliable localization of the target protein, the antibody quality and the target protein being confirmed in double stainings to stain in addition to the target protein also the coupled amino acid markers or other marker proteins whose localization has been described in the literature. GFP and its derivatives represents a special case that can be directly excited and itself fluoresces, so that no antibodies are necessary for the detection.

Immunohistochemistry

IHC serves specifically for (1) being able to estimate the amount of target protein in tumor and normal tissues, (2) analysing how many cells in the tumor and healthy tissue synthesize the target gene, and/or (3) defining the cell type in a tissue (tumor, healthy cells) in which the target protein is detectable. Different protocols must be used depending on the individual antibody (e.g. "Diagnostic Immunohistochemistry by David J., MD Dabbs ISBN: 0443065667" or in "Microscopy, Immunohistochemistry, and Antigen Retrieval Methods: For Light and Electron Microscopy ISBN: 0306467704").

Immunohistochemistry (IHC) on specific tissue samples serves to detect protein in the corresponding tissue. The aim of this method is to identify the localization of a protein in a functionally intact tissue aggregate.

IHC serves specifically for (1) being able to estimate the amount of target protein in tumor and normal tissues, (2) analysing how many cells in tumor and healthy tissue synthesize the target gene, and (3) defining the cell type in a tissue (tumor, healthy cells) in which the target protein is detectable. Alternatively, the amounts of protein of a target gene can be quantified by tissue immunofluorescence using a digital camera and suitable software (e.g. Tillvision, Till-photonics, Germany). The technology has frequently been published, and details of staining and microscopy can therefore be found for example in "Diagnostic Immunohistochemistry" by David J., MD Dabbs ISBN: 0443065667 or "Microscopy, Immunohistochemistry, and Antigen Retrieval Methods: For Light and Electron Microscopy" ISBN: 0306467704. It should be noted that, because of the properties of antibodies, different protocols have to be used (an example is described below) in order to obtain a valid result.

Ordinarily, histologically defined tumor tissues and, as reference, comparable healthy tissues are employed in the IHC. It is moreover possible to use as positive and negative controls cell lines in which the presence of the target gene is known through RT-PCR analyses. A background control must always be included.

Fixed tissue (e.g. fixation with aldehyde-containing substances, formaldehyde, paraformaldehyde or in alcoholic solutions) or shock-frozen tissue pieces with a thickness of 1-10 μm are applied to a glass support. Paraffin-embedded samples are deparaffinated for example with xylene. The samples are washed with TBS-T and blocked in serum. This is followed by incubation with the first antibody (dilution: 1:2 to 1:2000) for 1-18 hours, with affinity-purified antibodies normally being used. A washing step is followed by incubation with a second antibody which is coupled to an alkaline phosphatase (alternative: for example peroxidase), and is directed against the first antibody, for about 30-60 minutes. This is followed by color reaction using color substrates which are converted by the bound enzymes (cf. for example, Shi et al., *J. Histochem. Cytochem.* 39: 741-748, 1991; Shin et al., *Lab. Invest.* 64: 693-702, 1991). To demonstrate the antibody specificity, the reaction can be blocked by previous addition of the immunogen.

Immunization (See also Monoclonal Antibodies: A Practical Approach by Philip Shepherd, Christopher Dean isbn 0-19-963722-9; Antibodies: A Laboratory Manual by Ed Harlow, David Lane ISBN: 0879693142; Using Antibodies: A Laboratory Manual: Portable Protocol NO. by Edward Harlow, David Lane, Ed Harlow ISBN: 0879695447).

The process for preparing antibodies is described briefly below, and details can be found in the cited publications. Firstly, animals (e.g. rabbits) are immunized by a first injection of the desired target protein. The animal's immune response to the immunogen can be enhanced by a second or third immunization within a defined period (about 2-4 weeks after the preceding immunization). Again after various defined periods (first bleeding after 4 weeks, then about every 2 weeks with a total of up to 5 samplings), blood is taken from the animals, and an immune serum is obtained therefrom.

The animals are usually immunized by one of four well-established methods, with other methods also being available. It is moreover possible to immunize with peptides which are specific for the target protein, with the complete protein or with extracellular partial sequences of a protein which can be identified experimentally or via prediction programs.

(1) In the first case, peptides (length: 8-12 amino acids) conjugated to KLH (keyhole limpet hemocyanin) are synthesized by a standardized in vitro method, and these peptides are used for the immunization. Usually, 3 immunizations are carried out with a concentration of 5-1000 μg/immunization. The immunization can also be carried out as service from service providers.

(2) Alternatively, the immunization can be carried out with recombinant proteins. For this purpose, the cloned DNA of the target gene is cloned into an expression vector, and the target protein is synthesized in analogy to the conditions of the particular manufacturer (e.g. Roche Diagnostics, Invitrogen, Clontech, Qiagen) for example cell-free in vitro, in bacteria (e.g. *E. coli*), in yeast (e.g. *S. pombe*), in insect cells or in mammalian cells. After synthesis in one of the systems, the target protein is purified, the purification in this case usually taking place by standardized chromatographic methods. It is also possible in this connection to use for the immunization proteins which have a molecular anchor as aid for purification (e.g. His tag, Qiagen; FLAG tag, Roche Diagnostics; Gst fusion proteins). A large number of protocols is to be found for example in the "Current Protocols in Molecular Biology", John Wiley & Sons Ltd., Wiley Interscience.

(3) If a cell line which synthesizes the desired protein endogenously is available, this cell line can also be used to produce the specific antiserum. In this case, the immunization takes place in 1-3 injections in each case with about 1-5×$10^7$ cells.

(4) The immunization can also take place by injection of DNA (DNA immunization). For this purpose, the target gene is initially cloned into an expression vector so that the target sequence is under the control of a strong eukaryotic promoter (e.g. CMV promoter). Subsequently, 5-100 μg of DNA are transferred as immunogen using a "gene gun" into capillary regions with a strong blood flow in an organism (e.g. mouse, rabbit). The transferred DNA is taken up by the animal's cells, the target gene is expressed, and the animal finally develops an immune response to the target gene (Jung et al., Mol Cells 12:41-49, 2001; Kasinrerk et al., Hybrid Hybridomics 21:287-293, 2002).

Quality Control of the Polyclonal Serum or Antibody

Assays based on cell culture with subsequent Western blotting are most suitable for demonstrating specificity (various variations are described for example in "Current Protocols in Protein Chemistry", John Wiley & Sons Ltd., Wiley InterScience). For the demonstration, cells are transfected with a cDNA, which is under the control of a strong eukaryotic promoter (e.g. cytomegalovirus promoter), for the target protein. A wide variety of methods (e.g. electroporation, liposome-based transfection, calcium phosphate precipitation) are well established for transfecting cell lines with DNA (e.g. Lemoine et al., *Methods Mol. Biol.* 75:441-7, 1997). It is also possible alternatively to use cell lines which express the target gene endogenously (demonstration by target gene-specific RT-PCR). As control, in the ideal case homologous genes are also transfected in the experiment, in order to be able to demonstrate in the following Western blot the specificity of the analysed antibody.

In the subsequent Western blot, cells from cell culture or tissue samples which might contain the target protein are lysed in a 1% SDS solution, and the proteins are denatured thereby. The lysates are fractionated according to size by electrophoresis on 8-15% denaturing polyacrylamide gels (contain 1% SDS) (SDS polyacrylamide gel electrophoresis, SDS-PAGE). The proteins are then transferred by one of a plurality of blotting methods (e.g. semi-dry electroblot; Biorad) to a specific membrane (e.g. nitrocellulose, Schleicher & Schüll). The desired protein can be visualized on this membrane. For this purpose, the membrane is first incubated with the antibody which recognizes the target protein (dilution about 1:20-1:200, depending on the specificity of the antibody) for 60 minutes. After a washing step, the membrane is incubated with a second antibody which is coupled to a marker (e.g. enzymes such as peroxidase or alkaline phosphatase) and which recognizes the first antibody. It is then possible in a color or chemiluminescent reaction to visualize the target protein on the membrane (e.g. ECL, Amersham Bioscience). An antibody with a high specificity for the target protein should in the ideal case recognize only the desired protein itself.

Various methods are used to confirm the membrane localization of the target protein identified in the in silico approach. An important and well-established method using the antibodies described above is immuno-fluorescence (IF). Cells of established cell lines which either synthesize the target protein (detection of the RNA in an RT-PCR or of the protein in a Western blot) or else have been transfected with plasmid DNA are used for this. A wide variety of methods (e.g. electroporation, liposome-based transfection, calcium phosphate precipitation) are well established for transfection of cell lines with DNA (e.g. Lemoine et al., *Methods Mol. Biol.* 75:441-7, 1997). The plasmid transfected into the cells can in the immunofluorescence encode the unmodified protein or else couple various amino acid markers to the target protein. The principal markers are, for example, the fluorescent "green fluorescent protein" (GFP) in its various differentially fluorescent forms, short peptide sequences of 6-12 amino acids for which high-affinity and specific antibodies are available, or the short amino acid sequence Cys-Cys-X-X-Cys-Cys which can bind via its cysteine specific fluorescent substances (Invitrogen). Cells which synthesize the target protein are fixed for example with paraformaldehyde or methanol. The cells can then, if required, be permeabilized by incubation with detergents (e.g. 0.2% Triton X-100). The cells are then incubated with a primary antibody which is directed against the target protein or against one of the coupled markers. After a washing step, the mixture is incubated with a second antibody which is coupled to a fluorescent marker (e.g. fluorescin, Texas Red, Dako) and which binds to the first antibody. The cells labeled in this way are then covered with a layer of glycerol and analysed with the aid of a fluorescence microscope according to the manufacturer's instructions. Specific fluorescence emissions are achieved in this case by specific excitation depending on the substances employed. The analysis usually permits reliable localization of the target protein, the antibody quality and the target protein being confirmed in double stainings to stain in addition to the target protein also the coupled amino acid markers or other marker proteins whose localization has already been described in the literature. GFP and its derivatives represents a special case, being excitable directly and themselves fluorescing. The membrane permeability, which can be controlled through the use of detergents, permits demonstration in the immunofluorescence of whether an immunogenic epitope is located inside or outside the cell. The prediction of the selected proteins can thus be supported experimentally. An alternative possibility is to detect extracellular domains by means of flow cytometry. For this purpose, cells are fixed under non-permeabilizing conditions (e.g. with PBS/Na azide/2% FCS/5 mM EDTA) and analysed in a flow cytometer in accordance with the manufacturer's instructions. Only extracellular epitopes can be recognized by the antibody to be analysed in this method. A difference from immunofluorescence is that it is possible to distinguish between dead and living cells by use of, for example, propidium iodide or Trypan blue, and thus avoid false-positive results.

Affinity Purification

Purification of the polyclonal sera took place in the case of the peptide antibodies entirely, or in the case of the antibodies against recombinant proteins in part, as service by the contracted companies. For this purpose, in both cases, the appropriate peptide or recombinant protein was covalently bonded to a matrix, and the latter was, after the coupling, equilibrated with a native buffer (PBS: phosphate buffered saline) and then incubated with the crude serum. After a further PBS washing step, the antibody was eluted with 100 mM glycine, pH 2.7, and the eluate was immediately neutralized in 2M TRIS, pH 8. The antibodies purified in this way could then be employed for specific detection of the target proteins both by Western blotting and by immunofluorescence.

Preparation of EGFP Transfectants

For the immunofluorescence microscopy of heterologously expressed tumor-associated antigens, the complete ORF of the antigens was cloned in pEGFP-C1 and pEGFP-N3 vectors (Clontech). CHO and NIH3T3 cells cultivated on slides were transfected with the appropriate plasmid constructs using Fugene transfection reagent (Roche) in accordance with the manufacturer's instructions and, after 12-24 h, analysed by immunofluorescence microscopy.

Example 1

Identification of GPR35 as Diagnostic and Therapeutic Cancer Target

GPR35 (SEQ ID NO:1) and its translation product (SEQ ID NO:9) have been described as putative G protein-coupled receptor. The sequence is published in Genbank under accession No. AF089087. This transcript codes for a protein of 309 amino acids with a molecular weight of 34 kDa. It was predicted that GPR35 belongs to the superfamily of G protein-coupled receptors with 7 transmembrane domains (O'Dowd et al., *Genomics* 47:310-13, 1998). In order to confirm the predicted localization of GPR35 in the cell, the protein was fused to eGFP as reporter molecule and, after transfection of the appropriate plasmid, expressed heterologously in 293 cells. The localization was then analysed in a fluorescence microscope. It was confirmed according to the invention that GPR35 is an integral transmembrane molecule (FIG. 17). Investigation to date on human GPR35 (see, inter alia, Horikawa Y, Oda N, Cox N J, Li X, Orho-Melander M, Hara M, Hinokio Y, Lindner T H, Mashima H, Schwarz P E, del Bosque-Plata L, Horikawa Y, Oda Y, Yoshiuchi I, Colilla S, Polonsky K S, Wei S, Concannon P, Iwasaki N, Schulze J, Baier L J, Bogardus C, Groop L, Boerwinkle E, Hanis C L, Bell G I Nat Genet. 2000 October; 26(2):163-75) suggested that GPR35 is activated in many healthy tissues. The reading frame of the gene comprises a single exon. According to the invention, a gene-specific primer pair (SEQ ID NO:20, 21) for GPR35 was used in RT-PCR analyses to amplify cDNA in the colon and in colon carcinoma (13/26). By contrast, no significant expression is detectable in other normal tissues. Because of the particular fact that GPR35 consists of a single exon, genomic DNA impurities cannot be detected with intron-spanning primers. In order to preclude genomic contamination of the RNA samples, therefore, all RNAs were treated with DNAse. GPR35 transcripts were detected according to the invention only in the colon, in the rectum, in the testis and in colon carcinomas using DNA-free RNA.

TABLE 1

GPR35 expression in normal tissues

| Normal tissue | Expression |
|---|---|
| Brain | – |
| Cerebellum | – |
| Myocardium | – |
| Skeletal muscle | – |
| Rectum | ++ |
| Stomach | – |
| Colon | ++ |
| Pancreas | – |
| Kidney | – |
| Testis | – |
| Thymus | – |
| Mammary glands | – |
| Ovary | – |
| Uterus | n.d. |
| Skin | – |
| Lung | – |
| Thyroid | – |
| Lymph nodes | – |
| Spleen | – |
| PBMC | – |
| Adrenal | – |
| Esophagus | – |
| Small intestine | + |
| Prostate | – |

(nd = not determined)

Figure 1:
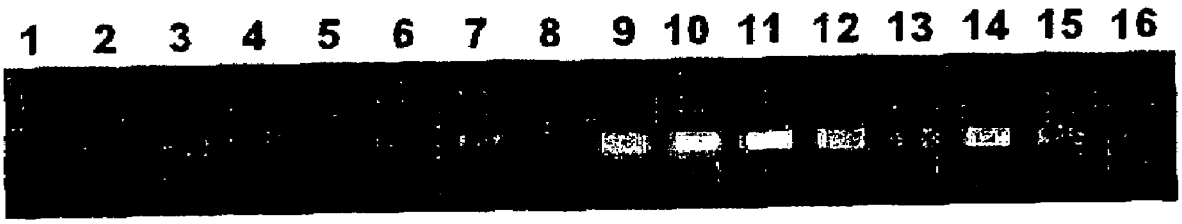
FIG. 1. GPR35 mRNA expression in colon carcinoma biopsies

The selective and high expression of GPR35 transcripts in normal colonic tissue and in colon carcinoma biopsies (FIG. 1) was not previously known and can be utilized according to the invention for molecular diagnostic methods such as RT-PCR for detecting disseminating tumor cells in the serum and bone marrow and for detecting metastases in other tissues. Quantitative RT-PCR with specific primers (SEQ ID NO:88 and 89) also confirms that GPR35 is a highly selective intestine-specific differentiation antigen which is also contained in intestinal tumors and in intestinal tumor metastases. In some intestinal tumors, it is in fact overexpressed by one log compared with normal intestine (FIG. 18). Antibodies were produced by immunizing rabbits for detecting GPR35 protein. The following peptides were used to propagate these antibodies:

```
GSSDLTWPPAIKLGC (AA 9-23)              SEQ ID NO:90
DRYVAVRHPLRARGLR (AA 112-127):         SEQ ID NO:91
VAPRAKAHKSQDSLC (C terminus):          SEQ ID NO:92
CFRSTRHNFNSMR (extracell. domain 2)    SEQ ID NO:93
```

Stainings with these antibodies for example in a Western blot confirm the expression in tumors. All 4 extracellular domains of GPR35 (position of the predicted extracellular domains in the sequence of SEQ ID NO:9 AA 1-22 (SEQ ID NO:94); AA 81-94 (SEQ ID NO:95); AA 156-176 (SEQ ID NO:96); AA 280-309 (SEQ ID NO:97)) can be used according to the invention as target structures of monoclonal antibodies. These antibodies bind specifically to the cell surface of tumor cells and can be used both for diagnostic and for therapeutic methods. Overexpression of GPR35 in tumors provides additional support for such a use. In addition, the sequences coding for proteins can be used according to the invention as vaccine (RNA, DNA, peptide, protein) for inducing tumor-specific immune responses (T-cell and B-cell-mediated immune responses). In addition, it has surprisingly been found that a further start codon exists 5' in front of the generally known start codon and expresses an N-terminally extended protein.

It has thus been found according to the invention that GPR35, a protein which was previously described as expressed ubiquitously, is tumor-associated overexpressed, selectively in gastrointestinal tumors, especially in tumors of the colon. GPR35 is therefore suitable in particular as molecular target structure for the diagnosis and treatment of these tumors. Investigation to date of human GPR35, cf., for example, Horikawa Y, Oda N, Cox N J, Li X, Orho-Melander M, Hara M, Hinokio Y, Lindner T H, Mashima H, Schwarz P E, del Bosque-Plata L, Horikawa Y, Oda Y, Yoshiuchi I, Colilla S, Polonsky K S, Wei S, Concannon P, Iwasaki N, Schulze J, Baier L J, Bogardus C, Groop L, Boerwinkle E, Hanis C L, Bell G I Nat Genet. 2000 October;26(2):163-75 suggested that GPR35 is activated in many healthy tissues. By contrast, the investigations according to the invention showed that GPR35 is surprisingly not significantly detectable in most normal tissues and, in contrast thereto, is highly activated in primary and metastatic colon tumors. In addition, besides the described GPR35 sequence, according to the invention a novel translation variant which makes use of an alternative start codon has been found (SEQ ID NO:10).

GPR35 is a member of the group of G-coupled receptors (GPCR), a very large protein family whose structure and function has been very well investigated. GPCR are outstandingly suitable as target structures for the development of pharmaceutically active substances, because the methods necessary therefor (e.g. receptor expression, purification, ligand screening, mutagenizing, functional inhibition, selection of agonistic and antagonistic ligands, radiolabeling of ligands) is very well developed and described in detail, cf., for example, "G Protein-Coupled Receptors" by Tatsuya Haga, Gabriel Berstein and Gabriel Bernstein ISBN: 0849333849 and in "Identification and Expression of G-Protein Coupled Receptors Receptor Biochemistry and Methodology" by Kevin R. Lynch ASIN: 0471183105. Realization according to the invention that GPR35 is undetectable in most healthy tissues but undergoes tumor-associated expression on the cell surface, enables it to be used as tumor-associated target structure for example for pharmaceutically active ligands, especially in conjugation for example with radioactive molecules as pharmaceutical substances. It is possible in a particular embodiment to use radiolabeled ligands which bind to GPR35 for detecting tumor cells or for treating colon tumors in vivo.

Example 2

Identification of GUCY2C in Hepatic and Ovarian Tumors and Novel GUCY2C Splice Variants as Diagnostic and Therapeutic Cancer Targets Guanylate cyclase 2 C (SEQ ID NO:2; translation product: SEQ ID NO:11)—a type I transmembrane protein—belongs to the family of natriuretic peptide receptors. The sequence is published in Genbank under the accession number NM_004963. Binding of the peptides guanylin and uroguanylin or else heat-stable enterotoxins (STa) increases the intracellular cGMP concentration, thus inducing signal transduction processes inside the cell.

Recent investigations indicate that expression of GUCY2C also extends to extraintestinal regions such as, for example, primary and metastatic adenocarcinomas of the stomach and of the esophagus (Park et al., *Cancer Epidemiol Biomarkers Prev.* 11: 739-44, 2002). A splice variant of GUCYC which is found both in normal and transformed tissue of the intestine comprises a 142 bp deletion in exon 1, thus preventing translation of a GUCY2C-like product (Pearlman et al., *Dig. Dis. Sci.* 45:298-05, 2000). The only splice variant described to date leads to no translation product.

The aim according to the invention was to identify tumor-associated splice variants for GUCY2C which can be utilized both for diagnosis and for therapy.

RT-PCR investigations with a GUCY2C-specific primer pair (SEQ ID NO:22, 23, 98, 99) show pronounced expression of GUCY2C transcripts in normal colon and stomach, and weak expression in liver, testis, ovary, thymus, spleen, brain and lung (tab. 2, FIG. 19). Expression in colon and stomach was at least 50 times higher than in all other normal tissues. Marked GUCY2C transcript levels were detected in colon carcinoma and stomach carcinoma (tab. 2). These results were specified by a quantitative PCR analysis and showed pronounced GUCY2C expression in normal colon, ileum, and in almost all colon carcinoma samples investigated (FIG. 2, 19B). A massive overexpression was detectable in some colon carcinoma samples. In addition, expression is found in 7/10 stomach tumors. We also surprisingly found that the gene is activated in many other previously undescribed tumors, inter alia ovarian, breast, liver and prostate tumors (FIG. 19B, tab. 2).

TABLE 2

GUC2C expression in normal and tumor tissues

| Normal tissues | Expression | Tumor type | Expression |
|---|---|---|---|
| Brain | + | Colon carcinoma | +++ |
| Cerebellum | | Pancreatic carcinoma | – |
| Myocardium | | | |

TABLE 2-continued

GUC2C expression in normal and tumor tissues

| Normal tissues | Expression | Tumor type | Expression |
|---|---|---|---|
| Skeletal muscle | – | Esophageal carcinoma | – |
| Myocardium | | Stomach carcinoma | +++ |
| Stomach | +++ | Bronchial | – |
| Colon | +++ | carcinoma | |
| Pancreas | – | Mammary carcinoma | –+ |
| Kidney | – | Ovarian carcinoma | + |
| Liver | + | Endometrial carci | |
| Testis | ++ | ENT tumors | |
| Thymus | + | Renal cell | |
| Breast | – | carcinoma | |
| Ovary | + | Prostate | + |
| Uterus | + | carcinoma | |
| Skin | | Liver carcinoma | + |
| Lung | + | | |
| Thyroid | | | |
| Lymph nodes | – | | |
| Spleen | + | | |
| PBMC | – | | |
| Prostate | – | | |

The following primer pairs were used to detect splice variants in colonic tissue and colon carcinoma tissue:

| | |
|---|---|
| GUCY2C-118s/GUCY2C-498as | (SEQ ID NO: 24, 29); |
| GUCY2C-621s/GUCY2C-1140as | (SEQ ID NO: 25, 30); |
| GUCY2C-1450s/GUCY2C-1790as | (SEQ ID NO: 26, 31); |
| GUCY2C-1993s/GUCY2C-2366as | (SEQ ID NO: 27, 32); |
| GUCY2C-2717s/GUCY2C-3200as | (SEQ ID NO: 28, 33); |
| GUCY2C-118s/GUCY2C-1140as | (SEQ ID NO: 24, 30); |
| GUCY2C-621s/GUCY2C-1790as | (SEQ ID NO: 25, 31); |
| GUCY2C-1450s/GUCY2C-2366as | (SEQ ID NO: 26, 32); |
| GUCY2C-1993s/GUCY2C-3200as | (SEQ ID NO: 27, 33). |

On investigation of splice variants in colon carcinoma tissue, three previously unknown forms were identified according to the invention.

a) A deletion of exon 3 (SEQ ID NO:3) which leads to a variant of GUCY2C which is only 111 amino acids long and in which the asparagine at position 111 is replaced by a proline.

b) A deletion of exon 6 (SEQ ID NO:4) which results in an expression product 258 amino acids long. This would generate a C-terminal neoepitope comprising 13 amino acids.

c) A variant in which the nucleotides at positions 1606-1614, and the corresponding amino acids L(536), L(537) and Q(538), are deleted (SEQ ID NO:5).

The splice variants according to the invention with deletions respectively in exon 3 and exon 6 (SEQ ID NO:3, 4) are distinguished in particular by the translation products (SEQ ID NO:12, 13) having no transmembrane domain. The result in the case of exon 6 deletion is a C-terminal neoepitope of 13 amino acids which shows no homology whatsoever with previously known proteins. This neoepitope is thus predestined to be a target structure for immunotherapy. The splice variant of the invention with base deletions at positions 1606-1614 (SEQ ID NO:5) and its translation product (SEQ ID NO:14) likewise comprises a neoepitope. Antibodies for detecting GUCY2C protein were produced by immunizing rabbits. The following peptides were used to propagate these antibodies:

SEQ ID NO:100: HNGSYEISVLMMGNS (AA 31-45)

SEQ ID NO:101: NLPTPPTVENQQRLA (AA 1009-1023)

Such antibodies can in principle be used for diagnostic and therapeutic purposes.

In particular, the extracellular domain of GUCY2C (position of the predicted extracellular domain from the sequence of SEQ ID NO:11: AA 454-1073 (SEQ ID NO:102)) can be used according to the invention as target structure of monoclonal antibodies. However, the structural prediction is somewhat ambiguous and not yet verified experimentally, so that an alternative membrane orientation is also conceivable. In this case, amino acids 1-431 would be outside the cell and be suitable as starting point for monoclonal antibodies. These antibodies bind specifically to the cell surface of tumor cells and can be used both for diagnostic and for therapeutic methods. Overexpression of GUCY2C, especially in the colon tumors, provides additional support for such a use. Sequences coding for proteins can moreover be used according to the invention as vaccine (RNA, DNA, peptides, protein) for inducing tumor-specific immune responses (T-cell- and B-cell-mediated immune responses).

It is moreover possible in accordance with the cellular function of the GUCY2C molecule to develop according to the invention substances, especially small molecules, which modulate the function of the enzyme on tumor cells. The product of the enzymic reaction, cGMP, is a known cellular signal molecule with a wide variety of functions (Tremblay et al. Mol Cell Biochem 230, 31).

Example 3

Identification of SCGB3A2 as Diagnostic and therapeutic Cancer Target

SCGB3A2 (SEQ ID NO:6) (translation product: SEQ ID NO:15) belongs to the secretoglobin gene family. The sequence is published in GenBank under accession number NM_054023. SCGB3A2 (UGRP1) is a homodimeric secretory protein with a size of 17 kDa, which is expressed exclusively in the lung and in the spiracles (Niimi et al., *Am J Hum Genet* 70:718-25, 2002). RT PCR investigations with a primer pair (SEQ ID NO:37, 38) confirmed selective expression in normal lung tissue. Lung- and trachea-specific genes, e.g. for surfactant proteins, are highly downregulated in malignant tumors during dedifferentiation and are normally undetectable in lung tumors. It was surprisingly found that SCGB3A2 is active in primary and metastatic lung tumors. The investigations according to the invention showed that SCGB3A2 is strongly and frequently expressed in bronchial carcinomas (FIG. 4). All the other 23 normal tissues tested, apart from lung and trachea, show no expression (cf. FIG. 20).

This was additionally confirmed in a specific quantitative RT-PCR (SEQ ID NO:103, 104) (FIG. 20) which additionally shows overexpression by at least one log in more than 50% of bronchial carcinomas.

The selective and high expression of SCGB3A2 in normal lung tissue and in lung carcinoma biopsies can be used according to the invention for molecular diagnostic methods such as RT-PCR for detecting disseminating tumor cells in blood and bone marrow, sputum, bronchial aspirate or lavage and for detecting metastases in other tissues, e.g. in local lymph nodes. In the healthy lung, SCGB3A2 is secreted by specialized cells exclusively into the bronchi. Accordingly, it is not to be expected that SCGB3A2 protein will be detectable in body fluids outside the respiratory tract in healthy individuals. By contrast, in particular metastatic tumor cells secrete their protein products directly into the bloodstream. One aspect of the invention therefore relates to detection of SCGB3A2 products in serum or plasma of patients via a specific antibody assay as diagnostic finding for lung tumors.

Antibodies for detecting SCGB3A2 protein were produced by immunizing rabbits. The following peptides were used to propagate these antibodies:

```
LINKVPLPVDKLAPL:        SEQ ID NO:105

SEAVKKLLEALSHLV:        SEQ ID NO:106
```

An SCGB3A2-specific reaction was detectable in immunofluorescence (FIG. 21). As expected for a secreted protein, the distribution of SCGB3A2 in the cell was assignable to the endoplasmic reticulum and secretion granules (FIG. 21A). To check the specificity, the cells were transfected in parallel with a plasmid that synthesizes an SCGB3A2-GFP fusion protein. Protein detection took place in this case via the autofluorescent GFP (green fluorescent protein) (FIG. 21B). Superimposition of the two fluorescence diagrams shows unambiguously that the immune serum specifically recognizes SCGB3A2 protein (FIG. 21C). Such antibodies can be used according to the invention for example in the form of immunoassays for diagnostic and therapeutic purposes.

Example 4

Identification of Claudin-18A1 and Claudin-18A2 Splice Variants as Diagnostic and Therapeutic Cancer Targets The claudin-18 gene codes for a surface membrane molecule having 4 transmembrane domains and intracellular N terminus and C terminus. Niimi and colleagues (*Mol. Cell. Biol.* 21:7380-90, 2001) describe two splice variants of the murine and human claudin-18 which have been described as expressed selectively in lung tissue (claudin-18A1) and in stomach tissue (claudin-18A2), respectively. These variants differ in the N terminus (FIG. 22).

It was investigated according to the invention how far the splice variants claudin-18A2 (SEQ ID NO:7) and claudin-18A1 (SEQ ID NO:117), and their respective translation products (SEQ ID NO:16 and 118), can be used as markers or therapeutic target structures for tumors. A quantitative PCR able to distinguish between the two variants was established by selecting A1-specific (SEQ ID NO:109 & 110) and A2-specific (SEQ ID NO:107 & 108) primer pairs. The A2 splice variant was additionally tested with a second primer pair in a conventional PCR (SEQ ID NO:39 & 40). The A1 variant is described to be active only in normal lung. However, it was surprisingly found according to the invention that the A1 variant is also active in the gastric mucosa. Stomach and lung are the only normal tissues showing significant activation. All other normal tissues are negative for claudin-A1. On investigating tumors, it was surprisingly found that claudin-A1 is highly activated in a large number of tumor tissues. Particularly strong expression is to be found in stomach tumors, lung tumors, pancreatic carcinomas, esophageal carcinomas (FIG. 23), ENT tumors and prostate carcinomas. The claudin-A1 expression levels in ENT, prostate, pancreatic and esophageal tumors are 100-10,000 higher than the levels in the corresponding normal tissues. The oligonucleotides used to investigate the claudin-A2 splice variant specifically enable this transcript to be amplified (SEQ ID NO:39 & 40 and 107 & 108). Investigation revealed that the A2 splice variant is expressed in none of the more than 20 normal tissues investigated apart from gastric mucosa and to a small extent also testis tissue. We have found that the A2 variant is also, like the A1 variant, activated in many tumors (depicted by way of example in FIG. 24). These include stomach tumors (8/10), pancreatic tumors (6/6), esophageal carcinomas (5/10) and liver carcinomas. Although no activation of claudin-18A2 is detectable in healthy lung, it was surprisingly found that some lung tumors express the A2.1 splice variant.

TABLE 3A

Expression of claudin-18A2 in normal and tumor tissues

| Normal tissue | Expression | Tumor type | Expression |
|---|---|---|---|
| Brain | – | Colon carcinoma | – |
| Cerebellum | – | | |
| Myocardium | – | Pancreatic carcinoma | ++ |
| Skeletal muscle | – | | |
| | | Esophageal carcinoma | ++ |
| Endometrium | – | | |
| Stomach | +++ | Gastric carcinoma | +++ |
| Colon | – | | |
| Pancreas | – | Bronchial carcinoma | ++ |
| Kidney | – | | |
| Liver | – | Breast carcinoma | – |
| Testis | + | | |
| Thymus | – | Ovarian carcinoma | – |
| Breast | – | | |
| Ovary | – | Endometrial carcinoma | n.i. |
| Uterus | – | | |
| Skin | – | ENT tumors | ++ |
| Lung | – | Renal cell carcinoma | – |
| Thyroid | – | | |
| Lymph nodes | – | Prostate carcinoma | – |
| Spleen | – | | |
| PBMC | – | | |
| Esophagus | – | | |

TABLE 3B

Expression of claudin-18A1 in normal and tumor tissues

| Normal tissue | Expression | Tumor type | Expression |
|---|---|---|---|
| Brain | – | Colon carcinoma | – |
| Cerebellum | – | | |
| Myocardium | – | Pancreatic carcinoma | ++ |
| Skeletal muscle | – | | |
| | | Esophageal carcinoma | ++ |
| Endometrium | – | | |
| Stomach | +++ | Gastric carcinoma | +++ |
| Colon | – | | |
| Pancreas | – | Bronchial carcinoma | ++ |
| Kidney | – | | |
| Liver | – | Breast carcinoma | + |
| Testis | + | | |
| Thymus | – | Ovarian carcinoma | n.i. |
| Breast | – | | |
| Ovary | – | Endometrial carcinoma | n.i. |
| Uterus | – | | |
| Skin | – | ENT tumors | ++ |
| Lung | +++ | Renal cell carcinoma | – |
| Thyroid | – | | |
| Lymph nodes | – | Prostate carcinoma | ++ |
| Spleen | – | | |
| PBMC | – | | |
| Esophagus | – | | |

Conventional PCR as independent control investigation also confirmed the results of the quantitative PCR. The oligonucleotides (SEQ ID NO:39, 40) used for this permit specific amplification of the A2 splice variant. It was shown according to the invention that 8/10 gastric carcinomas and half of the tested pancreatic carcinomas showed strong expression of this splice variant (FIG. 5). By contrast, expression is not detectable in other tissues by conventional PCR. In particular, there is no expression in lung, liver, blood, lymph nodes, breast tissue and kidney tissue (tab. 3).

The splice variants thus represent according to the invention highly specific molecular markers for tumors of the upper gastrointestinal tract as well as lung tumors, ENT tumors, prostate carcinomas and metastases thereof. These molecular markers can be used according to the invention for detecting tumor cells. Detection of the tumors is possible according to the invention with the oligonucleotides described (SEQ ID NO:39, 40, 107-110). Particularly suitable oligonucleotides are primer pairs of which at least one binds under stringent conditions to a segment of the transcript which is 180 base pairs long and is specific for one (SEQ ID NO:8) or the other splice variant (SEQ ID NO:119).

In order to confirm these data at the protein level, claudin-specific antibodies and immune sera were generated by immunizing animals. The plasma membrane localization of claudin-18 and the protein topology was confirmed by analysis of the transmembrane domains with bioinformatic tools (TMHMM, TMPRED) and immunofluorescence investigations of cells which expressed claudin-18 fusion proteins tagged with enhanced GFP. Claudin-18 has two extracellular domains. The N-terminal extracellular domain differs in sequence in the two splice variants (SEQ ID NO:111 for A1 and SEQ ID NO:112 for A2). The C-terminal extracellular domain is identical for both variants (SEQ ID NO:137) To date, no antibodies which bind to the extracellular domains of claudin-18 have yet been described. According to the invention, peptide epitopes which are located extracellularly and are specific for variant A1 or A2 or occur in both variants were selected for the immunization. Both variants of claudin-18 have no conventional glycosylation motifs and the glycosylation of the protein was therefore not to be expected. Nevertheless, account was taken in the selection of the epitopes that epitopes which comprise asparagine, serine, threonine are potentially glycosylated in rare cases even without conventional glycosylation sites. Glycosylation of an epitope may prevent the binding of an antibody specific for this epitope. Inter alia, epitopes were selected according to the invention so that the antibodies generated thereby permit the glycosylation status of the antigen to be distinguished. The following peptides, inter alia, were selected for producing antibodies for the immunization:

SEQ ID NO:17: DQWSTQDLYN (N-terminal extracellular domain, A2-specific, binding independent of glycosylation)

SEQ ID NO:18: NNPVTAVFNYQ (N-terminal extracellular domain, A2-specific, binding mainly to unglycosylated form, N37)

SEQ ID NO:113: STQDLYNNPVTAVF (N-terminal extracellular domain, A2-specific, binding only to non-glycosylated form, N37)

SEQ ID NO:114: DMWSTQDLYDNP (N-terminal extracellular domain, A1-specific)

SEQ ID NO:115: CRPYFTILGLPA (N-terminal extracellular domain, mainly specific for A1)

SEQ ID NO:116: TNFWMSTANMYTG (C-terminal extracellular domain, recognizes both A1 and A2).

The data for the A2-specific antibody produced by immunization with SEQ ID NO:17 are shown by way of example. The specific antibody can be utilized under various fixation conditions for immunofluorescence investigations. With comparative stainings of RT-PCR-positive and negative cell lines, in an amount which is readily detectable, the corresponding protein can be specifically detected in the gastric carcinoma cell lines typed as positive (FIG. 25). The endogenous protein is membrane-located and forms relatively large focal aggregates on the membrane. This antibody was additionally employed for protein detection in Western blotting. As expected, protein is detected only in stomach and in no other normal tissue, not even lung (FIG. 29). The comparative staining of stomach tumors and adjacent normal stomach tissue from patients surprisingly revealed that claudin-18 A2 has a smaller mass weight in all stomach tumors in which this protein is detected (FIG. 30, left). It was found according to the invention in a series of experiments that a band also appears at this level when lysate of normal stomach tissue is treated with the deglycosylating agent PNGase F (FIG. 30, right). Whereas exclusively the glycosylated form of the A2 variant is detectable in all normal stomach tissues, A2 is detectable as such in more than 60% of the investigated gastric carcinomas, in particular exclusively in the deglycosylated form. Although the A2 variant of claudin-18 is not detected in normal lung even at the protein level, it is to be found in bronchial carcinomas, as also previously in the quantitative RT-PCR. Once again, only the deglycosylated variant is present (FIG. 31). Antibodies which recognize the extracellular domain of the claudin-18-A2 splice variant have been produced according to the invention. In addition, antibodies which selectively recognize the N-terminal domain of the claudin-18-A1 splice variant (FIG. 28) and antibodies which bind to both variants in the region of the C-terminal extracellular domain (FIG. 27) have been produced. It is possible according to the invention to use such antibodies for diagnostic purposes, e.g. immunohistology (FIG. 32), but also for therapeutic purposes as explained above. A further important aspect relates to differentially glycosylated domains of claudin-18. Antibodies which exclusively bind to non-glycosylated epitopes have been produced according to the invention. Claudin-18 itself is a highly selective differentiating antigen for stomach tissue (A2) and for the lung and stomach (A1). Since it is evidently affected by changes in the glycosylation machinery in tumors, a particular, deglycosylated, variant of A2 is produced in tumors. This can be utilized diagnostically and therapeutically. Immune sera such as the one described here (against peptide of SEQ ID NO:17) can be utilized diagnostically for example in Western blotting. Antibodies which are entirely unable to bind to the glycosylated epitope as obtained for example by immunization with peptide of SEQ ID NO:113 (FIG. 26), can distinguish tumor tissue from normal tissue in the binding. It is possible in particular to employ such antibodies therapeutically because they are highly selective. The produced antibodies can be used directly also for producing chimeric or humanized recombinant antibodies. This can also take place directly with antibodies obtained from rabbits (concerning this, see J Biol Chem. 2000 May 5;275(18):13668-76 by Rader C, Ritter G, Nathan S, Elia M, Gout I, Jungbluth A A, Cohen L S, Welt S, Old L J, Barbas C F 3rd. "The rabbit antibody repertoire as a novel source for the generation of therapeutic human antibodies"). For this purpose, lymphocytes from the immunized animals were preserved. The amino acids 1-47 (SEQ ID NO:19 and 120) also represent particularly good epitopes for immunotherapeutic methods such as vaccines and the adoptive transfer of antigen-specific T lymphocytes.

Example 5

Identification of SLC13A1 as Diagnostic and Therapeutic Cancer Target

SLC13A1 belongs to the family of sodium sulfate cotransporters. The human gene is, in contrast to the mouse homolog of this gene, selectively expressed in the kidney (Lee et al., *Genomics* 70:354-63). SLC13A1 codes for a protein of 595 amino acids and comprises 13 putative transmembrane domains. Alternative splicing results in 4 different transcripts (SEQ ID NO:41-44) and its corresponding translation products (SEQ ID NO:45-48). It was investigated whether SLC13A1 can be used as marker for kidney tumors. Oligonucleotides (SEQ ID NO:49, 50) which enable specific amplification of SLC13A1 were used for this purpose.

TABLE 4

Expression of SLC13A1 in normal and tumor tissues

| Normal tissue | Expression | Tumor type | Expression |
|---|---|---|---|
| Brain | – | Colon | nd |
| Cerebellum | nd | carcinoma | |
| Myocardium | nd | Pancreatic | nd |
| Skeletal | nd | carcinoma | |
| muscle | | Esophageal | nd |
| Myocardium | – | carcinoma | |
| Stomach | – | Gastric | nd |
| Colon | – | carcinoma | |
| Pancreas | nd | Bronchial | nd |
| Kidney | +++ | carcinoma | |
| Liver | – | Breast | nd |
| Testis | + | carcinoma | |
| Thymus | – | Ovarian | nd |
| Breast | – | carcinoma | |
| Ovary | – | Endometrial | nd |
| Uterus | nd | carcinoma | |
| Skin | nd | ENT tumors | nd |
| Lung | – | Renal cell | +++ |
| Thyroid | – | carcinoma | |
| Lymph nodes | – | Prostate | nd |
| Spleen | – | carcinoma | |
| PBMC | – | | |
| Sigmoid | – | | |
| Esophagus | – | | |

RT-PCR investigations with an SLC13A1-specific primer pair (SEQ ID NO:49, 50) confirmed virtually selective expression in the kidney, and showed according to the invention a high expression in virtually all (7/8) investigated renal cell carcinoma biopsies (tab. 4, FIG. 6). Quantitative RT-PCR with specific primers (SEQ ID NO:121, 122) also confirmed these data (FIG. 34). Weak signals were detectable in the following normal tissues: colon, stomach, testis, breast, liver and brain. Expression in renal carcinomas was, however, at least 100 times higher than in all other normal tissues.

In order to analyse the subcellular localization of SLC13A1 in the cell, the protein was fused to eGFP as reporter molecule and, after transfection of the appropriate plasmid, expressed heterologously in 293 cells. The localization was then analysed under the fluorescence microscope. Our data impressively confirmed that SLC13A1 is an integral transmembrane molecule (FIG. 35).

Antibodies for detecting the SLC13A1 protein were produced by immunizing rabbits. The peptides of SEQ ID NO:123 and 124 were used for propagating these antibodies. Such antibodies can in principle be used for diagnostic and therapeutic purposes.

The SLC13A1 protein has 13 transmembrane domains and 7 extracellular regions. These extracellular domains of SLC13A1 in particular can be used according to the invention as target structures for monoclonal antibodies. SLC13A1 is involved as channel protein in the transport of ions. The extracellular domains of SLC13A1 in the healthy kidney are directed polarically in the direction of the urinary tract (luminally). However, high molecular weight monoclonal antibodies employed therapeutically are not excreted into the urinary tract, so that no binding to SLC13A1 takes place in the healthy kidney. By contrast, the polarity of SLC13A1 is abolished in tumor cells, and the protein is available for antibody targeting directly via the bloodstream. The pronounced expression and high incidence of SLC13A1 in renal cell carcinomas make this protein according to the invention a highly interesting diagnostic and therapeutic marker. This includes according to the invention the detection of disseminated tumor cells in serum, bone marrow, urine, and detection of metastases in other organs by means of RT-PCR. It is additionally possible to use the extracellular domains of SLC13A1 according to the invention as target structure for immunodiagnosis and therapy by means of monoclonal antibodies. SLC13A1 can moreover be employed according to the invention as vaccine (RNA, DNA, protein, peptides) for inducing tumor-specific immune responses (T and B cell-mediated immune responses). This includes according to the invention also the development of so-called small compounds which modulate the biological activity of SLC13A1 and can be employed for the therapy of renal tumors.

Example 6

Identification of CLCA1 as diagnostic and Therapeutic Cancer Target

CLCA1 (SEQ ID NO:51; translation product: SEQ ID NO:60) belongs to the family of $Ca^{++}$-activated $Cl^{-}$ channels. The sequence is published in Genbank under the accession No. NM_001285. CLCA1 is exclusively expressed in the intestinal crypt epithelium and in the goblet cells (Gruber et al., *Genomics* 54:200-14, 1998). It was investigated whether CLCA1 can be used as marker for colonic and gastric carcinoma. Oligonucleotides (SEQ ID NO:67, 68) which enable specific amplification of CLCA1 were used for this purpose. RT-PCR investigations with this primer set confirmed selective expression in the colon, and showed according to the invention high expression in (3/7) investigated colonic and (1/3) investigated gastric carcinoma samples (FIG. 7). The other normal tissues showed no or only very weak expression. This was additionally confirmed with a specific quantitative RT-PCR (SEQ ID NO:125, 126), in which case no expression could be detected in the normal tissues analyzed (FIG. 36). Of the tumor samples investigated in this experiment, 6/12 colonic carcinoma samples and 5/10 gastric carcinoma samples were positive for CLCA1. Overall, expression of the gene in tumors appears to be dysregulated. Besides samples with very strong expression, CLCA1 was markedly down-regulated in other samples.

The protein is predicted to have 4 transmembrane domains with a total of 2 extracellular regions. These extracellular domains of CLCA1 in particular can be used according to the invention as target structures for monoclonal antibodies.

The pronounced expression and high incidence of CLCA1 in gastric and colonic carcinomas make this protein according to the invention an interesting diagnostic and therapeutic marker. This includes according to the invention the detection of disseminated tumor cells in serum, bone marrow, urine, and detection of metastases in other organs by means of RT-PCR. It is additionally possible to use the extracellular domains of CLCA1 according to the invention as target structure for immunodiagnosis and therapy by means of monoclonal antibodies. CLCA1 can moreover be employed according to the invention as vaccine (RNA, DNA, protein, peptides) for inducing tumor-specific immune responses (T and B cell-mediated immune responses). This includes according to the invention also the development of so-called small compounds which modulate the biological activity as transport proteins of CLCA1 and can be employed for the therapy of gastrointestinal tumors.

Example 7

Identification of FLJ21477 as Diagnostic and Therapeutic Cancer Target

FLJ21477 (SEQ ID NO:52) and its predicted translation product (SEQ ID NO:61) was published as hypothetical protein in Genbank under the accession No. NM_025153. It is an integral membrane protein having ATPase activity and 4 transmembrane domains, which is accordingly suitable for therapy with specific antibodies. RT-PCR investigations with FLJ21477-specific primers (SEQ ID NO:69, 70) showed selective expression in the colon, and additionally various levels of expression in (7/12) investigated colonic carcinoma samples (FIG. 8). The other normal tissues showed no expression. This was confirmed additionally by a specific quantitative RT-PCR (SEQ ID NO:127, 128). FLJ21477-specific expression was detectable both in colon (FIG. 37A) and in 11/12 of colonic carcinomas. Besides the expression in colon tissue, expression was additionally detectable in stomach tissue. In addition, under the conditions of the quantitative RT-PCR, the expression detectable in brain, thymus and esophagus was distinctly weaker compared with colon and stomach (FIG. 37A). It was moreover additionally possible to detect FLJ21477-specific expression in the following tumor samples: stomach, pancreas, esophagus and liver.

The protein is predicted to have 4 transmembrane domains with a total of 2 extracellular regions. These extracellular domains of FLJ21477 in particular can be used according to the invention as target structures for monoclonal antibodies.

The expression and the high incidence of FLJ21477 for gastric and colonic carcinomas make this protein according to the invention a valuable diagnostic and therapeutic marker. This includes according to the invention the detection of disseminated tumor cells in serum, bone marrow, urine, and the detection of metastases in other organs by means of RT-PCR. In addition, the extracellular domains of FLJ21477 can be used according to the invention as target structure for immunodiagnosis and therapy by means of monoclonal antibodies. In addition, FLJ21477 can be employed according to the invention as vaccine (RNA, DNA, protein, peptides) for inducing tumor-specific immune responses (T and B cell-mediated immune responses).

Example 8

Identification of FLJ20694 as Diagnostic and Therapeutic Cancer Target

FLJ20694 (SEQ ID NO:53) and its translation product (SEQ ID NO:62) were published as hypothetical protein in Genbank under accession No. NM_017928. This protein is an integral transmembrane molecule (transmembrane domain AA 33-54), very probably with thioredoxin function. RT-PCR investigations with FLJ20694-specific primers (SEQ ID NO:71, 72) showed selective expression in the colon, and additionally various levels of expression in (5/9) investigated colonic carcinoma samples (FIG. 9). The other normal tissues showed no expression. This was additionally confirmed by a specific quantitative RT-PCR (SEQ ID NO:129, 130) (FIG. 38). FLJ29694 expression was undetectable in any other normal tissue apart from colon and stomach (not analysed in the first experiment).

The protein is predicted to have one transmembrane domain with an extracellular region. These extracellular domains of FLJ20694 in particular can be used according to the invention as target structures for monoclonal antibodies.

In addition, FLJ20694 can be employed according to the invention as vaccine (RNA, DNA, protein, peptides) for inducing tumor-specific immune responses (T and B cell-mediated immune responses). This includes according to the invention also the development of so-called small compounds which modulate the biological activity of FLJ20694 and can be employed for the therapy of gastrointestinal tumors.

Example 9

Identification of Von Ebner's Protein (c20orf114) as Diagnostic and Therapeutic Cancer Target von Ebner's protein (SEQ ID NO:54) and its translation product (SEQ ID NO:63) were published as Plunc-related protein of the upper airways and of the nasopharyngeal epithelium in Genbank under the accession No. AF364078. It was investigated according to the invention whether von Ebner's protein can be used as marker of lung carcinoma. Oligonucleotides (SEQ ID NO:73, 74) which enable specific amplification of Ebner's protein were used for this purpose. RT-PCR investigations with this primer set showed selective expression in the lung and in (5/10) investigated lung carcinoma samples (FIG. 10). In the group of normal tissues there was also expression in the stomach. The other normal tissues showed no expression.

Example 10

Identification of Plunc as Diagnostic and Therapeutic Cancer Target

Plunc (SEQ ID NO:55) and its translation product (SEQ ID NO:64) were published in Genbank under the accession No. NM_016583. Human Plunc codes for a protein of 256 amino acids and shows 72% homology with the murine Plunc protein (Bingle and Bingle, *Biochem Biophys Acta* 1493:363-7, 2000). Expression of Plunc is confined to the trachea, the upper airways, nasopharyngeal epithelium and salivary gland.

It was investigated according to the invention whether Plunc can be used as marker of lung carcinoma. Oligonucleotides (SEQ ID NO:75, 76) which enable specific amplification of Plunc were used for this purpose.

RT-PCR investigations with this primer set showed selective expression in the thymus, in the lung and in (6/10) investigated lung carcinoma samples (FIG. 11). Other normal tissues showed no expression.

Example 11

Identification of SLC26A9 as Diagnostic and Therapeutic Cancer Target

SLC26A9 (SEQ ID NO:56) and its translation product (SEQ ID NO:65) were published in Genbank under the accession No. NM_134325. SLC26A9 belongs to the family of anion exchangers. Expression of SLC26A9 is confined to the bronchiolar and alveolar epithelium of the lung (Lohi et al., J Biol Chem 277:14246-54, 2002).

It was investigated whether SLC26A9 can be used as marker of lung carcinoma. Oligonucleotides (SEQ ID NO:77, 78) which enable specific amplification of SLC26A9 were used for this purpose. RT-PCR investigations with SLC26A9-specific primers (SEQ ID NO:77, 78) showed selective expression in the lung and in all (13/13) investigated lung carcinoma samples (FIG. 12). The other normal tissues showed no expression, with the exception of the thyroid. It was possible in quantitative RT-PCR experiments with the primers of SEQ ID NO:131 and 132 firstly to confirm these results, and to obtain additional information. It was possible in pooled samples of 4-5 tumor tissues to detect high expression levels for SLC26A9-specific RNA in lung, colon, pancreas and stomach tumors. SLC26A9 is member of a family of transmembrane anion transporters. In the healthy lung, the protein is luminally directed in the direction of the airways and thus not directly available to IgG antibodies from the blood. By contrast, the polarity of the protein is abolished in tumors. It is therefore possible according to the invention to address SLC26A9 as therapeutic target using monoclonal antibodies in the defined tumors, inter alia lung tumors, gastric carcinomas, pancreatic carcinomas. The pronounced, high expression and high incidence of SLC26A9 for lung, stomach, pancreatic and esophageal carcinomas make this protein according to the invention an excellent diagnostic and therapeutic marker. This includes according to the invention the detection of disseminated tumor cells in serum, bone marrow and urine, and detection of metastases in other organs by means of RT-PCR. In addition, the extracellular domains of SLC26A9 can be used according to the invention as target structure for immunodiagnosis and therapy by means of monoclonal antibodies. It is additionally possible to employ SLC26A9 according to the invention as vaccine (RNA, DNA, protein, peptides) for inducing tumor-specific immune responses (T and B cell-mediated immune responses). This includes according to the invention also the development of so-called small compounds which modulate the biological activity of SLC26A9 and can be employed for the therapy of lung tumors and gastrointestinal tumors.

Example 12

Identification of THC1005163 as Diagnostic and Therapeutic Cancer Target

THC1005163 (SEQ ID NO:57) is a gene fragment from the TIGR gene index. The gene is defined only in the 3' region, while an ORF is lacking. RT-PCR investigations took place with a THC1005163-specific primer (SEQ ID NO:79) and an oligo $dT_{18}$ primer which had a specific tag of 21 specific bases at the 5' end. This tag was examined using database search programs for homology with known sequences. This specific primer was initially employed in the cDNA synthesis in order to preclude genomic DNA contaminations. RT-PCR investigations with this primer set showed expression in the stomach, ovary, lung and in (5/9) lung carcinoma biopsies (FIG. 13). Other normal tissues showed no expression.

Example 13

Identification of LOC134288 as mediated Diagnostic and Therapeutic Cancer Target LOC134288 (SEQ ID NO:58) and its predicted translation product (SEQ ID NO:66) were published in Genbank under accession No. XM_059703.

It was investigated according to the invention whether LOC134288 can be used as marker of renal cell carcinoma. Oligonucleotides (SEQ ID NO:80, 81) which enable specific amplification of LOC134288 were used for this purpose. RT-PCR investigations showed selective expression in the kidney and in (5/8) investigated renal cell carcinoma biopsies (FIG. 14).

Example 14

Identification of THC943866 as Diagnostic and Therapeutic Cancer Target

THC 943866 (SEQ ID NO:59) is a gene fragment from the TIGR gene index. It was investigated whether THC943866 can be used as marker of renal cell carcinoma. Oligonucleotides (SEQ ID NO:82, 83) which enable specific amplification of THC943866 were used for this purpose.

RT-PCR investigations with THC943866-specific primers (SEQ ID NO:82, 83) showed selective expression in the kidney and in (4/8) investigated renal cell carcinoma biopsies (FIG. 15).

Example 15

Identification of FLJ21458 as Diagnostic and Therapeutic Cancer Target

FLJ21458 (SEQ ID NO:84) and its predicted translation product (SEQ ID NO:85) were published in Genbank under the accession No. NM_034850. Sequence analyses revealed that the protein represents a new member of the butyrophillin family. Structural analyses revealed that it represents a type 1 transmembrane protein with an extracellular immunoglobulin domain. Oligonucleotides (SEQ ID NO:86, 87) which enable specific amplification of FLJ21458 were used for investigating expression. RT-PCR investigations with FLJ21458-specific primers (SEQ ID NO:86, 87) showed selective expression in colon and in (7/10) investigated colonic carcinoma biopsies (FIG. 16, tab. 5). Quantitative RT-PCR with specific primers (SEQ ID NO:133, 134) confirmed this selective expression profile (FIG. 39). It was additionally possible in the experiment to detect FLJ21458 gastrointestinal-specifically in the colon, and in stomach, in the rectum and cecum and in testis. 7/11 colon metastasis samples were also positive in the quantitative PCR. FLJ21458-specific expression was extended to other tumors, and a protein-specific expression was detectable in stomach, pancreas and liver tumors (tab. 5). Antibodies for detecting FLJ21458 protein were produced by immunizing rabbits. The following peptides were used to propagate these antibodies:

QWQVFGPDKPVQAL: SEQ ID NO:135

AKWKGPQGQDLSTDS: SEQ ID NO:136

An FLJ21458-specific reaction was detectable in immunofluorescence (FIG. 40). To check the specificity of the antibodies, 293 cells were transfected with a plasmid that codes for an FLJ21458-GFP fusion protein. Specificity was demonstrated on the one hand by colocalization investigations using the FLJ21458-specific antibody, and on the other hand via the auto-fluorescent GFP. Superimposition of the two fluorescent diagrams showed unambiguously that the immune serum specifically recognises FLJ21458 protein (FIG. 40*a*). Owing to the overexpression of the protein, the resultant cell staining was diffuse and did not allow unambiguous protein localization. For this reason, a further immunofluorescence experiment was carried out with the stomach tumor-specific cell line Snu16 which expresses FLJ21458 endogenously (FIG. 41B). The cells were stained with the FLJ21458-specific antiserum and with another antibody which recognizes the membrane protein E-cadherin. The FLJ21458-specific antibody stains the cell membranes at least weakly and is thus evidence that FLF21458 is localized in the cell membrane.

Bioinformatic investigations showed that the protein encoded by FLJ21458 represents a cell surface molecule and has an immunoglobulin supermolecule domain. Selective expression of this surface molecule makes it a good target for developing diagnostic methods for the detection of tumor cells and therapeutic methods for the elimination of tumor cells.

The pronounced expression and high incidence of FLJ21458 for gastric and colonic carcinomas make this protein according to the invention a highly interesting diagnostic and therapeutic marker. This includes according to the invention the detection of disseminated tumor cells in serum, bone marrow and urine, and the detection of metastases in other organs by means of RT-PCR. It is additionally possible to employ the extracellular domains of FLJ21458 according to the invention as target structure for immuno-diagnosis and therapy by means of monoclonal antibodies. It is additionally possible to employ FLJ21458 according to the invention as vaccine (RNA, DNA, protein, peptides) for inducing tumor-specific immune responses (T and B cell-mediated immune responses). This includes according to the invention also the development of so-called small compounds which modulate the biological activity of FLJ21458 and can be employed for the therapy of gastrointestinal tumors.

TABLE 5

FLJ21458 expression in normal and tumor tissues

| Normal tissue | Expression | Tumor type | Expression |
|---|---|---|---|
| Brain | – | Colonic | 7/10 |
| Cerebellum | – | carcinoma | |
| Myocardium | nd | Pancreatic | 5/6 |
| Skeletal | – | carcinoma | |
| muscle | | Esophageal | nd |
| Myocardium | – | carcinoma | |
| Stomach | ++ | Gastric | 8/10 |
| Colon | +++ | carcinoma | |
| Pancreas | – | Bronchial | nd |
| Kidney | – | carcinoma | |
| Liver | – | Breast | nd |
| Testis | ++ | carcinoma | |
| Thymus | nd | Ovarian | nd |
| Breast | nd | carcinoma | |
| Ovary | – | Endometrial | nd |
| Uterus | – | carcinoma | |
| Skin | – | ENT tumors | nd |
| Lung | – | Renal cell | nd |
| Thyroid | nd | carcinoma | |
| Lymph nodes | – | Prostate | nd |
| Spleen | – | carcinoma | |
| PBMC | – | Colonic | 7/11 |
| Adrenal | nd | metastases | |
| Esophagus | – | Liver | 5/8 |
| Small | – | carcinoma | |
| intestine | | | |
| Prostate | – | | |

The invention claimed is:

1. A method of diagnosing lung, pancreatic, or esophageal cancer, comprising detecting expression of a tumor-associated antigen in a biological sample, wherein the tumor-associated antigen is selected from the group consisting of:

(i) the polypeptide of SEQ ID NO: 16; and (ii) the polypeptide encoded by the nucleic acid of SEQ ID NO: 7, wherein detection of the tumor-associated antigen in a biological sample isolated from a patient in an amount greater than an amount of the tumor-associated antigen in a normal biological sample indicates the presence of lung, pancreatic, or esophageal cancer.

2. The method of claim 1, in which the detection comprises:

(i) contacting the biological sample with an antibody which binds specifically to the tumor-associated antigen; and (ii) detecting a complex formed between the antibody and the tumor-associated antigen.

3. The method of claim 2, wherein the antibody is labeled with a detectable marker.

4. The method of claim 3, wherein the detectable marker is a radioactive marker or an enzymatic marker.

5. The method of claim 1, wherein the biological sample comprises body fluid or body tissue.

* * * * *